US011117975B2

(12) United States Patent
Clarke et al.

(10) Patent No.: US 11,117,975 B2
(45) Date of Patent: *Sep. 14, 2021

(54) ANTI-CD38 ANTIBODIES AND FUSIONS TO ATTENUATED INTERFERON ALPHA-2B

(71) Applicant: Teva Pharmaceuticals Australia Pty Ltd, Macquarie Park (AU)

(72) Inventors: Adam Clarke, Macquarie Park (AU); Matthew Pollard, Macquarie Park (AU); Anthony Gerard Doyle, Macquarie Park (AU); Collette Behrens, Macquarie Park (AU); Tetsuo Yamagishi, Macquarie Park (AU); David S. Wilson, Jr., Redwood City, CA (US); Sarah L. Pogue, Fremont, CA (US); Tetsuya Taura, Palo Alto, CA (US)

(73) Assignee: Teva Pharmaceuticals Australia Pty Ltd, Macquarie Park (AU)

( * ) Notice: Subject to any disclaimer, the term of this patent is extended or adjusted under 35 U.S.C. 154(b) by 457 days.

This patent is subject to a terminal disclaimer.

(21) Appl. No.: 15/957,341

(22) Filed: Apr. 19, 2018

(65) Prior Publication Data
US 2018/0305460 A1 Oct. 25, 2018

Related U.S. Application Data

(60) Division of application No. 14/922,282, filed on Oct. 26, 2015, now Pat. No. 9,963,515, which is a continuation of application No. PCT/US2013/038659, filed on Apr. 29, 2013.

(51) Int. Cl.
| | |
|---|---|
| *A61K 39/395* | (2006.01) |
| *C07K 16/28* | (2006.01) |
| *C07K 14/56* | (2006.01) |
| *A61K 38/21* | (2006.01) |
| *A61K 38/00* | (2006.01) |
| *A61K 39/00* | (2006.01) |

(52) U.S. Cl.
CPC ........ *C07K 16/2896* (2013.01); *A61K 38/212* (2013.01); *A61K 39/39558* (2013.01); *C07K 14/56* (2013.01); *A61K 38/00* (2013.01); *A61K 2039/505* (2013.01); *C07K 2317/21* (2013.01); *C07K 2317/24* (2013.01); *C07K 2317/52* (2013.01); *C07K 2317/56* (2013.01); *C07K 2317/92* (2013.01); *C07K 2319/74* (2013.01)

(58) Field of Classification Search
CPC ............ A61K 2039/505; A61K 28/212; A61K 39/39558; A61K 38/00; C07K 16/2869; C07K 14/56; C07K 2317/52; C07K 2317/56; C07K 2317/21; C07K 2317/565; C07K 2319/00; C07K 2319/74
See application file for complete search history.

(56) References Cited

U.S. PATENT DOCUMENTS

| | | |
|---|---|---|
| 4,908,431 A | 3/1990 | Colman et al. |
| 5,055,289 A | 10/1991 | Frincke et al. |
| 5,225,539 A | 7/1993 | Winter |
| 5,441,734 A | 8/1995 | Reichert et al. |
| 5,545,405 A | 8/1996 | Page |
| 5,558,864 A | 9/1996 | Bendig et al. |
| 5,565,332 A | 10/1996 | Hoogenboom et al. |
| 5,585,089 A | 12/1996 | Queen et al. |
| 5,650,150 A | 7/1997 | Gillies |
| 5,677,171 A | 10/1997 | Hudziak et al. |
| 5,693,761 A | 12/1997 | Queen et al. |
| 5,770,195 A | 6/1998 | Hudziak et al. |
| 5,772,997 A | 6/1998 | Hudziak et al. |
| 5,795,965 A | 8/1998 | Tsuchiya et al. |
| 5,837,821 A | 11/1998 | Wu |
| 5,840,299 A | 11/1998 | Bendig et al. |
| 5,844,093 A | 12/1998 | Kettleborough et al. |
| 5,976,531 A | 11/1999 | Mezes et al. |
| 5,977,322 A | 11/1999 | Marks et al. |
| 6,054,297 A | 4/2000 | Carter et al. |
| 6,180,370 B1 | 1/2001 | Queen et al. |
| 6,217,866 B1 | 4/2001 | Sela et al. |
| 6,248,516 B1 | 6/2001 | Winter et al. |
| 6,277,375 B1 | 8/2001 | Ward |

(Continued)

FOREIGN PATENT DOCUMENTS

| | | |
|---|---|---|
| CN | 101045156 A | 10/2007 |
| EP | 0706799 A2 | 4/1996 |

(Continued)

OTHER PUBLICATIONS

Jiao, Y., et al. CD38: targeted therapy in multiple myeloma and therapeutic potential for solid cancers. Expert Opinion on Investigational Drugs., 2020, Sep. 2020, p. 1-14, published online ahead of print.*
Mihara, K., et al. Activated T-cell-mediated immunotherapy with a chimeric receptor against CD38 in B-cell Non-Hodgkin lymphoma. J. Immunotherapy, 2009, 32:737-743.*
Alkan et al., "Antiviral and Antiproliferative Effects of Interferons Delivered via Monoclonal Antibodies", Journal of Interferon Research, 1984, vol. 4, No. 3, p. 355-363.

(Continued)

*Primary Examiner* — Prema M Mertz
(74) *Attorney, Agent, or Firm* — BakerHostetler

(57) ABSTRACT

Antibodies that specifically bind to CD38, as well as constructs comprising such antibodies fused to attenuated interferon alpha-2B proteins are provided. Anti-CD38-attenuated interferon alpha-2b fusion constructs may be used to inhibit proliferation in cancerous cells that express both CD38 and the receptor for IFN-alpha2b, as well as to induce apoptosis in such cells. Inhibition of proliferation and induction of apoptosis in cancerous cells may serve as the basis for the treatment of the underlying cancer.

13 Claims, 42 Drawing Sheets

Specification includes a Sequence Listing.

(56) References Cited

U.S. PATENT DOCUMENTS

| | | |
|---|---|---|
| 6,300,064 B1 | 10/2001 | Knappik et al. |
| 6,339,070 B1 | 1/2002 | Emery et al. |
| 6,417,337 B1 | 7/2002 | Anderson et al. |
| 6,512,097 B1 | 1/2003 | Marks et al. |
| 6,569,430 B1 | 5/2003 | Waldmann et al. |
| 6,602,684 B1 | 8/2003 | Umana et al. |
| 6,800,735 B2 | 10/2004 | Whitty et al. |
| 6,821,505 B2 | 11/2004 | Ward |
| 6,872,392 B2 | 3/2005 | Nakamura et al. |
| 6,872,568 B1 | 3/2005 | Ni et al. |
| 6,903,203 B2 | 6/2005 | Copley et al. |
| 7,083,784 B2 | 8/2006 | Dall et al. |
| 7,091,321 B2 | 8/2006 | Gillies et al. |
| 7,166,697 B1 | 1/2007 | Galanis et al. |
| 7,202,346 B2 | 4/2007 | Payne et al. |
| 7,217,797 B2 | 5/2007 | Hinton et al. |
| 7,252,994 B2 | 8/2007 | Chuntharapai et al. |
| 7,312,318 B2 | 12/2007 | Hansen et al. |
| 7,317,089 B2 | 1/2008 | Kikly |
| 7,326,681 B2 | 2/2008 | Gerngross |
| 7,355,015 B1 | 4/2008 | Dickson et al. |
| 7,371,819 B2 | 5/2008 | Escary |
| 7,388,081 B2 | 6/2008 | Seki et al. |
| 7,456,257 B2 | 11/2008 | Jones et al. |
| 7,521,047 B2 | 4/2009 | Nagy et al. |
| 7,566,771 B1 | 7/2009 | Adair et al. |
| 7,666,422 B2 | 2/2010 | Siegall et al. |
| 7,670,595 B2 | 3/2010 | Gillies et al. |
| 7,700,742 B2 | 4/2010 | Cohen et al. |
| 7,709,610 B2 | 5/2010 | Williams et al. |
| 7,723,485 B2 | 5/2010 | Junutula et al. |
| 7,732,572 B2 | 6/2010 | Cox, III |
| 7,732,578 B2 | 6/2010 | Foote |
| 7,776,330 B2 | 8/2010 | Yazaki et al. |
| 7,790,415 B2 | 9/2010 | Gillies et al. |
| 7,829,673 B2 | 11/2010 | De et al. |
| 7,919,078 B2 | 4/2011 | Schreiber et al. |
| 7,943,744 B2 | 5/2011 | Frendeus et al. |
| 8,039,593 B2 | 10/2011 | Kuan et al. |
| 8,088,896 B2 | 1/2012 | Tesar et al. |
| 8,119,775 B2 | 2/2012 | Moretta et al. |
| 8,124,738 B2 | 2/2012 | Terret et al. |
| 8,153,765 B2 | 4/2012 | Park et al. |
| 8,187,601 B2 | 5/2012 | Weng et al. |
| 8,980,267 B2 | 3/2015 | Grewal et al. |
| 9,139,634 B2 | 9/2015 | Morrison et al. |
| 9,611,322 B2 | 4/2017 | Wilson et al. |
| 9,636,334 B2 | 5/2017 | Pogue et al. |
| 9,963,515 B2 | 5/2018 | Adam et al. |
| 10,232,041 B2 | 3/2019 | Pogue et al. |
| 2002/0142358 A1 | 10/2002 | Mikayama et al. |
| 2002/0164788 A1 | 11/2002 | Ellis et al. |
| 2002/0193569 A1 | 12/2002 | Hanna |
| 2003/0211100 A1 | 11/2003 | Bedian et al. |
| 2003/0211553 A1 | 11/2003 | Logtenberg et al. |
| 2004/0006215 A1 | 1/2004 | Keler et al. |
| 2004/0071696 A1 | 4/2004 | Adams et al. |
| 2006/0083736 A1 | 4/2006 | Law et al. |
| 2006/0099205 A1 | 5/2006 | Adams et al. |
| 2006/0269516 A1 | 11/2006 | Presta et al. |
| 2007/0098718 A1 | 5/2007 | Long et al. |
| 2007/0190068 A1 | 8/2007 | Hart et al. |
| 2008/0166319 A1 | 7/2008 | Schreiber et al. |
| 2008/0166352 A1 | 7/2008 | Siu et al. |
| 2009/0006815 A1 | 1/2009 | Loubier |
| 2009/0068175 A1 | 3/2009 | Lazar et al. |
| 2009/0076249 A1 | 3/2009 | De et al. |
| 2009/0092599 A1 | 4/2009 | Lazar et al. |
| 2009/0123950 A1 | 5/2009 | Tesar |
| 2009/0142340 A1 | 6/2009 | Lazar et al. |
| 2009/0148449 A1 | 6/2009 | De Weers et al. |
| 2009/0175863 A1 | 7/2009 | Kraus et al. |
| 2009/0202568 A1 | 8/2009 | Eriksson et al. |
| 2009/0304710 A1 | 12/2009 | Park et al. |
| 2010/0092489 A1 | 4/2010 | Van De Winkel et al. |
| 2010/0104557 A1 | 4/2010 | Bernett et al. |
| 2010/0172868 A1 | 7/2010 | Morrison et al. |
| 2010/0189689 A1 | 7/2010 | Chang et al. |
| 2010/0189729 A1 | 7/2010 | Hoerr et al. |
| 2010/0285004 A1 | 11/2010 | Tesar et al. |
| 2010/0297076 A1 | 11/2010 | Morrison et al. |
| 2011/0104112 A1 | 5/2011 | Morrison et al. |
| 2012/0201827 A1 | 8/2012 | Elias et al. |
| 2013/0230517 A1 | 9/2013 | Grewal et al. |
| 2013/0302318 A1 | 11/2013 | Rojkjaer et al. |
| 2014/0248238 A1 | 9/2014 | Wilson et al. |
| 2015/0031395 A1 | 1/2015 | Wachter et al. |
| 2015/0203560 A1 | 7/2015 | Grewal et al. |
| 2015/0313965 A1 | 11/2015 | Pogue et al. |
| 2015/0353485 A1 | 12/2015 | Hagen et al. |
| 2016/0068612 A1 | 3/2016 | Clarke et al. |
| 2016/0122410 A1 | 5/2016 | Behrens et al. |
| 2017/0202962 A1 | 7/2017 | Pogue et al. |
| 2017/0233449 A1 | 8/2017 | Wilson et al. |
| 2018/0305460 A1 | 10/2018 | Clarke et al. |

FOREIGN PATENT DOCUMENTS

| | | |
|---|---|---|
| FR | 2905375 A1 | 3/2008 |
| JP | 2008-533977 | 8/2008 |
| JP | 2009-501514 A | 1/2009 |
| JP | 2010-504363 | 2/2010 |
| JP | 2010-540453 | 12/2010 |
| JP | 2015-515453 A | 5/2015 |
| JP | 2016-511712 A | 4/2016 |
| JP | 6184965 B2 | 8/2017 |
| WO | 90/05144 A1 | 5/1990 |
| WO | 97/00271 A1 | 1/1997 |
| WO | 97/24137 A1 | 7/1997 |
| WO | 00/40265 A1 | 7/2000 |
| WO | 00/42072 A2 | 7/2000 |
| WO | 01/97844 A1 | 12/2001 |
| WO | 2004/022593 A2 | 3/2004 |
| WO | 2004/022747 A1 | 3/2004 |
| WO | 2005/103083 A2 | 11/2005 |
| WO | 2006/099875 A1 | 9/2006 |
| WO | 2006/125640 A2 | 11/2006 |
| WO | 2007/000769 A2 | 1/2007 |
| WO | 2007/042309 A2 | 4/2007 |
| WO | 2008/006554 A2 | 1/2008 |
| WO | 2008/037257 A2 | 4/2008 |
| WO | 2008/047242 A2 | 4/2008 |
| WO | 2008/124086 A2 | 10/2008 |
| WO | 2008/145139 A1 | 12/2008 |
| WO | 2009/017823 A2 | 2/2009 |
| WO | 2009/073975 A1 | 6/2009 |
| WO | 2010/105290 A1 | 9/2010 |
| WO | 2011/154453 A1 | 12/2011 |
| WO | 2012/041800 A1 | 4/2012 |
| WO | 2012/083370 A1 | 6/2012 |
| WO | 2012/092612 A1 | 7/2012 |
| WO | 2013/059885 A2 | 5/2013 |
| WO | 2013/107791 A1 | 7/2013 |
| WO | 2013/134138 A1 | 9/2013 |
| WO | 2014/028502 A1 | 2/2014 |
| WO | 2014/178820 A1 | 11/2014 |

OTHER PUBLICATIONS

Behr et al., "Low-Versus High-Dose Radioimmunotherapy with Humanized Anti-CD22 or Chimeric Anti-CD20 Antibodies in a Broad Spectrum of B Cell-associated Malignancies", Clin. Cancer Res., Oct. 1999, 5, 3304s-3314s.

Benhar, "Design of Synthetic Antibody Libraries", Expert Opin. Biol. Ther., May 2007, 7(5), 763-779.

Bhattacharya-Chatterjee et al., "Idiotype Vaccines against human T cell leukemia. II. Generation and Characterization of a Monoclonal idiotype cascade (Ab1, Ab2, and Ab3)", J. Immunol., 1988, 141, 1398-1403.

Bird et al., "Single-Chain Antigen-Binding Proteins", Science, Oct. 1988, 242, 423-426.

Brekke et al., "Human IgG3 Can Adopt the Disulfuide bond pattern characteristic for IgG1 without resembling it in complement mediated cell lysis", Mol. Immuol., May 1993, 30, 1419-1425.

(56) References Cited

OTHER PUBLICATIONS

Bumal et al., "Characterization of the Human Tumor and Normal Tissue Reactivity of the KS1/4 Monoclonal Antibody", Hybridoma, 1988, 7(4), 407-415.
Camploi et al., "Human High Molecular Weight-Melanoma-Associated Antigen (HMW-MAA): A Melanoma Cell Surface Chondroitin Sulfate Proteoglycan (MSCP) with Biological and Clinical Significance", Crit. Rev. Immunol, 2004, 24(4), 267-296.
Crowder et al., NEOPLASIA, PML mediates IFN-a-induced apoptosis in myeloma by regulating TRAIL induction, 2005, pp. 1280-1287.
Dall'Acqua et al., "Increasing the Affinity of a Human IgG1 for the Neonatal Fc Receptor: Biological Consequences", J. of Immunol, 2002, 169, 5171-5180.
Dall'Acqua et al., "Properties of Human IgG1s Engineered for Enhanced Binding to the Neonatal Fc Receptor (FcRn)", J. Biol. Chem., Aug. 2006, 281(33), 23514-23524.
Davies & Riechmann, "Camelising Human Antibody Fragments: NMR Studies on VH Domains", FEBS Letters, 1994, 339, 285-290.
Deaglio et al., "CD38 at the Junction between prognostic marker and therapeutic target", Trends in Mol. Med., 2008, 14(5), 210-218.
Divgi et al., "Clinical Comparison of Radiolocalization of Two Monoclonal Antibodies (mAbs) Against the TAG-72 Antigen", Nucl. Med. Biol., 1994, 21(1), 9-15.
During et al., "CD438 Expression is an Important Prognostic Marker in Chronic Lymphocytic Leukaemia", Leuk. Res., 2002, 16, 30-35.
Estin et al., "Transfected Mouse Melanoma Lines That Express Various Levels of Human Melanoma-Associated Antigen p97", J. Natl. Cancer Instit., Mar. 1989, 81(6), 445-448.
Feizi, "Demonstration by Monoclonal Antibodies that carbohydrate structures of glycoproteins and glycolipids are onco-developmental antigens", Nature, Mar. 1985, 314(7), 53-57.
Ferrara et al., "Modulation of Therapeutic Antibody Effector Functions by Glycosylation Engineering: Influence of Golgi Enzyme Localization Domain and Co-Expression of Heterologous B1,4-N-acetylglucosaminyltransferase III and Golgi a-mannosidase II", Biotechnol. Bioeng., Apr. 2006, 93(5), 851-861.
Fishburn, "The Pharmacology of PEGylation: Balancing PD with PK to Generate Novel Therapeutics", J. Pharm. Sci., 2008, 97, 4167-4183.
Foon et al., "Murine Anti-Idiotype (Id) Monoclonal Antibody (mAb) induces specific humoral responses to carcino-embryonic antigen (CEA) in Colorectal Cancer (CRC) Patients", Proc. Am. Soc. Clin. Oncol, 1994, 13, 294.
Fornier et al., "Update on the Management of Advanced Breast Cancer", Oncology, 1999, 13, 647-658.
Frankel et al., "Cell Surface Receptor-Targeted Therapy of Acute Myeloid Leukemia: A Review", Cancer Biother. Radiopharm, 2000, 15(5), 459-477.
Funaro et al., "CD38 Functions Are Regulated Through an Internalization Step", J. Immunol., 1998, 160, 2238-2247.
Gennaro, Ed., Remington's Pharmaceutical Sciences, 18th Edition, Mack Publishing Co., Easton, PA, 1990.
Harden et al., "Interleukin-6 Prevents Dexamethasone-induced myeloma cell death", Blood, 1994, 84, 3063-3070.
Hellstrom et al., "Monoclonal Antibodies to Cell Surface Antigens Shared by Chemically Induced Mouse Bladder Carcinomas", Cancer Res., 1985, 45, 2210-2188.
Henttu et al., "cDNA Coding for the Entire Human Prostate Specific Antigen Shows High Homologies to the Human Tissue Kallikrein Genes", Biochem. Biophys. Res. Comm., 1989, 160(2), 903-910.
Herlyn et al., "Monoclonal Antibody Detection of a Circulating Tumor-Associates Antigen. I. Presence of Antigen in Sera of Patients with Colorectal, Gastric and Pancreatic Carcinoma", J. Clin. Immunol., 1982, 2(2), 135-140.
Hilkens et al., "Cell Membrane-Associated mucins and their adhesion-modulating property", Trends in Bio. Chem. Sci., Sep. 1992, 17, 359-363.

Hinton et al., "An Engineered Human IgG1 Antibody with Longer Serum Half-Life", J. Immunol., 2006, 176, 346-356.
Hinton et al., "Engineered Human IgG Antibodies with Longer Serum Half-Lives in Primates", J. Biol. Chem., Feb. 2004, 279(8), 6213-6216.
Holliger et al., "Diabodies: Small Bivalent and Bispecific Antibody Fragments", PNAS USA, Jul. 1993, 90, 6444-6448.
Huston et al., "Protein Engineering of Antibody binding sites: Recovery of specific activity in an anti-digoxin single-chain Fv analogue produced in Escherichia coli", PNAS USA, Aug. 1988, 85, 5879-5883.
Idusogie et al., "Engineered Antibodies with Increased Activity to Recruit Complement", J. Immunol., 2001, 166, 2571-2575.
Jones et al., "Selective Clearance of Glycoforms of a Complex Glycoprotein pharmaceutical caused by terminal N-acetylglucosamine is similar in humans and cynomolgus monkeys", Glycobiology, 2007, 17(5), 529-540.
Kanda et al., "Comparison of Biological Activity among nonfucosylated therapeutic IgG1 antibodies with three different N-linked Fc oligosaccharides: the high-mannose, hybrid, and complex types", Glycobiology, 2006, 17(1), 104-118.
Kaneko et al., "Anti-Inflammatory Activity of Immunoglobulin G. Resulting from Fc Sialylation", Science, Aug. 2006, 313, 670-673.
Kolkman et al., "Directed Evolution of Proteins by Exon Shuffling", Nat. Biotechnol., May 2001, 19(5), 423-428.
Kopsidas et al., "In vitro Improvement of a Shark IgNAR antibody by QB replicase mutation and ribosome display mimics in vivo affinity maturation", Immunol. Lett., Nov. 15, 2006, 107(2), 163-168.
Li et al., "Optimization of Humanized IgGs in Glycoengineered Pichia Pastoris", Nat. Biotechnol., 2006, 24, 210-215.
Li et al., "The Epitope Specificity and Tissue Reactivity of Four Murine Monoclonal Anti-CD22 Antibodies", Cell Immunol., 1989, 111, 85-99.
Liu et al., "Crystal Structure of Human CD38 Extracellular Domain", Structure, 2005, 13, 1331-1339.
Livingston et al., "Improved Survival in Stage III Melanoma Patients with GM2 Antibodies: A Randomized Trail of Adjuvant Vaccination With GM2 Ganglioside" J. Clin. Oncol., 1994, 12, 1036-1044.
Malavasi et al., "CD38: A multi-lineage cell activation molecule with a split personality", Inti. J. Clin. Lab. Res., 1992, 22, 73-80.
Malavasi, et al, Human Immunology, Characterization of a Murine Monoclonal Antibody Specific for Human Early Lymphohemopoietic Cells ,1984, 9, 9-20.
Matsui, et al., British Journal of Haematology, Anti-tumour activity of interferon-alpha in multiple myeloma: role of interleukin 6 and tumor cell differentiation 2003, 121, pp. 251-258.
Michaelsen et al., "Enhancement of Complement Activation and Cytolysis of Human IgG3 by Deletion of Hinge Exons", Scand. J. Immunol, 1990, 32, 517-528.
Morabito, "Haematologica", Feb. 2002, 87(2), 217-218.
Natali et al., "Immunohistochemical Detection of Antigen in Human Primary and Metastatic Melanomas by the Monoclonal Antibody 140.240 and Its Possible Prognostic Significance", Cancer, 1987, 59, 55-63.
Natsume et al., "Engineered Antibodies of IgG1/IgG3 Mixed Isotype with Enhanced Cytotoxic Activities", Cancer Research, May 2008, 68(10), 3863-3872.
Norderhaug et al., "Chimeric mouse human IgG3 antibodies with an IgG4-like hinge region induce complement-mediated lysis more efficiently than IgG3 with normal hinge", Eur. J. Immunol., 1991, 21, 2379-2384.
Ono et al., "The humanized anti-HM1.24 antibody effectively kills multiple myeloma cells by human effector cell-mediated cytotoxicity", Mol. Immuno., 1999, 36, 387-395.
Otsuki et al., "Human Myeloma Cell Apoptosis induced by interferon-a", Jul. 1998, 103, 518-529.
Peled et al., "The Biochemistry of Somatic Hypermutation", Annu. Rev. Immunol., 2008, 26, 481-511.
Perez et al., "Isolation and Characterization of a cDNA encoding the KS1/4 epithelial carcinoma marker", J. Immunol., 1990, 142, 3662-3667.

(56) References Cited

OTHER PUBLICATIONS

Petkova et. al., "Enhanced half-life of genetically engineered human IgG1 antibodies in a humanized FcRn Mouse model: Potential Application in Humorally mediated autoimmune disease", Immunol., 2006, 18(12), 1759-1769.
Poljak, "Production and Structure of Diabodies", Structure, Dec. 1994, 2, 1121-1123.
Queen et al., "A Humanized antibody that binds to the interleukin 2 receptor", PNAS, Dec. 1989, 86(24), 10029-10033.
Ragnhammar et al., "Effect of Monoclonal Antibody 17-1A and GM-CSF in patients with advanced colorectal carcinoma—long-lasting, complete remissions can be induced", Int. J. Cancer, 1993, 53, 751-758.
Rossi et al., "CD20-Targeted Tetrameric Interferon-a, a novel and potent immunocytokine for the therapy of B-cell lymphomas", Blood, Oct. 2009, vol. 114, No. 18, 3864-3871.
Saleh et al., "Generation of a human anti-idiotypic antibody that mimics the GD2 antigen", J. Immunol., 1993, 151, 3390-3398.
Schier et al., "Isolation of High-Affinity Monomeric Human Anti-c-erbB-2 Single chain Fv Using Affinity-driven Selection", J. Mol. Biol. 1996, 255, 28-43.
Schier et al., "Isolation of Picomolar Affinity Anti-c-erbB-2 Single-Chain Fv by Molecular Evolution of the Complimentarity Determining Regions in the Center of the Antibody Binding Site", J. Mol. Biol., 1996, 263, 551-567.
Shields et al., "High Resolution Mapping of the Binding Site on Human LgG1 for FcyRI, FcyRII, FcyRIII and FcRn and Design of IgG1 Variants with Improved Binding to the FcyR", J. Biol. Chem., Mar. 2001, 276(9), 6591-6604.
Shitara et al., "A mouse/human chimeric anti-(ganglioside GD3) antibody with enhanced antitumor activities", Cancer Immunol. Immunother, 1993, 36, 373-380.
Stavenhagen et al., "Fc Optimization of Therapeutic Antibodies Enhances their ability to kill tumor cells in vitro and controls tumor expansion in vivo via low-affinity activating Fcy Receptors", Cancer Res., 2007, 67, 8882-8890.
Tan et al., "Influence of the hinge region on complement activation, C1q binding, and segmental flexibility in chimeric human immunoglobulins", PNAS, 1990, 87, 162-166.
Thie et al., "Affinity Maturation by Phage Display", Methods, Mol. Biol., 2009, 525, 309-322.
Trail et al., "Cure of Xenografted Human Carcinomas by BR96-Doxorubicin Immunoconjugates", Science, 1993, 261, 212-215.
Trauth et al., "Monoclonal Antibody-Mediated Tumore Regression by Induction of Apoptosis", Science, Jul. 1989, 245, 301-304.
Wahl et al., Cancer Res., 2002, 62(13), 3736-3742.
Ward et al., "Binding Activities of a Repertoire of Single Immunoglobulin variable domains secreted from *Escherichia coli*", Nature, Oct. 1989, 341, 544-546.
Xuan et al., "Targeted delivery of interferon-a via fusion to anti-CD20 results in potent antitumor activity against B-cell lymphoma", Blood, 2010, 115, 2864-2871.
Yu, et al., "Coexpression of Different Antigenic Markers on Moieties that Bear CA 125 Determinants", Can. Res., vol. 51, Jan. 15, 1991, pp. 468-475.
Yoshinaga et al., "Ig L-chain Shuffling for Affinity Maturation of Phage Lobrary-derived Human Anti-human MCP-1 Antibody Blocking its Chemotactic Activity", J Biochem, 2008, 143, 593-601.
Yokota, et al., "Rapid Tumor PeneliaLion of a Signle-Chain Fv and Comparison with other Immunoglobulin Forms", Can. Res., vol. 52, Jun. 15, 1992, pp. 3402-3408.
Wells, J. "Additivity of Mutational Effects in Proteins", Biochemistry, 1990, 29, 8509-8517.
Wahl, et al., "The Anti-CD30 Monoclonal Antibody SGN-30 Promotes Growth Arrest and DNA Fragmentation in Vitro and Afects Antibumor Activity in Models of Flodgkin's Disease", Can. Res., vol. 62, Jul. 1, 2002, pp. 3736-3742.
Vijayasaradhi, et al., "The Melanoma Antigen gp75 is the Human Homologue of the Mouse b (Brown) Locus Gene Product", J. Exp. Med., vol. 171, Apr. 1990, pp. 1375-1380.
Van Hof, et al., "Biodistribution of Indium-Labeled Engineered Human Antibody CTMO1 in Ovarian Cancer Patients: Influence of Protein Dose", Can. Res., vol. 56, Nov. 15, 1996, pp. 5179-5185.
Van Der Veer Michael S et al: "Towards effective immunotherapy of myeloma: enhanced elimination of myeloma cells by combination of lenalidomide with the human CD38 monoclonal antibody daratumumab", Haemat0l0, Ferrata Storti Foundation, Italy, vol. 96, No. 2, Feb. 1, 2011 (Feb. 1, 2011), pp. 284-290.
Tse, et al., "CR011, a Fully Human Monoclonal Antibody-Auristatin E Conjugate, for the Treatment of Melanoma", Clin. Cancer Res., 2006, 12(4): 1373-1382.
Trail, et al., "Effect of Linker Variation on the Stability, Porency, and Efficacy of Carcinoma-reactive BR64-Doxorubicin Immunoconjugates", Can. Res., vol. 57, Jan. 1, 1997, pp. 100-105.
Tomoyuki, et al., "Engineering the variable region of therapeutic IgG antibodies", MABS, Landes Bioscience, US, vol. 3, No. 3, May 1, 2011, p. 243-252.
Thalidomide-dexamethasone compared with melphalan-prednisolone in elderly patients with multiple myeloma, Heinz Ludwig, 1 Roman Hajek,2 Elena T6thova,3 Johannes Drach,4 Zdenek Adam,2 Boris Labar,5 Miklos Egyed,6, 3435-3442, 113/15.
Tailor, et al., "Nucleotide sequence of human prostatic acid phosphatase determined from a full-length cDNA clone", Nucleic Acids Research, vol. 18, No. 16, Jul. 11, 1990, p. 4928.
Sievers, et al., "Selective Ablation of Acute Myeloid Leukemia Using Antibody-Targeted Chemotherapy: a Phase I Study of Anti-CD33 Calichaemicin Immunoconjugate", Blood, vol. 93, No. 11, Jun. 1, 1999, pp. 3678-3784.
Shinkawa, T., et al., "The Absence of Fucose but Not the Presence of Galactose or Bisecting N-Acetylglucosamine of Human IgG1 Complex-type Oligosaccharides Shows the Critical Role of Enhancing Anti-body-dependent Cellular Cytotoxicty", 2003, Journal of Biological Chemistry, 278, 3466-3473.
Sgouros, et al., "Modeling and Dosimetry of Monoclonal Antibody M195 (Anti-CD33) in Acute Myelogenous Leukemia", J. Nucl. Med., vol. 34, No. 3, Mar. 1993, pp. 422-430.
Rossi et al., "Preclinical Studies on Targeted Delivery of Multiple IFNa2b to HLA-DR in Diverse Hemotologic Cancers" Lymphoid Neoplasia, Blood Journal, vol. 118, No. 7, Aug. 18, 2011.
Rosenblum, et al., "Recombinant Immunotoxins Directed against c-erb-3/HER2/neu Oncogene Product: In Vitro Cytotoxicity, Pharmacokinetics, and in Vivo Efficacy Studies in Xenograft Models", Clin. Can. Res., vol. 5, Apr. 1999, pp. 865-874.
Richardson, et al., "Monoclonal Antibodies in the Treatment of Multiple Myeloma", British Journal of Haematology, 2011, 154:745-754.
Results of a Phase II Trial Testing Interferon-Alpha 2b and Cytarabine Children and Adolescents With Chronic Myelogenous Leukemia, Frederic Millot, MD,, 555-559.
Reff, et al., "Depletion of B Cells In Vivo by a Chimeric Mouse Human Monoclonal Antibody to CD20", Blood, vol. 83, No. 2, Jan. 15, 1994, pp. 435-445.
Randomized clinical trial of zoledronic acid in multiple myeloma patients undergoing high-dose chemotherapy and stem-cell transplantation, A. Aviles Md,* N Neri MD/, e13-20, 20/1.
Pollack et al., "Treatment paraments modulating regression of human melanoma xenografts by an anti-body-drug conjugate (CR011-vcMMAE) targeting GPNMB", Cancer Chemother Pharmacol, 2007, 60, 423-435.
Piehler, et al., "New structural and functional aspects of the Type 1 interferon-receptor interaction revealed by comprehensive mutational analysis of the binding interface", vol. 275, No. 51, Dec. 2000, pp. 40425-40433.
Peterson, et al., "Effect of Multiple, Repeated Doses of Radioimmunotherapy on Target Antigen Expression (Breast MUC-1 Mucin) in Breast Carcinomas", Can. Res., vol. 57, Mar. 15, 1997, pp. 1103-1108.
Pavlinkova, et al., "Radioimmunotherapy of Human Colon Cancer Xenografts Using a Dimeric Single-Chain Fv Antibody Construct", vol. 5, Sep. 1999, pp. 2613-2619.
Padlan, et al., "Identification of specificity-determining residues in antibodies", FASEB Journal, vol. 9, Jan. 1995, pp. 133-139.

(56) References Cited

OTHER PUBLICATIONS

Ozzello, et al., "The use of natural interferon alpha conjugated to a monoclonal antibody anti mammary epithelial mucin (Mc5) for the treatment of human breast cancer xenograft", Breast Cancer Research and Treatment, 1993, 25, 265-276.

Ngo et al., "Computational Complexity, Protein Structure Prediction, and the Levinthal Paradox", The Protein Folding Problem and Tertiary Structure Prediction, 1994, 492-495.

Mittelman, et al., "Active Specific Immunotherapy in Patients with Melanoma", J. Clin. Invest., vol. 86, Dec. 1990, pp. 2136-2144.

Millot, F., et al., "Results of a Phase II trial testing interferon-alpha 2b and cytarabine in children and adolescents with chronic myelogenous leukemia", Pediatric Blood and Cancer, 2006, 47, 555-559.

Mason, et al., "Value of Monoclonal Anti-CD22 (p135) Antibodies for the Detection of Normal and Neoplastic B Lymphoid Cells", Blood, vol. 69, No. 3, Mar. 1987, pp. 836-840.

Maier, et al., "Requirements for the Internalization of a Murine Monoclonal Antibody Directed against the HER-2/neu Gene Product c-erB-2", Can. Res., vol. 51, Oct. 1, 2991, pp. 5361-5369.

Igawa, et al., "Engineering the variable region of therapeutic IgG antibodies", MABS, Landes Bioscience, US, vol. 3, No. 3, May 1, 2011, p. 243-252.

Lesinski, et al., "IFN-a Bortezomib Overcome Bcl-2 and Mcl-1 Overexpression in Melanoma Cells by Stimulating the Extrinsic Pathway of Apoptosis", Cancer Res., Oct. 2008; 68:(20), pp. 8351-8360.

Laubach, et al., "Daratumumab granted breakthrough drug status", Expert Opin. Investig. Drugs, 2014, 23 (4):445-452.

Laubach, et al., "CD38-Targeted Immunochemotherapy in Refractory Multiple Myeloma: A New Horizon", Clinical Cancer Research, 2015, 2660-2663.

Labrijn et al. "Therapeutic IgG4 antibodies engage in Fab-arm exchange with endogenous human IgG4 in vivo", Nature Biotechnology, 2009, 27:8; 767-771.

Ku, et al., "Alternate protein frameworks for molecular recognition", Proc. Natl. Acad. Sci. USA, vol. 92, Jul. 1995, pp. 6552-6556.

Kotchev, et al., "Synergy of Interferons and Bortezomib: Advantages of Combination Treatments in Facilitating Apoptosis in Multiple Myeloma Cells", Cytokine, 2010, 88.

Kossman, et al., "A Phase I Trial of Humanized Monoclonal Antibody HuM195 (anti-DC33) with Low-Dose Interleukin 2 in Acute Myelogenous Leukemia", Clin. Can. Res., vol. 5, Oct. 1999, pp. 2748-2755.

Koguma, T., et al., "Cloning and characterization of cDNA encoding rat ADP-ribosyl cyclase/cyclic ADP-ribose hydrolase (homologue to human CD38) from islets of Langerhans", Biochim. Biophys. Acta., 1994, 160-162.

Kodama, et al., "Mutated SEA-D227 A-conjgated antibodies greatly enhance antitumor activity against MUC1-expressing bile duct carcinoma", Cancer Immunology, Immnotherapy, vol. 50, No. 10, Dec. 2001, pp. 539-548.

Israeli, et al., "Molecular Cloning of a Complementary DNA Encoding a Prostate-specific Membrane Antigen", Can. Res., 1993, 53, 227-230.

International Search Report and Written Opinion issued in related application PCT/IB2015/001600 dated Nov. 23, 2015.

International Search Report and Written Opinion issued in related application PCT/AU2015/050654 dated Dec. 3, 2015.

International Search Report and Written Opinion from related application PCT/US2013/038659 dated Feb. 12, 2014.

International Search Report and Written Opinion from related application PCT/AU2012/001323 dated Mar. 13, 2013.

Igawa, et al., "Engineering the variable region of therapeutic IgG antibodies", MABS, Landes Bioscience, 2011, 3, 243-252.

Ibrahim, et al., "CD38 expression as an important prognostic factor in B-cell chronic lymphocytic leukemia", Blood, vol. 98, No. 1, Jul. 1, 2001, pp. 181-186.

Hoon, et al., "Molecular Cloning of a Human Monoclonal Antibody Reactive to Ganglioside Gm3 Antigen on Human Cancers", Can. Res. vol. 53, Nov. 1, 1993, pp. 5244-5250.

Honegger, et al., "Yet another numbering scheme for immunoglobulin variable domains: An automatic modeling and analysis tool", J. Mol. Biol., (2001) 309, 657-670.

Hellstroem, et al., "Monoclonal Mouse Antibodies Raised Against Human Lung Carcinoma", Can. Res., vol. 46, Aug. 1986, pp. 3917-3923.

Hamers-Casterman, et al., "Naturally occurring antibodies devoid of light chains", Nature, vol. 363, Jun. 3, 1993, pp. 446-448.

H. Ludwig et al: "Thaiidomide-dexamethasone compared with melphalan-prednisolone in elderly patients with multiple myeloma", BLOOD, vol. 113, No. 15, Oct. 27, 2008, pp. 3435-3442.

Giudicelli, et al., "IMGT, the international ImMunoGeneTics database", Nucleic Acids Research, 1997, vol. 25, No. 1, pp. 206-211.

Ghetie, et al., "Anti-CD19 Inhibits the Growth of Human B-Cell Tumor Lines In Vitro and of Daudi Cells in SCIO Mice b Inducing Cell Cycle Arrest", Blood, vol. 83, No. 5, Mar. 1, 1994, pp. 1329-1336.

Ghasriani et al., JBC, vol. 288, Jan. 4, 2013, No. 1, pp. 247-254.

Frey et al., Antibody-based Targeting of Interferon-Alpha to the Tumore Neovasculature: a Critical Evaluation; Royal Society of Chemistry, Integr. Biol., vol. 3, pp. 468-478, 2011.

Francisco, et al., "Agonistic Properties and in Vivo Antitumor Activity of the Anti-CD40 Antibody SGN-14", Can. Res., vol. 60, Jun. 15, 2000, pp. 3225-3231.

Edelman, et al., "The Covalent Structure of an Entire yG Immunoglobulin Molecule", Biochemistry, vol. 63, 1969, pp. 78-85.

De Weers, et al., "Daratumumab, a Novel Therapeutic Human CD38 Monoclonal Antibody, Induces Killing of Multiple Myeloma and other Hematological Tumors", J. Immunol., 2011, 186:1840-1848.

Cortes, J. et al., "Immune modulation of minimal residual disease in early chronic phase chronic myelogenous leukemia: A randomized trial of frontline high-dose imatinib mesylate with or without pegylated interferon alpha-2b and granulocyte-macrophage colony-stimulation factor", CANCER., 2010, 117, 572-580.

Chothia, et al., "Conformations of immunoglobulin hypervariable regions", Nature, vol. 342, Dec. 1989, pp. 877-883.

Chothia, et al., "Canonical Structures for the Hypervariable Regions of Immunoglobulins", J. Mol. Biol., (1987), No. 196, pp. 901-917.

Bork, P., "Powers and pitfalls in sequence analysis: the 70% hurdle.", Genome Research, 2000, 10, 398-400.

Bork, et al., "Go hunting in sequence databases but watch out for the traps", Trends in Genetics, 1996, 12, 425-427.

Bonardi, et al., "Delivery of Saporin to Human B-Cell Lymphoma Using Bispecific Antibody: Targeting via DC22 byt not CD19, CD37, or Immunoglobulin Results in Efficient Killing", Can. Res., 1991, 53, 3015-3021.

Aviles, A. et al., "Randomized clinical trial of zoledronic acid in multiple myeloma patients undergoing high-dose Chemotherapy and stem-cell transplantation", Current Oncology, 2013, e13-e20.

Ausiello, et al., "Functional topography of discrete domains of human CD38", Tissue Antigens, 2000, 56, 539-547.

Al-Lazikani, B. et al., "Standard Conformations for the Canonical Structures of Immunoglobulins", Journal of Molecular Biology, 1997, 273, 927-948.

"Peripheral blood CD38 expression predicts time to progression in B-cell chroonic lymphocytic leukemia after first-line therapy with high-does chlorambucil", Haematologica, vol. 87, No. 2, Feb. 2002, pp. 217-218.

Piehler et al., JBC, 2000, vol. 275, No. 51, pp. 40425-40433.

Trzpis, M. et al., Am. J. Pathol., (2007), vol. 171, No. 2, pp. 386-395.

Thomas, C. et al., Cell, (Aug. 19, 2011), vol. 146, pp. 621-632.

Stewart, A.G. et al., DNA, (1987), vol. 6, No. 2, pp. 119-128, abstract; 123, Table 1.

Pan, M. et al., Biochemistry, (2008), vol. 47, pp. 12018-12027, abstract.

Kalie, E. et al., J. Biol. Chem., (2007), vol. 282, No. 15, p. 11602-1161L.

Huang, T.-H. et al., J. Immunol., (2007), vol. 179, pp. 6881-6888,.

Ellis, J.H. et al., J. Immunol., (1995), vol. 155, No. 2, pp. 925-937.

\* cited by examiner

FIG. 2A

```
                 QLQLQESGPGLVKPSETLSLTCTVSGGSISSSSYYWSWIRQHPGKGLEWIGYIYYSGSTNYNPSLKS
SEQ ID NO: 13    ..................................................................
SEQ ID NO: 16    .V...........................V..G...........P....................
SEQ ID NO: 17    ..................................................................
SEQ ID NO: 18    ..................................................................
SEQ ID NO: 19    ..................................................................
SEQ ID NO: 20    ..................................................................
SEQ ID NO: 21    ..................................................................
SEQ ID NO: 22    .V................................................................
SEQ ID NO: 23    ..........................K.......................................
SEQ ID NO: 24    ..................................................................
SEQ ID NO: 25    ..................................................................
SEQ ID NO: 26    ...............................V..................................
SEQ ID NO: 27    ..................................................................
SEQ ID NO: 28    ..................................................................
SEQ ID NO: 29    .......................K..........................................
SEQ ID NO: 30    ..................................................................
SEQ ID NO: 31    .....................................P............................
SEQ ID NO: 32    ..................................................................
SEQ ID NO: 33    ..............................................G...................
SEQ ID NO: 34    ..................................................................
SEQ ID NO: 35    .....................................P............................
```

FIG. 2B

```
                RVTISVDTLKNQISLRLTSVTAADTAVYYCARVGGAGGWPMDVWGQGTTVTVSS
SEQ ID NO: 13   ......................................................
SEQ ID NO: 16   .....S...F..K.S.......................................
SEQ ID NO: 17   .....S................................................
SEQ ID NO: 18   ..................S...................................
SEQ ID NO: 19   ......................................................
SEQ ID NO: 20   .....S...F..K.S.......................................
SEQ ID NO: 21   ......................................................
SEQ ID NO: 22   ...........R..........................................
SEQ ID NO: 23   ......................................................
SEQ ID NO: 24   .............................R........................
SEQ ID NO: 25   ......................................................
SEQ ID NO: 26   ......................................................
SEQ ID NO: 27   ........K.............................................
SEQ ID NO: 28   .........................................LE.........
SEQ ID NO: 29   .........................................L..........
SEQ ID NO: 30   .........................................E..........
SEQ ID NO: 31   ......................................................
SEQ ID NO: 32   ........F.............................................
SEQ ID NO: 33   ........K.............................................
SEQ ID NO: 34   .....S...F..K.S..........................L..........
SEQ ID NO: 35   .....S...F..K.S..........................L..........
```

FIG. 3A

```
                 QAVLTQPASLSASPGESARLTCTLPSDINVRYNIYWYQQKPGSPPRYLLYYYSDSHKGQGS
SEQ ID NO: 14    ............................................................
SEQ ID NO: 37    .P....P.S...................GS..............................D
SEQ ID NO: 38    ............................................................
SEQ ID NO: 39    ............................................................
SEQ ID NO: 40    ............................................................
SEQ ID NO: 41    ............A...............................................
SEQ ID NO: 42    ............................................R...............
SEQ ID NO: 43    .........................G..................................
SEQ ID NO: 44    ..............................................R.R...........
SEQ ID NO: 45    ............................................................
SEQ ID NO: 46    .......................R....................................
SEQ ID NO: 47    ..................................R.........................
SEQ ID NO: 48    ............................................................
SEQ ID NO: 49    ............................................................
SEQ ID NO: 50    ............................................................
SEQ ID NO: 51    ............................................................
SEQ ID NO: 52    .P..........................................................
SEQ ID NO: 53    ...........S................................................
SEQ ID NO: 54    .............................G..............................
SEQ ID NO: 55    ..............................S.................R...........
SEQ ID NO: 56    ............................................................
SEQ ID NO: 57    ............................................................
SEQ ID NO: 58    ............................................................D
SEQ ID NO: 59    ............................................................
SEQ ID NO: 60    ............................................................
SEQ ID NO: 61    ............................................................
SEQ ID NO: 62    ............................................................
SEQ ID NO: 63    ............................................................
SEQ ID NO: 64    ............................................................
SEQ ID NO: 65    ............................................................
```

FIG. 3B

```
              GVPSRFSGSKDVSTNSGILLISGLQSEDEADYYCMTWSSNGSGVFGGGTQLTVLG
SEQ ID NO: 14 ..............A.A.T..................I.P.A..........
SEQ ID NO: 37 ......................................Q.............
SEQ ID NO: 38 ......................................................
SEQ ID NO: 39 ...............A......................................
SEQ ID NO: 40 ......................................................
SEQ ID NO: 41 ......................................................
SEQ ID NO: 42 ........-.............................................
SEQ ID NO: 43 ......................................................
SEQ ID NO: 44 ..........................................A...........
SEQ ID NO: 45 ......................................................
SEQ ID NO: 46 ......................................................
SEQ ID NO: 47 ......................................................
SEQ ID NO: 48 ......................................................
SEQ ID NO: 49 ...................................I..................
SEQ ID NO: 50 ....................................L.................
SEQ ID NO: 51 .............................................T........
SEQ ID NO: 52 ......................................................
SEQ ID NO: 53 ......................................................
SEQ ID NO: 54 ...............A......................................
SEQ ID NO: 55 ...............A......................................
SEQ ID NO: 56 ...............A.T...........................P.........
SEQ ID NO: 57 ......................................................
SEQ ID NO: 58 ......................................................
SEQ ID NO: 59 ......................................................
SEQ ID NO: 60 ......................................................
SEQ ID NO: 61 ......................................................
SEQ ID NO: 62 ......................................I.P............
SEQ ID NO: 63 ......................................................
SEQ ID NO: 64 ....................................................A.
SEQ ID NO: 65 .............................I.T......................
```

FIG. 4A

```
                QAVLTQPASLSASPGESARLTCTLPSDINVRYYNIYWYQQKPGSPPRYLLYYYSDSHKGQGS
SEQ ID NO: 14   ............................................................
SEQ ID NO: 66   ............................................................
SEQ ID NO: 67   ............................................................
SEQ ID NO: 68   ............................................................
SEQ ID NO: 69   ............................................................
SEQ ID NO: 70   ............................................................
SEQ ID NO: 71   ............................................................
SEQ ID NO: 72   ...............E............................................
SEQ ID NO: 73   ...............G............................................
SEQ ID NO: 74   ...............N............................................
SEQ ID NO: 75   ...............P............................................
SEQ ID NO: 76   ...............S............................................
SEQ ID NO: 77   ...............E............................................
SEQ ID NO: 78   ...............P............................................
SEQ ID NO: 79   ...............E..................D..........................
SEQ ID NO: 80   ...............Q..................E..........................
SEQ ID NO: 81   ...............P..................H..........................
SEQ ID NO: 82   ...............N..................Q..........................
SEQ ID NO: 83   ...............T..................N..........................
SEQ ID NO: 84   ...............D..................P..........................
SEQ ID NO: 85   ...............E..................D..........................
SEQ ID NO: 86   ...............H.........................................GS..
SEQ ID NO: 87   ...............Q.........................................GS..
SEQ ID NO: 88   ...............N.........................................GS..
SEQ ID NO: 89   ...............P.........................................GS..
SEQ ID NO: 90   ...............D..........................................S..
SEQ ID NO: 91   ..............................................................
SEQ ID NO: 92   ..........................................................Q..
SEQ ID NO: 93   ..........................................................Q..
SEQ ID NO: 94   ..........................................................Q..
SEQ ID NO: 95   ..........................................................Q..
```

Note: Exact column positions of substitutions may vary; figure shows sequence alignment with dots representing identity to the reference (SEQ ID NO: 14).

FIG. 4B

| | | |
|---|---|---|
| SEQ ID NO: 96 | GS | Q |
| SEQ ID NO: 97 | S | Q |
| SEQ ID NO: 98 | GS | E |
| SEQ ID NO: 99 | S | E |
| SEQ ID NO: 100 | GS | E |
| SEQ ID NO: 101 | S | E |
| SEQ ID NO: 102 | GS | Q |
| SEQ ID NO: 103 | S | Q |
| SEQ ID NO: 104 | GS | Q |
| SEQ ID NO: 105 | S | Q |
| SEQ ID NO: 106 | GS | E |
| SEQ ID NO: 107 | S | E |
| SEQ ID NO: 108 | GS | E |
| SEQ ID NO: 109 | S | E |

FIG. 4C

```
                 GVPSRFSGSKDVSTNSGILLISGLQSEDEADYCMTWSSNGSGVFGGGTQLTVLG
SEQ ID NO: 14    ......................................L...............
SEQ ID NO: 66    ..........................I.T..........................
SEQ ID NO: 67    ..........................I.T..........................
SEQ ID NO: 68    ..........................I.T..........................
SEQ ID NO: 69    .........Q................I.T..........................
SEQ ID NO: 70    ..........T...............I.T..........................
SEQ ID NO: 71    ..........................I.T..........................
SEQ ID NO: 72    ............G.............I.T..........................
SEQ ID NO: 73    .............H............I.T..........................
SEQ ID NO: 74    ..........................I.T..........................
SEQ ID NO: 75    ............K.............I.T..........................
SEQ ID NO: 76    ..........................I.T..........................
SEQ ID NO: 77    .............P............I.T..........................
SEQ ID NO: 78    ..........................I.T..........................
SEQ ID NO: 79    ..........................I.T..........................
SEQ ID NO: 80    ..........................I.T..........................
SEQ ID NO: 81    ..........................I.T..........................
SEQ ID NO: 82    ..........................I.T..........................
SEQ ID NO: 83    ..........................I.T..........................
SEQ ID NO: 84    ..........................I.T..........................
SEQ ID NO: 85    ..........................I.T..........................
SEQ ID NO: 86    ..........................I.T..........................
SEQ ID NO: 87    ..........................I.T..........................
SEQ ID NO: 88    ..........................I.T..........................
SEQ ID NO: 89    ..........................I.T..........................
SEQ ID NO: 90    ..........................I.T..........................
SEQ ID NO: 91    ..........................I.T.L.............Q.E........
SEQ ID NO: 92    ..........................I.T.L.............E..........
SEQ ID NO: 93    ..........................I.T.L.............E..........
SEQ ID NO: 94    ..........................I.T..........................
SEQ ID NO: 95    ..........................I.T.L.............E..........
```

```
                         CDR1                                CDR2
SEQ ID NO:  34   QLQLQESGPGLVKPSETLSLTCTVS GGSISSSSYYWS WIRQHPGKGLEWIG YIYYSGSTNYNPSLKS
SEQ ID NO:  18   ......................... ............ .............P ................
SEQ ID NO: 659   QLQLQESGPGLVKPSETLSLTCTVS GGSISSSSYYWS WIRQHPGKGLEWIG YIYYSGSTNYNPSLKS
                                                                    P

CDR3
SEQ ID NO:  34   RVTISVDTSKNQFSLKLSSVTAADTAVYYCAR VGGAGGWPLDV WGQGTTVTVSS
SEQ ID NO:  18   ........L..I..R.T............... .....M..... ...........
SEQ ID NO: 659   RVTISVDTSKNQFSLKLSSVTAADTAVYYCAR VGGAGGWPLDV WGQGTTVTVSS
                         L  I  R T                      M
```

```
                                                       CDR1                      CDR2
                                                TLPSDINVRYYNIY  WYQQKPGSPPRYLLY  YYSDSHKGQGS
SEQ ID NO: 65   QAVLTQPASLSASPGESARLTC  ..............  ...............  ...........
SEQ ID NO: 68   ....................   ..............  ...............  ....E......
SEQ ID NO: 86   ....................   ..............  ...............  .....Q.....
SEQ ID NO: 88   ....................   ..............  ...............  ...........
SEQ ID NO: 92   ....................   ............GS  ...............  ....E......
SEQ ID NO: 93   ....................   ............GS  ...............  ....E......
SEQ ID NO: 660  ....................   ............GS  ...............  .....Q.....
SEQ ID NO: 661  ....................   ............GS  ...............  .....Q.....
SEQ ID NO: 662  ....................   ............GS  ...............  ...........
SEQ ID NO: 663  ....................   ............GS  ...............  ...........
SEQ ID NO: 700  ....................   ............GS  ...............  ...........
SEQ ID NO: 701  ....................   ............GS  ...............  ...........
SEQ ID NO: 664  QAVLTQPASLSASPGESARLTC  TLPSDINVRYYNIY  WYQQKPGSPPRYLLY  YYSDSHKGQGS
                                                                        .....Q.....
                                                                        ....E......

CDR3
                                                          MTWSSNGSGV
SEQ ID NO: 65   GVPSRFSGSKDVSTNSGILLISGLQSEDIATYYC  ..........  FGGGTQLTVLG
SEQ ID NO: 68   ..................................  ..........  ...........
SEQ ID NO: 86   ..................................  ..........  ...........
SEQ ID NO: 88   .................T................  ..........  ...........
SEQ ID NO: 92   ..................................  ....Q.....  ...........
SEQ ID NO: 93   .................T................  ..L.E.....  ...........
SEQ ID NO: 660  .................T................  ..L.Q.....  ...........
SEQ ID NO: 661  .................T................  ..L.E.....  ...........
SEQ ID NO: 662  .................T................  ..L.Q.....  ...........
SEQ ID NO: 663  .................T................  ..L.E.....  ...........
SEQ ID NO: 700  .................T................  ..L.Q.....  ...........
SEQ ID NO: 701  ..................................  ..L.E.....  ...........
SEQ ID NO: 664  GVPSRFSGSKDVSTNSGILLISGLQSEDIATYYC  MTWSSNGSGV  FGGGTQLTVLG
                                 T                  L.Q
                                                    L.E
```

FIG. 7A

| | EVQLQQSGPEVGRPGSSVKISCKASGYTFTDYIMHWVKQSPGQGLEWIGWIDPEYGRTDYAEKFKK | |
|---|---|---|
| SEQ ID NO: 114 | ...............................................................  | |
| SEQ ID NO: 115 | ....V...A..KK..AT.....V..........................Q.A..K....M..... | QG |
| SEQ ID NO: 116 | ....V...A..KK..AT.....V..........................Q.A..K....M..... | QG |
| SEQ ID NO: 117 | ....V...A..KK..A......V..........................R.A..K....M..... | Q.LQG |
| SEQ ID NO: 118 | ....V...A..KK..A......V..........................R.A..K....M..... | Q.LQG |
| SEQ ID NO: 119 | Q...V...A..KK..A......V......L...................R.A..K....M..... | Q..QG |
| SEQ ID NO: 120 | Q...V...A..KK..A......V...........................R.A..K....M..... | Q..QG |
| SEQ ID NO: 121 | Q...V...A..KK..A......V......L...................R.A..K....M..... | Q..QG |
| SEQ ID NO: 122 | Q...V...A..KK..A......V...........................R.A..A....M..... | Q..QG |
| SEQ ID NO: 123 | QM..V...A..KKT........V...........................R.A..A....M..... | Q..QD |
| SEQ ID NO: 124 | QM..V...A..KKT........V...........................R.A..A....M..... | Q..QD |

| | KATLTADTSSSTAYIQLSSLASEDTATYFCARSAHTTGFGFAYWGQGTLVTVSS |
|---|---|
| SEQ ID NO: 114 | ...................................................... |
| SEQ ID NO: 115 | RV.I....TD...ME.....R.....V.Y..T...................... |
| SEQ ID NO: 116 | RV.I....TD...ME.....R.....V.Y.......................... |
| SEQ ID NO: 117 | RV.M.T..T....ME.R...R.D...V.Y.......................... |
| SEQ ID NO: 118 | RV.M....T....ME.R...R.D...V.Y.......................... |
| SEQ ID NO: 119 | RV.M.E..TD...ME.....R.....V.Y..T....................... |
| SEQ ID NO: 120 | RV.M....TD...ME.....R.....V.Y.......................... |
| SEQ ID NO: 121 | RV.M.E..TD...ME.....R.....V.Y..T....................... |
| SEQ ID NO: 122 | RV.M....TD...ME.....R.....V.Y.......................... |
| SEQ ID NO: 123 | RV.I.R.RM....ME.....R.....M.Y.......................... |
| SEQ ID NO: 124 | RV.I....R.M..ME.....R.....M.Y.......................... |

FIG. 7B

```
                 EVQLQQSGPEVGRPGSSVKISCKASGYIFTDYIMHWVKQSPGQGLEWIGWIDPEYGSTDYAEKFKK
SEQ ID NO: 132   ...V...A..KK..AT.........V...T..............Q.A..K....M.........QG
SEQ ID NO: 133   ...V...A..KK..AT.........V...T..............Q.A..K....M.........QG
SEQ ID NO: 134   ...V...A..KK..AT.........V...T..............Q.A..K....M.........QG
SEQ ID NO: 135   ...V...A..KK..A..........V...T..............R.A.......M.........QG
SEQ ID NO: 136   Q......A..KK..A..........V...T.............TL...............Q.LQG
SEQ ID NO: 137   Q......A..KK..A..........V...T.............TL...............Q.LQG
SEQ ID NO: 138   Q......A..KK..A..........V...T.............TL.......R.A..K....M.........Q..QG
SEQ ID NO: 139   Q......A..KK..A..........V...T..............R.A..K....M.........Q..QG
SEQ ID NO: 140   Q......A..KKT............V...T..............R.A..K....M.........Q..QG
SEQ ID NO: 141   QM.V...A..KKT............V...T..............R.A...A...M.........Q..QD
SEQ ID NO: 142   QM.V...A..KKT................T..............R.A...A...M.........Q..QD

KATLTADTSSSTAYIQLSSLTSEDTATYFCARVAITTVASGGFAYWGQGTLVTVSS
SEQ ID NO: 132   RV.I.....TD...ME........R.....V.Y..T....................
SEQ ID NO: 133   RV.I.....TD...ME........R.....V.Y..T....................
SEQ ID NO: 134   RV.I.....TD...ME........R.....V.Y.......................
SEQ ID NO: 135   RV.M.T...TD...ME........R.....V.Y.......................
SEQ ID NO: 136   RV.M.....T....ME.R...R.D......V.Y.......................
SEQ ID NO: 137   RV.M.....T....ME.R...R.D......V.Y.......................
SEQ ID NO: 138   RV.M.E...TD...ME........R.....V.Y..T....................
SEQ ID NO: 139   RV.M.....TD...ME........R.....V.Y..T....................
SEQ ID NO: 140   RV.M.E...TD...ME........R.....V.Y.......................
SEQ ID NO: 141   RV.I.R.R.M....ME........R.....M.Y.......................
SEQ ID NO: 142   RV.I.....R.M..ME........R.....M.Y.......................
```

FIG. 7C

```
SEQ ID NO: 148  EVQLQQSGPEVGRPGSSVKISCKASGYTFTDSVMNWVKQSPGQGLEWIGWIDPEYGRTDVAEKFKK
SEQ ID NO: 149  Q...V...A..KK..A....V....L.............R.A..K...M............Q..QG
SEQ ID NO: 150  Q...V...A..KK..A....V....L.............R.A..K...M............Q..QG
SEQ ID NO: 151  Q...V...A..KK..A....V....L.............R.A..K...M............Q..QG
SEQ ID NO: 152  Q...V...A..KK..A....V...................R.A..K...M............Q..QG
SEQ ID NO: 153  QM..V...A..KKT......V...................R.A...A..M............Q..QD
SEQ ID NO: 154  QM..V...A..KKT......V...................R.A...A..M............Q..QD
SEQ ID NO: 155  ....V...A..KK..AT.......................Q..A..K...M............Q..QG
SEQ ID NO: 156  ....V...A..KK..AT.......................Q..A..K...M............Q..QG

SEQ ID NO: 148  KATLTADSSSSTAYIYLSGLTSEDTATYFCARTKYNSGYGFPYWGQGSLVTVSS
SEQ ID NO: 149  RV.M.E.T.TD...ME..S.R.....V.Y..T...................TT...
SEQ ID NO: 150  RV.M...T.TD...ME..S.R.....V.Y..T...................TT...
SEQ ID NO: 151  RV.M.E.T.TD...ME..S.R.....V.Y......................TT...
SEQ ID NO: 152  RV.M...T.TD...ME..S.R.....V.Y......................TT...
SEQ ID NO: 153  RV.M...T.TD...ME..S.R.....M.Y......................TT...
SEQ ID NO: 154  RV.I..R.R.M...ME..S.R.....M.Y......................TT...
SEQ ID NO: 155  RV.I...T.TD...ME..S.R.....V.Y..T...................TT...
SEQ ID NO: 156  RV.I...T.TD...ME..S.R.....V.Y......................TT...
```

FIG. 8A

```
SEQ ID NO: 125   DIQMTQSPASLSASLGETVTIECRASEDIYSNLAWYQQKPGNSPQLLIYDANSLAD
SEQ ID NO: 126   ....ST....V.DR...T.........................KA.K........
SEQ ID NO: 127   ..L.SF....V.DR...T.........................KA.K........
SEQ ID NO: 128   ....S.V...V.DR...T.........................KA.K........
SEQ ID NO: 129   A.L...S...V.DR...T.........................KA.K........
SEQ ID NO: 130   ......S...V.DR...T.........................EKA.KS......
SEQ ID NO: 131   E.V.....T.V.P..RA.LS.......................QA.R........

SEQ ID NO: 125   GVPSRFSASGSGTQFSLKINSLRSEDVASYFCQQYNNYPYTFGAGTKLELKR
SEQ ID NO: 126   ......G.......E.T.T.S..QPD.F.T.Y..........Q.....I..
SEQ ID NO: 127   ......G.......E.T.T.S..QP..F.T.Y..........Q.....I..
SEQ ID NO: 128   ......G.......D.T.T.S..QP..F.T.Y..........Q.....I..
SEQ ID NO: 129   ......G.......D.T.T.S..QP..F.T.Y..........Q.....I..
SEQ ID NO: 130   ......G.......D.T.T.S..QP..F.T.Y..........Q.....I..
SEQ ID NO: 131   ..I.A.G.......E.T.T.S..Q...F.V.Y..........Q.....I..
```

FIG. 8B

```
                 DIVMTQGALPNPVPSGESASITCQSSESLLHSNGKTYLNWYLQRPGQSPQLLIYWMSTRAA
SEQ ID NO: 143   ............................................................
SEQ ID NO: 144   .......TP.SS..TL.QP...S.........................LQ....P.R...
SEQ ID NO: 145   .......SP.SL..TP..P...S.....................K................
SEQ ID NO: 146   .......TP.SLS.TP.QP...S..........................K..P........
SEQ ID NO: 147   .V.....SP.SL..TL.QP...S.......................FQ......RR....

GVSDRFSGSGSGTDFTLTISGVEAEDVGVYYCQQFLEYPPTFGSGTKLEIKR
SEQ ID NO: 143   ...................................................
SEQ ID NO: 144   ..P.........A......K..R...........Q................
SEQ ID NO: 145   ..P................K..R...........Q................
SEQ ID NO: 146   ..P................K..R...........Q................
SEQ ID NO: 147   ..P................K..R...........Q................
```

FIG. 8C

```
                  DIVMTQSPTSISISVGERVTMNCKASQNVDSDVDWYQQKTGQSPKLLIYKASNRYT
SEQ ID NO: 157    ..QL....SFL.A...D...IT................P.KA.............
SEQ ID NO: 158    ..Q.....S.V.A...D...IT................P.KA.............
SEQ ID NO: 159    A.QL....S.L.A...D...IT................P.KA.............
SEQ ID NO: 160    ..Q.....S.L.A...D...IT................P.KA.............
SEQ ID NO: 161    E.L.....ATL.L.P....A.LS...............P..A.R...........
SEQ ID NO: 162    E.......ATL.V.P....A.LS...............P..A.R...........
SEQ ID NO: 163    E.L.....DFQ.VTPK.K..IT................PD....K..........
SEQ ID NO: 164    ........................................................

GVPDRFTGSGSGTDFTFTISNMQAEDLAVYYCMQSNTHPRTFGGGTKLELKR
SEQ ID NO: 157    ...S..S........E..L...SL.P..F.T................V.I..
SEQ ID NO: 158    ...S..S...........L...SL.P..F.T................V.I..
SEQ ID NO: 159    ...S..S...........L...SL.P..F.T................V.I..
SEQ ID NO: 160    ...S..S...........L...SL.P..I.T................V.I..
SEQ ID NO: 161    ...S..S...............SL.P..I.T................V.I..
SEQ ID NO: 162    ..I.A..S.......R..L...SLEP..F..................V.I..
SEQ ID NO: 163    ..I.A..S..........E..L...SL.S..F................V.I..
SEQ ID NO: 164    ...S..S...............L..NSLE...A.T.............V.I..
```

FIG. 9A

```
              EVQLVQSGAEVKKPGATVKISCKVSGYTFTDSVMNWVQQAPGKGLEWMGWIDPEYGRTDVAEKFQG
SEQ ID NO: 156 ................................................................
SEQ ID NO: 165 ...........................................E....................
SEQ ID NO: 166 ...........................................G....................
SEQ ID NO: 167 ...........................................H....................
SEQ ID NO: 168 ...........................................Q....................
SEQ ID NO: 169 ...........................................S....................
SEQ ID NO: 170 ...........................................V....................
SEQ ID NO: 171 ..........................................E.....................
SEQ ID NO: 172 ..........................................P.....................
SEQ ID NO: 173 ..........................................Q.....................
SEQ ID NO: 174 ..........................................S.....................
SEQ ID NO: 175 ..................................................................
SEQ ID NO: 176 ..................................................................
SEQ ID NO: 177 ..................................................................
SEQ ID NO: 178 ..................................................................
SEQ ID NO: 179 ..................................................................
SEQ ID NO: 180 ..................................................................
SEQ ID NO: 197 ..................................................................
```

FIG. 9B

```
                RVTITADTSTDTAYMELSSLRSEDTAVYYCARTKYNSGYGFPYWGQGTTVTVSS
SEQ ID NO: 156  .....................................................
SEQ ID NO: 165  .....................................................
SEQ ID NO: 166  .....................................................
SEQ ID NO: 167  .....................................................
SEQ ID NO: 168  .....................................................
SEQ ID NO: 169  .....................................................
SEQ ID NO: 170  .....................................................
SEQ ID NO: 171  .....................................................
SEQ ID NO: 172  .....................................................
SEQ ID NO: 173  .....................................................
SEQ ID NO: 174  ...............................E.....................
SEQ ID NO: 175  ................................G....................
SEQ ID NO: 176  .................................P...................
SEQ ID NO: 177  ..................................T..................
SEQ ID NO: 178  ........................................G............
SEQ ID NO: 179  ..................................T..................
SEQ ID NO: 180  ............................................G........
SEQ ID NO: 197  .................................................Q...
```

FIG. 10A

```
                  DIQMTQSPSSLSASVGDRVTITCKASQNVDSDVDWYQQKPGKAPKLLIYKASNRYT
SEQ ID NO: 161    ........................................................
SEQ ID NO: 183    .......................P................................
SEQ ID NO: 184    ........................Q...............................
SEQ ID NO: 181    ........................E...............................
SEQ ID NO: 182    ........................G...............................
SEQ ID NO: 185    ........................................................
SEQ ID NO: 186    ............................................D...........
SEQ ID NO: 187    .............................................E..........
SEQ ID NO: 188    ........................................................
SEQ ID NO: 189    ........................................................
SEQ ID NO: 190    ........................................................
SEQ ID NO: 191    ........................................................
SEQ ID NO: 192    ........................................................
SEQ ID NO: 193    ........................................................
SEQ ID NO: 194    ........................................................
SEQ ID NO: 195    ........................................................
SEQ ID NO: 196    ........................................................
SEQ ID NO: 198    .....................................................Q..
```

FIG. 10B

```
SEQ ID NO: 161   GVPSRFSGSGSGTDFTFTISSLQPEDIATYYCMQSNTHPRTFGGGTKVEIKR
SEQ ID NO: 183   ...................................................
SEQ ID NO: 184   ...................................................
SEQ ID NO: 181   ...................................................
SEQ ID NO: 182   ...................................................
SEQ ID NO: 185   ...................................................
SEQ ID NO: 186   ...................................................
SEQ ID NO: 187   ...................................................
SEQ ID NO: 188   ............................A......................
SEQ ID NO: 189   ............................E......................
SEQ ID NO: 190   ............................H......................
SEQ ID NO: 191   ............................K......................
SEQ ID NO: 192   ............................P......................
SEQ ID NO: 193   ............................Q......................
SEQ ID NO: 194   ............................S......................
SEQ ID NO: 195   ............................V......................
SEQ ID NO: 196   .............................D.....................
SEQ ID NO: 198   ...................................................
```

FIG. 11a

| SEQ ID NO: | Framework 1<br>EVQLVQSGAEVKKPGATVKISCKVS | CDR1<br>GYTFTDSVMN | Framework 2<br>WVQQEPGKGLEWMG | CDR2<br>WIDPEYGRTDVAEKFQG |
|---|---|---|---|---|
| 165 | . . . . . . . . . . . . . . . . . . . . . . . . . | . . . . . . . . . . | . . . . . . . . . . . . . . | . . . . . . . . . . . . . . . . . |
| 166 | . . . . . . . . . . . . . . . . . . . . . . . . . | . . . . . . . . . . | . G . . . . . . . . . . . . | . . . . . . . . . . . . . . . . . |
| 167 | . . . . . . . . . . . . . . . . . . . . . . . . . | . . . . . . . . . . | . . H . . . . . . . . . . . | . . . . . . . . . . . . . . . . . |
| 179 | . . . . . . . . . . . . . . . . . . . . . . . . . | . . . . . . . . . . | . . . . A . . . . . . . . . | . . . . . . . . . . . . . . . . . |
| 180 | . . . . . . . . . . . . . . . . . . . . . . . . . | . . . . . . . . . . | . . . . A . . . . . . . . . | . . . . . . . . . . . . . . . . . |
| 156 | . . . . . . . . . . . . . . . . . . . . . . . . . | . . . . . . . . . . | . . . . A . . . . . . . . . | . . . . . . . . . . . . . . . . . |
| 197 | . . . . . . . . . . . . . . . . . . . . . . . . . | . . . . . . . . . . | . . . . A . . . . . . . . . | . . . . . . . . . . . . . . . . . |
| 152 | . . . Q . . . . . . . . . . . . . . . . . . . . . | . . . . . . . . . . | . . . . . . . . . R . A . . | . . . . . . . . . . . . . . . . . |
| 720 | . . . Q . . . . . . . . . . . . . . . . S . V . . | . . . . . L . . . . | . . . . . . . . . R . G . . | . . . . . . . . . . . . . . . . Q |
| 721 | . . . Q . . . . . . . . . . . . . . . . S . V . . | . . . . . L . . . . | . . . . . . . . . R . H . . | . . . . . . . . . . . . . . . . Q |
| 722 | . . . Q . . . . . . . . . . . . . . . . S . V . . | . . . . . L . . . . | . . . . . . . . . R . G . . | . . . . . . . . . . . . . . . . Q |
| 723 | . . . Q . . . . . . . . . . . . . . . . S . V . . | . . . . . L . . . . | . . . . . . . . . R . H . . | . . . . . . . . . . . . . . . . Q |
| 739 | . . . . . . . . . . . . . . . . . . . . . . . . . | . . . . . L . . . . | . . . . . . . . . . . G . . | . . . . . . . . . . . . . . . . Q |
| 740 | . . . . . . . . . . . . . . . . . . . . . . . . . | . . . . . . . . . . | . . . . . . . . . . . H . . | . . . . . . . . . . . . . . . . . |
| 741 | . . . . . . . . . . . . . . . . . . . . . . . . . | . . . . . . . . . . | . . . . . . . . . . . G . . | . . . . . . . . . . . . . . . . . |
| 742 | . . . . . . . . . . . . . . . . . . . . . . . . . | . . . . . . . . . . | . . . . . . . . . . . H . . | . . . . . . . . . . . . . . . . . |
| 665 | EVQLVQSGAEVKKPGATVKISCKVS<br>Q                    S  V | GYTFTDSVMN<br>     L | WVQQEPGKGLEWMG<br>         R G<br>           H<br>           A | WIDPEYGRTDVAEKFQG<br>                Q |

| SEQ ID NO: | | | CDR3 | |
|---|---|---|---|---|
| | RVTITADTSTDTAYMELSSLRSEDTAVYYCAR | TKYNSGYGFPY | WGQGTTVTVSS |
| SEQ ID NO: 165 | .................................. | .......... | ........... |
| SEQ ID NO: 166 | .................................. | .......... | ........... |
| SEQ ID NO: 167 | .................................. | .......... | ........... |
| SEQ ID NO: 179 | .................................. | ..G....... | ........... |
| SEQ ID NO: 180 | .................................. | .T........ | ........... |
| SEQ ID NO: 156 | .................................. | .......... | ........... |
| SEQ ID NO: 197 | .................................. | ......Q... | ........... |
| SEQ ID NO: 152 | ................M................. | ..G....... | ........... |
| SEQ ID NO: 720 | ................M................. | .......... | ........... |
| SEQ ID NO: 721 | ................M................. | ..G...Q... | ........... |
| SEQ ID NO: 722 | ................M................. | ..G...Q... | ........... |
| SEQ ID NO: 723 | ................M................. | ..G....... | ........... |
| SEQ ID NO: 739 | .................................. | ..G....... | ........... |
| SEQ ID NO: 740 | .................................. | ..G...Q... | ........... |
| SEQ ID NO: 741 | .................................. | ..G...Q... | ........... |
| SEQ ID NO: 742 | .................................. | ..G....... | ........... |
| SEQ ID NO: 665 | RVTITADTSTDTAYMELSSLRSEDTAVYYCAR | TKYNSGYGFPY | WGQGTTVTVSS |
| | M | G      Q | |
| | | T | |

| SEQ ID NO | Sequence | CDR1 | | CDR2 |
|---|---|---|---|---|
| | DIQMTQSPSSLSASVGDRVTITC | KASQNVDSDVD | WYQQKPGKAPKLLIY | KASNRYT |
| 161 | ....................... | ........... | ............... | ....... |
| 182 | ....................... | G.......... | ............... | ....... |
| 184 | ....................... | .Q......... | ............... | ...D... |
| 185 | ....................... | ........... | ............... | ....... |
| 188 | ....................... | ........... | ............... | ....... |
| 198 | ....................... | G.......... | ............... | ..Q.... |
| 704 | ....................... | G.......... | ............... | ...D... |
| 705 | ....................... | .Q......... | ............... | ...D... |
| 706 | ....................... | .Q......... | ............... | ....... |
| 707 | ....................... | G.......... | ............... | ..QD... |
| 708 | ....................... | G.......... | ............... | ..Q.... |
| 709 | ....................... | G.......... | ............... | ..QD... |
| 710 | ....................... | .Q......... | ............... | ..QD... |
| 711 | ....................... | .Q......... | ............... | ..Q.... |
| 666 | DIQMTQSPSSLSASVGDRVTITC | KASQNVDSDVD | WYQQKPGKAPKLLIY | KASNRYT |
| | | G Q | | Q D |

| SEQ ID NO | Sequence | CDR3 | |
|---|---|---|---|
| | GVPSRFSGSGSGTDFTFTISSLQPEDIATYYC | MQSNTHPRT | FGGGTKVEIKR |
| 161 | ............................... | ......... | ........... |
| 182 | ............................... | ......... | ........... |
| 184 | ............................... | ......... | ........... |
| 185 | ............................... | ......... | ........... |
| 188 | ............................... | ......... | ........... |
| 198 | ............................... | ...A..... | ........... |
| 704 | ............................... | ...A..... | ........... |
| 705 | ............................... | ...A..... | ........... |
| 706 | ............................... | ...A..... | ........... |
| 707 | ............................... | ...A..... | ........... |
| 708 | ............................... | ...A..... | ........... |
| 709 | ............................... | ...A..... | ........... |
| 710 | ............................... | ...A..... | ........... |
| 711 | ............................... | ...A..... | ........... |
| 666 | GVPSRFSGSGSGTDFTFTISSLQPEDIATYYC | MQSNTHPRT | FGGGTKVEIKR |
| | | A | |

```
                              CDR1                                    CDR2
SEQ ID NO: 110   EVQLVQSGAEVKKSGASVKVSCKAS GYTFTDYYIH WVRQAPGQGLEWMG WINPNNGGVTFAQKFQG
SEQ ID NO: 728   ........................  ..........  ....P.........  ..................
SEQ ID NO: 729   ........................  ..........  ....P.........  ..................
SEQ ID NO: 730   ........................  ..........  ....P.........  .............T....
SEQ ID NO: 731   ........................  ..........  ....P.........  ..................
SEQ ID NO: 736   EVQLVQSGAEVKKSGASVKVSCKAS GYTFTDYYIH WVRQAPGQGLEWMG WINPNNGGVTFAQKFQG
                                                         P                      T

CDR3
SEQ ID NO: 110   RVTMTRDTSISTAYMDLSSLRSDDTAVYFCAR DIRMSGWLAPFDY WGQGTLVTVSS
SEQ ID NO: 728   ................................ ............  ...........
SEQ ID NO: 729   ..............................Y. ............  ...........
SEQ ID NO: 730   ................................ ............  ...........
SEQ ID NO: 731   ................................ .......L....  ...........
SEQ ID NO: 736   RVTMTRDTSISTAYMDLSSLRSDDTAVYFCAR DIRMSGWLAPFDY WGQGTLVTVSS
                                                Y             L
```

FIG. 30

SEQUENCE LISTING

<160> NUMBER OF SEQ ID NOS: 753

<210> SEQ ID NO 1
<211> LENGTH: 258
<212> TYPE: PRT
<213> ORGANISM: Homo sapiens

<400> SEQUENCE: 1

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr
    50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
    130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
    210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 2
<211> LENGTH: 258
<212> TYPE: PRT
<213> ORGANISM: Macaca fascicularis

<400> SEQUENCE: 2

Leu Pro Arg Trp Arg Gln Gln Trp Ser Gly Ser Gly Thr Thr Ser Arg
1               5                   10                  15

Phe Pro Glu Thr Val Leu Ala Arg Cys Val Lys Tyr Thr Glu Val His
            20                  25                  30

Pro Glu Met Arg His Val Asp Cys Gln Ser Val Trp Asp Ala Phe Lys
        35                  40                  45

Gly Ala Phe Ile Ser Lys Tyr Pro Cys Asn Ile Thr Glu Glu Asp Tyr
    50                  55                  60

```
Gln Pro Leu Val Lys Leu Gly Thr Gln Thr Val Pro Cys Asn Lys Thr
 65                  70                  75                  80

Leu Leu Trp Ser Arg Ile Lys Asp Leu Ala His Gln Phe Thr Gln Val
                 85                  90                  95

Gln Arg Asp Met Phe Thr Leu Glu Asp Met Leu Leu Gly Tyr Leu Ala
            100                 105                 110

Asp Asp Leu Thr Trp Cys Gly Glu Phe Asn Thr Phe Glu Ile Asn Tyr
            115                 120                 125

Gln Ser Cys Pro Asp Trp Arg Lys Asp Cys Ser Asn Asn Pro Val Ser
130                 135                 140

Val Phe Trp Lys Thr Val Ser Arg Arg Phe Ala Glu Thr Ala Cys Gly
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Ala Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
210                 215                 220

Ser Lys Arg Asn Ile Arg Phe Phe Cys Lys Asn Ile Tyr Arg Pro Asp
225                 230                 235                 240

Lys Phe Leu Gln Cys Val Lys Asn Pro Glu Asp Ser Ser Cys Leu Ser
                245                 250                 255

Gly Ile

<210> SEQ ID NO 3
<211> LENGTH: 327
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210               215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 106
<212> TYPE: PRT
<213> ORGANISM: Homo sapiens

<400> SEQUENCE: 5

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
                35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 6
<211> LENGTH: 105
<212> TYPE: PRT
<213> ORGANISM: Homo sapiens

<400> SEQUENCE: 6

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
                35                  40                  45

Lys Ala Gly Val Glu Thr Thr Thr Pro Ser Lys Gln Ser Asn Asn Lys
            50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
```

100                 105

<210> SEQ ID NO 7
<211> LENGTH: 188
<212> TYPE: PRT
<213> ORGANISM: Homo sapiens

<400> SEQUENCE: 7

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Met Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 8
<211> LENGTH: 165
<212> TYPE: PRT
<213> ORGANISM: Homo sapiens

<400> SEQUENCE: 8

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Asn
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg

```
                130                 135                 140
Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 9
<211> LENGTH: 492
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335
```

```
Gly Ser Arg Arg Thr Leu Met Leu Leu Ala Gln Met Arg Ile Ser
                335                 340                 345                 350

Leu Phe Ser Cys Leu Lys Asp Arg His Asp Phe Gly Phe Pro Gln Glu
            355                 360                 365

Glu Phe Gly Asn Gln Phe Gln Lys Ala Glu Thr Ile Pro Val Leu His
        370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

Tyr Phe Gln Arg Ile Thr Leu Tyr Leu Lys Glu Lys Lys Tyr Ser Pro
    450                 455                 460

Cys Ala Trp Glu Val Val Arg Asp Glu Ile Met Arg Ser Phe Ser Leu
465                 470                 475                 480

Ser Thr Asn Leu Gln Glu Ser Leu Arg Ser Lys Glu
                485                 490

<210> SEQ ID NO 10
<211> LENGTH: 495
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Cys Asp Leu Pro Gln Thr
            325                 330                 335

His Ser Leu Gly Ser Arg Arg Thr Leu Met Leu Leu Ala Gln Met Arg
            340                 345                 350

Arg Ile Ser Leu Phe Ser Cys Leu Lys Asp Arg His Asp Phe Gly Phe
        355                 360                 365

Pro Gln Glu Glu Phe Gly Asn Gln Phe Gln Lys Ala Glu Thr Ile Pro
370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
            405                 410                 415

Glu Leu Tyr Gln Gln Leu Asn Asp Leu Glu Ala Cys Val Ile Gln Gly
            420                 425                 430

Val Gly Val Thr Glu Thr Pro Leu Met Lys Glu Asp Ser Ile Leu Ala
        435                 440                 445

Val Arg Lys Tyr Phe Gln Arg Ile Thr Leu Tyr Leu Lys Glu Lys Lys
        450                 455                 460

Tyr Ser Pro Cys Ala Trp Glu Val Val Arg Asp Glu Ile Met Arg Ser
465                 470                 475                 480

Phe Ser Leu Ser Thr Asn Leu Gln Glu Ser Leu Arg Ser Lys Glu
            485                 490                 495

<210> SEQ ID NO 11
<211> LENGTH: 121
<212> TYPE: PRT
<213> ORGANISM: Homo sapiens

<400> SEQUENCE: 11

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
            85                  90                  95

Cys Ala Arg Val Gly Gly Ala Gly Gly Trp Pro Met Asp Val Trp Gly

```
                    100                 105                 110
Gln Gly Thr Thr Val Thr Val Ser Ser
        115                 120
```

<210> SEQ ID NO 12
<211> LENGTH: 222
<212> TYPE: PRT
<213> ORGANISM: Homo sapiens

<400> SEQUENCE: 12

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly Gln Pro Lys Ala Ala Pro Ser Val Thr Leu Phe
        115                 120                 125

Pro Pro Ser Ser Glu Glu Leu Gln Ala Asn Lys Ala Thr Leu Val Cys
130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Cys Ser
    210                 215                 220
```

<210> SEQ ID NO 13
<211> LENGTH: 121
<212> TYPE: PRT
<213> ORGANISM: Homo sapiens

<400> SEQUENCE: 13

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
```

```
                    85                  90                  95
Cys Ala Arg Val Gly Ala Gly Gly Trp Pro Met Asp Val Trp Gly
                100                 105                 110
Gln Gly Thr Thr Val Thr Val Ser Ser
            115                 120

<210> SEQ ID NO 14
<211> LENGTH: 117
<212> TYPE: PRT
<213> ORGANISM: Homo sapiens

<400> SEQUENCE: 14

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
50              55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115

<210> SEQ ID NO 15
<211> LENGTH: 121
<212> TYPE: PRT
<213> ORGANISM: Homo sapiens

<400> SEQUENCE: 15

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 16
<211> LENGTH: 121
<212> TYPE: PRT
<213> ORGANISM: Homo sapiens

<400> SEQUENCE: 16
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Val Gly Gly Ala Gly Gly Trp Pro Met Asp Val Trp Gly
            100                 105                 110

Gln Gly Thr Thr Val Thr Val Ser Ser
            115                 120

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 17

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Ile
65                  70                  75                  80

Ser Leu Arg Leu Thr Ser Val Thr Ala Ala Asp Thr Ala Val Tyr Tyr
            85                  90                  95

Cys Ala Arg Val Gly Gly Ala Gly Gly Trp Pro Met Asp Val Trp Gly
            100                 105                 110

Gln Gly Thr Thr Val Thr Val Ser Ser
            115                 120

<210> SEQ ID NO 18
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 18

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser

```
                20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 19
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 19

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Leu Lys Asn Gln Ile
65                  70                  75                  80

Ser Leu Arg Leu Ser Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 20

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
            35                  40                  45
```

```
Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 21

Gln Leu Gln Leu Gln Glu Ser Gly Pro Gly Leu Val Lys Pro Ser Glu
 1               5                   10                  15

Thr Leu Ser Leu Thr Cys Lys Val Ser Gly Gly Ser Ile Ser Ser Ser
                20                  25                  30

Ser Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Leu Lys Asn Gln Ile
 65                  70                  75                  80

Ser Leu Arg Leu Thr Ser Val Thr Ala Ala Asp Thr Ala Val Tyr Tyr
                 85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 22

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Ser
                20                  25                  30

Ser Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Leu Lys Asn Gln Ile
 65                  70                  75                  80
```

```
Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 23

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Arg Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 24
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 24

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
```

```
              100                 105                 110

Gln Gly Thr Thr Val Thr Val Ser Ser
        115                 120
```

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 25

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Arg Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120
```

<210> SEQ ID NO 26
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 26

```
Gln Leu Gln Leu Gln Glu Ser Gly Pro Gly Leu Val Lys Pro Ser Glu
1               5                   10                  15

Thr Leu Lys Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120
```

```
<210> SEQ ID NO 27
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 27

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Leu Glu Val Trp Gly
            100                 105                 110

Gln Gly Thr Thr Val Thr Val Ser Ser
        115                 120

<210> SEQ ID NO 28
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 28

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Lys Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
            100                 105                 110

Gln Gly Thr Thr Val Thr Val Ser Ser
        115                 120

<210> SEQ ID NO 29
<211> LENGTH: 121
<212> TYPE: PRT
<213> ORGANISM: Artificial Sequence
```

<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Leu Asp Val Trp Gly
            100                 105                 110

Gln Gly Thr Thr Val Thr Val Ser Ser
            115                 120

<210> SEQ ID NO 30
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 30

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Glu Val Trp Gly
            100                 105                 110

Gln Gly Thr Thr Val Thr Val Ser Ser
            115                 120

<210> SEQ ID NO 31
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 32

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 33

Gln Leu Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Ser
                20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Leu Lys Asn Gln Ile
65                  70                  75                  80

Ser Leu Lys Leu Thr Ser Val Thr Ala Ala Asp Thr Ala Val Tyr Tyr
                85                  90                  95

Cys Ala Arg Val Gly Gly Ala Gly Gly Trp Pro Met Asp Val Trp Gly
                100                 105                 110

Gln Gly Thr Thr Val Thr Val Ser Ser
            115                 120
```

<210> SEQ ID NO 34
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 34

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly Gly Ala Gly Gly Trp Pro Leu Asp Val Trp Gly
                100                 105                 110

Gln Gly Thr Thr Val Thr Val Ser Ser
            115                 120
```

<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 35

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Ser Trp Ile Arg Gln Pro Pro Gly Lys Gly Leu Glu
```

```
            35                  40                  45

Trp Ile Gly Tyr Ile Tyr Tyr Ser Gly Ser Thr Asn Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Gly Ala Gly Gly Trp Pro Leu Asp Val Trp Gly
                100                 105                 110

Gln Gly Thr Thr Val Thr Val Ser Ser
            115                 120

<210> SEQ ID NO 36
<211> LENGTH: 117
<212> TYPE: PRT
<213> ORGANISM: Homo sapiens

<400> SEQUENCE: 36

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
             35                  40                  45

Leu Leu Tyr Tyr Tyr Ser Asp Ser His Lys Gly Gln Gly Ser Gly Val
 50                  55                  60

Pro Ser Arg Phe Ser Gly Ser Lys Asp Val Thr Asn Ser Gly Ile
 65                  70                  75                  80

Leu Leu Ile Ser Gly Leu Gln Ser Glu Asp Glu Ala Asp Tyr Tyr Cys
                 85                  90                  95

Met Thr Trp Ser Ser Asn Gly Ser Gly Val Phe Gly Gly Gly Thr Gln
                100                 105                 110

Leu Thr Val Leu Gly
            115

<210> SEQ ID NO 37
<211> LENGTH: 117
<212> TYPE: PRT
<213> ORGANISM: Homo sapiens

<400> SEQUENCE: 37

Gln Pro Val Leu Thr Gln Pro Pro Ser Ser Ala Ser Pro Gly Glu
 1               5                  10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
             35                  40                  45

Leu Leu Tyr Tyr Tyr Ser Asp Ser Asp Lys Gly Gln Gly Ser Gly Val
 50                  55                  60

Pro Ser Arg Phe Ser Gly Ser Lys Asp Ala Ser Ala Asn Thr Gly Ile
 65                  70                  75                  80

Leu Leu Ile Ser Gly Leu Gln Ser Glu Asp Glu Ala Asp Tyr Tyr Cys
                 85                  90                  95

Met Ile Trp Pro Ser Asn Ala Ser Gly Val Phe Gly Gly Gly Thr Gln
                100                 105                 110

Leu Thr Val Leu Gly
```

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 38

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Gln Gly Ser Gly Val Phe Gly Gly Gly Thr Gln
            100                 105                 110

Leu Thr Val Leu Gly
            115

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 39

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Ala Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115

<210> SEQ ID NO 40
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 40

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Arg Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 41

Gln Ala Val Leu Thr Gln Pro Ala Ser Leu Ser Ala Ser Pro Gly Ala
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: Completely synthesized

<400> SEQUENCE: 42

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Arg Tyr Arg Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 43
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 43

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Ser Thr Asn Ser Gly Ile Leu Leu
65                  70                  75                  80

Ile Ser Gly Leu Gln Ser Glu Asp Glu Ala Asp Tyr Tyr Cys Met Thr
                85                  90                  95

Trp Ser Ser Asn Gly Ser Gly Val Phe Gly Gly Gly Thr Gln Leu Thr
            100                 105                 110

Val Leu Gly
        115

<210> SEQ ID NO 44
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 44
```

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Gly Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115

<210> SEQ ID NO 45
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 45

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ala Gly Val Phe Gly Gly Gly Thr Gln
            100                 105                 110

Leu Thr Val Leu Gly
            115

<210> SEQ ID NO 46
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 46

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Arg Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 47
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 47

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Arg Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 48
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 48

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val

```
                50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Glu Ala Asp Tyr Tyr Cys
                    85                  90                  95

Met Thr Trp Ser Ser Thr Gly Ser Gly Val Phe Gly Gly Gly Thr Gln
                100                 105                 110

Leu Thr Val Leu Gly
        115
```

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 49

```
Gln Ala Val Leu Thr Gln Pro Ala Ser Leu Ser Ala Ser Pro Gly Glu
 1               5                  10                  15

Ser Ala Arg Leu Thr Cys Thr Leu Arg Ser Asp Ile Asn Val Arg Tyr
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Ser Asp Ser His Lys Gly Gln Gly Ser Gly Val
         50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Glu Ala Asp Tyr Tyr Cys
                    85                  90                  95

Met Thr Trp Ser Ser Asn Gly Ser Gly Val Phe Gly Gly Gly Thr Gln
                100                 105                 110

Leu Thr Val Leu Gly
        115
```

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 50

```
Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Ser Asp Ser His Lys Gly Gln Gly Ser Gly Val
         50                  55                  60

Pro Ser Arg Phe Ser Gly Ser Lys Asp Val Ser Thr Asn Ser Gly Ile
 65                  70                  75                  80
```

```
Leu Leu Ile Ser Gly Leu Gln Ser Glu Asp Glu Ala Asp Tyr Tyr Cys
                85                  90                  95

Met Thr Trp Ser Ser Asn Pro Ser Gly Val Phe Gly Gly Gly Thr Gln
            100                 105                 110

Leu Thr Val Leu Gly
        115

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 51

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Ile Thr Trp Ser Ser Asn Gly Ser Gly Val Phe Gly Gly Gly Thr Gln
            100                 105                 110

Leu Thr Val Leu Gly
        115

<210> SEQ ID NO 52
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 52

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Leu Thr Trp Ser Ser Asn Gly Ser Gly Val Phe Gly Gly Gly Thr Gln
            100                 105                 110
```

Leu Thr Val Leu Gly
        115

<210> SEQ ID NO 53
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 53

Gln Pro Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 54
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 54

Gln Ala Val Leu Thr Gln Pro Pro Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

```
<210> SEQ ID NO 55
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 55

Gln Ala Val Leu Thr Gln Pro Ala Ser Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115

<210> SEQ ID NO 56
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 56

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115

<210> SEQ ID NO 57
<211> LENGTH: 117
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: Completely synthesized

<400> SEQUENCE: 57

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 58
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 58

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 59

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Ser Asp Ser His Lys Gln Gly Ser Gly Val
    50                  55                  60

Pro Ser Arg Phe Ser Gly Ser Lys Asp Ala Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 60

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Ser Asp Ser His Lys Gln Gly Ser Gly Val
    50                  55                  60

Pro Ser Arg Phe Ser Gly Ser Lys Asp Val Ser Ala Asn Ser Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 61

Gln Ala Val Leu Thr Gln Pro Ala Ser Leu Ser Ala Ser Pro Gly Glu
1               5                   10                  15

-continued

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Thr Gly Ile
65                  70                  75                  80

Leu Leu Ile Ser Gly Leu Gln Ser Glu Asp Glu Ala Asp Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115

<210> SEQ ID NO 62
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 62

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Glu Ala Asp Tyr Tyr Cys
                85                  90                  95

Met Ile Trp Ser Ser Asn Gly Ser Gly Val Phe Gly Gly Gly Thr Gln
                100                 105                 110

Leu Thr Val Leu Gly
        115

<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 63

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

```
Leu Leu Tyr Tyr Tyr Ser Asp Ser His Lys Gly Gln Gly Ser Gly Val
         50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Glu Ala Asp Tyr Tyr Cys
                 85                  90                  95

Met Thr Trp Pro Ser Asn Gly Ser Gly Val Phe Gly Gly Gly Thr Gln
                100                 105                 110

Leu Thr Val Leu Gly
            115

<210> SEQ ID NO 64
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 64

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
             20                  25                  30

Tyr Asn Ile Tyr Trp Tyr Gln Gln Lys Pro Gly Ser Pro Pro Arg Tyr
         35                  40                  45

Leu Leu Tyr Tyr Tyr Ser Asp Ser His Lys Gly Gln Gly Ser Gly Val
         50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Glu Ala Asp Tyr Tyr Cys
                 85                  90                  95

Met Thr Trp Ser Ser Asn Ala Ser Gly Val Phe Gly Gly Gly Thr Gln
                100                 105                 110

Leu Thr Val Leu Gly
            115

<210> SEQ ID NO 65
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 65

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Tyr
             20                  25                  30

Tyr Asn Ile Tyr Trp Tyr Gln Gln Lys Pro Gly Ser Pro Pro Arg Tyr
         35                  40                  45

Leu Leu Tyr Tyr Tyr Ser Asp Ser His Lys Gly Gln Gly Ser Gly Val
         50                  55                  60

Pro Ser Arg Phe Ser Gly Ser Lys Asp Val Ser Thr Asn Ser Gly Ile
```

```
                 65                  70                  75                  80
Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115

<210> SEQ ID NO 66
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 66

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Asn Gly Ser Gly Val Phe Gly Gly Gly Thr Gln
            100                 105                 110

Leu Thr Val Leu Gly
            115

<210> SEQ ID NO 67
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 67

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95
```

```
Met Thr Trp Ser Ser Asn Gly Ser Gly Val Phe Gly Gly Gly Thr Gln
                100                 105                 110

Leu Thr Val Leu Gly
        115

<210> SEQ ID NO 68
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 68

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115

<210> SEQ ID NO 69
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 69

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Gly Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115
```

<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 70

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Ser Asp Ser His Lys Gly Gln Gly Ser Gly Val
        50                  55                  60

Pro Ser Arg Phe Ser Gly Ser Lys Asp Val Ser Thr His Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 71
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 71

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
                20                  25                  30

Tyr Asn Ile Tyr Trp Tyr Gln Gln Lys Pro Gly Ser Pro Pro Arg Tyr
            35                  40                  45

Leu Leu Tyr Tyr Ser Asp Ser His Lys Gly Gln Gly Ser Gly Val
        50                  55                  60

Pro Ser Arg Phe Ser Gly Ser Lys Asp Val Ser Thr Lys Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 72
<211> LENGTH: 117
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 72

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Pro Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115
```

<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 73

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Glu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115
```

<210> SEQ ID NO 74
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: Completely synthesized

<400> SEQUENCE: 74

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Gly Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115
```

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Completely synthesized

<400> SEQUENCE: 75

```
Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Asn Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115
```

<210> SEQ ID NO 76
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Completely synthesized

<400> SEQUENCE: 76

```
Gln Ala Val Leu Thr Gln Pro Ala Ser Leu Ser Ala Ser Pro Gly Glu
```

```
1               5                   10                  15
Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Pro Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115

<210> SEQ ID NO 77
<211> LENGTH: 117
<212> TYPE: PRT
<213> ORGANISM: Homo sapiens

<400> SEQUENCE: 77

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Ser Leu Tyr Tyr Tyr Ser Asp Ser His Lys Gly Gln Gly Ser Gly Val
        50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
            115

<210> SEQ ID NO 78
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 78

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Glu Tyr Tyr Tyr Ser Asp Ser His Lys Gly Gln Gly Ser Gly Val
        50                  55                  60
```

```
Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 79
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 79

Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
             35                  40                  45

Leu Pro Tyr Tyr Ser Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
                 85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 80
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 80

Gln Ala Val Leu Thr Gln Pro Ala Ser Leu Ser Ala Ser Pro Gly Glu
  1               5                  10                  15

Ser Ala Arg Leu Thr Cys Thr Leu Pro Ser Asp Ile Asn Val Arg Tyr
                 20                  25                  30

Tyr Asn Ile Tyr Trp Tyr Gln Gln Lys Pro Gly Ser Pro Pro Arg Tyr
             35                  40                  45

Leu Leu Glu Tyr Tyr Ser Asp Ser His Lys Gly Gln Gly Ser Gly Val
 50                  55                  60

Pro Ser Arg Phe Ser Gly Ser Lys Asp Val Ser Thr Asn Ser Gly Ile
 65                  70                  75                  80

Leu Leu Ile Ser Gly Leu Gln Ser Glu Asp Ile Ala Thr Tyr Tyr Cys
```

```
Met Thr Trp Ser Ser Asn Gly Ser Gly Val Phe Gly Gly Gly Thr Gln
            100                 105                 110

Leu Thr Val Leu Gly
        115

<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 81

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Gln Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 82

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Pro Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110
```

Leu Thr Val Leu Gly
        115

<210> SEQ ID NO 83
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 83

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Asn Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 84
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 84

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Thr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 85

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 85

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Asp Ser Ser His Lys Gly Gln Gly Ser Gly Val
    50                  55                  60

Pro Ser Arg Phe Ser Gly Ser Lys Asp Val Ser Thr Asn Ser Gly Ile
65              70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 86

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65              70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 87
<211> LENGTH: 117
<212> TYPE: PRT
<213> ORGANISM: Artificial Sequence
<220> FEATURE:
<223> OTHER INFORMATION: Description of Artificial Sequence: Synthetic
```

-continued

```
                         polypeptide
<220> FEATURE:
<223> OTHER INFORMATION: Completely synthesized

<400> SEQUENCE: 87

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr His Asp Ser His Lys Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 88

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Gln Asp Ser His Lys Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
        115

<210> SEQ ID NO 89
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 89
```

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser Asn Lys Gly Gln Gly Ser Gly Val
50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115

<210> SEQ ID NO 90
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 90

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser Pro Lys Gly Gln Gly Ser Gly Val
50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Met Thr Trp Ser Ser Asn Gly Ser Gly Val Phe Gly Gly Gly Thr Gln
                100                 105                 110

Leu Thr Val Leu Gly
        115

<210> SEQ ID NO 91
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 91

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr

```
                    20                  25                  30
Tyr Asn Ile Tyr Trp Tyr Gln Gln Lys Pro Gly Ser Pro Pro Arg Tyr
                35                  40                  45
Leu Leu Tyr Tyr Tyr Ser Asp Ser His Asp Gly Gln Gly Ser Gly Val
            50                  55                  60
Pro Ser Arg Phe Ser Gly Ser Lys Asp Val Ser Thr Asn Ser Gly Ile
65                  70                  75                  80
Leu Leu Ile Ser Gly Leu Gln Ser Glu Asp Ile Ala Thr Tyr Tyr Cys
                85                  90                  95
Met Thr Trp Ser Ser Asn Gly Ser Gly Val Phe Gly Gly Gly Thr Gln
                100                 105                 110
Leu Thr Val Leu Gly
            115

<210> SEQ ID NO 92
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 92

Gln Ala Val Leu Thr Gln Pro Ala Ser Leu Ser Ala Ser Pro Gly Glu
1               5                   10                  15
Ser Ala Arg Leu Thr Cys Thr Leu Pro Ser Asp Ile Asn Val Gly Ser
                20                  25                  30
Tyr Asn Ile Tyr Trp Tyr Gln Gln Lys Pro Gly Ser Pro Pro Arg Tyr
                35                  40                  45
Leu Leu Tyr Tyr Tyr Ser Asp Ser His Lys Gly Gln Gly Ser Gly Val
            50                  55                  60
Pro Ser Arg Phe Ser Gly Ser Lys Asp Val Ser Thr Asn Ser Gly Ile
65                  70                  75                  80
Leu Leu Ile Ser Gly Leu Gln Ser Glu Asp Ile Ala Thr Tyr Tyr Cys
                85                  90                  95
Leu Thr Trp Ser Ser Gln Gly Ser Gly Val Phe Gly Gly Gly Thr Gln
                100                 105                 110
Leu Thr Val Leu Gly
            115

<210> SEQ ID NO 93
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 93

Gln Ala Val Leu Thr Gln Pro Ala Ser Leu Ser Ala Ser Pro Gly Glu
1               5                   10                  15
Ser Ala Arg Leu Thr Cys Thr Leu Pro Ser Asp Ile Asn Val Gly Ser
                20                  25                  30
Tyr Asn Ile Tyr Trp Tyr Gln Gln Lys Pro Gly Ser Pro Pro Arg Tyr
                35                  40                  45
```

```
Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 94
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 94

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 95
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 95

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80
```

```
Leu Ile Ser Gly Leu Gln Ser Glu Asp Ile Ala Thr Tyr Tyr Cys
            85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 96
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 96

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
            85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 97
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 97

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
            85                  90                  95

Leu Thr Trp Ser Ser Gln Gly Ser Gly Val Phe Gly Gly Gly Thr Gln
```

Leu Thr Val Leu Gly
        115

<210> SEQ ID NO 98
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 98

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 99
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 100

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 101
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 101

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Asn Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 102
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Completely synthesized

<400> SEQUENCE: 102

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 103
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 103

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 104
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 104

Gln Ala Val Leu Thr Gln Pro Ala Ser Leu Ser Ala Ser Pro Gly Glu

```
                1               5                  10                  15
Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Gln Asp Ser His Lys Gly Gln Gly Ser Gly Val
        50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
                100                 105                 110

Leu Thr Val Leu Gly
        115

<210> SEQ ID NO 105
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 105

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
                20                  25                  30

Tyr Asn Ile Tyr Trp Tyr Gln Gln Lys Pro Gly Ser Pro Pro Arg Tyr
                35                  40                  45

Leu Leu Tyr Tyr Tyr Gln Asp Ser His Lys Gly Gln Gly Ser Gly Val
        50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
                100                 105                 110

Leu Thr Val Leu Gly
        115

<210> SEQ ID NO 106
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 106

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
                20                  25                  30
```

```
Tyr Asn Ile Tyr Trp Tyr Gln Gln Lys Pro Gly Ser Pro Arg Tyr
            35                  40                  45

Leu Leu Tyr Tyr Tyr Glu Asp Ser His Lys Gly Gln Gly Ser Gly Val
 50                  55                  60

Pro Ser Arg Phe Ser Gly Ser Lys Asp Val Ser Thr Gln Ser Gly Ile
 65                  70                  75                  80

Leu Leu Ile Ser Gly Leu Gln Ser Glu Asp Ile Ala Thr Tyr Tyr Cys
                 85                  90                  95

Leu Thr Trp Ser Ser Glu Gly Ser Gly Val Phe Gly Gly Gly Thr Gln
                100                 105                 110

Leu Thr Val Leu Gly
            115

<210> SEQ ID NO 107
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 107

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Arg Ser
             20                  25                  30

Tyr Asn Ile Tyr Trp Tyr Gln Gln Lys Pro Gly Ser Pro Pro Arg Tyr
            35                  40                  45

Leu Leu Tyr Tyr Tyr Glu Asp Ser His Lys Gly Gln Gly Ser Gly Val
 50                  55                  60

Pro Ser Arg Phe Ser Gly Ser Lys Asp Val Ser Thr Gln Ser Gly Ile
 65                  70                  75                  80

Leu Leu Ile Ser Gly Leu Gln Ser Glu Asp Ile Ala Thr Tyr Tyr Cys
                 85                  90                  95

Leu Thr Trp Ser Ser Glu Gly Ser Gly Val Phe Gly Gly Gly Thr Gln
                100                 105                 110

Leu Thr Val Leu Gly
            115

<210> SEQ ID NO 108
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 108

Gln Ala Val Leu Thr Gln Pro Ala Ser Leu Ser Ala Ser Pro Gly Glu
 1               5                  10                  15

Ser Ala Arg Leu Thr Cys Thr Leu Pro Ser Asp Ile Asn Val Gly Ser
             20                  25                  30

Tyr Asn Ile Tyr Trp Tyr Gln Gln Lys Pro Gly Ser Pro Pro Arg Tyr
            35                  40                  45

Leu Leu Tyr Tyr Tyr Glu Asp Ser His Lys Gly Gln Gly Ser Gly Val
 50                  55                  60
```

```
Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 109
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 109

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Glu Asp Ser His Lys Gly Gln Gly Ser Gly Val
    50                  55                  60

Pro Ser Arg Phe Ser Gly Ser Lys Asp Val Ser Thr Gln Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 110
<211> LENGTH: 122
<212> TYPE: PRT
<213> ORGANISM: Homo sapiens

<400> SEQUENCE: 110

Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Asn Pro Asn Asn Gly Gly Val Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Thr Ala Val Tyr Phe Cys
                85                  90                  95

Ala Arg Asp Ile Arg Met Ser Gly Trp Leu Ala Pro Phe Asp Tyr Trp
            100                 105                 110
```

Gly Gln Gly Thr Leu Val Thr Val Ser Ser
            115                 120

<210> SEQ ID NO 111
<211> LENGTH: 120
<212> TYPE: PRT
<213> ORGANISM: Homo sapiens

<400> SEQUENCE: 111

Gln Val Gln Leu Val Glu Ser Gly Gly Val Val Gln Gly Gly
1               5                   10                  15

Ser Leu Arg Leu Ser Cys Ala Ala Ser Gly Phe Thr Val Arg Ser Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Val Thr Thr Gly Trp Tyr Phe Asp Leu Trp Gly Arg
            100                 105                 110

Gly Thr Leu Val Thr Val Ser Ser
            115                 120

<210> SEQ ID NO 112
<211> LENGTH: 117
<212> TYPE: PRT
<213> ORGANISM: Homo sapiens

<400> SEQUENCE: 112

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr
            20                  25                  30

Tyr Asn Ile Tyr Trp Tyr Gln Gln Lys Pro Gly Ser Pro Pro Arg Tyr
        35                  40                  45

Leu Leu Tyr Tyr Ser Asp Ser His Lys Asp Gln Gly Ser Gly Val
    50                  55                  60

Pro Ser Arg Phe Ser Gly Ser Lys Asp Thr Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Ala Ser Asn Gly Ser Gly Val Leu Gly Gly Thr Gln
            100                 105                 110

Leu Thr Val Leu Gly
            115

<210> SEQ ID NO 113
<211> LENGTH: 117
<212> TYPE: PRT
<213> ORGANISM: Homo sapiens

<400> SEQUENCE: 113

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Arg Tyr

```
                20                  25                  30
His Asn Ile Tyr Trp Tyr Gln Glu Lys Pro Gly Ser Pro Arg Tyr
            35                  40                  45

Leu Leu Tyr Tyr Tyr Ser Asp Ser Ser Lys Gly Gln Gly Ser Gly Val
        50                  55                  60

Pro Ser Arg Phe Ser Gly Ser Lys Asp Val Ser Thr Asn Thr Gly Ile
65                  70                  75                  80

Leu Val Ile Ser Gly Leu Gln Ser Glu Asp Glu Ala Glu Tyr Tyr Cys
                85                  90                  95

Met Thr Trp Ser Ser Asn Gly Ser Gly Val Phe Gly Gly Gly Thr Gln
            100                 105                 110

Leu Thr Val Leu Gly
            115

<210> SEQ ID NO 114
<211> LENGTH: 120
<212> TYPE: PRT
<213> ORGANISM: Rattus norvegicus

<400> SEQUENCE: 114

Glu Val Gln Leu Gln Gln Ser Gly Pro Glu Val Gly Arg Pro Gly Ser
1               5                   10                  15

Ser Val Lys Ile Ser Cys Lys Ala Ser Gly Tyr Thr Phe Thr Asp Tyr
            20                  25                  30

Ile Met His Trp Val Lys Gln Ser Pro Gly Gln Gly Leu Glu Trp Ile
        35                  40                  45

Gly Trp Ile Asp Pro Glu Tyr Gly Arg Thr Asp Tyr Ala Glu Lys Phe
    50                  55                  60

Lys Lys Lys Ala Thr Leu Thr Ala Asp Thr Ser Ser Ser Thr Ala Tyr
65                  70                  75                  80

Ile Gln Leu Ser Ser Leu Ala Ser Glu Asp Thr Ala Thr Tyr Phe Cys
                85                  90                  95

Ala Arg Ser Ala His Thr Thr Gly Phe Gly Phe Ala Tyr Trp Gly Gln
            100                 105                 110

Gly Thr Leu Val Thr Val Ser Ser
        115                 120

<210> SEQ ID NO 115
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 115

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Ile Met His Trp Val Gln Gln Ala Pro Gly Lys Gly Leu Glu Trp Met
        35                  40                  45

Gly Trp Ile Asp Pro Glu Tyr Gly Arg Thr Asp Tyr Ala Glu Lys Phe
    50                  55                  60

Gln Gly Arg Val Thr Ile Thr Ala Asp Thr Ser Thr Asp Thr Ala Tyr
65                  70                  75                  80
```

```
Met Glu Leu Ser Ser Leu Arg Ser Glu Asp Thr Ala Val Tyr Tyr Cys
                85                  90                  95

Ala Thr Ser Ala His Thr Thr Gly Phe Gly Phe Ala Tyr Trp Gly Gln
            100                 105                 110

Gly Thr Leu Val Thr Val Ser Ser
        115                 120

<210> SEQ ID NO 116
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 116

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Ile Met His Trp Val Gln Gln Ala Pro Gly Lys Gly Leu Glu Trp Met
        35                  40                  45

Gly Trp Ile Asp Pro Glu Tyr Gly Arg Thr Asp Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala His Thr Thr Gly Phe Gly Phe Ala Tyr Trp Gly Gln
            100                 105                 110

Gly Thr Leu Val Thr Val Ser Ser
        115                 120

<210> SEQ ID NO 117
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Trp Ile Asp Pro Glu Tyr Gly Arg Thr Asp Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ala His Thr Thr Gly Phe Gly Phe Ala Tyr Trp Gly Gln
```

```
                    100                 105                 110

Gly Thr Leu Val Thr Val Ser Ser
        115                 120

<210> SEQ ID NO 118
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Trp Ile Asp Pro Glu Tyr Gly Arg Thr Asp Tyr Ala Gln Lys Leu
    50                  55                  60

Gln Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ala His Thr Thr Gly Phe Gly Phe Ala Tyr Trp Gly Gln
                100                 105                 110

Gly Thr Leu Val Thr Val Ser Ser
        115                 120

<210> SEQ ID NO 119
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
                20                  25                  30

Ile Met His Trp Val Arg Gln Ala Pro Gly Lys Gly Leu Glu Trp Met
            35                  40                  45

Gly Trp Ile Asp Pro Glu Tyr Gly Arg Thr Asp Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Ala His Thr Thr Gly Phe Gly Phe Ala Tyr Trp Gly Gln
                100                 105                 110

Gly Thr Leu Val Thr Val Ser Ser
        115                 120
```

<210> SEQ ID NO 120
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 120

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
            20                  25                  30

Ile Met His Trp Val Arg Gln Ala Pro Gly Lys Gly Leu Glu Trp Met
        35                  40                  45

Gly Trp Ile Asp Pro Glu Tyr Gly Arg Thr Asp Tyr Ala Gln Lys Phe
    50                  55                  60

Gln Gly Arg Val Thr Met Thr Ala Asp Thr Ser Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Ala His Thr Thr Gly Phe Gly Phe Ala Tyr Trp Gly Gln
            100                 105                 110

Gly Thr Leu Val Thr Val Ser Ser
        115                 120
```

<210> SEQ ID NO 121
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 121

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Ile Met His Trp Val Arg Gln Ala Pro Gly Lys Gly Leu Glu Trp Met
        35                  40                  45

Gly Trp Ile Asp Pro Glu Tyr Gly Arg Thr Asp Tyr Ala Gln Lys Phe
    50                  55                  60

Gln Gly Arg Val Thr Met Thr Glu Asp Thr Ser Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Ala His Thr Thr Gly Phe Gly Phe Ala Tyr Trp Gly Gln
            100                 105                 110

Gly Thr Leu Val Thr Val Ser Ser
        115                 120
```

<210> SEQ ID NO 122
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
            20                  25                  30

Ile Met His Trp Val Arg Gln Ala Pro Gly Lys Gly Leu Glu Trp Met
        35                  40                  45

Gly Trp Ile Asp Pro Glu Tyr Gly Arg Thr Asp Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala His Thr Thr Gly Phe Gly Phe Ala Tyr Trp Gly Gln
            100                 105                 110

Gly Thr Leu Val Thr Val Ser Ser
        115                 120

<210> SEQ ID NO 123
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 123

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Ala Leu Glu Trp Met
        35                  40                  45

Gly Trp Ile Asp Pro Glu Tyr Gly Arg Thr Asp Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Ser Ala His Thr Thr Gly Phe Gly Phe Ala Tyr Trp Gly Gln
            100                 105                 110

Gly Thr Leu Val Thr Val Ser Ser
        115                 120

<210> SEQ ID NO 124
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 124

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Ala Leu Glu Trp Met
        35                  40                  45

Gly Trp Ile Asp Pro Glu Tyr Gly Arg Thr Asp Tyr Ala Gln Lys Phe
    50                  55                  60

Gln Asp Arg Val Thr Ile Thr Ala Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Ser Ala His Thr Thr Gly Phe Gly Phe Ala Tyr Trp Gly Gln
            100                 105                 110

Gly Thr Leu Val Thr Val Ser Ser
            115                 120

<210> SEQ ID NO 125
<211> LENGTH: 108
<212> TYPE: PRT
<213> ORGANISM: Rattus norvegicus

<400> SEQUENCE: 125

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Ser Asn
            20                  25                  30

Leu Ala Trp Tyr Gln Gln Lys Pro Gly Asn Ser Pro Gln Leu Leu Ile
        35                  40                  45

Tyr Asp Ala Asn Ser Leu Ala Asp Gly Val Pro Ser Arg Phe Ser Ala
    50                  55                  60

Ser Gly Ser Gly Thr Gln Phe Ser Leu Lys Ile Asn Ser Leu Arg Ser
65                  70                  75                  80

Glu Asp Val Ala Ser Tyr Phe Cys Gln Gln Tyr Asn Asn Tyr Pro Tyr
                85                  90                  95

Thr Phe Gly Ala Gly Thr Lys Leu Glu Leu Lys Arg
            100                 105

<210> SEQ ID NO 126
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 126

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Asn Ser Leu Ala Asp Gly Val Pro Ser Arg Phe Ser Gly

```
                    50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Asn Tyr Pro Tyr
                 85                  90                  95

Thr Phe Gly Gln Gly Thr Lys Leu Glu Ile Lys Arg
            100                 105
```

<210> SEQ ID NO 127
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 127

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Glu Asp Ile Tyr Ser Asn
                 20                  25                  30

Leu Ala Trp Tyr Gln Gln Lys Pro Gly Lys Ala Pro Lys Leu Leu Ile
             35                  40                  45

Tyr Asp Ala Asn Ser Leu Ala Asp Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Tyr
                 85                  90                  95

Thr Phe Gly Gln Gly Thr Lys Leu Glu Ile Lys Arg
            100                 105
```

<210> SEQ ID NO 128
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 128

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Glu Asp Ile Tyr Ser Asn
                 20                  25                  30

Leu Ala Trp Tyr Gln Gln Lys Pro Gly Lys Ala Pro Lys Leu Leu Ile
             35                  40                  45

Tyr Asp Ala Asn Ser Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Tyr
                 85                  90                  95

Thr Phe Gly Gln Gly Thr Lys Leu Glu Ile Lys Arg
            100                 105
```

<210> SEQ ID NO 129
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 129

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Asn Ser Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Tyr
                85                  90                  95

Thr Phe Gly Gln Gly Thr Lys Leu Glu Ile Lys Arg
            100                 105

<210> SEQ ID NO 130
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Glu Lys Ala Pro Lys Ser Leu Ile
        35                  40                  45

Tyr Asp Ala Asn Ser Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Tyr
                85                  90                  95

Thr Phe Gly Gln Gly Thr Lys Leu Glu Ile Lys Arg
            100                 105

<210> SEQ ID NO 131
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 131

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Asp Ile Tyr Ser Asn
            20                  25                  30

Leu Ala Trp Tyr Gln Gln Lys Pro Gly Gln Ala Pro Arg Leu Leu Ile
        35                  40                  45

Tyr Asp Ala Asn Ser Leu Ala Asp Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Tyr
                85                  90                  95

Thr Phe Gly Gln Gly Thr Lys Leu Glu Ile Lys Arg
            100                 105

<210> SEQ ID NO 132
<211> LENGTH: 123
<212> TYPE: PRT
<213> ORGANISM: Rattus norvegicus

<400> SEQUENCE: 132

Glu Val Gln Leu Gln Gln Ser Gly Pro Glu Val Gly Arg Pro Gly Ser
1               5                   10                  15

Ser Val Lys Ile Ser Cys Lys Ala Ser Gly Tyr Ile Phe Thr Asp Tyr
            20                  25                  30

Ile Met His Trp Val Lys Gln Ser Pro Gly Gln Gly Leu Glu Trp Ile
        35                  40                  45

Gly Trp Ile Asp Pro Glu Tyr Gly Ser Thr Asp Tyr Ala Glu Lys Phe
50                  55                  60

Lys Lys Lys Ala Thr Leu Thr Ala Asp Thr Ser Ser Ser Thr Ala Tyr
65                  70                  75                  80

Ile Gln Leu Ser Ser Leu Thr Ser Glu Asp Thr Ala Thr Tyr Phe Cys
                85                  90                  95

Ala Arg Val Ala Ile Ile Thr Thr Val Ala Ser Gly Phe Ala Tyr
            100                 105                 110

Trp Gly Gln Gly Thr Leu Val Thr Val Ser Ser
        115                 120

<210> SEQ ID NO 133
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 133

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Ile Met His Trp Val Gln Gln Ala Pro Gly Lys Gly Leu Glu Trp Met
        35                  40                  45

Gly Trp Ile Asp Pro Glu Tyr Gly Ser Thr Asp Tyr Ala Glu Lys Phe
50                  55                  60

```
Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Val Ala Ile Ile Thr Val Ala Ser Gly Gly Phe Ala Tyr
            100                 105                 110

Trp Gly Gln Gly Thr Leu Val Thr Val Ser Ser
        115                 120
```

<210> SEQ ID NO 134
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 134

```
Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Ile Phe Thr Asp Tyr
                 20                  25                  30

Ile Met His Trp Val Gln Gln Ala Pro Gly Lys Gly Leu Glu Trp Met
             35                  40                  45

Gly Trp Ile Asp Pro Glu Tyr Gly Ser Thr Tyr Ala Glu Lys Phe
         50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Val Ala Ile Ile Thr Val Ala Ser Gly Gly Phe Ala Tyr
            100                 105                 110

Trp Gly Gln Gly Thr Leu Val Thr Val Ser Ser
        115                 120
```

<210> SEQ ID NO 135
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 135

```
Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Asp Tyr
                 20                  25                  30

Ile Met His Trp Val Gln Gln Ala Pro Gly Lys Gly Leu Glu Trp Met
             35                  40                  45

Gly Trp Ile Asp Pro Glu Tyr Gly Ser Thr Asp Tyr Ala Glu Lys Phe
         50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
```

85                  90                  95

Ala Arg Val Ala Ile Ile Thr Thr Val Ala Ser Gly Gly Phe Ala Tyr
                100                 105                 110

Trp Gly Gln Gly Thr Leu Val Thr Val Ser Ser
            115                 120

<210> SEQ ID NO 136
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Trp Ile Asp Pro Glu Tyr Gly Ser Thr Asp Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Ile Ile Thr Thr Val Ala Ser Gly Gly Phe Ala Tyr
                100                 105                 110

Trp Gly Gln Gly Thr Leu Val Thr Val Ser Ser
            115                 120

<210> SEQ ID NO 137
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Trp Ile Asp Pro Glu Tyr Gly Ser Thr Asp Tyr Ala Gln Lys Leu
    50                  55                  60

Gln Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Ile Ile Thr Thr Val Ala Ser Gly Gly Phe Ala Tyr
                100                 105                 110

Trp Gly Gln Gly Thr Leu Val Thr Val Ser Ser
            115                 120

<210> SEQ ID NO 138
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
            20                  25                  30

Ile Met His Trp Val Arg Gln Ala Pro Gly Lys Gly Leu Glu Trp Met
        35                  40                  45

Gly Trp Ile Asp Pro Glu Tyr Gly Ser Thr Asp Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Val Ala Ile Ile Thr Thr Val Ala Ser Gly Gly Phe Ala Tyr
            100                 105                 110

Trp Gly Gln Gly Thr Leu Val Thr Val Ser Ser
            115                 120

<210> SEQ ID NO 139
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
            20                  25                  30

Ile Met His Trp Val Arg Gln Ala Pro Gly Lys Gly Leu Glu Trp Met
        35                  40                  45

Gly Trp Ile Asp Pro Glu Tyr Gly Ser Thr Asp Tyr Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Val Ala Ile Ile Thr Thr Val Ala Ser Gly Gly Phe Ala Tyr
            100                 105                 110

Trp Gly Gln Gly Thr Leu Val Thr Val Ser Ser
            115                 120

<210> SEQ ID NO 140

```
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Tyr
            20                  25                  30

Ile Met His Trp Val Arg Gln Ala Pro Gly Lys Gly Leu Glu Trp Met
        35                  40                  45

Gly Trp Ile Asp Pro Glu Tyr Gly Ser Thr Asp Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Ile Ile Thr Thr Val Ala Ser Gly Phe Ala Tyr
            100                 105                 110

Trp Gly Gln Gly Thr Leu Val Thr Val Ser Ser
        115                 120

<210> SEQ ID NO 141
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 141

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Ala Leu Glu Trp Met
        35                  40                  45

Gly Trp Ile Asp Pro Glu Tyr Gly Ser Thr Asp Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Val Ala Ile Ile Thr Thr Val Ala Ser Gly Phe Ala Tyr
            100                 105                 110

Trp Gly Gln Gly Thr Leu Val Thr Val Ser Ser
        115                 120

<210> SEQ ID NO 142
<211> LENGTH: 123
<212> TYPE: PRT
<213> ORGANISM: Artificial Sequence
<220> FEATURE:
<223> OTHER INFORMATION: Description of Artificial Sequence: Synthetic
```

```
                              polypeptide
<220> FEATURE:
<223> OTHER INFORMATION: Completely synthesized

<400> SEQUENCE: 142

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Ala Leu Glu Trp Met
            35                  40                  45

Gly Trp Ile Asp Pro Glu Tyr Gly Ser Thr Tyr Ala Gln Lys Phe
        50                  55                  60

Gln Asp Arg Val Thr Ile Thr Ala Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Val Ala Ile Ile Thr Val Ala Ser Gly Gly Phe Ala Tyr
            100                 105                 110

Trp Gly Gln Gly Thr Leu Val Thr Val Ser Ser
        115                 120

<210> SEQ ID NO 143
<211> LENGTH: 113
<212> TYPE: PRT
<213> ORGANISM: Rattus norvegicus

<400> SEQUENCE: 143

Asp Ile Val Met Thr Gln Gly Ala Leu Pro Asn Pro Val Pro Ser Gly
1               5                   10                  15

Glu Ser Ala Ser Ile Thr Cys Gln Ser Ser Glu Ser Leu Leu His Ser
                20                  25                  30

Asn Gly Lys Thr Tyr Leu Asn Trp Tyr Leu Gln Arg Pro Gly Gln Ser
            35                  40                  45

Pro Gln Leu Leu Ile Tyr Trp Met Ser Thr Arg Ala Ala Gly Val Ser
        50                  55                  60

Asp Arg Phe Ser Gly Ser Gly Ser Gly Thr Asp Phe Thr Leu Thr Ile
65                  70                  75                  80

Ser Gly Val Glu Ala Glu Asp Val Gly Val Tyr Tyr Cys Gln Gln Phe
                85                  90                  95

Leu Glu Tyr Pro Pro Thr Phe Gly Ser Gly Thr Lys Leu Glu Ile Lys
            100                 105                 110

Arg

<210> SEQ ID NO 144
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 144

Asp Ile Val Met Thr Gln Thr Pro Leu Ser Ser Pro Val Thr Leu Gly
1               5                   10                  15

Gln Pro Ala Ser Ile Ser Cys Gln Ser Ser Glu Ser Leu Leu His Ser
                20                  25                  30
```

Asn Gly Lys Thr Tyr Leu Asn Trp Leu Gln Gln Arg Pro Gly Gln Pro
            35                  40                  45

Pro Arg Leu Leu Ile Tyr Trp Met Ser Thr Arg Ala Ala Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Gln Gln Phe
                 85                  90                  95

Leu Glu Tyr Pro Pro Thr Phe Gly Gln Gly Thr Lys Leu Glu Ile Lys
            100                 105                 110

Arg

<210> SEQ ID NO 145
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 145

Asp Ile Val Met Thr Gln Ser Pro Leu Ser Leu Pro Val Thr Pro Gly
 1               5                  10                  15

Glu Pro Ala Ser Ile Ser Cys Gln Ser Ser Glu Ser Leu Leu His Ser
             20                  25                  30

Asn Gly Lys Thr Tyr Leu Asn Trp Tyr Leu Gln Lys Pro Gly Gln Ser
            35                  40                  45

Pro Gln Leu Leu Ile Tyr Trp Met Ser Thr Arg Ala Ala Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Phe
                 85                  90                  95

Leu Glu Tyr Pro Pro Thr Phe Gly Gln Gly Thr Lys Leu Glu Ile Lys
            100                 105                 110

Arg

<210> SEQ ID NO 146
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 146

Asp Ile Val Met Thr Gln Thr Pro Leu Ser Leu Ser Val Thr Pro Gly
 1               5                  10                  15

Gln Pro Ala Ser Ile Ser Cys Gln Ser Ser Glu Ser Leu Leu His Ser
             20                  25                  30

Asn Gly Lys Thr Tyr Leu Asn Trp Tyr Leu Gln Lys Pro Gly Gln Pro
            35                  40                  45

Pro Gln Leu Leu Ile Tyr Trp Met Ser Thr Arg Ala Ala Gly Val Pro
 50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Phe
                 85                  90                  95

Leu Glu Tyr Pro Pro Thr Phe Gly Gln Gly Thr Lys Leu Glu Ile Lys
                100                 105                 110

Arg
```

<210> SEQ ID NO 147
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 147

```
Asp Val Val Met Thr Gln Ser Pro Leu Ser Leu Pro Val Thr Leu Gly
 1               5                  10                  15

Gln Pro Ala Ser Ile Ser Cys Gln Ser Ser Glu Ser Leu Leu His Ser
                 20                  25                  30

Asn Gly Lys Thr Tyr Leu Asn Trp Phe Gln Gln Arg Pro Gly Gln Ser
             35                  40                  45

Pro Arg Arg Leu Ile Tyr Trp Met Ser Thr Arg Ala Ala Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Phe
                 85                  90                  95

Leu Glu Tyr Pro Pro Thr Phe Gly Gln Gly Thr Lys Leu Glu Ile Lys
                100                 105                 110

Arg
```

<210> SEQ ID NO 148
<211> LENGTH: 120
<212> TYPE: PRT
<213> ORGANISM: Rattus norvegicus

<400> SEQUENCE: 148

```
Glu Val Gln Leu Gln Gln Ser Gly Pro Glu Val Gly Arg Pro Gly Ser
 1               5                  10                  15

Ser Val Lys Ile Ser Cys Lys Ala Ser Gly Tyr Thr Phe Thr Asp Ser
                 20                  25                  30

Val Met Asn Trp Val Lys Gln Ser Pro Gly Gln Gly Leu Glu Trp Ile
             35                  40                  45

Gly Trp Ile Asp Pro Glu Tyr Gly Arg Thr Asp Val Ala Glu Lys Phe
 50                  55                  60

Lys Lys Lys Ala Thr Leu Thr Ala Asp Ser Ser Ser Thr Ala Tyr
 65                  70                  75                  80

Ile Tyr Leu Ser Gly Leu Thr Ser Glu Asp Thr Ala Thr Tyr Phe Cys
                 85                  90                  95

Ala Arg Thr Lys Tyr Asn Ser Gly Tyr Gly Phe Pro Tyr Trp Gly Gln
                100                 105                 110

Gly Ser Leu Val Thr Val Ser Ser
            115                 120
```

```
<210> SEQ ID NO 149
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 150
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 151
<211> LENGTH: 120
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 152
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Ala Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 153
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized
```

<400> SEQUENCE: 153

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Ser
            20                  25                  30

Val Met Asn Trp Val Arg Gln Ala Pro Gly Gln Ala Leu Glu Trp Met
        35                  40                  45

Gly Trp Ile Asp Pro Glu Tyr Gly Arg Thr Asp Val Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Gly Asp Thr Ala Met Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 154
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 154

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Ser
            20                  25                  30

Val Met Asn Trp Val Arg Gln Ala Pro Gly Gln Ala Leu Glu Trp Met
        35                  40                  45

Gly Trp Ile Asp Pro Glu Tyr Gly Arg Thr Asp Val Ala Gln Lys Phe
    50                  55                  60

Gln Asp Arg Val Thr Ile Thr Ala Asp Arg Ser Met Ser Thr Ala Tyr
65                  70                  75                  80

Met Glu Leu Ser Ser Leu Arg Ser Gly Asp Thr Ala Met Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 155
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 155

Glu Val Gln Leu Val Gln Ser Gly Ala Glu Val Lys Lys Pro Gly Ala
1               5                   10                  15

```
Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 156
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 156

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 157
<211> LENGTH: 108
<212> TYPE: PRT
<213> ORGANISM: Rattus norvegicus

<400> SEQUENCE: 157

Asp Ile Val Met Thr Gln Ser Pro Thr Ser Ile Ser Ile Ser Val Gly
1               5                   10                  15

Glu Arg Val Thr Met Asn Cys Lys Ala Ser Gln Asn Val Asp Ser Asp
            20                  25                  30

Val Asp Trp Tyr Gln Gln Lys Thr Gly Gln Ser Pro Lys Leu Leu Ile
        35                  40                  45

Tyr Lys Ala Ser Asn Arg Tyr Thr Gly Val Pro Asp Arg Phe Thr Gly
    50                  55                  60
```

-continued

Ser Gly Ser Gly Thr Asp Phe Thr Phe Thr Ile Ser Asn Met Gln Ala
 65                  70                  75                  80

Glu Asp Leu Ala Val Tyr Tyr Cys Met Gln Ser Asn Thr His Pro Arg
                 85                  90                  95

Thr Phe Gly Gly Gly Thr Lys Leu Glu Leu Lys Arg
            100                 105

<210> SEQ ID NO 158
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 158

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Met Gln Ser Asn Thr His Pro Arg
                 85                  90                  95

Thr Phe Gly Gly Gly Thr Lys Val Glu Ile Lys Arg
            100                 105

<210> SEQ ID NO 159
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 159

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Met Gln Ser Asn Thr His Pro Arg
                 85                  90                  95

Thr Phe Gly Gly Gly Thr Lys Val Glu Ile Lys Arg
            100                 105

<210> SEQ ID NO 160

<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Completely synthesized

<400> SEQUENCE: 160

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 161
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Completely synthesized

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 162
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Completely synthesized

<400> SEQUENCE: 162

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asn Val Asp Ser Asp
            20                  25                  30

Val Asp Trp Tyr Gln Gln Lys Pro Gly Gln Ala Pro Arg Leu Leu Ile
        35                  40                  45

Tyr Lys Ala Ser Asn Arg Tyr Thr Gly Ile Pro Ala Arg Phe Ser Gly
50                  55                  60

Ser Gly Ser Gly Arg Asp Phe Thr Leu Thr Ile Ser Ser Leu Glu Pro
65                  70                  75                  80

Glu Asp Phe Ala Val Tyr Tyr Cys Met Gln Ser Asn Thr His Pro Arg
                85                  90                  95

Thr Phe Gly Gly Gly Thr Lys Val Glu Ile Lys Arg
            100                 105
```

<210> SEQ ID NO 163
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 163

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Asp Ser Asp
            20                  25                  30

Val Asp Trp Tyr Gln Gln Lys Pro Gly Gln Ala Pro Arg Leu Leu Ile
        35                  40                  45

Tyr Lys Ala Ser Asn Arg Tyr Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Met Gln Ser Asn Thr His Pro Arg
                85                  90                  95

Thr Phe Gly Gly Gly Thr Lys Val Glu Ile Lys Arg
            100                 105
```

<210> SEQ ID NO 164
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 164

```
Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asn Val Asp Ser Asp
            20                  25                  30

Val Asp Trp Tyr Gln Gln Lys Pro Asp Gln Ser Pro Lys Leu Leu Ile
        35                  40                  45

Lys Lys Ala Ser Asn Arg Tyr Thr Gly Val Pro Ser Arg Phe Ser Gly
50                  55                  60
```

```
Ser Gly Ser Gly Thr Asp Phe Thr Leu Thr Ile Asn Ser Leu Glu Ala
 65                  70                  75                  80

Glu Asp Ala Ala Thr Tyr Tyr Cys Met Gln Ser Asn Thr His Pro Arg
                 85                  90                  95

Thr Phe Gly Gly Gly Thr Lys Val Glu Ile Lys Arg
            100                 105
```

<210> SEQ ID NO 165
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 165

```
Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Asp Ser
             20                  25                  30

Val Met Asn Trp Val Gln Gln Glu Pro Gly Lys Gly Leu Glu Trp Met
         35                  40                  45

Gly Trp Ile Asp Pro Glu Tyr Gly Arg Thr Asp Val Ala Glu Lys Phe
     50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120
```

<210> SEQ ID NO 166
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 166

```
Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Asp Ser
             20                  25                  30

Val Met Asn Trp Val Gln Gln Gly Pro Gly Lys Gly Leu Glu Trp Met
         35                  40                  45

Gly Trp Ile Asp Pro Glu Tyr Gly Arg Thr Asp Val Ala Glu Lys Phe
     50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Lys Tyr Asn Ser Gly Tyr Gly Phe Pro Tyr Trp Gly Gln
```

Gly Thr Thr Val Thr Val Ser Ser
        115                 120

<210> SEQ ID NO 167
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 167

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln His Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 168
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 168

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Gln Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 169
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 169

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ser Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 170
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 170

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Val Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 171
<211> LENGTH: 120
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 171

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Glu Trp Val Gln Gln Ala Pro Gly Lys Gly Leu Glu Trp Met
            35                  40                  45

Gly Trp Ile Asp Pro Glu Tyr Gly Arg Thr Asp Val Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 172
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 172

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Pro Trp Val Gln Gln Ala Pro Gly Lys Gly Leu Glu Trp Met
            35                  40                  45

Gly Trp Ile Asp Pro Glu Tyr Gly Arg Thr Asp Val Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 173
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized
```

<400> SEQUENCE: 173

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Gln Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 174
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 174

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Ser Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 175
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 175

Glu Val Gln Leu Val Gln Ser Gly Ala Glu Val Lys Lys Pro Gly Ala
1               5                   10                  15

```
Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Glu Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 176
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 176

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Gly Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 177
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 177

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
```

```
                35                  40                  45

Gly Trp Ile Asp Pro Glu Tyr Gly Arg Thr Asp Val Ala Glu Lys Phe
         50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Pro Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 178
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 178

Glu Val Gln Leu Val Gln Ser Gly Ala Glu Val Lys Lys Pro Gly Ala
  1               5                  10                  15

Thr Val Lys Ile Ser Cys Lys Val Ser Gly Tyr Thr Phe Thr Asp Ser
             20                  25                  30

Val Met Asn Trp Val Gln Gln Ala Pro Gly Lys Gly Leu Glu Trp Met
         35                  40                  45

Gly Trp Ile Asp Pro Glu Tyr Gly Arg Thr Asp Val Ala Glu Lys Phe
         50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Thr Lys Tyr Asn Ser Gly Tyr Gly Phe Pro Tyr Trp Gly Gln
            100                 105                 110

Gly Thr Thr Val Thr Val Ser Ser
            115                 120

<210> SEQ ID NO 179
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 179

Glu Val Gln Leu Val Gln Ser Gly Ala Glu Val Lys Lys Pro Gly Ala
  1               5                  10                  15

Thr Val Lys Ile Ser Cys Lys Val Ser Gly Tyr Thr Phe Thr Asp Ser
             20                  25                  30

Val Met Asn Trp Val Gln Gln Ala Pro Gly Lys Gly Leu Glu Trp Met
         35                  40                  45

Gly Trp Ile Asp Pro Glu Tyr Gly Arg Thr Asp Val Ala Glu Lys Phe
         50                  55                  60
```

```
Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Gly Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 180
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 180

Glu Val Gln Leu Val Gln Ser Gly Ala Glu Val Lys Lys Pro Gly Ala
  1               5                  10                  15

Thr Val Lys Ile Ser Cys Lys Val Ser Gly Tyr Thr Phe Thr Asp Ser
             20                  25                  30

Val Met Asn Trp Val Gln Gln Ala Pro Gly Lys Gly Leu Glu Trp Met
         35                  40                  45

Gly Trp Ile Asp Pro Glu Tyr Gly Arg Thr Asp Val Ala Glu Lys Phe
     50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Thr Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 181
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 181

Asp Ile Gln Met Thr Gln Ser Pro Ser Ser Leu Ser Ala Ser Val Gly
  1               5                  10                  15

Asp Arg Val Thr Ile Thr Cys Glu Ala Ser Gln Asn Val Asp Ser Asp
             20                  25                  30

Val Asp Trp Tyr Gln Gln Lys Pro Gly Lys Ala Pro Lys Leu Leu Ile
         35                  40                  45

Tyr Lys Ala Ser Asn Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Met Gln Ser Asn Thr His Pro Arg
                 85                  90                  95
```

Thr Phe Gly Gly Gly Thr Lys Val Glu Ile Lys Arg
            100                 105

<210> SEQ ID NO 182
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 183
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Pro Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 184
<211> LENGTH: 108
<212> TYPE: PRT
<213> ORGANISM: Artificial Sequence
<220> FEATURE:
<223> OTHER INFORMATION: Description of Artificial Sequence: Synthetic

```
              polypeptide
<220> FEATURE:
<223> OTHER INFORMATION: Completely synthesized

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 185
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 186
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30
```

Val Asp Trp Tyr Gln Gln Lys Pro Gly Lys Ala Pro Lys Leu Leu Asp
         35                  40                  45

Tyr Lys Ala Ser Asn Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                 85                  90                  95

Thr Phe Gly Gly Gly Thr Lys Val Glu Ile Lys Arg
             100                 105

<210> SEQ ID NO 187
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
             20                  25                  30

Val Asp Trp Tyr Gln Gln Lys Pro Gly Lys Ala Pro Lys Leu Leu Ile
         35                  40                  45

Glu Lys Ala Ser Asn Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                 85                  90                  95

Thr Phe Gly Gly Gly Thr Lys Val Glu Ile Lys Arg
             100                 105

<210> SEQ ID NO 188
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
             20                  25                  30

Val Asp Trp Tyr Gln Gln Lys Pro Gly Lys Ala Pro Lys Leu Leu Ile
         35                  40                  45

Tyr Lys Ala Ser Asn Arg Tyr Thr Gly Val Pro Ser Arg Phe Ser Gly
     50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg

```
                    85                  90                  95

Thr Phe Gly Gly Gly Thr Lys Val Glu Ile Lys Arg
            100                 105

<210> SEQ ID NO 189
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Glu Gln Ser Asn Thr His Pro Arg
                85                  90                  95

Thr Phe Gly Gly Gly Thr Lys Val Glu Ile Lys Arg
            100                 105

<210> SEQ ID NO 190
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Ser Asn Thr His Pro Arg
                85                  90                  95

Thr Phe Gly Gly Gly Thr Lys Val Glu Ile Lys Arg
            100                 105

<210> SEQ ID NO 191
<211> LENGTH: 108
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: Completely synthesized

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Lys Gln Ser Asn Thr His Pro Arg
                85                  90                  95

Thr Phe Gly Gly Gly Thr Lys Val Glu Ile Lys Arg
            100                 105

<210> SEQ ID NO 192
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Pro Gln Ser Asn Thr His Pro Arg
                85                  90                  95

Thr Phe Gly Gly Gly Thr Lys Val Glu Ile Lys Arg
            100                 105

<210> SEQ ID NO 193
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp

```
                20                  25                  30

Val Asp Trp Tyr Gln Gln Lys Pro Gly Lys Ala Pro Lys Leu Leu Ile
            35                  40                  45

Tyr Lys Ala Ser Asn Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asn Thr His Pro Arg
                85                  90                  95

Thr Phe Gly Gly Gly Thr Lys Val Glu Ile Lys Arg
            100                 105

<210> SEQ ID NO 194
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ser Gln Ser Asn Thr His Pro Arg
                85                  90                  95

Thr Phe Gly Gly Gly Thr Lys Val Glu Ile Lys Arg
            100                 105

<210> SEQ ID NO 195
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys Val Gln Ser Asn Thr His Pro Arg
                85                  90                  95

Thr Phe Gly Gly Gly Thr Lys Val Glu Ile Lys Arg
            100                 105

<210> SEQ ID NO 196
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Asp Ser Asn Thr His Pro Arg
                85                  90                  95

Thr Phe Gly Gly Gly Thr Lys Val Glu Ile Lys Arg
            100                 105

<210> SEQ ID NO 197
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 197

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Gln Ser Gly Tyr Gly Phe Pro Tyr Trp Gly Gln
            100                 105                 110

Gly Thr Thr Val Thr Val Ser Ser
        115                 120

<210> SEQ ID NO 198

<211> LENGTH: 108
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Completely synthesized

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Gln Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Met Gln Ser Asn Thr His Pro Arg
                85                  90                  95

Thr Phe Gly Gly Gly Thr Lys Val Glu Ile Lys Arg
            100                 105

<210> SEQ ID NO 199
<211> LENGTH: 30
<212> TYPE: PRT
<213> ORGANISM: Homo sapiens

<400> SEQUENCE: 199

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 200
<211> LENGTH: 7
<212> TYPE: PRT
<213> ORGANISM: Homo sapiens

<400> SEQUENCE: 200

Ser Ser Ser Tyr Tyr Trp Ser
1               5

<210> SEQ ID NO 201
<211> LENGTH: 14
<212> TYPE: PRT
<213> ORGANISM: Homo sapiens

<400> SEQUENCE: 201

Trp Ile Arg Gln His Pro Gly Lys Gly Leu Glu Trp Ile Gly
1               5                   10

<210> SEQ ID NO 202
<211> LENGTH: 16
<212> TYPE: PRT
<213> ORGANISM: Homo sapiens

<400> SEQUENCE: 202

Tyr Ile Tyr Tyr Ser Gly Ser Thr Asn Tyr Asn Pro Ser Leu Lys Ser
1               5                   10                  15

<210> SEQ ID NO 203
<211> LENGTH: 32
<212> TYPE: PRT
<213> ORGANISM: Homo sapiens

<400> SEQUENCE: 203

Arg Val Thr Ile Ser Val Asp Thr Leu Lys Asn Gln Ile Ser Leu Arg
1               5                   10                  15
Leu Thr Ser Val Thr Ala Ala Asp Thr Ala Val Tyr Tyr Cys Ala Arg
            20                  25                  30

<210> SEQ ID NO 204
<211> LENGTH: 11
<212> TYPE: PRT
<213> ORGANISM: Homo sapiens

<400> SEQUENCE: 204

Val Gly Gly Ala Gly Gly Trp Pro Met Asp Val
1               5                   10

<210> SEQ ID NO 205
<211> LENGTH: 11
<212> TYPE: PRT
<213> ORGANISM: Homo sapiens

<400> SEQUENCE: 205

Trp Gly Gln Gly Thr Thr Val Thr Val Ser Ser
1               5                   10

<210> SEQ ID NO 206
<211> LENGTH: 30
<212> TYPE: PRT
<213> ORGANISM: Homo sapiens

<400> SEQUENCE: 206

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser
            20                  25                  30

<210> SEQ ID NO 207
<211> LENGTH: 7
<212> TYPE: PRT
<213> ORGANISM: Homo sapiens

<400> SEQUENCE: 207

Ser Gly Ser Tyr Tyr Trp Ser
1               5

<210> SEQ ID NO 208
<211> LENGTH: 14
<212> TYPE: PRT
<213> ORGANISM: Homo sapiens

<400> SEQUENCE: 208

Trp Ile Arg Gln Pro Pro Gly Lys Gly Leu Glu Trp Ile Gly
1               5                   10

<210> SEQ ID NO 209
<211> LENGTH: 32
<212> TYPE: PRT
<213> ORGANISM: Homo sapiens

<400> SEQUENCE: 209

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 210

```
Arg Val Thr Ile Ser Val Asp Thr Ser Lys Asn Gln Ile Ser Leu Arg
1               5                   10                  15

Leu Thr Ser Val Thr Ala Ala Asp Thr Ala Val Tyr Tyr Cys Ala Arg
            20                  25                  30
```

<210> SEQ ID NO 211
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 211

```
Trp Ile Arg Gln Pro Pro Gly Lys Gly Leu Glu Trp Ile Gly
1               5                   10
```

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 212

```
Arg Val Thr Ile Ser Val Asp Thr Leu Lys Asn Gln Ile Ser Leu Arg
1               5                   10                  15

Leu Ser Ser Val Thr Ala Ala Asp Thr Ala Val Tyr Tyr Cys Ala Arg
            20                  25                  30
```

<210> SEQ ID NO 213
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 213

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 214
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 214

Gln Leu Gln Leu Gln Glu Ser Gly Pro Gly Leu Val Lys Pro Ser Glu
1               5                   10                  15

Thr Leu Ser Leu Thr Cys Lys Val Ser Gly Gly Ser Ile Ser
            20                  25                  30

<210> SEQ ID NO 215
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 215

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 216
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 216

Arg Val Thr Ile Ser Arg Asp Thr Leu Lys Asn Gln Ile Ser Leu Arg
1               5                   10                  15

Leu Thr Ser Val Thr Ala Ala Asp Thr Ala Val Tyr Tyr Cys Ala Arg
            20                  25                  30

<210> SEQ ID NO 217
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 217

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser
            20                  25                  30

<210> SEQ ID NO 218

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 218

Arg Val Thr Ile Ser Val Asp Thr Leu Lys Asn Gln Ile Ser Leu Arg
1               5                   10                  15

Leu Thr Ser Val Arg Ala Ala Asp Thr Ala Val Tyr Tyr Cys Ala Arg
            20                  25                  30

<210> SEQ ID NO 219
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 219

Gln Leu Gln Leu Gln Glu Ser Gly Pro Gly Leu Val Lys Pro Ser Glu
1               5                   10                  15

Thr Leu Lys Leu Thr Cys Thr Val Ser Gly Gly Ser Ile Ser
            20                  25                  30

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 220

Val Gly Gly Ala Gly Gly Trp Pro Leu Glu Val
1               5                   10

<210> SEQ ID NO 221
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 221

Arg Val Thr Ile Ser Val Asp Lys Leu Lys Asn Gln Ile Ser Leu Arg
1               5                   10                  15

Leu Thr Ser Val Thr Ala Ala Asp Thr Ala Val Tyr Tyr Cys Ala Arg
            20                  25                  30

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Completely synthesized

<400> SEQUENCE: 222

Val Gly Gly Ala Gly Gly Trp Pro Leu Asp Val
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 223

Val Gly Gly Ala Gly Gly Trp Pro Met Glu Val
1               5                   10

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 224

Ser Gly Ser Tyr Tyr Trp Ser
1               5

<210> SEQ ID NO 225
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 225

Arg Val Thr Ile Ser Val Asp Thr Leu Lys Asn Gln Phe Ser Leu Arg
1               5                   10                  15

Leu Thr Ser Val Thr Ala Ala Asp Thr Ala Val Tyr Tyr Cys Ala Arg
            20                  25                  30

<210> SEQ ID NO 226
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 226

Arg Val Thr Ile Ser Val Asp Thr Leu Lys Asn Gln Ile Ser Leu Lys
1               5                   10                  15

Leu Thr Ser Val Thr Ala Ala Asp Thr Ala Val Tyr Tyr Cys Ala Arg
            20                  25                  30
```

```
<210> SEQ ID NO 227
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 227

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 228

Val Gly Gly Ala Gly Gly Trp Pro Leu Asp Val
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 229

Trp Ile Arg Gln Pro Pro Gly Lys Gly Leu Glu Trp Ile Gly
1               5                   10

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 230

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized
```

<400> SEQUENCE: 231

Val Gly Gly Ala Gly Gly Trp Pro Met Asp Val
1               5                   10

<210> SEQ ID NO 232
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 232

Gln Ala Val Leu Thr Gln Pro Ala Ser Leu Ser Ala Ser Pro Gly Glu
1               5                   10                  15

Ser Ala Arg Leu Thr Cys
            20

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 233

Thr Leu Pro Ser Asp Ile Asn Val Arg Tyr Tyr Asn Ile Tyr
1               5                   10

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 234

Trp Tyr Gln Gln Lys Pro Gly Ser Pro Pro Arg Tyr Leu Leu Tyr
1               5                   10                  15

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 235

Tyr Tyr Ser Asp Ser His Lys Gly Gln Gly Ser
1               5                   10

<210> SEQ ID NO 236
<211> LENGTH: 34
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: Completely synthesized

<400> SEQUENCE: 236

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 237

Met Thr Trp Ser Ser Asn Gly Ser Gly Val
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 238

Phe Gly Gly Gly Thr Gln Leu Thr Val Leu Gly
1               5                   10

<210> SEQ ID NO 239
<211> LENGTH: 22
<212> TYPE: PRT
<213> ORGANISM: Homo sapiens

<400> SEQUENCE: 239

Gln Pro Val Leu Thr Gln Pro Pro Ser Ser Ala Ser Pro Gly Glu
1               5                   10                  15

Ser Ala Arg Leu Thr Cys
            20

<210> SEQ ID NO 240
<211> LENGTH: 14
<212> TYPE: PRT
<213> ORGANISM: Homo sapiens

<400> SEQUENCE: 240

Thr Leu Pro Ser Asp Ile Asn Val Gly Ser Tyr Asn Ile Tyr
1               5                   10

<210> SEQ ID NO 241
<211> LENGTH: 11
<212> TYPE: PRT
<213> ORGANISM: Homo sapiens

<400> SEQUENCE: 241

```
Tyr Tyr Ser Asp Ser Asp Lys Gly Gln Gly Ser
1               5                   10

<210> SEQ ID NO 242
<211> LENGTH: 34
<212> TYPE: PRT
<213> ORGANISM: Homo sapiens

<400> SEQUENCE: 242

Gly Val Pro Ser Arg Phe Ser Gly Ser Lys Asp Ala Ser Ala Asn Thr
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 243
<211> LENGTH: 8
<212> TYPE: PRT
<213> ORGANISM: Homo sapiens

<400> SEQUENCE: 243

Met Ile Trp Pro Ser Asn Ala Ser
1               5

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 244

Met Thr Trp Ser Ser Gln Gly Ser Gly Val
1               5                   10

<210> SEQ ID NO 245
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 245

Gly Val Pro Ser Arg Phe Ser Gly Ser Lys Asp Val Ser Thr Ala Ser
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized
```

-continued

<400> SEQUENCE: 246

Trp Tyr Gln Gln Lys Pro Gly Ser Pro Pro Arg Tyr Leu Leu Arg
1               5                   10                  15

<210> SEQ ID NO 247
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 247

Gln Ala Val Leu Thr Gln Pro Ala Ser Leu Ser Ala Ser Pro Gly Ala
1               5                   10                  15

Ser Ala Arg Leu Thr Cys
            20

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 248

Trp Tyr Gln Gln Lys Pro Gly Ser Pro Pro Arg Tyr Leu Leu Arg
1               5                   10                  15

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 249

Tyr Arg Ser Asp Ser His Lys Gly Gln Gly Ser
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 250

Thr Leu Pro Ser Gly Ile Asn Val Arg Tyr Tyr Asn Ile Tyr
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic

```
                peptide
<220> FEATURE:
<223> OTHER INFORMATION: Completely synthesized

<400> SEQUENCE: 251

Met Thr Trp Ser Ser Asn Gly Ala Gly Val
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 252

Thr Leu Pro Ser Asp Ile Asn Val Arg Tyr Tyr Arg Ile Tyr
1               5                   10

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 253

Tyr Arg Ser Asp Ser His Lys Gly Gln Gly Ser
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 254

Met Thr Trp Ser Ser Thr Gly Ser Gly Val
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 255

Thr Leu Arg Ser Asp Ile Asn Val Arg Tyr Tyr Asn Ile Tyr
1               5                   10

<210> SEQ ID NO 256
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<223> OTHER INFORMATION: Completely synthesized

<400> SEQUENCE: 256

Met Thr Trp Ser Ser Asn Pro Ser Gly Val
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 257

Ile Thr Trp Ser Ser Asn Gly Ser Gly Val
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 258

Leu Thr Trp Ser Ser Asn Gly Ser Gly Val
1               5                   10

<210> SEQ ID NO 259
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 259

Gln Pro Val Leu Thr Gln Pro Ala Ser Leu Ser Ala Ser Pro Gly Glu
1               5                   10                  15

Ser Ala Arg Leu Thr Cys
            20

<210> SEQ ID NO 260
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 260

Gln Ala Val Leu Thr Gln Pro Pro Ser Leu Ser Ala Ser Pro Gly Glu
1               5                   10                  15

Ser Ala Arg Leu Thr Cys
            20

<210> SEQ ID NO 261
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 261

Gln Ala Val Leu Thr Gln Pro Ala Ser Ser Ala Ser Pro Gly Glu
1               5                   10                  15

Ser Ala Arg Leu Thr Cys
            20

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Thr Leu Pro Ser Asp Ile Asn Val Gly Tyr Tyr Asn Ile Tyr
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 263

Thr Leu Pro Ser Asp Ile Asn Val Arg Ser Tyr Asn Ile Tyr
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 264

Tyr Tyr Ser Asp Ser Asp Lys Gly Gln Gly Ser
1               5                   10

<210> SEQ ID NO 265
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 265

```
Gly Val Pro Ser Arg Phe Ser Gly Ser Lys Asp Ala Ser Thr Asn Ser
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 266
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 266

Gly Val Pro Ser Arg Phe Ser Gly Ser Lys Asp Val Ser Ala Asn Ser
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 267
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 267

Gly Val Pro Ser Arg Phe Ser Gly Ser Lys Asp Val Ser Thr Asn Thr
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 268

Met Ile Trp Ser Ser Asn Gly Ser Gly Val
1               5                   10

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 269
```

```
Met Thr Trp Pro Ser Asn Gly Ser Gly Val
1               5                   10

<210> SEQ ID NO 270
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 270

Met Thr Trp Ser Ser Asn Ala Ser Gly Val
1               5                   10

<210> SEQ ID NO 271
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 271

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 272
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 272

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 273

Leu Thr Trp Ser Ser Asn Gly Ser Gly Val
1               5                   10

<210> SEQ ID NO 274
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 274

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 275

Met Thr Trp Ser Ser Asn Gly Ser Gly Val
1               5                   10

<210> SEQ ID NO 276
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Gly Val Pro Ser Arg Phe Ser Gly Ser Lys Asp Val Ser Thr Thr Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 277
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 277

Gly Val Pro Ser Arg Phe Ser Gly Ser Lys Asp Val Ser Thr Gly Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 278
<211> LENGTH: 34
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 278

Gly Val Pro Ser Arg Phe Ser Gly Ser Lys Asp Val Ser Thr His Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 279
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 279

Gly Val Pro Ser Arg Phe Ser Gly Ser Lys Asp Val Ser Thr Lys Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 280
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 280

Gly Val Pro Ser Arg Phe Ser Gly Ser Lys Asp Val Ser Thr Pro Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 281
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 281

Trp Tyr Gln Gln Lys Pro Gly Ser Pro Pro Arg Tyr Glu Leu Tyr
1               5                   10                  15

<210> SEQ ID NO 282
<211> LENGTH: 34
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 282

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 283

Trp Tyr Gln Gln Lys Pro Gly Ser Pro Pro Arg Tyr Gly Leu Tyr
1               5                   10                  15

<210> SEQ ID NO 284
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 284

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 285

Trp Tyr Gln Gln Lys Pro Gly Ser Pro Pro Arg Tyr Asn Leu Tyr
1               5                   10                  15

<210> SEQ ID NO 286
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: Completely synthesized

<400> SEQUENCE: 286

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 287
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 287

Trp Tyr Gln Gln Lys Pro Gly Ser Pro Pro Arg Tyr Pro Leu Tyr
1               5                   10                  15

<210> SEQ ID NO 288
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 288

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 289

Trp Tyr Gln Gln Lys Pro Gly Ser Pro Pro Arg Tyr Ser Leu Tyr
1               5                   10                  15

<210> SEQ ID NO 290
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 290

Gly Val Pro Ser Arg Phe Ser Gly Ser Lys Asp Val Ser Thr Asn Ser

```
                1               5                  10                 15
Gly Ile Leu Leu Ile Ser Gly Leu Gln Ser Glu Asp Ile Ala Thr Tyr
                20                 25                 30

Tyr Cys

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 291

Trp Tyr Gln Gln Lys Pro Gly Ser Pro Pro Arg Tyr Leu Glu Tyr
1               5                  10                 15

<210> SEQ ID NO 292
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 292

Gly Val Pro Ser Arg Phe Ser Gly Ser Lys Asp Val Ser Thr Asn Ser
1               5                  10                 15

Gly Ile Leu Leu Ile Ser Gly Leu Gln Ser Glu Asp Ile Ala Thr Tyr
                20                 25                 30

Tyr Cys

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 293

Trp Tyr Gln Gln Lys Pro Gly Ser Pro Pro Arg Tyr Leu Pro Tyr
1               5                  10                 15

<210> SEQ ID NO 294
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 294

Gly Val Pro Ser Arg Phe Ser Gly Ser Lys Asp Val Ser Thr Asn Ser
1               5                  10                 15

Gly Ile Leu Leu Ile Ser Gly Leu Gln Ser Glu Asp Ile Ala Thr Tyr
                20                 25                 30
```

Tyr Cys

<210> SEQ ID NO 295
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 295

Trp Tyr Gln Gln Lys Pro Gly Ser Pro Pro Arg Tyr Leu Leu Glu
1               5                   10                  15

<210> SEQ ID NO 296
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 296

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 297

Trp Tyr Gln Gln Lys Pro Gly Ser Pro Pro Arg Tyr Leu Leu Gln
1               5                   10                  15

<210> SEQ ID NO 298
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 298

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 299
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 299

Pro Tyr Ser Asp Ser His Lys Gly Gln Gly Ser
1               5                   10

<210> SEQ ID NO 300
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 300

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 301
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 301

Asn Tyr Ser Asp Ser His Lys Gly Gln Gly Ser
1               5                   10

<210> SEQ ID NO 302
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 302

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 303
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide <220> FEATURE:
<223> OTHER INFORMATION: Completely synthesized

<400> SEQUENCE: 303

Thr Tyr Ser Asp Ser His Lys Gly Gln Gly Ser
1               5                   10

<210> SEQ ID NO 304
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 304

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 305
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 305

Tyr Asp Ser Asp Ser His Lys Gly Gln Gly Ser
1               5                   10

<210> SEQ ID NO 306
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 306

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 307

Tyr Tyr Glu Asp Ser His Lys Gly Gln Gly Ser
1               5                   10

<210> SEQ ID NO 308
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 308

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
                20                  25                  30

Tyr Cys

<210> SEQ ID NO 309
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 309

Tyr Tyr His Asp Ser His Lys Gly Gln Gly Ser
1               5                   10

<210> SEQ ID NO 310
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 310

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
                20                  25                  30

Tyr Cys

<210> SEQ ID NO 311
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 311

Tyr Tyr Gln Asp Ser His Lys Gly Gln Gly Ser
1               5                   10

<210> SEQ ID NO 312

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 312

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 313

Tyr Tyr Ser Asp Ser Asn Lys Gly Gln Gly Ser
1               5                   10

<210> SEQ ID NO 314
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 314

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 315

Tyr Tyr Ser Asp Ser Pro Lys Gly Gln Gly Ser
1               5                   10

<210> SEQ ID NO 316
<211> LENGTH: 34
<212> TYPE: PRT
<213> ORGANISM: Artificial Sequence
<220> FEATURE:
<223> OTHER INFORMATION: Description of Artificial Sequence: Synthetic
```

```
            polypeptide
<220> FEATURE:
<223> OTHER INFORMATION: Completely synthesized

<400> SEQUENCE: 316

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 317
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 317

Tyr Tyr Ser Asp Ser His Asp Gly Gln Gly Ser
1               5                   10

<210> SEQ ID NO 318
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 318

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 319
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 319

Thr Leu Pro Ser Asp Ile Asn Val Gly Ser Tyr Asn Ile Tyr
1               5                   10

<210> SEQ ID NO 320
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 320
```

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 321
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 321

Leu Thr Trp Ser Ser Gln Gly Ser Gly Val
1               5                   10

<210> SEQ ID NO 322
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 322

Thr Leu Pro Ser Asp Ile Asn Val Gly Ser Tyr Asn Ile Tyr
1               5                   10

<210> SEQ ID NO 323
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 323

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 324
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 324

Leu Thr Trp Ser Ser Glu Gly Ser Gly Val
1               5                   10

```
<210> SEQ ID NO 325
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 325

Thr Leu Pro Ser Asp Ile Asn Val Gly Ser Tyr Asn Ile Tyr
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 326

Tyr Tyr Gln Asp Ser His Lys Gly Gln Gly Ser
1               5                   10

<210> SEQ ID NO 327
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 327

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 328

Leu Thr Trp Ser Ser Glu Gly Ser Gly Val
1               5                   10

<210> SEQ ID NO 329
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized
```

```
<400> SEQUENCE: 329

Thr Leu Pro Ser Asp Ile Asn Val Arg Ser Tyr Asn Ile Tyr
1               5                   10

<210> SEQ ID NO 330
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 330

Tyr Tyr Gln Asp Ser His Lys Gly Gln Gly Ser
1               5                   10

<210> SEQ ID NO 331
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 331

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 332

Leu Thr Trp Ser Ser Glu Gly Ser Gly Val
1               5                   10

<210> SEQ ID NO 333
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 333

Thr Leu Pro Ser Asp Ile Asn Val Gly Ser Tyr Asn Ile Tyr
1               5                   10

<210> SEQ ID NO 334
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 334

Tyr Tyr Gln Asp Ser His Lys Gly Gln Gly Ser
1               5                   10

<210> SEQ ID NO 335
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 335

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 336
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 336

Leu Thr Trp Ser Ser Gln Gly Ser Gly Val
1               5                   10

<210> SEQ ID NO 337
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 337

Thr Leu Pro Ser Asp Ile Asn Val Arg Ser Tyr Asn Ile Tyr
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 338

Tyr Tyr Gln Asp Ser His Lys Gly Gln Gly Ser
1               5                   10
```

<210> SEQ ID NO 339
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 339

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 340

Leu Thr Trp Ser Ser Gln Gly Ser Gly Val
1               5                   10

<210> SEQ ID NO 341
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 341

Thr Leu Pro Ser Asp Ile Asn Val Gly Ser Tyr Asn Ile Tyr
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 342

Tyr Tyr Glu Asp Ser His Lys Gly Gln Gly Ser
1               5                   10

<210> SEQ ID NO 343
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: Completely synthesized

<400> SEQUENCE: 343

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 344

Leu Thr Trp Ser Ser Glu Gly Ser Gly Val
1               5                   10

<210> SEQ ID NO 345
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 345

Thr Leu Pro Ser Asp Ile Asn Val Arg Ser Tyr Asn Ile Tyr
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 346

Tyr Tyr Glu Asp Ser His Lys Gly Gln Gly Ser
1               5                   10

<210> SEQ ID NO 347
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 347

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 348
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 348

Leu Thr Trp Ser Ser Glu Gly Ser Gly Val
1               5                   10

<210> SEQ ID NO 349
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 349

Thr Leu Pro Ser Asp Ile Asn Val Gly Ser Tyr Asn Ile Tyr
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 350

Tyr Tyr Glu Asp Ser His Lys Gly Gln Gly Ser
1               5                   10

<210> SEQ ID NO 351
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 351

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Completely synthesized

<400> SEQUENCE: 352

Leu Thr Trp Ser Ser Gln Gly Ser Gly Val
1               5                   10

<210> SEQ ID NO 353
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 353

Thr Leu Pro Ser Asp Ile Asn Val Arg Ser Tyr Asn Ile Tyr
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 354

Tyr Tyr Glu Asp Ser His Lys Gly Gln Gly Ser
1               5                   10

<210> SEQ ID NO 355
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 355

Gly Val Pro Ser Arg Phe Ser Gly Ser Lys Asp Val Ser Thr Asn Ser
1               5                   10                  15

Gly Ile Leu Leu Ile Ser Gly Leu Gln Ser Glu Asp Ile Ala Thr Tyr
                20                  25                  30

Tyr Cys

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 356

Leu Thr Trp Ser Ser Gln Gly Ser Gly Val
1               5                   10

<210> SEQ ID NO 357
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 357

Thr Leu Pro Ser Asp Ile Asn Val Gly Ser Tyr Asn Ile Tyr
1               5                   10

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 358

Tyr Tyr Gln Asp Ser His Lys Gly Gln Gly Ser
1               5                   10

<210> SEQ ID NO 359
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 359

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 360
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 360

Leu Thr Trp Ser Ser Glu Gly Ser Gly Val
1               5                   10

<210> SEQ ID NO 361
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 361
```

Thr Leu Pro Ser Asp Ile Asn Val Arg Ser Tyr Asn Ile Tyr
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 362

Tyr Tyr Gln Asp Ser His Lys Gly Gln Gly Ser
1               5                   10

<210> SEQ ID NO 363
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 363

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 364
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 364

Leu Thr Trp Ser Ser Glu Gly Ser Gly Val
1               5                   10

<210> SEQ ID NO 365
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 365

Thr Leu Pro Ser Asp Ile Asn Val Gly Ser Tyr Asn Ile Tyr
1               5                   10

<210> SEQ ID NO 366
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: Completely synthesized

<400> SEQUENCE: 366

Tyr Tyr Gln Asp Ser His Lys Gly Gln Gly Ser
1               5                   10

<210> SEQ ID NO 367
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 367

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 368
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 368

Leu Thr Trp Ser Ser Gln Gly Ser Gly Val
1               5                   10

<210> SEQ ID NO 369
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 369

Thr Leu Pro Ser Asp Ile Asn Val Arg Ser Tyr Asn Ile Tyr
1               5                   10

<210> SEQ ID NO 370
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 370

Tyr Tyr Gln Asp Ser His Lys Gly Gln Gly Ser
1               5                   10

<210> SEQ ID NO 371
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 371

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 372
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 372

Leu Thr Trp Ser Ser Gln Gly Ser Gly Val
1               5                   10

<210> SEQ ID NO 373
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 373

Thr Leu Pro Ser Asp Ile Asn Val Gly Ser Tyr Asn Ile Tyr
1               5                   10

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 374

Tyr Tyr Glu Asp Ser His Lys Gly Gln Gly Ser
1               5                   10

<210> SEQ ID NO 375
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

```
<400> SEQUENCE: 375

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 376

Leu Thr Trp Ser Ser Glu Gly Ser Gly Val
1               5                   10

<210> SEQ ID NO 377
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 377

Thr Leu Pro Ser Asp Ile Asn Val Arg Ser Tyr Asn Ile Tyr
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 378

Tyr Tyr Glu Asp Ser His Lys Gly Gln Gly Ser
1               5                   10

<210> SEQ ID NO 379
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 379

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys
```

<210> SEQ ID NO 380
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 380

Leu Thr Trp Ser Ser Glu Gly Ser Gly Val
1               5                   10

<210> SEQ ID NO 381
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 381

Thr Leu Pro Ser Asp Ile Asn Val Gly Ser Tyr Asn Ile Tyr
1               5                   10

<210> SEQ ID NO 382
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 382

Tyr Tyr Glu Asp Ser His Lys Gly Gln Gly Ser
1               5                   10

<210> SEQ ID NO 383
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 383

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 384
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: Completely synthesized

<400> SEQUENCE: 384

Leu Thr Trp Ser Ser Gln Gly Ser Gly Val
1               5                   10

<210> SEQ ID NO 385
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 385

Thr Leu Pro Ser Asp Ile Asn Val Arg Ser Tyr Asn Ile Tyr
1               5                   10

<210> SEQ ID NO 386
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 386

Tyr Tyr Glu Asp Ser His Lys Gly Gln Gly Ser
1               5                   10

<210> SEQ ID NO 387
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 387

Gly Val Pro Ser Arg Phe Ser Gly Ser Lys Asp Val Ser Thr Gln Ser
1               5                   10                  15

Gly Ile Leu Leu Ile Ser Gly Leu Gln Ser Glu Asp Ile Ala Thr Tyr
            20                  25                  30

Tyr Cys

<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 388

Leu Thr Trp Ser Ser Gln Gly Ser Gly Val
1               5                   10

<210> SEQ ID NO 389
<211> LENGTH: 30

```
<212> TYPE: PRT
<213> ORGANISM: Rattus norvegicus

<400> SEQUENCE: 389

Glu Val Gln Leu Gln Gln Ser Gly Pro Glu Val Gly Arg Pro Gly Ser
1               5                   10                  15

Ser Val Lys Ile Ser Cys Lys Ala Ser Gly Tyr Thr Phe Thr
            20                  25                  30

<210> SEQ ID NO 390
<211> LENGTH: 5
<212> TYPE: PRT
<213> ORGANISM: Rattus norvegicus

<400> SEQUENCE: 390

Asp Tyr Ile Met His
1               5

<210> SEQ ID NO 391
<211> LENGTH: 14
<212> TYPE: PRT
<213> ORGANISM: Rattus norvegicus

<400> SEQUENCE: 391

Trp Val Lys Gln Ser Pro Gly Gln Gly Leu Glu Trp Ile Gly
1               5                   10

<210> SEQ ID NO 392
<211> LENGTH: 17
<212> TYPE: PRT
<213> ORGANISM: Rattus norvegicus

<400> SEQUENCE: 392

Trp Ile Asp Pro Glu Tyr Gly Arg Thr Asp Tyr Ala Glu Lys Phe Lys
1               5                   10                  15

Lys

<210> SEQ ID NO 393
<211> LENGTH: 32
<212> TYPE: PRT
<213> ORGANISM: Rattus norvegicus

<400> SEQUENCE: 393

Lys Ala Thr Leu Thr Ala Asp Thr Ser Ser Thr Ala Tyr Ile Gln
1               5                   10                  15

Leu Ser Ser Leu Ala Ser Glu Asp Thr Ala Thr Tyr Phe Cys Ala Arg
            20                  25                  30

<210> SEQ ID NO 394
<211> LENGTH: 11
<212> TYPE: PRT
<213> ORGANISM: Rattus norvegicus

<400> SEQUENCE: 394

Ser Ala His Thr Thr Gly Phe Gly Phe Ala Tyr
1               5                   10

<210> SEQ ID NO 395
<211> LENGTH: 11
<212> TYPE: PRT
<213> ORGANISM: Rattus norvegicus

<400> SEQUENCE: 395
```

```
Trp Gly Gln Gly Thr Leu Val Thr Val Ser Ser
1               5                   10
```

<210> SEQ ID NO 396
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 396

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30
```

<210> SEQ ID NO 397
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 397

```
Trp Val Gln Gln Ala Pro Gly Lys Gly Leu Glu Trp Met Gly
1               5                   10
```

<210> SEQ ID NO 398
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

```
Trp Ile Asp Pro Glu Tyr Gly Arg Thr Asp Tyr Ala Glu Lys Phe Gln
1               5                   10                  15

Gly
```

<210> SEQ ID NO 399
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 399

```
Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30
```

<210> SEQ ID NO 400
<211> LENGTH: 30
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<223> OTHER INFORMATION: Completely synthesized

<400> SEQUENCE: 400

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 401
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 401

Trp Val Gln Gln Ala Pro Gly Lys Gly Leu Glu Trp Met Gly
1               5                   10

<210> SEQ ID NO 402
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 402

Trp Ile Asp Pro Glu Tyr Gly Arg Thr Asp Tyr Ala Glu Lys Phe Gln
1               5                   10                  15

Gly

<210> SEQ ID NO 403
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 403

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 404
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 404
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 405
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 405

Trp Val Arg Gln Ala Pro Gly Gln Gly Leu Glu Trp Met Gly
1               5                   10

<210> SEQ ID NO 406
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 406

Trp Ile Asp Pro Glu Tyr Gly Arg Thr Asp Tyr Ala Gln Lys Leu Gln
1               5                   10                  15

Gly

<210> SEQ ID NO 407
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 407

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 408
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 408

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

```
<210> SEQ ID NO 409
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 409

Trp Val Arg Gln Ala Pro Gly Gln Gly Leu Glu Trp Met Gly
1               5                   10

<210> SEQ ID NO 410
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 410

Trp Ile Asp Pro Glu Tyr Gly Arg Thr Asp Tyr Ala Gln Lys Leu Gln
1               5                   10                  15

Gly

<210> SEQ ID NO 411
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 411

Arg Val Thr Met Thr Ala Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 412
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 412

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 413
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Completely synthesized

<400> SEQUENCE: 413

Trp Val Arg Gln Ala Pro Gly Lys Gly Leu Glu Trp Met Gly
1               5                  10

<210> SEQ ID NO 414
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 414

Trp Ile Asp Pro Glu Tyr Gly Arg Thr Asp Tyr Ala Gln Lys Phe Gln
1               5                  10                  15

Gly

<210> SEQ ID NO 415
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 415

Arg Val Thr Met Thr Glu Asp Thr Ser Thr Asp Thr Ala Tyr Met Glu
1               5                  10                  15

Leu Ser Ser Leu Arg Ser Glu Asp Thr Ala Val Tyr Tyr Cys Ala Thr
                20                  25                  30

<210> SEQ ID NO 416
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 416

Gln Val Gln Leu Val Gln Ser Gly Ala Glu Val Lys Lys Pro Gly Ala
1               5                  10                  15

Ser Val Lys Val Ser Cys Lys Val Ser Gly Tyr Thr Leu Thr
                20                  25                  30

<210> SEQ ID NO 417
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 417

Trp Val Arg Gln Ala Pro Gly Lys Gly Leu Glu Trp Met Gly
1               5                  10
```

<210> SEQ ID NO 418
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 418

Trp Ile Asp Pro Glu Tyr Gly Arg Thr Asp Tyr Ala Gln Lys Phe Gln
1               5                   10                  15

Gly

<210> SEQ ID NO 419
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 419

Arg Val Thr Met Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 420
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 420

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr
            20                  25                  30

<210> SEQ ID NO 421
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 421

Trp Val Arg Gln Ala Pro Gly Lys Gly Leu Glu Trp Met Gly
1               5                   10

<210> SEQ ID NO 422
<211> LENGTH: 17
<212> TYPE: PRT
<213> ORGANISM: Artificial Sequence
<220> FEATURE:

-continued

```
<223> OTHER INFORMATION: Description of Artificial Sequence: Synthetic
      peptide
<220> FEATURE:
<223> OTHER INFORMATION: Completely synthesized

<400> SEQUENCE: 422

Trp Ile Asp Pro Glu Tyr Gly Arg Thr Asp Tyr Ala Gln Lys Phe Gln
1               5                   10                  15

Gly

<210> SEQ ID NO 423
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 423

Arg Val Thr Met Thr Glu Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 424
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 424

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 425
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 425

Trp Val Arg Gln Ala Pro Gly Lys Gly Leu Glu Trp Met Gly
1               5                   10

<210> SEQ ID NO 426
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 426
```

```
<210> SEQ ID NO 427
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 427

Arg Val Thr Met Thr Glu Asp Thr Ser Thr Asp Thr Ala Tyr Met Glu
1               5                   10                  15
Leu Ser Ser Leu Arg Ser Glu Asp Thr Ala Val Tyr Tyr Cys Ala Arg
            20                  25                  30

<210> SEQ ID NO 428
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 428

Gln Met Gln Leu Val Gln Ser Gly Ala Glu Val Lys Lys Thr Gly Ser
1               5                   10                  15
Ser Val Lys Val Ser Cys Lys Ala Ser Gly Tyr Thr Phe Thr
            20                  25                  30

<210> SEQ ID NO 429
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 429

Trp Val Arg Gln Ala Pro Gly Gln Ala Leu Glu Trp Met Gly
1               5                   10

<210> SEQ ID NO 430
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 430

Trp Ile Asp Pro Glu Tyr Gly Arg Thr Asp Tyr Ala Gln Lys Phe Gln
1               5                   10                  15
Asp

<210> SEQ ID NO 431
```

(preceding sequence, continued from previous page:)

```
Trp Ile Asp Pro Glu Tyr Gly Arg Thr Asp Tyr Ala Gln Lys Phe Gln
1               5                   10                  15
Gly
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 431

Arg Val Thr Ile Thr Arg Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 432
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 432

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30

<210> SEQ ID NO 433
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 433

Trp Val Arg Gln Ala Pro Gly Gln Ala Leu Glu Trp Met Gly
1               5                   10

<210> SEQ ID NO 434
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 434

Trp Ile Asp Pro Glu Tyr Gly Arg Thr Asp Tyr Ala Gln Lys Phe Gln
1               5                   10                  15

Asp

<210> SEQ ID NO 435
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Completely synthesized

<400> SEQUENCE: 435

Arg Val Thr Ile Thr Ala Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 436
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 436

Asp Ile Gln Met Thr Gln Ser Pro Ala Ser Leu Ser Ala Ser Leu Gly
1               5                   10                  15

Glu Thr Val Thr Ile Glu Cys
            20

<210> SEQ ID NO 437
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 437

Arg Ala Ser Glu Asp Ile Tyr Ser Asn Leu Ala
1               5                   10

<210> SEQ ID NO 438
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 438

Trp Tyr Gln Gln Lys Pro Gly Asn Ser Pro Gln Leu Leu Ile Tyr
1               5                   10                  15

<210> SEQ ID NO 439
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 439

Asp Ala Asn Ser Leu Ala Asp
1               5

<210> SEQ ID NO 440

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 440

Gly Val Pro Ser Arg Phe Ser Ala Ser Gly Ser Gly Thr Gln Phe Ser
1               5                   10                  15

Leu Lys Ile Asn Ser Leu Arg Ser Glu Asp Val Ala Ser Tyr Phe Cys
            20                  25                  30

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 441

Gln Gln Tyr Asn Asn Tyr Pro Tyr Thr
1               5

<210> SEQ ID NO 442
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 442

Phe Gly Ala Gly Thr Lys Leu Glu Leu Lys Arg
1               5                   10

<210> SEQ ID NO 443
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 443

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 444
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized
```

```
<400> SEQUENCE: 444

Trp Tyr Gln Gln Lys Pro Gly Lys Ala Pro Lys Leu Leu Ile Tyr
1               5                   10                  15

<210> SEQ ID NO 445
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 445

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 446
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 446

Phe Gly Gln Gly Thr Lys Leu Glu Ile Lys Arg
1               5                   10

<210> SEQ ID NO 447
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 447

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 448
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 448

Trp Tyr Gln Gln Lys Pro Gly Lys Ala Pro Lys Leu Leu Ile Tyr
1               5                   10                  15

<210> SEQ ID NO 449
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 449

Gly Val Pro Ser Arg Phe Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 450
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 450

Phe Gly Gln Gly Thr Lys Leu Glu Ile Lys Arg
1               5                   10

<210> SEQ ID NO 451
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 451

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 452
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 452

Trp Tyr Gln Gln Lys Pro Gly Lys Ala Pro Lys Leu Leu Ile Tyr
1               5                   10                  15

<210> SEQ ID NO 453
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 453
```

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 454
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 454

Phe Gly Gln Gly Thr Lys Leu Glu Ile Lys Arg
1               5                   10

<210> SEQ ID NO 455
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 455

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 456
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 456

Trp Tyr Gln Gln Lys Pro Gly Lys Ala Pro Lys Leu Leu Ile Tyr
1               5                   10                  15

<210> SEQ ID NO 457
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 457

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 458
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 458

Phe Gly Gln Gly Thr Lys Leu Glu Ile Lys Arg
1               5                   10

<210> SEQ ID NO 459
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 459

Asp Ile Gln Met Thr Gln Ser Pro Ser Ser Leu Ser Ala Ser Val Gly
1               5                   10                  15

Glu Asp Arg Thr Ile Thr Cys
            20

<210> SEQ ID NO 460
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 460

Trp Tyr Gln Gln Lys Pro Glu Lys Ala Pro Lys Ser Leu Ile Tyr
1               5                   10                  15

<210> SEQ ID NO 461
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 461

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 462
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 462
```

Phe Gly Gln Gly Thr Lys Leu Glu Ile Lys Arg
1               5                   10

<210> SEQ ID NO 463
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 463

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 464
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 464

Trp Tyr Gln Gln Lys Pro Gly Gln Ala Pro Arg Leu Leu Ile Tyr
1               5                   10                  15

<210> SEQ ID NO 465
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 465

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 466
<211> LENGTH: 30
<212> TYPE: PRT
<213> ORGANISM: Rattus norvegicus

<400> SEQUENCE: 466

Glu Val Gln Leu Gln Gln Ser Gly Pro Glu Val Gly Arg Pro Gly Ser
1               5                   10                  15

Ser Val Lys Ile Ser Cys Lys Ala Ser Gly Tyr Ile Phe Thr
            20                  25                  30

<210> SEQ ID NO 467
<211> LENGTH: 17
<212> TYPE: PRT
<213> ORGANISM: Rattus norvegicus

<400> SEQUENCE: 467

```
Trp Ile Asp Pro Glu Tyr Gly Ser Thr Asp Tyr Ala Glu Lys Phe Lys
1               5                   10                  15

Lys
```

<210> SEQ ID NO 468
<211> LENGTH: 32
<212> TYPE: PRT
<213> ORGANISM: Rattus norvegicus

<400> SEQUENCE: 468

```
Lys Ala Thr Leu Thr Ala Asp Thr Ser Ser Thr Ala Tyr Ile Gln
1               5                   10                  15

Leu Ser Ser Leu Thr Ser Glu Asp Thr Ala Thr Tyr Phe Cys Ala Arg
            20                  25                  30
```

<210> SEQ ID NO 469
<211> LENGTH: 14
<212> TYPE: PRT
<213> ORGANISM: Rattus norvegicus

<400> SEQUENCE: 469

```
Val Ala Ile Ile Thr Thr Val Ala Ser Gly Gly Phe Ala Tyr
1               5                   10
```

<210> SEQ ID NO 470
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 470

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30
```

<210> SEQ ID NO 471
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 471

```
Trp Ile Asp Pro Glu Tyr Gly Ser Thr Asp Tyr Ala Glu Lys Phe Gln
1               5                   10                  15

Gly
```

<210> SEQ ID NO 472
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

```
<400> SEQUENCE: 472

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr
            20                  25                  30

<210> SEQ ID NO 473
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 473

Trp Ile Asp Pro Glu Tyr Gly Ser Thr Asp Tyr Ala Glu Lys Phe Gln
1               5                   10                  15

Gly

<210> SEQ ID NO 474
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 474

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 475
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 475

Trp Ile Asp Pro Glu Tyr Gly Ser Thr Asp Tyr Ala Glu Lys Phe Gln
1               5                   10                  15

Gly

<210> SEQ ID NO 476
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 476

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr
            20                  25                  30

<210> SEQ ID NO 477
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Trp Ile Asp Pro Glu Tyr Gly Ser Thr Asp Tyr Ala Gln Lys Leu Gln
1               5                   10                  15

Gly

<210> SEQ ID NO 478
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 479
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 479

Trp Ile Asp Pro Glu Tyr Gly Ser Thr Asp Tyr Ala Gln Lys Leu Gln
1               5                   10                  15

Gly

<210> SEQ ID NO 480
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 480

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 481
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: Completely synthesized

<400> SEQUENCE: 481

Trp Ile Asp Pro Glu Tyr Gly Ser Thr Asp Tyr Ala Gln Lys Phe Gln
1               5                   10                  15

Gly

<210> SEQ ID NO 482
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 482

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 483
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Trp Ile Asp Pro Glu Tyr Gly Ser Thr Asp Tyr Ala Gln Lys Phe Gln
1               5                   10                  15

Gly

<210> SEQ ID NO 484
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 484

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 485
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 485

```
Trp Ile Asp Pro Glu Tyr Gly Ser Thr Asp Tyr Ala Gln Lys Phe Gln
1               5                   10                  15

Gly
```

<210> SEQ ID NO 486
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 486

```
Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30
```

<210> SEQ ID NO 487
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 487

```
Trp Ile Asp Pro Glu Tyr Gly Ser Thr Asp Tyr Ala Gln Lys Phe Gln
1               5                   10                  15

Asp
```

<210> SEQ ID NO 488
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 488

```
Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30
```

<210> SEQ ID NO 489
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 489

```
Trp Ile Asp Pro Glu Tyr Gly Ser Thr Asp Tyr Ala Gln Lys Phe Gln
1               5                   10                  15

Asp
```

<210> SEQ ID NO 490
<211> LENGTH: 23
<212> TYPE: PRT
<213> ORGANISM: Rattus norvegicus

<400> SEQUENCE: 490

Asp Ile Val Met Thr Gln Gly Ala Leu Pro Asn Pro Val Pro Ser Gly
1               5                   10                  15

Glu Ser Ala Ser Ile Thr Cys
            20

<210> SEQ ID NO 491
<211> LENGTH: 16
<212> TYPE: PRT
<213> ORGANISM: Rattus norvegicus

<400> SEQUENCE: 491

Gln Ser Ser Glu Ser Leu Leu His Ser Asn Gly Lys Thr Tyr Leu Asn
1               5                   10                  15

<210> SEQ ID NO 492
<211> LENGTH: 15
<212> TYPE: PRT
<213> ORGANISM: Rattus norvegicus

<400> SEQUENCE: 492

Trp Tyr Leu Gln Arg Pro Gly Gln Ser Pro Gln Leu Leu Ile Tyr
1               5                   10                  15

<210> SEQ ID NO 493
<211> LENGTH: 7
<212> TYPE: PRT
<213> ORGANISM: Rattus norvegicus

<400> SEQUENCE: 493

Trp Met Ser Thr Arg Ala Ala
1               5

<210> SEQ ID NO 494
<211> LENGTH: 32
<212> TYPE: PRT
<213> ORGANISM: Rattus norvegicus

<400> SEQUENCE: 494

Gly Val Ser Asp Arg Phe Ser Gly Ser Gly Ser Gly Thr Asp Phe Thr
1               5                   10                  15

Leu Thr Ile Ser Gly Val Glu Ala Glu Asp Val Gly Val Tyr Tyr Cys
            20                  25                  30

<210> SEQ ID NO 495
<211> LENGTH: 9
<212> TYPE: PRT
<213> ORGANISM: Rattus norvegicus

<400> SEQUENCE: 495

Gln Gln Phe Leu Glu Tyr Pro Pro Thr
1               5

<210> SEQ ID NO 496
<211> LENGTH: 11
<212> TYPE: PRT
<213> ORGANISM: Rattus norvegicus

<400> SEQUENCE: 496

```
Phe Gly Ser Gly Thr Lys Leu Glu Ile Lys Arg
1               5                   10
```

<210> SEQ ID NO 497
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 497

```
Asp Ile Val Met Thr Gln Thr Pro Leu Ser Ser Pro Val Thr Leu Gly
1               5                   10                  15

Gln Pro Ala Ser Ile Ser Cys
            20
```

<210> SEQ ID NO 498
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 498

```
Trp Leu Gln Gln Arg Pro Gly Gln Pro Pro Arg Leu Leu Ile Tyr
1               5                   10                  15
```

<210> SEQ ID NO 499
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 499

```
Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30
```

<210> SEQ ID NO 500
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 500

```
Phe Gly Gln Gly Thr Lys Leu Glu Ile Lys Arg
1               5                   10
```

<210> SEQ ID NO 501
<211> LENGTH: 23
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 501

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 502
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 502

Trp Tyr Leu Gln Lys Pro Gly Gln Ser Pro Gln Leu Leu Ile Tyr
1               5                   10                  15

<210> SEQ ID NO 503
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 503

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 504
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 504

Phe Gly Gln Gly Thr Lys Leu Glu Ile Lys Arg
1               5                   10

<210> SEQ ID NO 505
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 505

Asp Ile Val Met Thr Gln Thr Pro Leu Ser Leu Ser Val Thr Pro Gly
```

```
Gln Pro Ala Ser Ile Ser Cys
            20

<210> SEQ ID NO 506
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 506

Trp Tyr Leu Gln Lys Pro Gly Gln Pro Pro Gln Leu Leu Ile Tyr
1               5                   10                  15

<210> SEQ ID NO 507
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 507

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 508
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 508

Phe Gly Gln Gly Thr Lys Leu Glu Ile Lys Arg
1               5                   10

<210> SEQ ID NO 509
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 509

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 510
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 510

Trp Phe Gln Gln Arg Pro Gly Gln Ser Pro Arg Arg Leu Ile Tyr
1               5                   10                  15

<210> SEQ ID NO 511
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 511

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 512
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 512

Phe Gly Gln Gly Thr Lys Leu Glu Ile Lys Arg
1               5                   10

<210> SEQ ID NO 513
<211> LENGTH: 30
<212> TYPE: PRT
<213> ORGANISM: Rattus norvegicus

<400> SEQUENCE: 513

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 514
<211> LENGTH: 5
<212> TYPE: PRT
<213> ORGANISM: Rattus norvegicus

<400> SEQUENCE: 514

Asp Ser Val Met Asn
1               5

<210> SEQ ID NO 515
<211> LENGTH: 14
<212> TYPE: PRT
<213> ORGANISM: Rattus norvegicus

<400> SEQUENCE: 515

Trp Val Gln Gln Ala Pro Gly Lys Gly Leu Glu Trp Met Gly
1               5                   10

<210> SEQ ID NO 516
<211> LENGTH: 17
<212> TYPE: PRT
<213> ORGANISM: Rattus norvegicus

<400> SEQUENCE: 516

Trp Ile Asp Pro Glu Tyr Gly Arg Thr Asp Val Ala Glu Lys Phe Gln
1               5                   10                  15

Gly

<210> SEQ ID NO 517
<211> LENGTH: 32
<212> TYPE: PRT
<213> ORGANISM: Rattus norvegicus

<400> SEQUENCE: 517

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 518
<211> LENGTH: 11
<212> TYPE: PRT
<213> ORGANISM: Rattus norvegicus

<400> SEQUENCE: 518

Thr Lys Tyr Asn Ser Gly Tyr Gly Phe Pro Tyr
1               5                   10

<210> SEQ ID NO 519
<211> LENGTH: 11
<212> TYPE: PRT
<213> ORGANISM: Rattus norvegicus

<400> SEQUENCE: 519

Trp Gly Gln Gly Thr Thr Val Thr Val Ser Ser
1               5                   10

<210> SEQ ID NO 520
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 520

Trp Val Gln Gln Glu Pro Gly Lys Gly Leu Glu Trp Met Gly
1               5                   10

<210> SEQ ID NO 521
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 521

Trp Val Gln Gln Gly Pro Gly Lys Gly Leu Glu Trp Met Gly
1               5                   10

<210> SEQ ID NO 522
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 522

Trp Val Gln Gln His Pro Gly Lys Gly Leu Glu Trp Met Gly
1               5                   10

<210> SEQ ID NO 523
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 523

Trp Val Gln Gln Gln Pro Gly Lys Gly Leu Glu Trp Met Gly
1               5                   10

<210> SEQ ID NO 524
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 524

Trp Val Gln Gln Ser Pro Gly Lys Gly Leu Glu Trp Met Gly
1               5                   10

<210> SEQ ID NO 525
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 525

Trp Val Gln Gln Val Pro Gly Lys Gly Leu Glu Trp Met Gly
1               5                   10

<210> SEQ ID NO 526
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: Completely synthesized

<400> SEQUENCE: 526

Asp Ser Val Met Glu
1               5

<210> SEQ ID NO 527
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 527

Asp Ser Val Met Pro
1               5

<210> SEQ ID NO 528
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 528

Asp Ser Val Met Gln
1               5

<210> SEQ ID NO 529
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 529

Asp Ser Val Met Ser
1               5

<210> SEQ ID NO 530
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 530

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Glu
            20                  25                  30

<210> SEQ ID NO 531
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 531

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Gly
            20                  25                  30

<210> SEQ ID NO 532
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 532

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Pro
            20                  25                  30

<210> SEQ ID NO 533
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 533

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 534
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 534

Thr Gly Tyr Asn Ser Gly Tyr Gly Phe Pro Tyr
1               5                   10

<210> SEQ ID NO 535
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized
```

-continued

```
<400> SEQUENCE: 535

Thr Thr Tyr Asn Ser Gly Tyr Gly Phe Pro Tyr
1               5                   10

<210> SEQ ID NO 536
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 536

Thr Lys Tyr Gln Ser Gly Tyr Gly Phe Pro Tyr
1               5                   10

<210> SEQ ID NO 537
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 537

Glu Val Gln Leu Gln Gln Ser Gly Pro Glu Val Gly Arg Pro Gly Ser
1               5                   10                  15

Ser Val Lys Ile Ser Cys Lys Ala Ser Gly Tyr Thr Phe Thr
            20                  25                  30

<210> SEQ ID NO 538
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Trp Val Lys Gln Ser Pro Gly Gln Gly Leu Glu Trp Ile Gly
1               5                   10

<210> SEQ ID NO 539
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 539

Trp Ile Asp Pro Glu Tyr Gly Arg Thr Asp Val Ala Glu Lys Phe Lys
1               5                   10                  15

Lys

<210> SEQ ID NO 540
<211> LENGTH: 32
<212> TYPE: PRT
<213> ORGANISM: Artificial Sequence
<220> FEATURE:
<223> OTHER INFORMATION: Description of Artificial Sequence: Synthetic
``` polypeptide
<220> FEATURE:
<223> OTHER INFORMATION: Completely synthesized

<400> SEQUENCE: 540

Lys Ala Thr Leu Thr Ala Asp Ser Ser Ser Thr Ala Tyr Ile Tyr
1               5                   10                  15

Leu Ser Gly Leu Thr Ser Glu Asp Thr Ala Thr Tyr Phe Cys Ala Arg
            20                  25                  30

<210> SEQ ID NO 541
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 541

Trp Gly Gln Gly Ser Leu Val Thr Val Ser Ser
1               5                   10

<210> SEQ ID NO 542
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 542

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 543
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 543

Trp Val Arg Gln Ala Pro Gly Lys Gly Leu Glu Trp Met Gly
1               5                   10

<210> SEQ ID NO 544
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 544

Trp Ile Asp Pro Glu Tyr Gly Arg Thr Asp Val Ala Gln Lys Phe Gln
1               5                   10                  15

Gly

<210> SEQ ID NO 545
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 545

```
Gly Arg Val Thr Met Thr Glu Asp Thr Ser Thr Asp Thr Ala Tyr Met
1               5                   10                  15

Glu Leu Ser Ser Leu Arg Ser Glu Asp Thr Ala Val Tyr Tyr Cys Ala
            20                  25                  30

Thr
```

<210> SEQ ID NO 546
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 546

```
Trp Gly Gln Gly Thr Thr Val Thr Val Ser Ser
1               5                   10
```

<210> SEQ ID NO 547
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 547

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30
```

<210> SEQ ID NO 548
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 548

```
Trp Val Arg Gln Ala Pro Gly Lys Gly Leu Glu Trp Met Gly
1               5                   10
```

<210> SEQ ID NO 549
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 549

Trp Ile Asp Pro Glu Tyr Gly Arg Thr Asp Val Ala Gln Lys Phe Gln
1               5                   10                  15

Gly

<210> SEQ ID NO 550
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 550

Arg Val Thr Met Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 551
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 551

Trp Gly Gln Gly Thr Thr Val Thr Val Ser Ser
1               5                   10

<210> SEQ ID NO 552
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 552

Gln Val Gln Leu Val Gln Ser Gly Ala Glu Lys Lys Pro Gly Ala
1               5                   10                  15

Ser Val Lys Val Ser Cys Lys Val Ser Gly Tyr Thr Leu Thr
            20                  25                  30

<210> SEQ ID NO 553
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 553

Trp Val Arg Gln Ala Pro Gly Lys Gly Leu Glu Trp Met Gly
1               5                   10

<210> SEQ ID NO 554
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 554

Trp Ile Asp Pro Glu Tyr Gly Arg Thr Asp Val Ala Gln Lys Phe Gln
1               5                   10                  15

Gly

<210> SEQ ID NO 555
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 555

Arg Val Thr Met Thr Glu Asp Thr Ser Thr Asp Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 556
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 556

Trp Gly Gln Gly Thr Thr Val Thr Val Ser Ser
1               5                   10

<210> SEQ ID NO 557
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 557

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 558
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 558

Trp Val Arg Gln Ala Pro Gly Lys Gly Leu Glu Trp Met Gly
1               5                   10

<210> SEQ ID NO 559
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 559

Trp Ile Asp Pro Glu Tyr Gly Arg Thr Asp Val Ala Gln Lys Phe Gln
1               5                   10                  15

Gly

<210> SEQ ID NO 560
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 560

Gly Arg Val Thr Met Thr Ala Asp Thr Ser Thr Asp Thr Ala Tyr Met
1               5                   10                  15

Glu Leu Ser Ser Leu Arg Ser Glu Asp Thr Ala Val Tyr Tyr Cys Ala
            20                  25                  30

Arg

<210> SEQ ID NO 561
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 561

Trp Gly Gln Gly Thr Thr Val Thr Val Ser Ser
1               5                   10

<210> SEQ ID NO 562
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized
```

<400> SEQUENCE: 562

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30

<210> SEQ ID NO 563
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 563

Trp Val Arg Gln Ala Pro Gly Gln Ala Leu Glu Trp Met Gly
1               5                   10

<210> SEQ ID NO 564
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 564

Trp Ile Asp Pro Glu Tyr Gly Arg Thr Asp Val Ala Gln Lys Phe Gln
1               5                   10                  15

Asp

<210> SEQ ID NO 565
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 565

Arg Val Thr Ile Thr Arg Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 566
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 566

Trp Gly Gln Gly Thr Thr Val Thr Val Ser Ser
1               5                   10

<210> SEQ ID NO 567

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 567

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30

<210> SEQ ID NO 568
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 568

Trp Val Arg Gln Ala Pro Gly Gln Ala Leu Glu Trp Met Gly
1               5                   10

<210> SEQ ID NO 569
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 569

Trp Ile Asp Pro Glu Tyr Gly Arg Thr Asp Val Ala Gln Lys Phe Gln
1               5                   10                  15

Asp

<210> SEQ ID NO 570
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 570

Arg Val Thr Ile Thr Ala Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 571
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: Completely synthesized

<400> SEQUENCE: 571

Trp Gly Gln Gly Thr Thr Val Thr Val Ser Ser
1               5                   10

<210> SEQ ID NO 572
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 572

Glu Val Gln Leu Val Gln Ser Gly Pro Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 573
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 573

Trp Val Gln Gln Ala Pro Gly Lys Gly Leu Glu Trp Met Gly
1               5                   10

<210> SEQ ID NO 574
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 574

Trp Ile Asp Pro Glu Tyr Gly Arg Thr Asp Val Ala Glu Lys Phe Gln
1               5                   10                  15

Gly

<210> SEQ ID NO 575
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 575

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
            20                  25                  30

<210> SEQ ID NO 576
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 576

Trp Gly Gln Gly Thr Thr Val Thr Val Ser Ser
1               5                   10

<210> SEQ ID NO 577
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 577

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 578
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 578

Trp Val Gln Gln Ala Pro Gly Lys Gly Leu Glu Trp Met Gly
1               5                   10

<210> SEQ ID NO 579
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 579

Trp Ile Asp Pro Glu Tyr Gly Arg Thr Asp Val Ala Glu Lys Phe Gln
1               5                   10                  15

Gly

<210> SEQ ID NO 580
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 580

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 581
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 581

Trp Gly Gln Gly Thr Thr Val Thr Val Ser Ser
1               5                   10

<210> SEQ ID NO 582
<211> LENGTH: 23
<212> TYPE: PRT
<213> ORGANISM: Rattus norvegicus

<400> SEQUENCE: 582

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 583
<211> LENGTH: 11
<212> TYPE: PRT
<213> ORGANISM: Rattus norvegicus

<400> SEQUENCE: 583

Lys Ala Ser Gln Asn Val Asp Ser Asp Val Asp
1               5                   10

<210> SEQ ID NO 584
<211> LENGTH: 15
<212> TYPE: PRT
<213> ORGANISM: Rattus norvegicus

<400> SEQUENCE: 584

Trp Tyr Gln Gln Lys Pro Gly Lys Ala Pro Lys Leu Leu Ile Tyr
1               5                   10                  15

<210> SEQ ID NO 585
<211> LENGTH: 7
<212> TYPE: PRT
<213> ORGANISM: Rattus norvegicus

<400> SEQUENCE: 585

Lys Ala Ser Asn Arg Tyr Thr
1               5

<210> SEQ ID NO 586
<211> LENGTH: 32
<212> TYPE: PRT
<213> ORGANISM: Rattus norvegicus

<400> SEQUENCE: 586

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 587
<211> LENGTH: 9
<212> TYPE: PRT
<213> ORGANISM: Rattus norvegicus

<400> SEQUENCE: 587

Met Gln Ser Asn Thr His Pro Arg Thr
1               5

<210> SEQ ID NO 588
<211> LENGTH: 11
<212> TYPE: PRT
<213> ORGANISM: Rattus norvegicus

<400> SEQUENCE: 588

Phe Gly Gly Gly Thr Lys Val Glu Ile Lys Arg
1               5                   10

<210> SEQ ID NO 589
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 589

Pro Ala Ser Gln Asn Val Asp Ser Asp Val Asp
1               5                   10

<210> SEQ ID NO 590
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 590

Gln Ala Ser Gln Asn Val Asp Ser Asp Val Asp
1               5                   10

<210> SEQ ID NO 591
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 591

Lys Ala Ser Asn Asp Tyr Thr
1               5

<210> SEQ ID NO 592

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 592

Trp Tyr Gln Gln Lys Pro Gly Lys Ala Pro Lys Leu Leu Asp Tyr
1               5                   10                  15

<210> SEQ ID NO 593
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 593

Trp Tyr Gln Gln Lys Pro Gly Lys Ala Pro Lys Leu Leu Ile Glu
1               5                   10                  15

<210> SEQ ID NO 594
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 594

Ala Gln Ser Asn Thr His Pro Arg Thr
1               5

<210> SEQ ID NO 595
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 595

Glu Gln Ser Asn Thr His Pro Arg Thr
1               5

<210> SEQ ID NO 596
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 596

His Gln Ser Asn Thr His Pro Arg Thr
1               5
```

```
<210> SEQ ID NO 597
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 597

Lys Gln Ser Asn Thr His Pro Arg Thr
1               5

<210> SEQ ID NO 598
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 598

Pro Gln Ser Asn Thr His Pro Arg Thr
1               5

<210> SEQ ID NO 599
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 599

Gln Gln Ser Asn Thr His Pro Arg Thr
1               5

<210> SEQ ID NO 600
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 600

Ser Gln Ser Asn Thr His Pro Arg Thr
1               5

<210> SEQ ID NO 601
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 601

Val Gln Ser Asn Thr His Pro Arg Thr
1               5
```

```
<210> SEQ ID NO 602
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 602

Met Asp Ser Asn Thr His Pro Arg Thr
1               5

<210> SEQ ID NO 603
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 603

Met Gln Glu Asn Thr His Pro Arg Thr
1               5

<210> SEQ ID NO 604
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 604

Met Gln Ser Thr Thr His Pro Arg Thr
1               5

<210> SEQ ID NO 605
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 605

Lys Ala Ser Gln Arg Tyr Thr
1               5

<210> SEQ ID NO 606
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 606

Met Gln Ser Gln Thr His Pro Arg Thr
1               5
```

<210> SEQ ID NO 607
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 607

Asp Ile Val Met Thr Gln Ser Pro Thr Ser Ile Ser Val Gly
1               5                   10                  15

Glu Arg Val Thr Met Asn Cys
            20

<210> SEQ ID NO 608
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 608

Lys Ala Ser Gln Asn Val Asp Ser Asp Val Asp
1               5                   10

<210> SEQ ID NO 609
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 609

Trp Tyr Gln Gln Lys Thr Gly Gln Ser Pro Lys Leu Leu Ile Tyr
1               5                   10                  15

<210> SEQ ID NO 610
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 610

Lys Ala Ser Asn Arg Tyr Thr
1               5

<210> SEQ ID NO 611
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 611

Gly Val Pro Asp Arg Phe Thr Gly Ser Gly Ser Gly Thr Asp Phe Thr
1               5                   10                  15

Phe Thr Ile Ser Asn Met Gln Ala Glu Asp Leu Ala Val Tyr Tyr Cys
            20                  25                  30

<210> SEQ ID NO 612
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 612

Met Gln Ser Asn Thr His Pro Arg Thr
1               5

<210> SEQ ID NO 613
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 613

Phe Gly Gly Gly Thr Lys Leu Glu Leu Lys Arg
1               5                   10

<210> SEQ ID NO 614
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 614

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 615
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 615

Trp Tyr Gln Gln Lys Pro Gly Lys Ala Pro Lys Leu Leu Ile Tyr
1               5                   10                  15

<210> SEQ ID NO 616
<211> LENGTH: 32
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 616

Gly Val Pro Ser Arg Phe Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 617
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 617

Phe Gly Gly Gly Thr Lys Val Glu Ile Lys Arg
1               5                   10

<210> SEQ ID NO 618
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 618

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 619
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 619

Trp Tyr Gln Gln Lys Pro Gly Lys Ala Pro Lys Leu Leu Ile Tyr
1               5                   10                  15

<210> SEQ ID NO 620
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 620

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 621
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 621

Phe Gly Gly Gly Thr Lys Val Glu Ile Lys Arg
1               5                   10

<210> SEQ ID NO 622
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 622

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 623
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 623

Trp Tyr Gln Gln Lys Pro Gly Lys Ala Pro Lys Leu Leu Ile Tyr
1               5                   10                  15

<210> SEQ ID NO 624
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 624

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 625
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 625

Phe Gly Gly Gly Thr Lys Val Glu Ile Lys Arg
1               5                  10

<210> SEQ ID NO 626
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 626

Asp Ile Gln Met Thr Gln Ser Pro Ser Ser Leu Ser Ala Ser Val Gly
1               5                  10                  15

Asp Arg Val Thr Ile Thr Cys
            20

<210> SEQ ID NO 627
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 627

Trp Tyr Gln Gln Lys Pro Gly Lys Ala Pro Lys Leu Leu Ile Tyr
1               5                  10                  15

<210> SEQ ID NO 628
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 628

Gly Val Pro Ser Arg Phe Ser Gly Ser Gly Ser Gly Thr Asp Phe Thr
1               5                  10                  15

Phe Thr Ile Ser Ser Leu Gln Pro Glu Asp Ile Ala Thr Tyr Tyr Cys
            20                  25                  30

<210> SEQ ID NO 629
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 629
```

Phe Gly Gly Gly Thr Lys Val Glu Ile Lys Arg
1               5                   10

<210> SEQ ID NO 630
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 630

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 631
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 631

Trp Tyr Gln Gln Lys Pro Gly Gln Ala Pro Arg Leu Leu Ile Tyr
1               5                   10                  15

<210> SEQ ID NO 632
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 632

Gly Ile Pro Ala Arg Phe Ser Gly Ser Gly Ser Gly Arg Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 633
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 633

Phe Gly Gly Gly Thr Lys Val Glu Ile Lys Arg
1               5                   10

<210> SEQ ID NO 634
<211> LENGTH: 23
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 634

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 635
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 635

Trp Tyr Gln Gln Lys Pro Gly Gln Ala Pro Arg Leu Leu Ile Tyr
1               5                   10                  15

<210> SEQ ID NO 636
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 636

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 637
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 637

Phe Gly Gly Gly Thr Lys Val Glu Ile Lys Arg
1               5                   10

<210> SEQ ID NO 638
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 638

Glu Ile Val Leu Thr Gln Ser Pro Asp Phe Gln Ser Val Thr Pro Lys
```

```
1               5                   10                  15
Glu Lys Val Thr Ile Thr Cys
            20

<210> SEQ ID NO 639
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 639

Trp Tyr Gln Gln Lys Pro Asp Gln Ser Pro Lys Leu Leu Ile Lys
1               5                   10                  15

<210> SEQ ID NO 640
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 640

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 641
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 641

Phe Gly Gly Gly Thr Lys Val Glu Ile Lys Arg
1               5                   10

<210> SEQ ID NO 642
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 642

Gly Gly Gly Gly Ser
1               5

<210> SEQ ID NO 643
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<223> OTHER INFORMATION: Completely synthesized

<400> SEQUENCE: 643

Gly Gly Gly Gly Ser Gly Gly Gly Gly Ser
1               5                   10

<210> SEQ ID NO 644
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 644

Gly Gly Gly Gly Ser Gly Gly Gly Gly Ser Gly Gly Gly Gly Ser
1               5                   10                  15

<210> SEQ ID NO 645
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 645

Gly Gly Gly Gly Ser Gly Gly Gly Gly Ser Gly Gly Gly Gly Ser Gly
1               5                   10                  15

Gly Gly Gly Ser
            20

<210> SEQ ID NO 646
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 646

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 647
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 647

Met Ala Leu Thr Phe Ala Leu Leu Val Ala Leu Leu Val Leu Ser Cys
1               5                   10                  15
```

Lys Ser Ser Cys Ser Val Gly Cys Asp Leu Pro Gln Thr His Ser Leu
               20                  25                  30

Gly Ser Arg Arg Thr Leu Met Leu Leu Ala Gln Met Arg Arg Ile Ser
           35                  40                  45

Leu Phe Ser Cys Leu Lys Asp Arg His Asp Phe Gly Phe Pro Gln Glu
50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Met Asp Ser Ser
               85                  90                  95

Ala Ala Trp Asp Glu Thr Leu Leu Asp Lys Phe Tyr Thr Glu Leu Tyr
           100                 105                 110

Gln Gln Leu Asn Asp Leu Glu Ala Cys Val Ile Gln Gly Val Gly Val
       115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Asp Glu Ile Met Arg Ser Phe Ser Leu
               165                 170                 175

Ser Thr Asn Leu Gln Glu Ser Leu Arg Ser Lys Glu
           180                 185

<210> SEQ ID NO 648
<211> LENGTH: 165
<212> TYPE: PRT
<213> ORGANISM: Homo sapiens

<400> SEQUENCE: 648

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
           20                  25                  30

Arg His Asp Phe Gly Phe Pro Gln Glu Glu Phe Gly Asn Gln Phe Gln
       35                  40                  45

Lys Ala Glu Thr Ile Pro Val Leu His Glu Met Ile Gln Gln Ile Phe
50                  55                  60

Asn Leu Phe Ser Thr Met Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
               85                  90                  95

Ala Cys Val Ile Gln Gly Val Gly Val Thr Glu Thr Pro Leu Met Lys
           100                 105                 110

Glu Asp Ser Ile Leu Ala Val Arg Lys Tyr Phe Gln Arg Ile Thr Leu
       115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
               165

<210> SEQ ID NO 649
<211> LENGTH: 165
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 649

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Met Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Asp Glu Ile Met Arg Ser Phe Ser Leu Ser Thr Asn Leu Gln Glu Ser
145                 150                 155                 160

Leu Arg Ser Lys Glu
                165

<210> SEQ ID NO 650
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 650

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Met Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
```

```
                130                 135                 140
Tyr Phe Gln Arg Ile Thr Leu Tyr Leu Lys Glu Lys Tyr Ser Pro
145                 150                 155                 160

Cys Ala Trp Glu Val Val Arg Gly Glu Ile Met Arg Ser Phe Ser Leu
                165                 170                 175

Ser Thr Asn Leu Gln Glu Ser Leu Arg Ser Lys Glu
                180                 185

<210> SEQ ID NO 651
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 651

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Met Asp Ser Ser Ala Ala Trp Asp Glu Thr Leu
65              70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Gly Glu Ile Met Arg Ser Phe Ser Leu Ser Thr Asn Leu Gln Glu Ser
145                 150                 155                 160

Leu Arg Ser Lys Glu
                165

<210> SEQ ID NO 652
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 652

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

Tyr Phe Gln Arg Ile Thr Leu Tyr Leu Lys Glu Lys Lys Tyr Ser Pro
450                 455                 460

Cys Ala Trp Glu Val Val Arg Asp Glu Ile Met Arg Ser Phe Ser Leu
```

465                 470                 475                 480
Ser Thr Asn Leu Gln Glu Ser Leu Arg Ser Lys Glu
                485                 490

<210> SEQ ID NO 653
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 653

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu

|   |   | 325 |   |   |   | 330 |   |   |   | 335 |   |
|---|---|---|---|---|---|---|---|---|---|---|---|

```
Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
            355                 360                 365

Glu Phe Gly Asn Gln Phe Gln Lys Ala Glu Thr Ile Pro Val Leu His
            370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
                420                 425                 430

Thr Glu Thr Pro Leu Met Lys Glu Asp Ser Ile Leu Ala Val Arg Lys
                435                 440                 445

Tyr Phe Gln Arg Ile Thr Leu Tyr Leu Lys Glu Lys Lys Tyr Ser Pro
            450                 455                 460

Cys Ala Trp Glu Val Val Arg Gly Glu Ile Met Arg Ser Phe Ser Leu
465                 470                 475                 480

Ser Thr Asn Leu Gln Glu Ser Leu Arg Ser Lys Glu
                485                 490
```

<210> SEQ ID NO 654
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 654

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
```

```
                180                 185                 190
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
    370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

Tyr Phe Gln Arg Ile Thr Leu Tyr Leu Lys Glu Lys Lys Tyr Ser Pro
    450                 455                 460

Cys Ala Trp Glu Val Val Arg Gly Glu Ile Met Arg Ser Phe Ser Leu
465                 470                 475                 480

Ser Thr Asn Leu Gln Glu Ser Leu Arg Ser Lys Glu
                485                 490

<210> SEQ ID NO 655
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 655

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys Cys Asp Leu Pro Gln Thr
                325                 330                 335
His Ser Leu Gly Ser Arg Arg Thr Leu Met Leu Leu Ala Gln Met Arg
            340                 345                 350
Arg Ile Ser Leu Phe Ser Cys Leu Lys Asp Arg His Asp Phe Gly Phe
            355                 360                 365
Pro Gln Glu Glu Phe Gly Asn Gln Phe Gln Lys Ala Glu Thr Ile Pro
            370                 375                 380
Val Leu His Glu Met Ile Gln Gln Ile Phe Asn Leu Phe Ser Thr Lys
385                 390                 395                 400
Asp Ser Ser Ala Ala Trp Asp Glu Thr Leu Leu Asp Lys Phe Tyr Thr
                405                 410                 415
Glu Leu Tyr Gln Gln Leu Asn Asp Leu Glu Ala Cys Val Ile Gln Gly
            420                 425                 430
Val Gly Val Thr Glu Thr Pro Leu Met Lys Glu Asp Ser Ile Leu Ala
            435                 440                 445
Val Arg Lys Tyr Phe Gln Arg Ile Thr Leu Tyr Leu Lys Glu Lys Lys
            450                 455                 460
```

```
Tyr Ser Pro Cys Ala Trp Glu Val Val Arg Gly Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 656
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 656

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

-continued

```
Gln Lys Ser Leu Ser Leu Ser Pro Gly Lys Cys Asp Leu Pro Gln Thr
            325                 330                 335

His Ser Leu Gly Ser Arg Arg Thr Leu Met Leu Leu Ala Gln Met Arg
        340                 345                 350

Arg Ile Ser Leu Phe Ser Cys Leu Lys Asp Arg His Asp Phe Gly Phe
        355                 360                 365

Pro Gln Glu Glu Phe Gly Asn Gln Phe Gln Lys Ala Glu Thr Ile Pro
    370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
                405                 410                 415

Glu Leu Tyr Gln Gln Leu Asn Asp Leu Glu Ala Cys Val Ile Gln Gly
            420                 425                 430

Val Gly Val Thr Glu Thr Pro Leu Met Lys Glu Asp Ser Ile Leu Ala
        435                 440                 445

Val Arg Lys Tyr Phe Gln Arg Ile Thr Leu Tyr Leu Lys Glu Lys Lys
    450                 455                 460

Tyr Ser Pro Cys Ala Trp Glu Val Val Arg Asp Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 657
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 657

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Cys Asp Leu Pro Gln Thr
                325                 330                 335

His Ser Leu Gly Ser Arg Arg Thr Leu Met Leu Leu Ala Gln Met Arg
            340                 345                 350

Arg Ile Ser Leu Phe Ser Cys Leu Lys Asp Arg His Asp Phe Gly Phe
        355                 360                 365

Pro Gln Glu Glu Phe Gly Asn Gln Phe Gln Lys Ala Glu Thr Ile Pro
    370                 375                 380

Val Leu His Glu Met Ile Gln Gln Ile Phe Asn Leu Phe Ser Thr Lys
385                 390                 395                 400

Asp Ser Ser Ala Ala Trp Asp Glu Thr Leu Leu Asp Lys Phe Tyr Thr
                405                 410                 415

Glu Leu Tyr Gln Gln Leu Asn Asp Leu Glu Ala Cys Val Ile Gln Gly
            420                 425                 430

Val Gly Val Thr Glu Thr Pro Leu Met Lys Glu Asp Ser Ile Leu Ala
        435                 440                 445

Val Arg Lys Tyr Phe Gln Arg Ile Thr Leu Tyr Leu Lys Glu Lys Lys
    450                 455                 460

Tyr Ser Pro Cys Ala Trp Glu Val Val Arg Gly Glu Ile Met Arg Ser
465                 470                 475                 480

Phe Ser Leu Ser Thr Asn Leu Gln Glu Ser Leu Arg Ser Lys Glu
                485                 490                 495

<210> SEQ ID NO 658
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 658

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Tyr Ile Thr Arg Glu Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

```
Tyr Phe Gln Arg Ile Thr Leu Tyr Leu Lys Glu Lys Lys Tyr Ser Pro
        450                 455                 460

Cys Ala Trp Glu Val Val Arg Asp Glu Ile Met Arg Ser Phe Ser Leu
465                 470                 475                 480

Ser Thr Asn Leu Gln Glu Ser Leu Arg Ser Lys Glu
                485                 490

<210> SEQ ID NO 659
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized
<220> FEATURE:
<221> NAME/KEY: MOD_RES
<222> LOCATION: (42)..(42)
<223> OTHER INFORMATION: His or Pro
<220> FEATURE:
<221> NAME/KEY: MOD_RES
<222> LOCATION: (76)..(76)
<223> OTHER INFORMATION: Ser or Leu
<220> FEATURE:
<221> NAME/KEY: MOD_RES
<222> LOCATION: (80)..(80)
<223> OTHER INFORMATION: Phe or Ile
<220> FEATURE:
<221> NAME/KEY: MOD_RES
<222> LOCATION: (83)..(83)
<223> OTHER INFORMATION: Lys or Arg
<220> FEATURE:
<221> NAME/KEY: MOD_RES
<222> LOCATION: (85)..(85)
<223> OTHER INFORMATION: Ser or Thr
<220> FEATURE:
<221> NAME/KEY: MOD_RES
<222> LOCATION: (108)..(108)
<223> OTHER INFORMATION: Leu or Met

<400> SEQUENCE: 659

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln Xaa Pro Gly Lys Gly Leu Glu
        35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Val Asp Thr Xaa Lys Asn Gln Xaa
65                  70                  75                  80

Ser Leu Xaa Leu Xaa Ser Val Thr Ala Ala Asp Thr Ala Val Tyr Tyr
                85                  90                  95

Cys Ala Arg Val Gly Gly Ala Gly Gly Trp Pro Xaa Asp Val Trp Gly
            100                 105                 110

Gln Gly Thr Thr Val Thr Val Ser Ser
            115                 120

<210> SEQ ID NO 660
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Completely synthesized

<400> SEQUENCE: 660

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
            115

<210> SEQ ID NO 661
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 661

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Glu Asp Ser His Lys Gly Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
            115

<210> SEQ ID NO 662
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 662

Gln Ala Val Leu Thr Gln Pro Ala Ser Leu Ser Ala Ser Pro Gly Glu

```
1               5                   10                  15
Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
        50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 663
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 663

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
            35                  40                  45

Leu Leu Tyr Tyr Tyr Gln Asp Ser His Lys Gly Gln Gly Ser Gly Val
        50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 664
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized
<220> FEATURE:
<221> NAME/KEY: MOD_RES
<222> LOCATION: (31)..(31)
<223> OTHER INFORMATION: Arg or Gly
<220> FEATURE:
<221> NAME/KEY: MOD_RES
<222> LOCATION: (32)..(32)
<223> OTHER INFORMATION: Tyr or Ser
<220> FEATURE:
```

```
<221> NAME/KEY: MOD_RES
<222> LOCATION: (54)..(54)
<223> OTHER INFORMATION: Ser, Glu or Gln
<220> FEATURE:
<221> NAME/KEY: MOD_RES
<222> LOCATION: (77)..(77)
<223> OTHER INFORMATION: Asn or Thr
<220> FEATURE:
<221> NAME/KEY: MOD_RES
<222> LOCATION: (97)..(97)
<223> OTHER INFORMATION: Met or Leu
<220> FEATURE:
<221> NAME/KEY: MOD_RES
<222> LOCATION: (102)..(102)
<223> OTHER INFORMATION: Asn, Gln or Glu

<400> SEQUENCE: 664

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Xaa Xaa
            20                  25                  30

Tyr Asn Ile Tyr Trp Tyr Gln Gln Lys Pro Gly Ser Pro Pro Arg Tyr
        35                  40                  45

Leu Leu Tyr Tyr Xaa Asp Ser His Lys Gly Gln Gly Ser Gly Val
50                  55                  60

Pro Ser Arg Phe Ser Gly Ser Lys Asp Val Ser Thr Xaa Ser Gly Ile
65                  70                  75                  80

Leu Leu Ile Ser Gly Leu Gln Ser Glu Asp Ile Ala Thr Tyr Tyr Cys
                85                  90                  95

Xaa Thr Trp Ser Ser Xaa Gly Ser Gly Val Phe Gly Gly Thr Gln
            100                 105                 110

Leu Thr Val Leu Gly
        115

<210> SEQ ID NO 665
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (20)..(20)
<223> OTHER INFORMATION: Ile or Val
<220> FEATURE:
<221> NAME/KEY: MOD_RES
<222> LOCATION: (29)..(29)
<223> OTHER INFORMATION: Phe or Leu
<220> FEATURE:
<221> NAME/KEY: MOD_RES
<222> LOCATION: (38)..(38)
<223> OTHER INFORMATION: Gln or Arg
<220> FEATURE:
<221> NAME/KEY: MOD_RES
<222> LOCATION: (40)..(40)
<223> OTHER INFORMATION: Glu, Gly, His or Ala
<220> FEATURE:
<221> NAME/KEY: MOD_RES
<222> LOCATION: (62)..(62)
```

```
<223> OTHER INFORMATION: Glu or Gln
<220> FEATURE:
<221> NAME/KEY: MOD_RES
<222> LOCATION: (70)..(70)
<223> OTHER INFORMATION: Ile or Met
<220> FEATURE:
<221> NAME/KEY: MOD_RES
<222> LOCATION: (100)..(100)
<223> OTHER INFORMATION: Lys, Gly or Thr
<220> FEATURE:
<221> NAME/KEY: MOD_RES
<222> LOCATION: (102)..(102)
<223> OTHER INFORMATION: Asn or Gln

<400> SEQUENCE: 665

Xaa Val Gln Leu Val Gln Ser Gly Ala Glu Val Lys Lys Pro Gly Ala
1               5                   10                  15

Xaa Val Lys Xaa Ser Cys Lys Val Ser Gly Tyr Thr Xaa Thr Asp Ser
            20                  25                  30

Val Met Asn Trp Val Xaa Gln Xaa Pro Gly Lys Gly Leu Glu Trp Met
        35                  40                  45

Gly Trp Ile Asp Pro Glu Tyr Gly Arg Thr Asp Val Ala Xaa Lys Phe
    50                  55                  60

Gln Gly Arg Val Thr Xaa Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Xaa Tyr Xaa Ser Gly Tyr Gly Phe Pro Tyr Trp Gly Gln
            100                 105                 110

Gly Thr Thr Val Thr Val Ser Ser
            115                 120

<210> SEQ ID NO 666
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized
<220> FEATURE:
<221> NAME/KEY: MOD_RES
<222> LOCATION: (24)..(24)
<223> OTHER INFORMATION: Lys, Gly or Gln
<220> FEATURE:
<221> NAME/KEY: MOD_RES
<222> LOCATION: (53)..(53)
<223> OTHER INFORMATION: Asn or Gln
<220> FEATURE:
<221> NAME/KEY: MOD_RES
<222> LOCATION: (54)..(54)
<223> OTHER INFORMATION: Arg or Asp
<220> FEATURE:
<221> NAME/KEY: MOD_RES
<222> LOCATION: (89)..(89)
<223> OTHER INFORMATION: Met or Ala

<400> SEQUENCE: 666

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Xaa Xaa Tyr Thr Gly Val Pro Ser Arg Phe Ser Gly
```

```
                  50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Xaa Gln Ser Asn Thr His Pro Arg
                 85                  90                  95

Thr Phe Gly Gly Gly Thr Lys Val Glu Ile Lys Arg
            100                 105
```

<210> SEQ ID NO 667
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 667
cagctgcagc tgcaggaatc cggccctggc ctggtcaagc cctccgagac actgagcctg     60
acctgcaccg tgtccggcgg ctccatctcc tccagctcct actactggtc ctggatccgg    120
cagcaccccg gcaagggcct ggaatggatc ggctacatct actactccgg ctccaccaac    180
tacaacccca gcctgaagtc cagagtgacc atctccgtgg acacctccaa gaaccagttc    240
tccctgaagc tgtcctccgt gaccgccgct gacaccgccg tgtactactg tgccagagtg    300
ggcggagctg gcggctggcc tctggatgtg tggggccagg gcaccaccgt caccgtgtcc    360
tca                                                                  363

<210> SEQ ID NO 668
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 668
cagctgcagc tgcaggaatc cggccctggc ctggtcaagc cctccgagac actgagcctg     60
acctgcaccg tgtccggcgg ctccatctcc tccagctcct actactggtc ctggatccgg    120
cagcctcccg gcaagggcct ggaatggatc ggctacatct actactccgg ctccaccaac    180
tacaacccca gcctgaagtc cagagtgacc atctccgtgg acaccctgaa gaaccagatc    240
tccctgcggc tgacctccgt gaccgccgct gacaccgccg tgtactactg tgccagagtg    300
ggcggagctg gcggctggcc tatggatgtg tggggccagg gcaccaccgt caccgtgtcc    360
tca                                                                  363

<210> SEQ ID NO 669
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 669
caggccgtgc tgacccagcc tgcctccctg tctgcctctc ctggcgagtc cgccagactg     60

```
acctgcaccc tgccctccga catcaacgtg cggtactaca acatctactg gtatcagcag    120
aagcccggca gccccccag atacctgctg tactactact ccgactccca aagggccag      180 ggctccggcg tgcctccag attctccggc tccaaggacg tgtccaccaa ctccggcatc    240
ctgctgatct ccggcctgca gtccgaggac attgccacct actactgcat gacttggagc    300
agcaacggca gcggcgtgtt cggcggaggc acccagctga ccgtcctagg t             351
```

<210> SEQ ID NO 670
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 670

```
caggccgtgc tgacccagcc tgcctccctg tctgcctctc ctggcgagtc cgccagactg     60
acctgcaccc tgccctccga catcaacgtg cggtactaca acatctactg gtatcagcag    120
aagcccggca gccccccag atacctgctg tactactact ccgactccca aagggccag      180 ggctccggcg tgcctccag attctccggc tccaaggacg tgtccaccac ctccggcatc    240
ctgctgatct ccggcctgca gtccgaggac attgccacct actactgcat gacttggagc    300
agcaacggca gcggcgtgtt cggcggaggc acccagctga ccgtcctagg t             351
```

<210> SEQ ID NO 671
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 671

```
caggccgtgc tgacccagcc tgcctccctg tctgcctctc ctggcgagtc cgccagactg     60
acctgcaccc tgccctccga catcaacgtg cggtactaca acatctactg gtatcagcag    120
aagcccggca gccccccag atacctgctg tactactacg aggactccca aagggccag      180 ggctccggcg tgcctccag attctccggc tccaaggacg tgtccaccaa ctccggcatc    240
ctgctgatct ccggcctgca gtccgaggac attgccacct actactgcat gacttggagc    300
agcaacggca gcggcgtgtt cggcggaggc acccagctga ccgtcctagg t             351
```

<210> SEQ ID NO 672
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 672

```
caggccgtgc tgacccagcc tgcctccctg tctgcctctc ctggcgagtc cgccagactg     60
acctgcaccc tgccctccga catcaacgtg cggtactaca acatctactg gtatcagcag    120
aagcccggca gccccccag atacctgctg tactactacc aggactccca aagggccag      180
```

```
ggctccggcg tgccctccag attctccggc tccaaggacg tgtccaccaa ctccggcatc    240
ctgctgatct ccggcctgca gtccgaggac attgccacct actactgcat gacttggagc    300
agcaacggca gcggcgtgtt cggcggaggc acccagctga ccgtcctagg t             351
```

<210> SEQ ID NO 673
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 673

```
caggctgtgc tgacgcagcc ggccagcctc tccgcgtccc ctggcgaatc cgcacggctg     60
acttgcaccc tgccgagcga cattaacgtc ggtagctaca atatctactg gtaccaacaa    120
aagccgggga gcccacccg ctacttactg tattactact cggattccca taaaggacag    180
ggatcgggag tgccatcacg cttcagcgga tcgaaggatg tgtcgaccaa ttcgggaatc    240
ctgctcatct caggcttgca gagcgaggac atcgccacct actactgtct gacttggtca    300
tcccaggggt caggcgtgtt tggaggaggt acccagctga ctgtcctagg t             351
```

<210> SEQ ID NO 674
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 674

```
caggctgtgc tgacgcagcc ggccagcctc tccgcgtccc ctggcgaatc cgcacggctg     60
acttgcaccc tgccgagcga cattaacgtc ggtagctaca atatctactg gtaccaacaa    120
aagccgggga gcccacccg ctacttactg tattactact cggattccca taaaggacag    180
ggatcgggag tgccatcacg cttcagcgga tcgaaggatg tgtcgaccaa ttcgggaatc    240
ctgctcatct caggcttgca gagcgaggac atcgccacct actactgtct gacttggtca    300
tccgaagggt caggcgtgtt tggaggaggt acccagctga ctgtcctagg t             351
```

<210> SEQ ID NO 675
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 675

```
caggctgtgc tgacgcagcc ggccagcctc tccgcgtccc ctggcgaatc cgcacggctg     60
acttgcaccc tgccgagcga cattaacgtc ggtagctaca atatctactg gtaccaacaa    120
aagccgggga gcccacccg ctacttactg tattactacg aggattccca taaaggacag    180
ggatcgggag tgccatcacg cttcagcgga tcgaaggatg tgtcgaccac ctcgggaatc    240
ctgctcatct caggcttgca gagcgaggac atcgccacct actactgtct gacttggtca    300
```

```
tcccaggggt caggcgtgtt tggaggaggt acccagctga ctgtcctagg t          351
```

<210> SEQ ID NO 676
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 676

```
caggctgtgc tgacgcagcc ggccagcctc tccgcgtccc ctggcgaatc cgcacggctg   60
acttgcaccc tgccgagcga cattaacgtc ggtagctaca atatctactg gtaccaacaa  120
aagccgggga gcccaccccg ctacttactg tattactacg aggattccca taaaggacag  180
ggatcgggag tgccatcacg cttcagcgga tcgaaggatg tgtcgaccac ctcgggaatc  240
ctgctcatct caggcttgca gagcgaggac atcgccacct actactgtct gacttggtca  300
tccgaagggt caggcgtgtt tggaggaggt acccagctga ctgtcctagg t           351
```

<210> SEQ ID NO 677
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 677

```
caggctgtgc tgacgcagcc ggccagcctc tccgcgtccc ctggcgaatc cgcacggctg   60
acttgcaccc tgccgagcga cattaacgtc ggtagctaca atatctactg gtaccaacaa  120
aagccgggga gcccaccccg ctacttactg tattactacc aggattccca taaaggacag  180
ggatcgggag tgccatcacg cttcagcgga tcgaaggatg tgtcgaccac ctcgggaatc  240
ctgctcatct caggcttgca gagcgaggac atcgccacct actactgtct gacttggtca  300
tcccaggggt caggcgtgtt tggaggaggt acccagctga ctgtcctagg t           351
```

<210> SEQ ID NO 678
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 678

```
caggctgtgc tgacgcagcc ggccagcctc tccgcgtccc ctggcgaatc cgcacggctg   60
acttgcaccc tgccgagcga cattaacgtc ggtagctaca atatctactg gtaccaacaa  120
aagccgggga gcccaccccg ctacttactg tattactacc aggattccca taaaggacag  180
ggatcgggag tgccatcacg cttcagcgga tcgaaggatg tgtcgaccac ctcgggaatc  240
ctgctcatct caggcttgca gagcgaggac atcgccacct actactgtct gacttggtca  300
tccgaagggt caggcgtgtt tggaggaggt acccagctga ctgtcctagg t           351
```

<210> SEQ ID NO 679
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 679
gaggtgcagc tggtgcagtc cggcgctgaa gtgaagaaac ccggcgctac cgtgaagatc      60
tcctgcaagg tgtccggcta caccttcacc gactccgtga tgaactgggt gcagcaggag     120
cctggcaagg gcctggaatg gatgggctgg atcgaccccg agtacggcag aaccgacgtg     180
gccgagaagt tccagggcag agtgaccatc accgccgaca cctccaccga caccgcctac     240
atggaactgt cctccctgcg gagcgaggac accgccgtgt actactgcgc ccggaccaag     300
tacaactccg gctacggctt ccccctactgg ggccagggca ccaccgtgac agtgtcctca     360

<210> SEQ ID NO 680
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 680
gaggtgcagc tggtgcagtc cggcgctgaa gtgaagaaac ccggcgctac cgtgaagatc      60
tcctgcaagg tgtccggcta caccttcacc gactccgtga tgaactgggt gcagcagggc     120
cctggcaagg gcctggaatg gatgggctgg atcgaccccg agtacggcag aaccgacgtg     180
gccgagaagt tccagggcag agtgaccatc accgccgaca cctccaccga caccgcctac     240
atggaactgt cctccctgcg gagcgaggac accgccgtgt actactgcgc ccggaccaag     300
tacaactccg gctacggctt ccccctactgg ggccagggca ccaccgtgac agtgtcctca     360

<210> SEQ ID NO 681
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 681
gaggtgcagc tggtgcagtc cggcgctgaa gtgaagaaac ccggcgctac cgtgaagatc      60
tcctgcaagg tgtccggcta caccttcacc gactccgtga tgaactgggt gcagcagcac     120
cctggcaagg gcctggaatg gatgggctgg atcgaccccg agtacggcag aaccgacgtg     180
gccgagaagt tccagggcag agtgaccatc accgccgaca cctccaccga caccgcctac     240
atggaactgt cctccctgcg gagcgaggac accgccgtgt actactgcgc ccggaccaag     300
tacaactccg gctacggctt ccccctactgg ggccagggca ccaccgtgac agtgtcctca     360

<210> SEQ ID NO 682
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 682
gaggtgcagc tggtgcagtc cggcgctgaa gtgaagaaac ccggcgctac cgtgaagatc    60
tcctgcaagg tgtccggcta caccttcacc gactccgtga tgaactgggt gcagcagcag   120
cctggcaagg gcctggaatg gatgggctgg atcgaccccg agtacggcag aaccgacgtg   180
gccgagaagt tccagggcag agtgaccatc accgccgaca cctccaccga caccgcctac   240
atggaactgt cctccctgcg gagcgaggac accgccgtgt actactgcgc ccggaccaag   300
tacaactccg gctacggctt cccctactgg ggccagggca ccaccgtgac agtgtcctca   360

<210> SEQ ID NO 683
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 683
gaggtgcagc tggtgcagtc cggcgctgaa gtgaagaaac ccggcgctac cgtgaagatc    60
tcctgcaagg tgtccggcta caccttcacc gactccgtga tgaactgggt gcagcaggcc   120
cctggcaagg gcctggaatg gatgggctgg atcgaccccg agtacggcag aaccgacgtg   180
gccgagaagt tccagggcag agtgaccatc accgccgaca cctccaccga caccgcctac   240
atggaactgt cctccctgcg gagcgaggac accgccgtgt actactgcgc ccggaccggc   300
tacaactccg gctacggctt cccctactgg ggccagggca ccaccgtgac agtgtcctca   360

<210> SEQ ID NO 684
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 684
gaggtgcagc tggtgcagtc cggcgctgaa gtgaagaaac ccggcgctac cgtgaagatc    60
tcctgcaagg tgtccggcta caccttcacc gactccgtga tgaactgggt gcagcaggcc   120
cctggcaagg gcctggaatg gatgggctgg atcgaccccg agtacggcag aaccgacgtg   180
gccgagaagt tccagggcag agtgaccatc accgccgaca cctccaccga caccgcctac   240
atggaactgt cctccctgcg gagcgaggac accgccgtgt actactgcgc ccggaccacc   300
tacaactccg gctacggctt cccctactgg ggccagggca ccaccgtgac agtgtcctca   360

<210> SEQ ID NO 685
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: Completely synthesized

<400> SEQUENCE: 685

```
gaggtgcagc tggtgcagtc cggcgctgaa gtgaagaaac ccggcgctac cgtgaagatc      60
tcctgcaagg tgtccggcta caccttcacc gactccgtga tgaactgggt gcagcaggcc     120
cctggcaagg gcctggaatg gatgggctgg atcgacaccg agtacggcag aaccgacgtg     180
gccgagaagt tccagggcag agtgaccatc accgccgaca cctccaccga caccgcctac     240
atggaactgt cctccctgcg gagcgaggac accgccgtgt actactgcgc ccggaccaag     300
tacaactccg gctacggctt ccctactgg ggccagggca ccaccgtgac agtgtcctca      360
```

<210> SEQ ID NO 686
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 686

```
gaggtgcagc tggtgcagtc cggcgctgaa gtgaagaaac ccggcgctac cgtgaagatc      60
tcctgcaagg tgtccggcta caccttcacc gactccgtga tgaactgggt gcagcaggcc     120
cctggcaagg gcctggaatg gatgggctgg atcgaccccg agtacggcag aaccgacgtg     180
gccgagaagt tccagggcag agtgaccatc accgccgaca cctccaccga caccgcctac     240
atggaactgt cctccctgcg gagcgaggac accgccgtgt actactgcgc ccctaccaag     300
tacaactccg gctacggctt ccctactgg ggccagggca ccaccgtgac agtgtcctca      360
```

<210> SEQ ID NO 687
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 687

```
caggtgcagc tggtgcagtc cggcgctgaa gtgaagaaac ccggcgcttc cgtgaaggtg      60
tcctgcaagg tgtccggcta caccctgacc gactccgtga tgaactgggt gcgacaggcc     120
cctggcaagg gcctggaatg gatgggctgg atcgaccccg agtacggcag aaccgacgtg     180
gcccagaaat tccagggcag agtgaccatg accgccgaca cctccaccga caccgcctac     240
atggaactgt cctccctgcg gagcgaggac accgccgtgt actactgcgc ccggaccaag     300
tacaactccg gctacggctt ccctactgg ggccagggca ccaccgtgac cgtgtcctca      360
```

<210> SEQ ID NO 688
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 688

| | |
|---|---|
| gacatccaga tgacccagag cccttccagc ctgtccgcct ctgtgggcga cagagtgacc | 60 |
| atcacatgca aggcctccca gaacgtggac agcgacgtgg actggtatca gcagaagccc | 120 |
| ggcaaggccc ctaagctgct gatctacaag gccagcaaca gatacaccgg cgtgccctcc | 180 |
| agattctccg gctctggatc tggcaccgac ttcaccttca ccatcagctc cctgcagccc | 240 |
| gaggacattg ccacctacta ctgtatgcag tccaacaccc accccggac cttcggcgga | 300 |
| ggcaccaagg tggaaatcaa gcgt | 324 |

<210> SEQ ID NO 689
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 689

| | |
|---|---|
| gacatccaga tgacccagag cccttccagc ctgtccgcct ctgtgggcga cagagtgacc | 60 |
| atcacatgcg gcgcctccca gaacgtggac agcgacgtgg actggtatca gcagaagccc | 120 |
| ggcaaggccc ctaagctgct gatctacaag gccagcaaca gatacaccgg cgtgccctcc | 180 |
| agattctccg gctctggatc tggcaccgac ttcaccttca ccatcagctc cctgcagccc | 240 |
| gaggacattg ccacctacta ctgtatgcag tccaacaccc accccggac cttcggcgga | 300 |
| ggcaccaagg tggaaatcaa gcgt | 324 |

<210> SEQ ID NO 690
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 690

| | |
|---|---|
| gacatccaga tgacccaatc cccttcctca ttgtccgctt cggtcggcga ccgcgtgact | 60 |
| atcacttgcc aggcatcaca aaacgtggat tcggatgtgg attggtacca gcagaagccc | 120 |
| ggaaaggccc cgaaactgct gatctacaag gcgtccaacc ggtacactgg cgtcccgtcg | 180 |
| agattcagcg gaagcgggtc gggaaccgac tttaccttca ctatcagctc actccagcca | 240 |
| gaggacattg ccacctatta ctgtatgcag agcaataccc acccgcgcac cttcggagga | 300 |
| ggtactaaag tggaaatcaa gcgt | 324 |

<210> SEQ ID NO 691
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 691

| | |
|---|---|
| gacatccaga tgacccagag cccttccagc ctgtccgcct ctgtgggcga cagagtgacc | 60 |
| atcacatgca aggcctccca gaacgtggac agcgacgtgg actggtatca gcagaagccc | 120 |

```
ggcaaggccc ctaagctgct gatctacaag gccagcaacg actacaccgg cgtgccctcc    180
agattctccg gctctggatc tggcaccgac ttcaccttca ccatcagctc cctgcagccc    240
gaggacattg ccacctacta ctgtatgcag tccaacaccc accccggac cttcggcgga    300 ggcaccaagg tggaaatcaa gcgt                                          324
```

<210> SEQ ID NO 692
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 692

```
gacatccaga tgacccagag cccttccagc ctgtccgcct ctgtgggcga cagagtgacc     60
atcacatgca aggcctccca gaacgtggac agcgacgtgg actggtatca gcagaagccc    120
ggcaaggccc ctaagctgct gatctacaag gccagcaaca gatacaccgg cgtgccctcc    180
agattctccg gctctggatc tggcaccgac ttcaccttca ccatcagctc cctgcagccc    240
gaggacattg ccacctacta ctgtgcgcag tccaacaccc accccggac cttcggcgga    300 ggcaccaagg tggaaatcaa gcgt                                          324
```

<210> SEQ ID NO 693
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 693

```
gacatccaga tgacccaatc cccttcctca ttgtccgctt cggtcggcga ccgcgtgact     60
atcacttgca aagcatcaca aaacgtggat tcggatgtgg attggtacca gcagaagccc    120
ggaaaggccc cgaaactgct gatctacaag gcgtcccagc ggtacactgg cgtcccgtcg    180
agattcagcg gaagcgggtc gggaaccgac tttaccttca ctatcagctc actccagcca    240
gaggacattg ccacctatta ctgtatgcag agcaataccc accgcgcac cttcggagga    300 ggtactaaag tggaaatcaa gcgt                                          324
```

<210> SEQ ID NO 694
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 694

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys Cys Asp Leu Pro Gln Thr His Ser Leu
                325                 330                 335

Gly Ser Arg Arg Thr Leu Met Leu Leu Ala Gln Met Arg Arg Ile Ser
            340                 345                 350

Leu Phe Ser Cys Leu Lys Asp Arg His Asp Phe Gly Phe Pro Gln Glu
        355                 360                 365

Glu Phe Gly Asn Gln Phe Gln Lys Ala Glu Thr Ile Pro Val Leu His
    370                 375                 380

Glu Met Ile Gln Gln Ile Phe Asn Leu Phe Ser Thr Lys Asp Ser Ser
385                 390                 395                 400

Ala Ala Trp Asp Glu Thr Leu Leu Asp Lys Phe Tyr Thr Glu Leu Tyr
                405                 410                 415

Gln Gln Leu Asn Asp Leu Glu Ala Cys Val Ile Gln Gly Val Gly Val
            420                 425                 430

Thr Glu Thr Pro Leu Met Lys Glu Asp Ser Ile Leu Ala Val Arg Lys
        435                 440                 445

Tyr Phe Gln Arg Ile Thr Leu Tyr Leu Lys Glu Lys Lys Tyr Ser Pro
    450                 455                 460
```

```
Cys Ala Trp Glu Val Val Arg Gly Glu Ile Met Arg Ser Phe Ser Leu
465                 470                 475                 480

Ser Thr Asn Leu Gln Glu Ser Leu Arg Ser Lys Glu
                485                 490
```

<210> SEQ ID NO 695
<211> LENGTH: 366
<212> TYPE: DNA
<213> ORGANISM: Homo sapiens

<400> SEQUENCE: 695

```
gaggtccagc tggtacagtc tggggctgag gtgaagaagt ctggggcctc agtgaaggtc      60
tcctgcaagg cttctggata caccttcacc gactactata tacactgggt gcgacaggcc     120
cctggacaag ggcttgagtg gatgggatgg atcaaccctaa acaatggtgg cgtaaccttt    180
gcccagaagt ttcagggcag ggtcaccatg accagggaca cgtccatcag cacagcctac    240
atggacctga gcagcctgag atctgacgac acggccgtct acttctgtgc gagagatatt    300
cgaatgagcg gtggctggc gccatttgac tactggggcc agggaaccct ggtcaccgtc     360
tcctca                                                                366
```

<210> SEQ ID NO 696
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 696

```
Gly Ala Ser Gln Asn Val Asp Ser Asp Val Asp
1               5                   10
```

<210> SEQ ID NO 697
<211> LENGTH: 5
<212> TYPE: PRT
<213> ORGANISM: Homo sapiens

<400> SEQUENCE: 697

```
Asp Tyr Tyr Ile His
1               5
```

<210> SEQ ID NO 698
<211> LENGTH: 17
<212> TYPE: PRT
<213> ORGANISM: Homo sapiens

<400> SEQUENCE: 698

```
Trp Ile Asn Pro Asn Asn Gly Gly Val Thr Phe Ala Gln Lys Phe Gln
1               5                   10                  15

Gly
```

<210> SEQ ID NO 699
<211> LENGTH: 13
<212> TYPE: PRT
<213> ORGANISM: Homo sapiens

<400> SEQUENCE: 699

```
Asp Ile Arg Met Ser Gly Trp Leu Ala Pro Phe Asp Tyr
1               5                   10
```

-continued

```
<210> SEQ ID NO 700
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 700

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Gln Gly Ser Gly Val Phe Gly Gly Gly Thr Gln
            100                 105                 110

Leu Thr Val Leu Gly
        115

<210> SEQ ID NO 701
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 701

Gln Ala Val Leu Thr Gln Pro Ala Ser Leu Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser His Lys Gly Gln Gly Ser Gly Val
    50                  55                  60

Pro Ser Arg Phe Ser Gly Ser Lys Asp Val Ser Thr Thr Ser Gly Ile
65                  70                  75                  80

Leu Leu Ile Ser Gly Leu Gln Ser Glu Asp Ile Ala Thr Tyr Tyr Cys
                85                  90                  95

Leu Thr Trp Ser Ser Glu Gly Ser Gly Val Phe Gly Gly Gly Thr Gln
            100                 105                 110

Leu Thr Val Leu Gly
        115

<210> SEQ ID NO 702
<211> LENGTH: 351
<212> TYPE: DNA
<213> ORGANISM: Artificial Sequence
```

<220> FEATURE:
<223> OTHER INFORMATION: Description of Artificial Sequence: Synthetic
    polynucleotide
<220> FEATURE:
<223> OTHER INFORMATION: Completely synthesized

<400> SEQUENCE: 702
caagccgtcc tgactcagcc agccagcctg tccgcgtcac cgggagaatc cgctcgcctg    60
acttgcactc tgccctcaga catcaatgtc ggttcgtaca acatctactg gtaccaacaa   120
aagccggggt cgcctccgcg gtatctgttg tactactact cggatagcca caagggacag   180
ggctcgggag tgccatccag attttccggg tcaaaagatg tgagcacgac ctcgggcatc   240
ctcctcatca gcggacttca gtccgaggac attgcgacct actactgcct cacttggtcg   300
tcacagggaa gcggagtgtt cggaggaggc acccagctga ccgtcctagg t            351

<210> SEQ ID NO 703
<211> LENGTH: 351
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Completely synthesized

<400> SEQUENCE: 703
caagccgtcc tgactcagcc agccagcctg tccgcgtcac cgggagaatc cgctcgcctg    60
acttgcactc tgccctcaga catcaatgtc ggttcgtaca acatctactg gtaccaacaa   120
aagccggggt cgcctccgcg gtatctgttg tactactact cggatagcca caagggacag   180
ggctcgggag tgccatccag attttccggg tcaaaagatg tgagcacgac ctcgggcatc   240
ctcctcatca gcggacttca gtccgaggac attgcgacct actactgcct cacttggtcg   300
tcagaaggaa gcggagtgtt cggaggaggc acccagctga ccgtcctagg t            351

<210> SEQ ID NO 704
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Completely synthesized

<400> SEQUENCE: 704

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105

<210> SEQ ID NO 705
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 705

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105
```

<210> SEQ ID NO 706
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 706

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
            100                 105
```

<210> SEQ ID NO 707
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 707

| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Gln | Ala | Ser | Gln | Asn | Val | Asp | Ser | Asp |
| | | | 20 | | | | | 25 | | | | | 30 | | |

| Val | Asp | Trp | Tyr | Gln | Gln | Lys | Pro | Gly | Lys | Ala | Pro | Lys | Leu | Leu | Ile |
| | | | 35 | | | | | 40 | | | | | 45 | | |

| Tyr | Lys | Ala | Ser | Asn | Arg | Tyr | Thr | Gly | Val | Pro | Ser | Arg | Phe | Ser | Gly |
| | 50 | | | | | 55 | | | | | 60 | | | | |

| Ser | Gly | Ser | Gly | Thr | Asp | Phe | Thr | Phe | Thr | Ile | Ser | Ser | Leu | Gln | Pro |
| 65 | | | | | 70 | | | | | 75 | | | | | 80 |

| Glu | Asp | Ile | Ala | Thr | Tyr | Tyr | Cys | Ala | Gln | Ser | Asn | Thr | His | Pro | Arg |
| | | | | 85 | | | | | 90 | | | | | 95 | |

| Thr | Phe | Gly | Gly | Gly | Thr | Lys | Val | Glu | Ile | Lys | Arg |
| | | | | 100 | | | | | 105 | | |

<210> SEQ ID NO 708
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Completely synthesized

<400> SEQUENCE: 708

| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Gly | Ala | Ser | Gln | Asn | Val | Asp | Ser | Asp |
| | | | 20 | | | | | 25 | | | | | 30 | | |

| Val | Asp | Trp | Tyr | Gln | Gln | Lys | Pro | Gly | Lys | Ala | Pro | Lys | Leu | Leu | Ile |
| | | | 35 | | | | | 40 | | | | | 45 | | |

| Tyr | Lys | Ala | Ser | Gln | Asp | Tyr | Thr | Gly | Val | Pro | Ser | Arg | Phe | Ser | Gly |
| | 50 | | | | | 55 | | | | | 60 | | | | |

| Ser | Gly | Ser | Gly | Thr | Asp | Phe | Thr | Phe | Thr | Ile | Ser | Ser | Leu | Gln | Pro |
| 65 | | | | | 70 | | | | | 75 | | | | | 80 |

| Glu | Asp | Ile | Ala | Thr | Tyr | Tyr | Cys | Ala | Gln | Ser | Asn | Thr | His | Pro | Arg |
| | | | | 85 | | | | | 90 | | | | | 95 | |

| Thr | Phe | Gly | Gly | Gly | Thr | Lys | Val | Glu | Ile | Lys | Arg |
| | | | | 100 | | | | | 105 | | |

<210> SEQ ID NO 709
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Completely synthesized

<400> SEQUENCE: 709

| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Gly | Ala | Ser | Gln | Asn | Val | Asp | Ser | Asp |
| | | | 20 | | | | | 25 | | | | | 30 | | |

| Val | Asp | Trp | Tyr | Gln | Gln | Lys | Pro | Gly | Lys | Ala | Pro | Lys | Leu | Leu | Ile |
| | | | 35 | | | | | 40 | | | | | 45 | | |

```
Tyr Lys Ala Ser Gln Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
                100                 105
```

<210> SEQ ID NO 710
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 710

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Gln Asp Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
                100                 105
```

<210> SEQ ID NO 711
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 711

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Gln Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Gln Ser Asn Thr His Pro Arg
                85                  90                  95

Thr Phe Gly Gly Gly Thr Lys Val Glu Ile Lys Arg
                100                 105
```

<210> SEQ ID NO 712
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 712

```
gacatccaga tgactcagag cccgtcctcg ctttcggctt ccgtcggcga ccgcgtgacc      60
atcacttgtg gcgcgtcgca gaacgtcgat tccgacgtgg actggtacca acagaagccg     120
gggaaagcgc ccaagctgct gatctacaag gcctccaatg attacactgg agtgcctagc     180
cggttcagcg gatcagggtc gggaacggac ttcactttta ccatctcaag cctccaacca    240
gaagatattg ccacctatta ctgcgcacaa tcaaacaccc acccgagaac cttcggcgga    300
ggaaccaagg tggagatcaa acgt                                           324
```

<210> SEQ ID NO 713
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 713

```
gacatccaga tgactcagag cccgtcctcg ctttcggctt ccgtcggcga ccgcgtgacc      60
atcacttgtg gcgcgtcgca gaacgtcgat tccgacgtgg actggtacca acagaagccg     120
gggaaagcgc ccaagctgct gatctacaag gcctccaatc gctacactgg agtgcctagc     180
cggttcagcg gatcagggtc gggaacggac ttcactttta ccatctcaag cctccaacca    240
gaagatattg ccacctatta ctgcgcacaa tcaaacaccc acccgagaac cttcggcgga    300
ggaaccaagg tggagatcaa acgt                                           324
```

<210> SEQ ID NO 714
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 714

```
gacatccaga tgactcagag cccgtcctcg ctttcggctt ccgtcggcga ccgcgtgacc      60
atcacttgtc aggcgtcgca gaacgtcgat tccgacgtgg actggtacca acagaagccg     120
gggaaagcgc ccaagctgct gatctacaag gcctccaatg attacactgg agtgcctagc     180
cggttcagcg gatcagggtc gggaacggac ttcactttta ccatctcaag cctccaacca    240
gaagatattg ccacctatta ctgcgcacaa tcaaacaccc acccgagaac cttcggcgga    300
ggaaccaagg tggagatcaa acgt                                           324
```

<210> SEQ ID NO 715
<211> LENGTH: 324

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 715
gacatccaga tgactcagag cccgtcctcg ctttcggctt ccgtcggcga ccgcgtgacc     60
atcacttgtc aggcgtcgca gaacgtcgat tccgacgtgg actggtacca acagaagccg    120
gggaaagcgc ccaagctgct gatctacaag gcctccaatc gctacactgg agtgcctagc    180
cggttcagcg gatcagggtc gggaacggac ttcacttta ccatctcaag cctccaacca     240
gaagatattg ccacctatta ctgcgcacaa tcaaacaccc acccgagaac cttcggcgga    300
ggaaccaagg tggagatcaa acgt                                           324

<210> SEQ ID NO 716
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 716
gacatccaga tgactcagag cccgtcctcg ctttcggctt ccgtcggcga ccgcgtgacc     60
atcacttgtg gcgcgtcgca gaacgtcgat tccgacgtgg actggtacca acagaagccg    120
gggaaagcgc ccaagctgct gatctacaag gcctcccagg attacactgg agtgcctagc    180
cggttcagcg gatcagggtc gggaacggac ttcacttta ccatctcaag cctccaacca     240
gaagatattg ccacctatta ctgcgcacaa tcaaacaccc acccgagaac cttcggcgga    300
ggaaccaagg tggagatcaa acgt                                           324

<210> SEQ ID NO 717
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 717
gacatccaga tgactcagag cccgtcctcg ctttcggctt ccgtcggcga ccgcgtgacc     60
atcacttgtg gcgcgtcgca gaacgtcgat tccgacgtgg actggtacca acagaagccg    120
gggaaagcgc ccaagctgct gatctacaag gcctcccagc gctacactgg agtgcctagc    180
cggttcagcg gatcagggtc gggaacggac ttcacttta ccatctcaag cctccaacca     240
gaagatattg ccacctatta ctgcgcacaa tcaaacaccc acccgagaac cttcggcgga    300
ggaaccaagg tggagatcaa acgt                                           324

<210> SEQ ID NO 718
<211> LENGTH: 324
<212> TYPE: DNA
<213> ORGANISM: Artificial Sequence
<220> FEATURE:
<223> OTHER INFORMATION: Description of Artificial Sequence: Synthetic

```
polynucleotide
<220> FEATURE:
<223> OTHER INFORMATION: Completely synthesized

<400> SEQUENCE: 718
gacatccaga tgactcagag cccgtcctcg ctttcggctt ccgtcggcga ccgcgtgacc    60
atcacttgtc aggcgtcgca gaacgtcgat tccgacgtgg actggtacca acagaagccg   120
gggaaagcgc ccaagctgct gatctacaag gcctcccagg attacactgg agtgcctagc   180
cggttcagcg gatcagggtc gggaacggac ttcacttta ccatctcaag cctccaacca    240
gaagatattg ccacctatta ctgcgcacaa tcaaacaccc acccgagaac cttcggcgga   300
ggaaccaagg tggagatcaa acgt                                          324

<210> SEQ ID NO 719
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 719
gacatccaga tgactcagag cccgtcctcg ctttcggctt ccgtcggcga ccgcgtgacc    60
atcacttgtc aggcgtcgca gaacgtcgat tccgacgtgg actggtacca acagaagccg   120
gggaaagcgc ccaagctgct gatctacaag gcctcccagc gctacactgg agtgcctagc   180
cggttcagcg gatcagggtc gggaacggac ttcacttta ccatctcaag cctccaacca    240
gaagatattg ccacctatta ctgcgcacaa tcaaacaccc acccgagaac cttcggcgga   300
ggaaccaagg tggagatcaa acgt                                          324

<210> SEQ ID NO 720
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 720

Gln Val Gln Leu Val Gln Ser Gly Ala Glu Val Lys Lys Pro Gly Ala
1               5                  10                  15

Ser Val Lys Val Ser Cys Lys Val Ser Gly Tyr Thr Leu Thr Asp Ser
            20                  25                  30

Val Met Asn Trp Val Arg Gln Gly Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Asn Ser Gly Tyr Gly Phe Pro Tyr Trp Gly Gln
            100                 105                 110

Gly Thr Thr Val Thr Val Ser Ser
        115                 120
```

```
<210> SEQ ID NO 721
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 721

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln His Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 722
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 722

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln Gly Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Gln Ser Gly Tyr Gly Phe Pro Tyr Trp Gly Gln
            100                 105                 110

Gly Thr Thr Val Thr Val Ser Ser
        115                 120

<210> SEQ ID NO 723
<211> LENGTH: 120
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 723

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Ser
            20                  25                  30

Val Met Asn Trp Val Arg Gln His Pro Gly Lys Gly Leu Glu Trp Met
        35                  40                  45

Gly Trp Ile Asp Pro Glu Tyr Gly Arg Thr Asp Val Ala Gln Lys Phe
    50                  55                  60

Gln Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Gln Ser Gly Tyr Gly Phe Pro Tyr Trp Gly Gln
            100                 105                 110

Gly Thr Thr Val Thr Val Ser Ser
        115                 120
```

<210> SEQ ID NO 724
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 724

```
caagtgcaac tggtgcagtc cggtgccgaa gtgaagaaac cgggtgcgtc cgtcaaagtg     60
agctgcaagg tgtccgggta caccttgact gattcagtga tgaattgggt gcggcagggg    120
ccaggaaagg gactggagtg gatgggatgg atcgaccctg aatacggaag gactgacgtc    180
gcccagaagt ttcagggacg cgtcacgatg actgccgata cttcgaccga cacggcttac    240
atggaactct cgtccctgag atcggaggac accgcagtct actactgtgc tcgcactggc    300
tataactcag gctacggctt cccgtactgg ggacaaggaa ccaccgtgac agtgtcctca    360
```

<210> SEQ ID NO 725
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 725

```
caagtgcaac tggtgcagtc cggtgccgaa gtgaagaaac cgggtgcgtc cgtcaaagtg     60
agctgcaagg tgtccgggta caccttgact gattcagtga tgaattgggt gcggcagcac    120
ccaggaaagg gactggagtg gatgggatgg atcgaccctg aatacggaag gactgacgtc    180
gcccagaagt ttcagggacg cgtcacgatg actgccgata cttcgaccga cacggcttac    240
```

```
atggaactct cgtccctgag atcggaggac accgcagtct actactgtgc tcgcactggc    300
tataactcag gctacggctt cccgtactgg ggacaaggaa ccaccgtgac agtgtcctca    360
```

<210> SEQ ID NO 726
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 726

```
caagtgcaac tggtgcagtc cggtgccgaa gtgaagaaac cgggtgcgtc cgtcaaagtg     60
agctgcaagg tgtccgggta caccttgact gattcagtga tgaattgggt gcggcagggg    120
ccaggaaagg gactggagtg gatgggatgg atcgaccctg aatacggaag gactgacgtc    180
gcccagaagt tcagggacg cgtcacgatg actgccgata cttcgaccga cacggcttac    240
atggaactct cgtccctgag atcggaggac accgcagtct actactgtgc tcgcactggc    300
tatcagtcag gctacggctt cccgtactgg ggacaaggaa ccaccgtgac agtgtcctca    360
```

<210> SEQ ID NO 727
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 727

```
caagtgcaac tggtgcagtc cggtgccgaa gtgaagaaac cgggtgcgtc cgtcaaagtg     60
agctgcaagg tgtccgggta caccttgact gattcagtga tgaattgggt gcggcagcac    120
ccaggaaagg gactggagtg gatgggatgg atcgaccctg aatacggaag gactgacgtc    180
gcccagaagt tcagggacg cgtcacgatg actgccgata cttcgaccga cacggcttac    240
atggaactct cgtccctgag atcggaggac accgcagtct actactgtgc tcgcactggc    300
tatcagtcag gctacggctt cccgtactgg ggacaaggaa ccaccgtgac agtgtcctca    360
```

<210> SEQ ID NO 728
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 728

```
Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Pro Pro Gly Gln Gly Leu Glu Trp Met
        35                  40                  45

Gly Trp Ile Asn Pro Asn Asn Gly Gly Val Thr Phe Ala Gln Lys Phe
    50                  55                  60
```

```
Gln Gly Arg Val Thr Met Thr Arg Asp Thr Ser Ile Ser Thr Ala Tyr
 65                  70                  75                  80

Met Asp Leu Ser Ser Leu Arg Ser Asp Thr Ala Val Tyr Phe Cys
                 85                  90                  95

Ala Arg Asp Ile Arg Met Ser Gly Trp Leu Ala Pro Phe Asp Tyr Trp
            100                 105                 110

Gly Gln Gly Thr Leu Val Thr Val Ser Ser
        115                 120

<210> SEQ ID NO 729
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 729

Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Pro Pro Gly Gln Gly Leu Glu Trp Met
        35                  40                  45

Gly Trp Ile Asn Pro Asn Asn Gly Gly Val Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Thr Ala Val Tyr Tyr Cys
                85                  90                  95

Ala Arg Asp Ile Arg Met Ser Gly Trp Leu Ala Pro Phe Asp Tyr Trp
            100                 105                 110

Gly Gln Gly Thr Leu Val Thr Val Ser Ser
        115                 120

<210> SEQ ID NO 730
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 730

Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Pro Pro Gly Gln Gly Leu Glu Trp Met
        35                  40                  45

Gly Trp Ile Asn Pro Asn Asn Gly Gly Thr Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Asp Thr Ala Val Tyr Phe Cys
                85                  90                  95
```

-continued

Ala Arg Asp Ile Arg Met Ser Gly Trp Leu Ala Pro Phe Asp Tyr Trp
            100                 105                 110

Gly Gln Gly Thr Leu Val Thr Val Ser Ser
        115                 120

<210> SEQ ID NO 731
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 731

Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Pro Pro Gly Gln Gly Leu Glu Trp Met
        35                  40                  45

Gly Trp Ile Asn Pro Asn Asn Gly Gly Val Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Asp Thr Ala Val Tyr Phe Cys
                85                  90                  95

Ala Arg Asp Ile Arg Leu Ser Gly Trp Leu Ala Pro Phe Asp Tyr Trp
            100                 105                 110

Gly Gln Gly Thr Leu Val Thr Val Ser Ser
        115                 120

<210> SEQ ID NO 732
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 732
gaagtccaac tggtccagtc gggcgcagag gtgaagaagt caggggcgag cgtgaaagtg      60
tcatgtaaag cctccggcta cactttacc gattactaca ttcactgggt gagacagcct     120
ccgggacaag gactcgaatg gatgggctgg atcaatccaa acaacggagg tgtcaccttc     180
gctcagaagt tccaaggtcg ggtgaccatg acccgcgaca cgtcaatcag cactgcctac     240
atggatttgt cgtccctgcg gtccgatgac actgcggtgt acttctgcgc aagggacatc     300
cgcatgtcgg ggtggctggc cccgttcgac tattgggac agggaactct cgtgacagtg     360
tcctca                                                                366

<210> SEQ ID NO 733
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: Completely synthesized

<400> SEQUENCE: 733

```
gaagtccaac tggtccagtc gggcgcagag gtgaagaagt caggggcgag cgtgaaagtg    60
tcatgtaaag cctccggcta cacttttacc gattactaca ttcactgggt gagacagcct   120
ccgggacaag gactcgaatg gatgggctgg atcaatccaa acaacggagg tgtcaccttc   180
gctcagaagt tccaaggtcg ggtgaccatg acccgcgaca cgtcaatcag cactgcctac   240
atggatttgt cgtccctgcg gtccgatgac actgcggtgt actactgcgc aagggacatc   300
cgcatgtcgg ggtggctggc cccgttcgac tattggggac agggaactct cgtgacagtg   360
tcctca                                                              366
```

<210> SEQ ID NO 734
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Completely synthesized

<400> SEQUENCE: 734

```
gaagtccaac tggtccagtc gggcgcagag gtgaagaagt caggggcgag cgtgaaagtg    60
tcatgtaaag cctccggcta cacttttacc gattactaca ttcactgggt gagacagcct   120
ccgggacaag gactcgaatg gatgggctgg atcaatccaa acaacggagg taccaccttc   180
gctcagaagt tccaaggtcg ggtgaccatg acccgcgaca cgtcaatcag cactgcctac   240
atggatttgt cgtccctgcg gtccgatgac actgcggtgt acttctgcgc aagggacatc   300
cgcatgtcgg ggtggctggc cccgttcgac tattggggac agggaactct cgtgacagtg   360
tcctca                                                              366
```

<210> SEQ ID NO 735
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Completely synthesized

<400> SEQUENCE: 735

```
gaagtccaac tggtccagtc gggcgcagag gtgaagaagt caggggcgag cgtgaaagtg    60
tcatgtaaag cctccggcta cacttttacc gattactaca ttcactgggt gagacagcct   120
ccgggacaag gactcgaatg gatgggctgg atcaatccaa acaacggagg tgtcaccttc   180
gctcagaagt tccaaggtcg ggtgaccatg acccgcgaca cgtcaatcag cactgcctac   240
atggatttgt cgtccctgcg gtccgatgac actgcggtgt acttctgcgc aagggacatc   300
cgcctgtcgg ggtggctggc cccgttcgac tattggggac agggaactct cgtgacagtg   360
tcctca                                                              366
```

<210> SEQ ID NO 736
<211> LENGTH: 122
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: Completely synthesized
<220> FEATURE:
<221> NAME/KEY: MOD_RES
<222> LOCATION: (40)..(40)
<223> OTHER INFORMATION: Ala or Pro
<220> FEATURE:
<221> NAME/KEY: MOD_RES
<222> LOCATION: (58)..(58)
<223> OTHER INFORMATION: Val or Thr
<220> FEATURE:
<221> NAME/KEY: MOD_RES
<222> LOCATION: (95)..(95)
<223> OTHER INFORMATION: Phe or Tyr
<220> FEATURE:
<221> NAME/KEY: MOD_RES
<222> LOCATION: (102)..(102)
<223> OTHER INFORMATION: Met or Leu

<400> SEQUENCE: 736

Glu Val Gln Leu Val Gln Ser Gly Ala Glu Val Lys Lys Ser Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Xaa Pro Gly Gln Gly Leu Glu Trp Met
        35                  40                  45

Gly Trp Ile Asn Pro Asn Asn Gly Gly Xaa Thr Phe Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Ser Leu Arg Ser Asp Thr Ala Val Tyr Xaa Cys
                85                  90                  95

Ala Arg Asp Ile Arg Xaa Ser Gly Trp Leu Ala Pro Phe Asp Tyr Trp
            100                 105                 110

Gly Gln Gly Thr Leu Val Thr Val Ser Ser
        115                 120

<210> SEQ ID NO 737
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 737

Trp Ile Asn Pro Asn Asn Gly Gly Thr Thr Phe Ala Gln Lys Phe Gln
1               5                   10                  15

Gly

<210> SEQ ID NO 738
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 738

Asp Ile Arg Leu Ser Gly Trp Leu Ala Pro Phe Asp Tyr

<210> SEQ ID NO 739
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Completely synthesized

<400> SEQUENCE: 739

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Asn Trp Val Gln Gln Gly Pro Gly Lys Gly Leu Glu Trp Met
            35                  40                  45

Gly Trp Ile Asp Pro Glu Tyr Gly Arg Thr Asp Val Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 740
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Completely synthesized

<400> SEQUENCE: 740

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Asn Trp Val Gln Gln His Pro Gly Lys Gly Leu Glu Trp Met
            35                  40                  45

Gly Trp Ile Asp Pro Glu Tyr Gly Arg Thr Asp Val Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Asn Ser Gly Tyr Gly Phe Pro Tyr Trp Gly Gln
                100                 105                 110

Gly Thr Thr Val Thr Val Ser Ser
            115                 120

<210> SEQ ID NO 741
<211> LENGTH: 120

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 741

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Asn Trp Val Gln Gln Gly Pro Gly Lys Gly Leu Glu Trp Met
            35                  40                  45

Gly Trp Ile Asp Pro Glu Tyr Gly Arg Thr Asp Val Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Gln Ser Gly Tyr Gly Phe Pro Tyr Trp Gly Gln
                100                 105                 110

Gly Thr Thr Val Thr Val Ser Ser
            115                 120

<210> SEQ ID NO 742
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 742

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
                20                  25                  30

Val Met Asn Trp Val Gln Gln His Pro Gly Lys Gly Leu Glu Trp Met
            35                  40                  45

Gly Trp Ile Asp Pro Glu Tyr Gly Arg Thr Asp Val Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Tyr Gln Ser Gly Tyr Gly Phe Pro Tyr Trp Gly Gln
                100                 105                 110

Gly Thr Thr Val Thr Val Ser Ser
            115                 120

<210> SEQ ID NO 743
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide <220> FEATURE:
<223> OTHER INFORMATION: Completely synthesized

<400> SEQUENCE: 743
gaagtgcagc tggtgcagtc gggtgcagag gtcaagaaac cgggagcgac cgtgaaaatc    60
agctgcaagg tgtccgggta cactttcacg gactcggtga tgaattgggt ccaacaggga    120
ccggggaagg gattggagtg gatgggatgg attgacccag aatacggccg caccgacgtc    180
gcagaaaagt ttcaaggacg ggtcactatc accgcggaca cctcaaccga tactgcctac    240
atggagctct cctcgctgag aagcgaagat actgccgtgt actactgtgc caggaccggt    300
tacaactcgg gatacggctt cccttattgg ggacagggca ccactgtgac agtgtcctca    360

<210> SEQ ID NO 744
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 744
gaggtgcagc tggtccagtc aggagcagaa gtcaaaaagc cgggagccac cgtcaagatt    60
tcgtgtaagg tgtcgggcta cactttcact gattccgtca tgaattgggt gcagcaacac    120
ccagggaaag ggttggaatg gatgggatgg atcgaccctg aatacggccg caccgacgtg    180
gcggagaagt ttcaaggaag agtgacgatc actgccgata cctcgaccga caccgcatac    240
atggaactga gctcgctccg gtccgaggac accgccgtgt actactgcgc gaggactggc    300
tacaacagcg gatacggatt cccgtattgg ggccagggta ccactgtgac agtgtcctca    360

<210> SEQ ID NO 745
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 745
gaggtccagc tggtgcaatc aggagccgaa gtgaaaaagc cgggagcaac cgtcaagatt    60
agctgtaagg tgtcggggta caccttcact gactccgtga tgaactgggt gcagcaaggg    120
ccaggaaagg gactggagtg gatgggctgg atcgaccctg aatacggcag gactgacgtc    180
gccgagaaat tccagggtag agtgaccatc actgcggata cctcgaccga cactgcgtac    240
atggaactct ccagcttgcg gtcggaagat accgccgtct actactgcgc acgcaccggt    300
tatcagtcgg gctacggatt tccgtactgg ggacaaggaa ctacggtgac agtgtcctca    360

<210> SEQ ID NO 746
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized

<400> SEQUENCE: 746

```
gaagtccagc tcgtgcagtc gggagccgaa gtgaagaagc cgggagcgac tgtcaagatt    60
tcgtgtaagg tcagcggata taccttcacc gattccgtga tgaactgggt gcagcagcac   120
ccaggcaaag gccttgagtg gatggggtgg atcgacccgg agtacgggag aaccgacgtg   180
gcagagaaat ttcaaggacg ggtcaccatc actgccgaca cttccactga cactgcatac   240
atggaactgt catcgctgcg ctcggaagat accgccgtgt actactgcgc gaggacgggt   300
taccaaagcg gatacggatt cccttactgg ggccaaggta ccaccgtgac agtgtcctca   360
```

<210> SEQ ID NO 747
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 747

Lys Ala Ser Gln Asp Tyr Thr
1               5

<210> SEQ ID NO 748
<211> LENGTH: 30
<212> TYPE: PRT
<213> ORGANISM: Homo sapiens

<400> SEQUENCE: 748

Glu Val Gln Leu Val Gln Ser Gly Ala Glu Val Lys Lys Ser Gly Ala
1               5                  10                  15

Ser Val Lys Val Ser Cys Lys Ala Ser Gly Tyr Thr Phe Thr
            20                  25                  30

<210> SEQ ID NO 749
<211> LENGTH: 14
<212> TYPE: PRT
<213> ORGANISM: Homo sapiens

<400> SEQUENCE: 749

Trp Val Arg Gln Ala Pro Gly Gln Gly Leu Glu Trp Met Gly
1               5                  10

<210> SEQ ID NO 750
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Completely synthesized

<400> SEQUENCE: 750

Trp Val Arg Gln Pro Pro Gly Gln Gly Leu Glu Trp Met Gly
1               5                  10

<210> SEQ ID NO 751
<211> LENGTH: 32
<212> TYPE: PRT
<213> ORGANISM: Homo sapiens

```
<400> SEQUENCE: 751

Arg Val Thr Met Thr Arg Asp Thr Ser Ile Ser Thr Ala Tyr Met Asp
1               5                   10                  15

Leu Ser Ser Leu Arg Ser Asp Asp Thr Ala Val Tyr Phe Cys Ala Arg
            20                  25                  30

<210> SEQ ID NO 752
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Completely synthesized

<400> SEQUENCE: 752

Arg Val Thr Met Thr Arg Asp Thr Ser Ile Ser Thr Ala Tyr Met Asp
1               5                   10                  15

Leu Ser Ser Leu Arg Ser Asp Asp Thr Ala Val Tyr Tyr Cys Ala Arg
            20                  25                  30

<210> SEQ ID NO 753
<211> LENGTH: 11
<212> TYPE: PRT
<213> ORGANISM: Homo sapiens

<400> SEQUENCE: 753

Trp Gly Gln Gly Thr Leu Val Thr Val Ser Ser
1               5                   10
```

ANTI-CD38 ANTIBODIES AND FUSIONS TO ATTENUATED INTERFERON ALPHA-2B

CROSS REFERENCE TO RELATED APPLICATIONS

This application is a divisional of U.S. application Ser. No. 14/922,282, filed Oct. 26, 2015, which is a continuation of International Application No. PCT/US2013/038659, filed on Apr. 29, 2013, the disclosure of each of which are hereby incorporated by reference their entirety.

REFERENCE TO A SEQUENCE LISTING

This application includes a Sequence Listing submitted electronically as a text file named 102085 000916 SL.txt, created on Jul. 11, 2018 with a size of 519,931 bytes. The Sequence Listing is incorporated by reference herein.

FIELD OF THE DISCLOSURE

This disclosure relates generally to the field of antibody engineering. More specifically, this disclosure relates to antibodies that bind specifically to CD38, as well as constructs comprising such antibodies and attenuated interferon-alpha ligands, and methods of treatment using these constructs. In these constructs, the antibodies direct the ligands to cells that express both CD38 and receptors for the ligands, and the attenuated interferon-alpha reduces interferon signaling in cells that do not express CD38.

BACKGROUND OF THE DISCLOSURE

Various publications, including patents, published applications, technical articles, scholarly articles, and gene or protein accession numbers are cited throughout the specification. Each of these materials is incorporated by reference herein, in its entirety and for all purposes.

CD38 is a 46 kDa type II transmembrane glycoprotein. It has a short N-terminal cytoplasmic tail of 20 amino acids, a single transmembrane helix and a long extracellular domain of 256 amino acids. It is expressed on the surface of many immune cells including CD4 and CD8 positive T cells, B cells, NK cells, monocytes, plasma cells and on a significant proportion of normal bone marrow precursor cells. In some instances, the expression of CD38 in lymphocytes may be dependent on the differentiation and activation state of the cell, for example, resting T and B cells may be negative while immature and activated lymphocytes may be predominantly positive for CD38 expression. CD38 mRNA expression has been detected in non-hemopoeitic organs such as the pancreas, brain, spleen and liver (Koguma, T. (1994) Biochim. Biophys. Acta 1223:160).

CD38 is a multifunctional ectoenzyme that is involved in transmembrane signaling and cell adhesion. It is also known as cyclic ADP ribose hydrolase because it can transform $NAD^+$ and $NADP^+$ into cADPR, ADPR and NAADP, depending on extracellular pH. These products induce $Ca^{2+}$-mobilization inside the cell, which can lead to tyrosine phosphorylation and activation of the cell. CD38 is also a receptor that can interact with a ligand, CD31. Activation of receptor via CD31 leads to intracellular events including $Ca^{2+}$ mobilization, cell activation, proliferation, differentiation and migration.

CD38 is expressed at high levels on multiple myeloma cells, in most cases of T- and B-lineage acute lymphoblastic leukemias, some acute myelocyticleukemias, follicular center cell lymphomas and T lymphoblastic lymphomas. CD38 is also expressed on B-lineage chronic lymphoblastic leukemia (B-CLL) cells. In some cases, B-CLL patients presenting with a CD38+ clone are characterized by an unfavorable clinical course with a more advanced stage of disease, poor responsiveness to chemotherapy and shorter survival time. The use of antibodies to CD38 has been proposed for the treatment of CD38-expressing cancers and hematological malignancies. It may therefore be advantageous to provide alternative antibodies to CD38 which have desirable manufacturing, stability and immunogenic properties.

Numerous peptide and polypeptide ligands have been described to function by interacting with a receptor on a cell surface, and thereby stimulating, inhibiting, or otherwise modulating a biological response, usually involving signal transduction pathways inside the cell that bears the said receptor. Examples of such ligands include peptide and polypeptide hormones, cytokines, chemokines, growth factors, and apoptosis-inducing factors.

Due to the biological activities of such ligands, many have potential uses as therapeutics. Several peptide or polypeptide ligands have been approved by regulatory agencies as therapeutic products including, for example, human growth hormone, insulin, interferon (IFN)-alpha2b, IFN-alpha2a, IFNβ, erythropoietin, G-CSF and GM-CSF.

While these and other ligands have demonstrated potential in therapeutic applications, they may also exhibit toxicity when administered to human patients. One reason for toxicity is that most of these ligands trigger receptors on a variety of cells, including cells other than those that mediate the desired therapeutic effect. A consequence of such "off target" activity of ligands is that many ligands are currently not suitable for use as therapeutic agents because the ligands cannot be administered at sufficiently high dosages to produce maximal or optimal therapeutic effects on the target cells which mediate the therapeutic effect.

For example it has been known since the mid-1980's that interferons, in particular IFN-alpha, are able to increase apoptosis and decrease proliferation of certain cancer cells. IFN-alpha has been approved by the FDA for the treatment of several cancers including melanoma, renal cell carcinoma, B cell lymphoma, multiple myeloma, chronic myelogenous leukemia (CML) and hairy cell leukemia. A direct effect of IFN-alpha on the tumor cells is mediated by the IFN-alpha binding directly to the type I IFN receptor on those cells and stimulating apoptosis, terminal differentiation or reduced proliferation. A further indirect effect of IFN-alpha on non-cancer cells is to stimulate the immune system, which may produce an additional anti-cancer effect by causing the immune system to reject the tumor.

These biological activities are mediated by type I interferon receptors on the surface of the cancer cells which, when stimulated, initiate various signal transduction pathways leading to reduced proliferation and/or the induction of terminal differentiation or apoptosis. The type I interferon receptor is, however, also present on most non-cancerous cells. Activation of this receptor on non-cancerous cells by IFN-alpha causes the expression of numerous pro-inflammatory cytokines and chemokines, leading to toxicity and untoward effects. Such toxicity may cause severe flu-like symptoms, which prevents the dosing of IFN-alpha to a subject at levels that exert the maximum anti-proliferative and pro-apoptotic activity on the cancer cells.

When IFN-alpha2b is used to treat multiple myeloma, its utility resides, at least in part, in its binding to type I interferon receptors on the myeloma cells, which in turn triggers apoptosis and/or reduced proliferation and hence limits disease progression. Unfortunately, however, this IFN also binds healthy cells within the body, triggering a variety of other cellular responses, some of which are harmful.

A publication by Ozzello (Breast Cancer Research and Treatment 25:265-76, 1993) describes chemically conjugating human IFN-alpha to a tumor-targeting antibody, thereby localizing the direct inhibitory activity of IFN-alpha to the tumor as a way of reducing tumor growth rates, and demonstrated that such conjugates have anti-tumor activity in a xenograft model of a human cancer. The mechanism of the observed anti-cancer activity was attributed to a direct effect of IFN-alpha on the cancer cells, since the human IFN-alpha used in the experiments did not interact appreciably with the murine type I IFN receptor, which could have led to an indirect anti-cancer effect. Because of this lack of binding of the human IFN-alpha to the murine cells, the toxicity of the antibody-IFN-alpha conjugate relative to free INF-alpha was not assessed.

Antibodies and IFN-alpha may also be connected together in the form of a fusion protein. For example, WO 01/97844 describes a direct fusion of human IFN-alpha to the C-terminus of the heavy chain of an IgG specific for the tumor antigen CD20.

In general, IFN may be targeted to cancer cells. While this approach may result in an increase in activity of the IFN against cancer cells, it does not completely address the issue of undesired activity of the IFN on healthy cells. Fusing IFN-alpha to the C-terminus of the heavy chain of an IgG may prolong the half-life of the IFN alpha leading to undesirable adverse events. Accordingly, there exists a need to decrease off-target activity of ligand-based drugs, while retaining the "on-target" therapeutic effect of such ligands.

SUMMARY OF THE DISCLOSURE

The disclosure features new anti-CD38 antibodies and constructs comprising an anti-CD38 antibody and attenuated IFN-alpha. The antibodies, which comprise one or a plurality of mutations in their heavy and/or light chain variable regions retain the ability to specifically bind to CD38, including CD38 expressed on the surface of cells. The antibodies may be fused, for example, to an attenuated form of interferon alpha to form an anti-CD38 antibody-attenuated interferon fusion construct.

In some aspects, an isolated antibody that binds specifically to CD38 comprises a heavy chain variable region comprising the amino acid sequence of SEQ ID NO: 559 and a light chain variable region comprising the amino acid sequence of SEQ ID NO: 664. In some aspects, an isolated antibody that binds specifically to CD38 comprising a heavy chain variable region comprising the amino acid sequence of SEQ ID NO: 665 and a light chain variable region comprising the amino acid sequence of SEQ ID NO: 666. In some aspects, an isolated antibody that binds specifically to CD38 comprises a heavy chain variable region comprising the amino acid sequence of SEQ ID NO: 739 and a light chain variable region comprising the amino acid sequence of SEQ ID NO: 664. The heavy chain variable region amino acid sequence of SEQ ID NO: 559 excludes the amino acid sequence of SEQ ID NO: 13. The light chain variable region amino acid sequence of SEQ ID NO: 664 excludes the amino acid sequence of SEQ ID NO: 14. In some aspects, an isolated antibody that binds specifically to CD38 comprises a heavy chain CDR1 comprising the amino acid sequence of, SEQ ID NO: 200, SEQ ID NO: 514 or SEQ ID NO: 697, a heavy chain CDR2 comprising the amino acid sequence of SEQ ID NO: 202, SEQ ID NO: 516, SEQ ID NO: 544, SEQ ID NO: 698 or SEQ ID NO: 737, and a heavy chain CDR3 comprising the amino acid sequence of SEQ ID NO: 204, SEQ ID NO: 222, SEQ ID NO: 518, SEQ ID NO: 534, SEQ ID NO: 535, SEQ ID NO: 536, SEQ ID NO: 699 or SEQ ID NO: 738, and may further comprise a light chain CDR1 comprising the amino acid sequence of SEQ ID NO: 233, SEQ ID NO: 319, SEQ ID NO: 583, SEQ ID NO: 590 or SEQ ID NO: 696, a light chain CDR2 comprising the amino acid sequence of SEQ ID NO: 235, SEQ ID NO: 307, SEQ ID NO: 311, SEQ ID NO: 585, SEQ ID NO: 591 or SEQ ID NO: 605, a light chain CDR3 comprising the amino acid sequence of SEQ ID NO: 237, SEQ ID NO: 321, SEQ ID NO: 324, SEQ ID NO: 587 or SEQ ID NO: 594.

In preferred aspects, the heavy chain variable region comprises the amino acid sequence of SEQ ID NO: 34, SEQ ID NO: 18, SEQ ID NO: 665, SEQ ID NO: 165, SEQ ID NO: 166, SEQ ID NO: 167, SEQ ID NO: 179, SEQ ID NO: 180, SEQ ID NO: 156, SEQ ID NO: 197, SEQ ID NO: 152, SEQ ID NO: 720, SEQ ID NO: 721, SEQ ID NO: 722, SEQ ID NO: 723, SEQ ID NO: 739, SEQ ID NO: 740, SEQ ID NO: 741, SEQ ID NO: 742, SEQ ID NO: 728, SEQ ID NO: 730, SEQ ID NO: 731. In preferred aspects, the light chain variable region comprises the amino acid sequence of SEQ ID NO: 65, SEQ ID NO: 68, SEQ ID NO: 86, SEQ ID NO: 88, SEQ ID NO: 92, SEQ ID NO: 93, SEQ ID NO: 660, SEQ ID NO: 661, SEQ ID NO: 662, SEQ ID NO: 663. SEQ ID NO: 161, SEQ ID NO: 184, SEQ ID NO: 185, SEQ ID NO: 188, SEQ ID NO: 198 or SEQ ID NO: 700, SEQ ID NO: 701, SEQ ID NO: 704, SEQ ID NO: 705, SEQ ID NO: 706, SEQ ID NO: 707, SEQ ID NO: 708, SEQ ID NO: 709, SEQ ID NO: 710, SEQ ID NO: 711.

The antibody preferably is capable of binding to CD38-positive cells. The antibody may bind to a CD38-positive cell with an EC50 value of less than about 100 nM. The antibody may bind to a CD38-positive cell with an $EC_{50}$ value of less than about 75 nM. The antibody may bind to a CD38-positive cell with an $EC_{50}$ value of less than about 50 nM. The antibody may bind to a CD38-positive cell with an $EC_{50}$ value of less than about 30 nM. The antibody may bind to a CD38-positive cell with an $EC_{50}$ value of less than about 25 nM. The antibody may bind to a CD38-positive cell with an $EC_{50}$ value of less than about 20 nM. The antibody may bind to a CD38-positive cell with an $EC_{50}$ value of less than about 15 nM. The antibody may bind to a CD38-positive cell with an $EC_{50}$ value of less than about 13 nM. The antibody may bind to a CD38-positive cell with an $EC_{50}$ value of less than about 10 nM.

The antibody may be a monoclonal antibody, and is preferably a fully human antibody. The antibody may comprise an FAb. The antibody may comprise a human IgG1 constant region or a human IgG4 constant region. The IgG1 or the IgG4 constant region may comprise a tyrosine at position 252, a threonine at position 254, and a glutamic acid at position 256 according to the EU numbering system. The IgG4 constant region may comprise a proline at position 228 according to the EU numbering system, and the proline at position 228 may be in addition to a tyrosine at position 252, a threonine at position 254, and a glutamic acid at position 256.

In some aspects, the antibody is fused to attenuated interferon alpha-2b. The interferon alpha-2b may comprise a substitution of the alanine at position 145 to glycine or aspartic acid, including an interferon alpha-2b having the amino acid sequence of SEQ ID NO: 649 or SEQ ID NO: 651. The attenuated interferon alpha-2b may be fused directly to the C-terminus of the IgG1 or IgG4 constant region, and the antibody may comprise the amino acid sequence of SEQ ID NO: 9, SEQ ID NO: 10, SEQ ID NO: 652, SEQ ID NO: 653, SEQ ID NO: 654, SEQ ID NO: 655, SEQ ID NO: 656, SEQ ID NO: 657, SEQ ID NO: 658, or SEQ ID NO: 694. The antibody, including the antibody fused to an attenuated interferon alpha-2b may be comprised in a composition comprising a pharmaceutically acceptable carrier.

Isolated polynucleotides encoding the antibody and the antibody fused to an attenuated interferon alpha-2b are provided. The polynucleotide may comprise the nucleic acid sequence of SEQ ID NO: 667, SEQ ID NO: 670, SEQ ID NO: 671, SEQ ID NO: 672, SEQ ID NO: 673, SEQ ID NO: 674, SEQ ID NO: 668, SEQ ID NO: 669, SEQ ID NO: 675, SEQ ID NO: 676, or SEQ ID NO: 677, SEQ ID NO: 678, SEQ ID NO: 679, SEQ ID NO: 680, SEQ ID NO: 681, SEQ ID NO: 682, SEQ ID NO: 683, SEQ ID NO: 684, SEQ ID NO: 685, SEQ ID NO: 686, SEQ ID NO: 687, SEQ ID NO: 688, SEQ ID NO: 689, SEQ ID NO: 690, SEQ ID NO: 691, SEQ ID NO: 692, SEQ ID NO: 693, SEQ ID NO: 695 SEQ ID NO: 702, SEQ ID NO: 703, SEQ ID NO: 712, SEQ ID NO: 713, SEQ ID NO: 714, SEQ ID NO: 715, SEQ ID NO: 716, SEQ ID NO: 717, SEQ ID NO: 718, SEQ ID NO: 719, SEQ ID NO: 724, SEQ ID NO: 725, SEQ ID NO: 726, SEQ ID NO: 727 SEQ ID NO: 732, SEQ ID NO: 733, SEQ ID NO: 734, SEQ ID NO: 735, SEQ ID NO: 743, SEQ ID NO: 744, SEQ ID NO: 745, SEQ ID NO: 746. The polynucleotides may comprise a vector. The vector may be used, for example, to transform a cell. A transformed cell comprising such polynucleotides is also provided. The transformed cell may comprise a mammalian cell, a yeast cell, or an insect cell.

Stable cells that express the antibodies are also provided. Antibody-expressing cells may be mammalian cells. Preferred cells are Chinese Hamster Ovary (CHO) cells.

Kits comprising antibodies fused to attenuated interferon alpha-2b are provided. The kits comprise the anti-CD38-attenuated interferon alpha-2b fusion construct, and instructions for using the construct in a method for inhibiting the proliferation of a tumor cell expressing CD38 and a receptor for interferon alpha-2b on its surface, instructions for using the construct in a method for inducing apoptosis in a tumor cell expressing CD38 and a receptor for interferon alpha-2b on its surface, instructions for using the construct in a method for treating a tumor comprising cells expressing CD38 and a receptor for interferon alpha-2b on their surface in a subject in need thereof, and optionally, a pharmaceutically acceptable carrier. Kits comprising anti-CD38 antibodies are provided, and such kits comprise the anti-CD38 antibody and instructions for using the antibody in a method for detecting a CD38-positive tumor cell in a tissue sample isolated from a subject, the antibody may optionally be fused to an attenuated interferon alpha-2b protein.

The anti-CD38 antibody-attenuated interferon alpha-2b fusion constructs may be used as a therapy in the treatment of a tumor comprising cells expressing CD38 and a receptor for interferon alpha-2b on their surface. Generally, a treatment method comprises administering to a subject having the tumor an anti-CD38 antibody-attenuated interferon alpha-2b fusion construct in an amount effective to treat the tumor. The construct may comprise any construct described or exemplified herein. The subject is preferably a mammal, more preferably a non-human primate, and most preferably a human being. The tumor may comprise a B-cell lymphoma, multiple myeloma, non-Hodgkin's lymphoma, chronic myelogenous leukemia, chronic lymphocytic leukemia or acute myelogenous leukemia.

The anti-CD38 antibodies, optionally fused to an attenuated interferon alpha-2b protein, may be used in a method for detecting a CD38-positive tumor cell in a tissue sample isolated from a subject. Generally, the method comprises contacting an antibody that binds specifically to CD38 with a tissue sample isolated from a subject and detecting a complex of the antibody and a CD38-positive cell in the tissue sample. The tissue sample may be known to have or be suspected of having CD38-positive tumor cells. The tissue may comprise blood or bone marrow. The CD38-positive tumor cell may be a CD38-positive B-cell lymphoma cell, multiple myeloma cell, non-Hodgkin's lymphoma cell, chronic myelogenous leukemia cell, chronic lymphocytic leukemia cell, or acute myelogenous leukemia cell. The subject is preferably a mammal, more preferably a non-human primate, and most preferably a human being. The method may include the step of isolating the tissue sample from the subject. The method may further comprise contacting the antibody with a tissue sample that does not include any CD38-positive cells, for example, to serve as a negative control.

BRIEF DESCRIPTION OF THE DRAWINGS

FIGS. 2A and 2B show sequences of heavy chain variable regions of X02.1, related constructs and the most homologous germline antibody sequence. CDRs defined by the Kabat numbering system are underlined.

FIGS. 3A and 3B show sequences of light chain variable regions of X02.1, related constructs and the most homologous germline antibody sequence. CDRs defined by the Kabat numbering system are underlined.

FIGS. 4A-4D show the sequences of light chain variable regions of A02.1 and related constructs. CDRs defined by the Kabat numbering system are underlined FIG. 5 shows the consensus variable heavy chain sequence of A02.1 and related constructs. Boxed regions contain CDRs (as indicated) as defined by the Kabat numbering system and the enhanced Chothia numbering system. CDRs defined by the Kabat numbering system are shown in bold. CDRs defined by the enhanced Chothia numbering system are underlined.

FIG. 6 shows the consensus variable light chain sequence of A02.1 and related constructs. Boxed regions contain CDRs (as indicated) as defined by the Kabat numbering system and the enhanced Chothia numbering system. CDRs defined by the Kabat numbering system are shown in bold. CDRs defined by the enhanced Chothia numbering system are underlined FIGS. 7A-7C show sequences of heavy chain variable regions of humanized heavy chain variable regions. CDRs defined by the Kabat numbering system are underlined.

FIGS. 8A-8C show sequences of heavy chain variable regions of humanized light chain variable regions. CDRs defined by the Kabat numbering system are underlined.

FIGS. 9A and 9B show the variable heavy chain of A10.0 and related constructs. CDRs defined by the Kabat numbering system are underlined.

FIGS. 10A and 10B show the variable light chain of A10.0 and related constructs. CDRs defined by the Kabat numbering system are underlined.

FIGS. 11A and 11B show the variable heavy chain consensus sequence of A10.0 and related constructs. Boxed regions contain CDRs (as indicated) as defined by the Kabat numbering system and the enhanced Chothia numbering system. CDRs defined by the Kabat numbering system are shown in bold. CDRs defined by the enhanced Chothia numbering system are underlined.

FIG. 12 shows the variable light chain consensus sequence of A10.0 and related constructs. Boxed regions contain CDRs (as indicated) as defined by the Kabat numbering system and the enhanced Chothia numbering system. CDRs defined by the Kabat numbering system are shown in bold. CDRs defined by the enhanced Chothia numbering system are underlined.

FIG. 30 shows variable heavy chain consensus sequences of X910/12-HC-L0-Interferon-alpha (A145D) IgG4 and related sequences. Boxed regions contain CDRs (as indicated) as defined by the Kabat numbering system and the enhanced Chothia numbering system. CDRs defined by the Kabat numbering system are shown in bold. CDRs defined by the enhanced Chothia numbering system are underlined.

DETAILED DESCRIPTION OF THE DISCLOSURE

Figure 1:
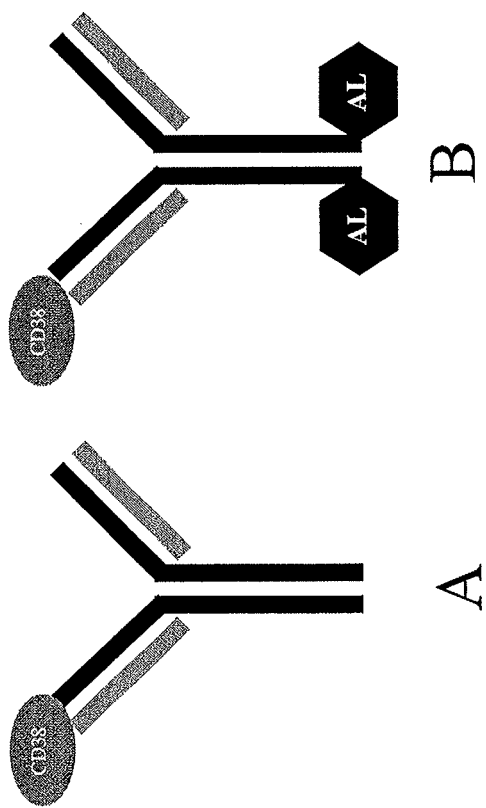
FIG. 1 shows an example of an anti-CD38-attenuated interferon fusion construct.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

The terms subject and patient are used interchangeably and include any animal. Mammals are preferred, including companion and farm mammals, as well as rodents, including mice, rabbits, and rats, and other rodents. Non-human primates, such as Cynomolgus monkeys, are more preferred, and human beings are highly preferred.

A molecule such as an antibody has been "isolated" if it has been altered and/or removed from its natural environment by the hand of a human being.

As used herein, the singular forms "a," "an," and "the" include plural referents unless expressly stated otherwise.

An anti-CD38 antibody-attenuated interferon alpha-2b fusion construct includes, but is not limited to, any antibody described or exemplified herein that binds specifically to CD38 that is fused to an attenuated interferon alpha-2b protein, including an interferon alpha-2b of SEQ ID NO: 647, SEQ ID NO: 648, SEQ ID NO: 649, SEQ ID NO: 650, or SEQ ID NO: 651. In some aspects, fusing an unmutated interferon alpha-2b protein, such as SEQ ID NO: 7, to an anti-CD38 antibody attenuates the biologic activities of the interferon molecule. In this disclosure, attenuated interferon, attenuated interferon alpha-2b, IFN-alpha2b A145D, and IFN-alpha2b A145G are used interchangeably.

Specificity is not necessarily an absolute designation but may constitute a relative term signifying the degree of selectivity of an antibody IFN-alpha fusion protein construct for an antigen-positive cell compared to an antigen-negative cell. Specificity of an antibody IFN-alpha fusion protein construct for an antigen-positive cell is mediated by the variable regions of the antibody, and usually by the complementarity determining regions (CDRs) of the antibody. A construct may have 100-fold specificity for antigen-positive cells compared to antigen-negative cells.

Human CD38 comprises the amino acid sequence of SEQ ID NO: 1, and cynomolgus monkey CD38 comprises the amino acid sequence of SEQ ID NO: 2.

It has been further observed that interferon-alpha2b can be attenuated in terms of its biologic activity which is mediated through the interferon binding to an interferon receptor on a cell surface by introducing certain amino acid changes into the protein sequence. An attenuated interferon molecule can be fused to antibodies that specifically bind to CD38, such that the antibody may serve as a delivery vehicle for the attenuated interferon to CD38-positive cells with a resulting diminution of off target interferon activity caused by the attenuated interferon molecule. It has been further observed that fusing the attenuated interferon to the CD38 antibodies does not significantly affect the capacity of the antibody to specifically bind to CD38 on cells expressing CD38, including cells in the body of animals. It has been further observed that variants of the CD38 antibodies can be engineered and expressed such that the antibodies have reduced immunogenicity and enhanced stability and half life without a significant loss of specificity or affinity of the antibody to the CD38 antigen. These variant antibodies can be fused to an attenuated interferon.

Accordingly, antibodies that specifically bind to CD38 are featured. It has also been observed that such anti-CD38 antibodies may be employed as delivery vehicles for attenuated ligands such as interferon alpha. Without intending to be limited to any particular theory or mechanism of action, it is believed that the antibodies direct the interferon alpha to which they are attached to CD38-positive cells, where the interferon may interact with its receptor. It is believed that the antibody, as a delivery vehicle, compensates for the diminished capacity of the interferon molecule to bind to its receptor. In this sense, the attenuated interferon has reduced capacity to interact with its receptor on healthy cells, and particularly cells that do not express CD38. It is believed that by bringing the attenuated interferon into proximity with its receptor on CD38-positive cells, the antibodies may enhance the capacity of the attenuated interferon to bind to its relevant receptor and induce a therapeutic effect, while exhibiting a diminished capacity to induce undesirable effects on healthy cells that do not express CD38.

The antibodies may be polyclonal, but in some aspects, are not polyclonal. The antibodies preferably are monoclonal. The antibodies are preferably full length antibodies. Full length antibodies generally comprise a variable region heavy chain and a variable region light chain. The antibodies may comprise derivatives or fragments or portions of antibodies that retain the antigen-binding specificity, and also preferably retain most or all of the affinity, of the parent antibody molecule (e.g., for CD38). For example, derivatives may comprise at least one variable region (either a heavy chain or light chain variable region). Other examples of suitable antibody derivatives and fragments include, without limitation, antibodies with polyepitopic specificity, bispecific antibodies, multi-specific antibodies, diabodies, single-chain molecules, as well as FAb, F(Ab')2, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or dimers, light chain monomers or dimers, dimers consisting of one heavy and one light chain, and other multimers. Single chain Fv antibodies may be multi-valent. All antibody isotypes may be used to produce antibody derivatives, fragments, and portions. Antibody derivatives, fragments, and/or portions may be recombinantly produced and expressed by any cell type, prokaryotic or eukaryotic.

In some embodiments an isolated antibody may refer to a monoclonal antibody to which IFN-alpha, or an attenuated IFN-alpha, has been fused to the C-terminus of the heavy chain IgG constant region. When the monoclonal antibody has a binding specificity to CD38 and the IFN-alpha is attenuated IFN-alpha 2b, the isolated antibody is also referred to as an Anti-CD38 attenuated IFN-alpha fusion protein, or an Anti-CD38 attenutated IFN-alpha fusion construct herein.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FWR or FR). Each VH and VL is composed of three CDRs and four FWRs, arranged from amino-terminus to carboxy-terminus in the following order: FWR1, CDR1, FWR2, CDR2, FWR3, CDR3, FWR4. Typically, the antigen binding properties of an antibody are less likely to be disturbed by changes to FWR sequences than by changes to the CDR sequences. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The antibodies may be derived from any species. For example, the antibodies may be mouse, rat, goat, horse, swine, bovine, camel, chicken, rabbit, donkey, llama, dromedary, shark, or human antibodies, as well as antibodies from any other animal species. For use in the treatment of humans, non-human derived antibodies may be structurally altered to be less antigenic upon administration to a human patient, including by chimerization or humanization or superhumanization.

In some aspects, the antibodies are humanized antibodies. Humanized antibodies are those wherein the amino acids directly involved in antigen binding, e.g., the complementarity determining regions (CDR), and in some cases the framework regions (FWR), or portions thereof, of the heavy and/or light chains are not of human origin, while the rest of the amino acids in the antibody are human or otherwise of human origin, e.g., a human antibody scaffold. Humanized antibodies also include antibodies in which one or more residues of the human protein are modified by one or more amino acid substitutions and/or one or more FWR residues of the human protein are replaced by corresponding non-human residues. Humanized antibodies may also comprise residues which are found in neither the human antibody or in the non-human antibody. A humanized antibody may be a super-humanized antibody, e.g., as described in U.S. Pat. No. 7,732,578. The antibodies may be humanized chimeric antibodies.

In highly preferred aspects, the antibodies are fully human. Fully human antibodies are those where the whole molecule is human or otherwise of human origin, or includes an amino acid sequence identical to a human form of the antibody. Fully human antibodies include those obtained from a human V gene library, for example, where human genes encoding variable regions of antibodies are recombinantly expressed. Fully human antibodies may be expressed in other organisms (e.g., mice and xenomouse technology) or cells from other organisms transformed with genes encoding human antibodies. Fully human antibodies may nevertheless include amino acid residues not encoded by human sequences, e.g., mutations introduced by random or site directed mutations.

The antibodies may be full length antibodies of any class, for example, IgG1, IgG2 or IgG4. The constant domains of such antibodies are preferably human. The variable regions of such antibodies may be of non-human origin, or preferably are human in origin or are humanized. Antibody fragments may also be used in place of the full length antibodies.

The antibodies may be minibodies. Minibodies comprise small versions of whole antibodies, which encode in a single chain the essential elements of a whole antibody. For example, the minibody may be comprised of the VH and VL domains of a native antibody fused to the hinge region and CH3 domain of an immunoglobulin molecule.

In some aspects, the antibody may comprise non-immunoglobulin derived protein frameworks. For example, reference may be made to (Ku & Schutz, Proc. Natl. Acad. Sci. USA 92: 6552-6556, 1995) which describes a four-helix bundle protein cytochrome b562 having two loops randomized to create CDRs, which have been selected for antigen binding.

Natural sequence variations may exist among heavy and light chains and the genes encoding them, and therefore, persons having ordinary skill in the art would expect to find some level of variation within the amino acid sequences, or the genes encoding them, of the antibodies described and exemplified herein. These variants preferably maintain the unique binding properties (e.g., specificity and affinity) of the parent antibody. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the disclosure. The antibodies thus include variants having single or multiple amino acid substitutions, deletions, additions, or replacements that retain the biological properties (e.g., binding specificity and binding affinity) of the parent antibodies. The variants are preferably conservative, but may be non-conservative.

Amino acid positions assigned to CDRs and FWRs may be defined according to Kabat Sequences of Proteins of Immunological Interest, National Institutes of Health, Bethesda, Md., 1987 and 1991 (also referred to herein as the Kabat numbering system). In addition, the amino acid positions assigned to CDRs and FWRs may be defined according to the Enhanced Chothia Numbering Scheme (www_bioinfo_org_uk/index). The heavy chain constant region of an antibody can be defined by the EU numbering system (Edelman, G M et al. (1969), Proc. Natl. Acad. USA, 63, 78-85).

According to the numbering system of Kabat, VH FWRs and CDRs may be positioned as follows: residues 1-30 (FWR1), 31-35 (CDR1), 36-49 (FWR2), 50-65 (CDR2), 66-94 (FWR3), 95-102 (CDR3) and 103-113 (FWR4), and VL FWRs and CDRs are positioned as follows: residues 1-23 (FWR1), 24-34 (CDR1), 35-49 (FWR2), 50-56 (CDR2), 57-88 (FWR3), 89-97 (CDR3) and 98-107 (FWR4). In some instances, variable regions may increase in length and according to the Kabat numbering system some amino acids may be designated by a number followed by a letter. This specification is not limited to FWRs and CDRs as defined by the Kabat numbering system, but includes all numbering systems, including the canonical numbering system or of Chothia et al. (1987) J. Mol Biol. 196:901-17; Chothia et al. (1989) Nature 342:877-83; and/or Al-Lazikani et al. (1997) J. Mol. Biol. 273:927-48; the numbering system of Honnegher et al. (2001) J. Mol. Biol., 309:657-70; or the IMGT system discussed in Giudicelli et al., (1997) Nucleic Acids Res. 25:206-11. In some aspects, the CDRs are defined according to the Kabat numbering system.

In some particular aspects, for any of the heavy chain CDR2 subdomains described herein, according to the Kabat numbering system, the five C-terminal amino acids may not participate directly in antigen binding, and accordingly, it will be understood that any one or more of these five C-terminal amino acids may be substituted with another naturally-occurring amino acid without substantially adversely affecting antigen binding. In some aspects, for any of the light chain CDR1 subdomains described herein, according to the Kabat numbering system, the four N-terminal amino acids may not participate directly in antigen binding, and accordingly, it will be understood that any one or more of these four amino acids may be substituted with another naturally-occurring amino acid without substantially adversely affecting antigen binding. For example, as described by Padlan et al. (1995) FASEB J. 9:133-139, the five C terminal amino acids of heavy chain CDR2 and/or the four N-terminal amino acids of light chain CDR1 may not participate in antigen binding. In some aspects, both the heavy chain CDR2 and the light chain CDR1 do not directly participate in antigen binding.

In some aspects, chemical analogues of amino acids may be used in the antibodies described and/or exemplified herein. The use of chemical analogues of amino acids is useful, for example, for stabilizing the molecules such as if required to be administered to a subject. The analogues of the amino acids contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogues.

The antibodies may comprise post-translational modifications or moieties, which may impact antibody activity or stability. These modifications or moieties include, but are not limited to, methylated, acetylated, glycosylated, sulfated, phosphorylated, carboxylated, and amidated moieties and other moieties that are well known in the art. Moieties include any chemical group or combinations of groups commonly found on immunoglobulin molecules in nature or otherwise added to antibodies by recombinant expression systems, including prokaryotic and eukaryotic expression systems.

Examples of side chain modifications contemplated by the disclosure include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivation, for example, to a corresponding amide.

Sulphydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers may be used, for example, to stabilize 3D conformations of the antibodies and constructs, using homo-bifunctional crosslinkers such as the bifunctionalimido esters having (CH$_2$)n spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH).

The antibodies may be affinity matured, or may comprise amino acid changes that decrease immunogenicity, for example, by removing predicted MHC class II-binding motifs. The therapeutic utility of the antibodies described herein may be further enhanced by modulating their functional characteristics, such as antibody-dependent cell-mediated cytotoxicity (ADCC), complement-dependent cytotoxicity (CDC), serum half-life, biodistribution and binding to Fc receptors or the combination of any of these. This modulation can be achieved by protein-engineering, glyco-engineering or chemical methods. Depending on the therapeutic application required, it could be advantageous to either increase or decrease any of these activities. An example of glyco-engineering used the Potelligent® method as described in Shinkawa T. et al. (2003) J. Biol. Chem. 278: 3466-73.

The antibodies may include modifications that modulate its serum half-life and biodistribution, including modifications that modulate the antibody's interaction with the neonatal Fc receptor (FcRn), a receptor with a key role in protecting IgG from catabolism, and maintaining high serum antibody concentration. Serum half-life modulating modifications may occur in the Fc region of IgG1 or IgG4, including the triple substitution of M252Y/S254T/T256E (Numbering according to the EU numbering system (Edelman, G. M. et al. (1969) Proc. Natl. Acad. USA 63, 78-85)), (e.g., SEQ ID NO: 656, SEQ ID NO: 657, SEQ ID NO: 658, SEQ ID NO: 694), as described in U.S. Pat. No. 7,083,784. Other substitutions may occur at positions 250 and 428, see e.g., U.S. Pat. No. 7,217,797, as well as at positions 307, 380 and 434, see, e.g., WO 00/42072. Examples of constant domain amino acid substitutions which modulate binding to Fc receptors and subsequent function mediated by these receptors, including FcRn binding and serum half-life, are described in U.S. Publ. Nos. 2009/0142340, 2009/0068175, and 2009/0092599. Naked antibodies may have the heavy chain C-terminal lysine omitted or removed to reduce heterogeneity. The substitution of S228P (EU numbering) in the human IgG4 can stabilize antibody Fab-arm exchange in vivo (Labrin et al. (2009) Nature Biotechnology 27:8; 767-773).

The glycans linked to antibody molecules are known to influence interactions of antibody with Fc receptors and glycan receptors and thereby influence antibody activity, including serum half-life. Hence, certain glycoforms that modulate desired antibody activities can confer therapeutic advantage. Methods for generating engineered glycoforms include but are not limited to those described in U.S. Pat. Nos. 6,602,684, 7,326,681, and 7,388,081 and PCT Publ. No. WO 08/006554. Alternatively, the antibody sequences may be modified to remove relevant glycoform attachment sites.

The antibodies may be labeled or conjugated to any chemical or biomolecule moieties. Labeled antibodies may find use in therapeutic, diagnostic, or basic research applications. Such labels/conjugates can be detectable, such as fluorochromes, radiolabels, enzymes, fluorescent proteins, and biotin. The labels/conjugates may be chemotherapeutic agents, toxins, isotopes, and other agents used for treating conditions such as the killing of cancer cells. Chemotherapeutic agents may be any which is suitable for the purpose to which the antibody is being used.

The antibodies may be derivatized by known protecting/blocking groups to prevent proteolytic cleavage or enhance activity or stability.

The antibodies preferably have a binding affinity for an epitope on CD38 that includes a dissociation constant (Kd) of less than about $1 \times 10^{-2}$ M. In some embodiments, the Kd is less than about $1 \times 10^{-3}$ M. In other embodiments, the Kd is less than about $1 \times 10^{-4}$ M. In some embodiments, the Kd is less than about $1 \times 10^{-5}$ M. In still other embodiments, the Kd is less than about $1 \times 10^{-6}$ M. In other embodiments, the Kd is less than about $1 \times 10^{-7}$ M. In other embodiments, the Kd is less than about $1 \times 10^{-8}$ M. In other embodiments, the Kd is less than about $1 \times 10^{-9}$ M. In other embodiments, the Kd is less than about $1 \times 10^{-10}$ M. In still other embodiments, the Kd is less than about $1 \times 10^{-11}$ M. In some embodiments, the Kd is less than about $1 \times 10^{-12}$ M. In other embodiments, the Kd is less than about $1 \times 10^{-13}$ M. In other embodiments, the Kd is less than about $1 \times 10^{-14}$ M. In still other embodiments, the Kd is less than about $1 \times 10^{-15}$ M. Affinity values refer to those obtained by standard methodologies, including surface plasmon resonance such as Biacore™ analyses or analysis using an Octet® Red 96 (Forte Bio) Dip-and-Read system.

The antibodies may comprise a single chain Fv molecule (scFv), Fab, or full IgG. Any such antibodies may comprise a heavy chain having an amino acid sequence having at least about 85%, at least about 90%, at least about 95%, at least about 96%, at least about 97%, at least about 98%, at least about 99%, or at least about 100% sequence identity with the amino acid sequence of SEQ ID NO: 659 or SEQ ID NO: 665 or SEQ ID NO: 736, provided that a heavy chain comprising the amino acid sequence of SEQ ID NO: 659 or variant thereof excludes the amino acid sequence of SEQ ID NO: 13. It will be understood that antibodies comprising amino acid changes in their heavy chain retain the capability to specifically bind to CD38. The retained CD38 specific binding activity (including affinity) is preferably about the same as the binding activity (including affinity) of an antibody without any amino acid changes in the heavy chain, although the binding activity (including affinity) may be lesser or greater than an antibody without any amino acid changes in the heavy chain. The antibody may comprise a light chain having an amino acid sequence having at least about 85%, at least about 90%, at least about 95%, at least about 96%, at least about 97%, at least about 98%, at least about 99%, or at least about 100% sequence identity with the amino acid sequence of SEQ ID NO: 664 or SEQ ID NO: 666, provided that a light chain comprising the amino acid sequence of SEQ ID NO: 664 or variant thereof excludes the amino acid sequence of SEQ ID NO: 14. It will be understood that antibodies comprising amino acid changes in their light chain retain the capability to specifically bind to CD38. The retained CD38 specific binding activity (including affinity) is preferably about the same as the binding activity (including affinity) of an antibody without any amino acid changes in the light chain, although the binding activity (including affinity) may be lesser or greater than an antibody without any amino acid changes in the light chain.

In some aspects, the heavy chain FWR1 comprises the amino acid sequence of SEQ ID NO: 199, SEQ ID NO: 206, SEQ ID NO: 214, SEQ ID NO: 215, SEQ ID NO: 217, SEQ ID NO: 219, SEQ ID NO: 389, SEQ ID NO: 396, SEQ ID NO: 400, SEQ ID NO: 404, SEQ ID NO: 408, SEQ ID NO: 412, SEQ ID NO: 416, SEQ ID NO: 420, SEQ ID NO: 424, SEQ ID NO: 428, SEQ ID NO: 432, SEQ ID NO: 466, SEQ ID NO: 470, SEQ ID NO: 472, SEQ ID NO: 474, SEQ ID NO: 476, SEQ ID NO: 478, SEQ ID NO: 480, SEQ ID NO: 482, SEQ ID NO: 486, SEQ ID NO: 488, SEQ ID NO: 513, SEQ ID NO: 537, SEQ ID NO: 542, SEQ ID NO: 547, SEQ ID NO: 552, SEQ ID NO: 557, SEQ ID NO: 562, SEQ ID NO: 567, SEQ ID NO: 572, SEQ ID NO: 577 or SEQ ID NO: 748, and in some aspects, the heavy chain FWR1 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 199, SEQ ID NO: 214, SEQ ID NO: 215, SEQ ID NO: 217, SEQ ID NO: 219, SEQ ID NO: 389, SEQ ID NO: 396, SEQ ID NO: 400, SEQ ID NO: 404, SEQ ID NO: 408, SEQ ID NO: 412, SEQ ID NO: 416, SEQ ID NO: 420, SEQ ID NO: 424, SEQ ID NO: 428, SEQ ID NO: 432, SEQ ID NO: 466, SEQ ID NO: 470, SEQ ID NO: 472, SEQ ID NO: 474, SEQ ID NO: 476, SEQ ID NO: 478, SEQ ID NO: 480, SEQ ID NO: 482, SEQ ID NO: 486, SEQ ID NO: 488, SEQ ID NO: 513, SEQ ID NO: 537, SEQ ID NO: 542, SEQ ID NO: 547, SEQ ID NO: 552, SEQ ID NO: 557, SEQ ID NO: 562, SEQ ID NO: 567, SEQ ID NO: 572, SEQ ID NO: 577 or SEQ ID NO: 748. In some aspects, the heavy chain FWR2 comprises the amino acid sequence of SEQ ID NO: 201, SEQ ID NO: 211, SEQ ID NO: 229, SEQ ID NO: 391, SEQ ID NO: 397, SEQ ID NO: 401, SEQ ID NO: 405, SEQ ID NO: 409, SEQ ID NO: 413, SEQ ID NO: 417, SEQ ID NO: 421, SEQ ID NO: 425, SEQ ID NO: 429, SEQ ID NO: 433, SEQ ID NO: 515, SEQ ID NO: 520, SEQ ID NO: 521, SEQ ID NO: 522, SEQ ID NO: 523, SEQ ID NO: 524, SEQ ID NO: 525, SEQ ID NO: 538, SEQ ID NO: 543, SEQ ID NO: 548, SEQ ID NO: 553, SEQ ID NO: 558, SEQ ID NO: 563, SEQ ID NO: 568, SEQ ID NO: 573, SEQ ID NO: 578, SEQ ID NO: 749 or SEQ ID NO: 750, and in some aspects, the heavy chain FWR2 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 201, SEQ ID NO: 211, SEQ ID NO: 229, SEQ ID NO: 391, SEQ ID NO: 397, SEQ ID NO: 401, SEQ ID NO: 405, SEQ ID NO: 409, SEQ ID NO: 413, SEQ ID NO: 417, SEQ ID NO: 421, SEQ ID NO: 425, SEQ ID NO: 429, SEQ ID NO: 433, SEQ ID NO: 515, SEQ ID NO: 520, SEQ ID NO: 521, SEQ ID NO: 522, SEQ ID NO: 523, SEQ ID NO: 524, SEQ ID NO: 525, SEQ ID NO: 538, SEQ ID NO: 543, SEQ ID NO: 548, SEQ ID NO: 553, SEQ ID NO: 558, SEQ ID NO: 563, SEQ ID NO: 568, SEQ ID NO: 573, SEQ ID NO: 578, SEQ ID NO: 749 or SEQ ID NO: 750. In some aspects, the heavy chain FWR3 comprises the amino acid sequence of SEQ ID NO: 203, SEQ ID NO: 210, SEQ ID NO: 212, SEQ ID NO: 213, SEQ ID NO: 216, SEQ ID NO: 218, SEQ ID NO: 221, SEQ ID NO: 226, SEQ ID NO: 227, SEQ ID NO: 230, SEQ ID NO: 393, SEQ ID NO: 399, SEQ ID NO: 403, SEQ ID NO: 407, SEQ ID NO: 411, SEQ ID NO: 415, SEQ ID NO: 419, SEQ ID NO: 423, SEQ ID NO: 427, SEQ ID NO: 431, SEQ ID NO: 435, SEQ ID NO: 468, SEQ ID NO: 517, SEQ ID NO: 530, SEQ ID NO: 531, SEQ ID NO: 532, SEQ ID NO: 533, SEQ ID NO: 540, SEQ ID NO: 545, SEQ ID NO: 550, SEQ ID NO: 555, SEQ ID NO: 560, SEQ ID NO: 565, SEQ ID NO: 570, SEQ ID NO: 575, SEQ ID NO: 580, SEQ ID NO: 751 or SEQ ID NO: 752 and in some aspects, the heavy chain FWR3 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 203, SEQ ID NO: 210, SEQ ID NO: 212, SEQ ID NO: 213, SEQ ID NO: 216, SEQ ID NO: 218, SEQ ID NO: 221, SEQ ID NO: 226, SEQ ID NO: 227, SEQ ID NO: 230, SEQ ID NO: 393, SEQ ID NO: 399, SEQ ID NO: 403, SEQ ID NO: 407, SEQ ID NO: 411, SEQ ID NO: 415, SEQ ID NO: 419, SEQ ID NO: 423, SEQ ID NO: 427, SEQ ID NO: 431, SEQ ID NO: 435, SEQ ID NO: 468, SEQ ID NO: 517, SEQ ID NO: 530, SEQ ID NO: 531, SEQ ID NO: 532, SEQ ID NO: 533, SEQ ID NO: 540, SEQ ID NO: 545, SEQ ID NO: 550, SEQ ID NO: 555, SEQ ID NO: 560, SEQ ID NO: 565, SEQ ID NO: 570, SEQ ID NO: 575, SEQ ID NO: 580, SEQ ID NO: 751 or SEQ ID NO: 752. In some aspects, the heavy chain FWR4 comprises the amino acid sequence of SEQ ID NO: 205, SEQ ID NO: 395, SEQ ID NO: 519, SEQ ID NO: 541, SEQ ID NO: 546, SEQ ID NO: 551, SEQ ID NO: 556, SEQ ID NO: 561, SEQ ID NO: 566, SEQ ID NO: 571, SEQ ID NO: 576, SEQ ID NO: 581 or SEQ ID NO: 753, and in some aspects, the heavy chain FWR4 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 205, SEQ ID NO: 395, SEQ ID NO: 519, SEQ ID NO: 541, SEQ ID NO: 546, SEQ ID NO: 551, SEQ ID NO: 556, SEQ ID NO: 561, SEQ ID NO: 566, SEQ ID NO: 571, SEQ ID NO: 576, SEQ ID NO: 581 or SEQ ID NO: 753. It will be understood that antibodies comprising amino acid changes in the heavy chain framework region(s) (FWR1, FWR2, FWR3, and/or FWR4) retain the capability to specifically bind to CD38. The retained CD38 specific binding activity (including affinity) is preferably about the same as the binding activity (including affinity) of an antibody without any amino acid changes in any heavy chain framework region(s), although the binding activity (including affinity) may be lesser or greater than an antibody without any amino acid changes in any heavy chain framework region(s).

In some aspects, the heavy chain CDR1 comprises the amino acid sequence of SEQ ID NO: 200, SEQ ID NO: 224, SEQ ID NO: 390, SEQ ID NO: 514, SEQ ID NO: 526, SEQ ID NO: 527, SEQ ID NO: 528, SEQ ID NO: 529, or SEQ ID NO: 697 and in some aspects, the heavy chain CDR1 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 200, SEQ ID NO: 224, SEQ ID NO: 390, SEQ ID NO: 514, SEQ ID NO: 526, SEQ ID NO: 527, SEQ ID NO: 528, SEQ ID NO: 529, or SEQ ID NO: 697. In some aspects, the heavy chain CDR2 comprises the amino acid sequence of SEQ ID NO: 202, SEQ ID NO: 392, SEQ ID NO: 398, SEQ ID NO: 402, SEQ ID NO: 406, SEQ ID NO: 410, SEQ ID NO: 414, SEQ ID NO: 418, SEQ ID NO: 422, SEQ ID NO: 426, SEQ ID NO: 430, SEQ ID NO: 434, SEQ ID NO: 467, SEQ ID NO: 471, SEQ ID NO: 473, SEQ ID NO: 475, SEQ ID NO: 477, SEQ ID NO: 479, SEQ ID NO: 481, SEQ ID NO: 483, SEQ ID NO: 485, SEQ ID NO: 487, SEQ ID NO: 489, SEQ ID NO: 516, SEQ ID NO: 539, SEQ ID NO: 544, SEQ ID NO: 549, SEQ ID NO: 554, SEQ ID NO: 559, SEQ ID NO: 564, SEQ ID NO: 569, SEQ ID NO: 574, SEQ ID NO: 579, SEQ ID NO: 698 or SEQ ID NO: 737 and in some aspects, the heavy chain CDR2 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 202, SEQ ID NO: 392, SEQ ID NO: 398, SEQ ID NO: 402, SEQ ID NO: 406, SEQ ID NO: 410, SEQ ID NO: 414, SEQ ID NO: 418, SEQ ID NO: 422, SEQ ID NO: 426, SEQ ID NO: 430, SEQ ID NO: 434, SEQ ID NO: 467, SEQ ID NO: 471, SEQ ID NO: 473, SEQ ID NO: 475, SEQ ID NO: 477, SEQ ID NO: 479, SEQ ID NO: 481, SEQ ID NO: 483, SEQ ID NO: 485, SEQ ID NO: 487, SEQ ID NO: 489, SEQ ID NO: 516, SEQ ID NO: 539, SEQ ID NO: 544, SEQ ID NO: 549, SEQ ID NO: 554, SEQ ID NO: 559, SEQ ID NO: 564, SEQ ID NO: 569, SEQ ID NO: 574, SEQ ID NO: 579, SEQ ID NO: 698 or SEQ ID NO: 737. In some aspects, the heavy chain CDR3 comprises the amino acid sequence of SEQ ID NO: 204, SEQ ID NO: 220, SEQ ID NO: 222, SEQ ID NO: 223, SEQ ID NO: 228, SEQ ID NO: 231, SEQ ID NO: 394, SEQ ID NO: 469, SEQ ID NO: 518, SEQ ID NO: 534, SEQ ID NO: 535, SEQ ID NO: 536, SEQ ID NO: 699 or SEQ ID NO: 738 and in some aspects, the heavy chain CDR3 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 204, SEQ ID NO: 220, SEQ ID NO: 222, SEQ ID NO: 223, SEQ ID NO: 228, SEQ ID NO: 231, SEQ ID NO: 394, SEQ ID NO: 469, SEQ ID NO: 518, SEQ ID NO: 534, SEQ ID NO: 535, SEQ ID NO: 536, SEQ ID NO: 699 or SEQ ID NO: 738. It will be understood that antibodies comprising amino acid changes in the heavy chain complementarity determining region(s) (CDR1, CDR2, and/or CDR3) retain the capability to specifically bind to CD38. The retained CD38 specific binding activity (including affinity) is preferably about the same as the binding activity (including affinity) of an antibody without any amino acid changes in any heavy chain complementarity determining region(s), although the binding activity (including affinity) may be lesser or greater than an antibody without any amino acid changes in any heavy chain complementarity determining region(s).

In some aspects, the light chain FWR1 comprises the amino acid sequence of SEQ ID NO: 232, SEQ ID NO: 247, SEQ ID NO: 259, SEQ ID NO: 260, SEQ ID NO: 261, SEQ ID NO: 436, SEQ ID NO: 443, SEQ ID NO: 447, SEQ ID NO: 451, SEQ ID NO: 455, SEQ ID NO: 459, SEQ ID NO: 463, SEQ ID NO: 490, SEQ ID NO: 497, SEQ ID NO: 501, SEQ ID NO: 509, SEQ ID NO: 582, SEQ ID NO: 607, SEQ ID NO: 614, SEQ ID NO: 618, SEQ ID NO: 622, SEQ ID NO: 626, SEQ ID NO: 630, SEQ ID NO: 634 or SEQ ID NO: 638 and in some aspects, the light chain FWR1 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 232, SEQ ID NO: 247, SEQ ID NO: 259, SEQ ID NO: 260, SEQ ID NO: 261, SEQ ID NO: 436, SEQ ID NO: 443, SEQ ID NO: 447, SEQ ID NO: 451, SEQ ID NO: 455, SEQ ID NO: 459, SEQ ID NO: 463, SEQ ID NO: 490, SEQ ID NO: 497, SEQ ID NO: 501, SEQ ID NO: 509, SEQ ID NO: 582, SEQ ID NO: 607, SEQ ID NO: 614, SEQ ID NO: 618, SEQ ID NO: 622, SEQ ID NO: 626, SEQ ID NO: 630, SEQ ID NO: 634 or SEQ ID NO: 638. In some aspects, the light chain FWR2 comprises the amino acid sequence of SEQ ID NO: 234, SEQ ID NO: 246, SEQ ID NO: 248, SEQ ID NO: 281, SEQ ID NO: 283, SEQ ID NO: 285, SEQ ID NO: 287, SEQ ID NO: 289, SEQ ID NO: 291, SEQ ID NO: 293, SEQ ID NO: 295, SEQ ID NO: 297, SEQ ID NO: 438, SEQ ID NO: 444, SEQ ID NO: 448, SEQ ID NO: 452, SEQ ID NO: 456, SEQ ID NO: 460, SEQ ID NO: 464, SEQ ID NO: 492, SEQ ID NO: 498, SEQ ID NO: 502, SEQ ID NO: 506, SEQ ID NO: 510, SEQ ID NO: 584, SEQ ID NO: 592, SEQ ID NO: 593, SEQ ID NO: 609, SEQ ID NO: 615, SEQ ID NO: 619, SEQ ID NO: 623, SEQ ID NO: 627, SEQ ID NO: 631, SEQ ID NO: 635 or SEQ ID NO: 639 and in some aspects, the light chain FWR2 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 234, SEQ ID NO: 246, SEQ ID NO: 248, SEQ ID NO: 281, SEQ ID NO: 283, SEQ ID NO: 285, SEQ ID NO: 287, SEQ ID NO: 289, SEQ ID NO: 291, SEQ ID NO: 293, SEQ ID NO: 295, SEQ ID NO: 297, SEQ ID NO: 438, SEQ ID NO: 444, SEQ ID NO: 448, SEQ ID NO: 452, SEQ ID NO: 456, SEQ ID NO: 460, SEQ ID NO: 464, SEQ ID NO: 492, SEQ ID NO: 498, SEQ ID NO: 502, SEQ ID NO: 506, SEQ ID NO: 510, SEQ ID NO: 584, SEQ ID NO: 592, SEQ ID NO: 593, SEQ ID NO: 609, SEQ ID NO: 615, SEQ ID NO: 619, SEQ ID NO: 623, SEQ ID NO: 627, SEQ ID NO: 631, SEQ ID NO: 635 or SEQ ID NO: 639. In some aspects, the light chain FWR3 comprises the amino acid sequence of SEQ ID NO: 236, SEQ ID NO: 245, SEQ ID NO: 265, SEQ ID NO: 266, SEQ ID NO: 267, SEQ ID NO: 271, SEQ ID NO: 272, SEQ ID NO: 274, SEQ ID NO: 276, SEQ ID NO: 277, SEQ ID NO: 278, SEQ ID NO: 279, SEQ ID NO: 280, SEQ ID NO: 282, SEQ ID NO: 284, SEQ ID NO: 286, SEQ ID NO: 288, SEQ ID NO: 290, SEQ ID NO: 292, SEQ ID NO: 294, SEQ ID NO: 296, SEQ ID NO: 298, SEQ ID NO: 300, SEQ ID NO: 302, SEQ ID NO: 304, SEQ ID NO: 306, SEQ ID NO: 308, SEQ ID NO: 310, SEQ ID NO: 312, SEQ ID NO: 314, SEQ ID NO: 316, SEQ ID NO: 318, SEQ ID NO: 320, SEQ ID NO: 323, SEQ ID NO: 327, SEQ ID NO: 331, SEQ ID NO: 335, SEQ ID NO: 339, SEQ ID NO: 343, SEQ ID NO: 347, SEQ ID NO: 351, SEQ ID NO: 355, SEQ ID NO: 359, SEQ ID NO: 363, SEQ ID NO: 367, SEQ ID NO: 371, SEQ ID NO: 375, SEQ ID NO: 379, SEQ ID NO: 383, SEQ ID NO: 387, SEQ ID NO: 440, SEQ ID NO: 445, SEQ ID NO: 449, SEQ ID NO: 453, SEQ ID NO: 457, SEQ ID NO: 461, SEQ ID NO: 465, SEQ ID NO: 494, SEQ ID NO: 499, SEQ ID NO: 503, SEQ ID NO: 507, SEQ ID NO: 511, SEQ ID NO: 586, SEQ ID NO: 611, SEQ ID NO: 616, SEQ ID NO: 620, SEQ ID NO: 624, SEQ ID NO: 628, SEQ ID NO: 632, SEQ ID NO: 636 or SEQ ID NO: 640, and in some aspects, the light chain FWR3 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 236, SEQ ID NO: 245, SEQ ID NO: 265, SEQ ID NO: 266, SEQ ID NO: 267, SEQ ID NO: 271, SEQ ID NO: 272, SEQ ID NO: 274, SEQ ID NO: 276, SEQ ID NO: 277, SEQ ID NO: 278, SEQ ID NO: 279, SEQ ID NO: 280, SEQ ID NO: 282, SEQ ID NO: 284, SEQ ID NO: 286, SEQ ID NO: 288, SEQ ID NO: 290, SEQ ID NO: 292, SEQ ID NO: 294, SEQ ID NO: 296, SEQ ID NO: 298, SEQ ID NO: 300, SEQ ID NO: 302, SEQ ID NO: 304, SEQ ID NO: 306, SEQ ID NO: 308, SEQ ID NO: 310, SEQ ID NO: 312, SEQ ID NO: 314, SEQ ID NO: 316, SEQ ID NO: 318, SEQ ID NO: 320, SEQ ID NO: 323, SEQ ID NO: 327, SEQ ID NO: 331, SEQ ID NO: 335, SEQ ID NO: 339, SEQ ID NO: 343, SEQ ID NO: 347, SEQ ID NO: 351, SEQ ID NO: 355, SEQ ID NO: 359, SEQ ID NO: 363, SEQ ID NO: 367, SEQ ID NO: 371, SEQ ID NO: 375, SEQ ID NO: 379, SEQ ID NO: 383, SEQ ID NO: 387, SEQ ID NO: 440, SEQ ID NO: 445, SEQ ID NO: 449, SEQ ID NO: 453, SEQ ID NO: 457, SEQ ID NO: 461, SEQ ID NO: 465, SEQ ID NO: 494, SEQ ID NO: 499, SEQ ID NO: 503, SEQ ID NO: 507, SEQ ID NO: 511, SEQ ID NO: 586, SEQ ID NO: 611, SEQ ID NO: 616, SEQ ID NO: 620, SEQ ID NO: 624, SEQ ID NO: 628, SEQ ID NO: 632, SEQ ID NO: 636 or SEQ ID NO: 640. In some aspects, the light chain FWR4 comprises the amino acid sequence of SEQ ID NO: 238, SEQ ID NO: 442, SEQ ID NO: 446, SEQ ID NO: 450, SEQ ID NO: 454, SEQ ID NO: 458, SEQ ID NO: 462, SEQ ID NO: 496, SEQ ID NO: 500, SEQ ID NO: 504, SEQ ID NO: 508, SEQ ID NO: 512, SEQ ID NO: 588, SEQ ID NO: 613, SEQ ID NO: 617, SEQ ID NO: 621, SEQ ID NO: 625, SEQ ID NO: 629, SEQ ID NO: 633, SEQ ID NO: 637 or SEQ ID NO: 641 and in some aspects, the light chain FWR4 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 238, SEQ ID NO: 442, SEQ ID NO: 446, SEQ ID NO: 450, SEQ ID NO: 454, SEQ ID NO: 458, SEQ ID NO: 462, SEQ ID NO: 496, SEQ ID NO: 500, SEQ ID NO: 504, SEQ ID NO: 508, SEQ ID NO: 512, SEQ ID NO: 588, SEQ ID NO: 613, SEQ ID NO: 617, SEQ ID NO: 621, SEQ ID NO: 625, SEQ ID NO: 629, SEQ ID NO: 633, SEQ ID NO: 637 or SEQ ID NO: 641. It will be understood that antibodies comprising amino acid changes in the light chain framework region(s) (FWR1, FWR2, FWR3, and/or FWR4) retain the capability to specifically bind to CD38. The retained CD38 specific binding activity (including affinity) is preferably about the same as the binding activity (including affinity) of an antibody without any amino acid changes in any light chain framework region(s), although the binding activity (including affinity) may be lesser or greater than an antibody without any amino acid changes in any light chain framework region(s).

In some aspects, the light chain CDR1 comprises the amino acid sequence of SEQ ID NO: 233, SEQ ID NO: 250, SEQ ID NO: 525, SEQ ID NO: 255, SEQ ID NO: 262, SEQ ID NO: 263, SEQ ID NO: 319, SEQ ID NO: 322, SEQ ID NO: 325, SEQ ID NO: 329, SEQ ID NO: 333, SEQ ID NO: 337, SEQ ID NO: 341, SEQ ID NO: 345, SEQ ID NO: 349, SEQ ID NO: 353, SEQ ID NO: 357, SEQ ID NO: 361, SEQ ID NO: 365, SEQ ID NO: 369, SEQ ID NO: 373, SEQ ID NO: 377, SEQ ID NO: 381, SEQ ID NO: 385, SEQ ID NO: 437, SEQ ID NO: 491, SEQ ID NO: 583, SEQ ID NO: 589, SEQ ID NO: 590, SEQ ID NO: 608, or SEQ ID NO: 696, and in some aspects, the light chain CDR1 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 233, SEQ ID NO: 250, SEQ ID NO: 525, SEQ ID NO: 255, SEQ ID NO: 262, SEQ ID NO: 263, SEQ ID NO: 319, SEQ ID NO: 322, SEQ ID NO: 325, SEQ ID NO: 329, SEQ ID NO: 333, SEQ ID NO: 337, SEQ ID NO: 341, SEQ ID NO: 345, SEQ ID NO: 349, SEQ ID NO: 353, SEQ ID NO: 357, SEQ ID NO: 361, SEQ ID NO: 365, SEQ ID NO: 369, SEQ ID NO: 373, SEQ ID NO: 377, SEQ ID NO: 381, SEQ ID NO: 385, SEQ ID NO: 437, SEQ ID NO: 491, SEQ ID NO: 583, SEQ ID NO: 589, SEQ ID NO: 590, SEQ ID NO: 608, or SEQ ID NO: 696. In some aspects, the light chain CDR2 comprises the amino acid sequence of SEQ ID NO: 235, SEQ ID NO: 249, SEQ ID NO: 253, SEQ ID NO: 264, SEQ ID NO: 299, SEQ ID NO: 301, SEQ ID NO: 303, SEQ ID NO: 305, SEQ ID NO: 307, SEQ ID NO: 309, SEQ ID NO: 311, SEQ ID NO: 313, SEQ ID NO: 315, SEQ ID NO: 317, SEQ ID NO: 326, SEQ ID NO: 330, SEQ ID NO: 334, SEQ ID NO: 338, SEQ ID NO: 342, SEQ ID NO: 346, SEQ ID NO: 350, SEQ ID NO: 354, SEQ ID NO: 358, SEQ ID NO: 362, SEQ ID NO: 366, SEQ ID NO: 370, SEQ ID NO: 374, SEQ ID NO: 378, SEQ ID NO: 382, SEQ ID NO: 386, SEQ ID NO: 439, SEQ ID NO: 493, SEQ ID NO: 585, SEQ ID NO: 591, SEQ ID NO: 605, SEQ ID NO: 610 or SEQ ID NO: 747, and in some aspects, the light chain CDR2 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 235, SEQ ID NO: 249, SEQ ID NO: 253, SEQ ID NO: 264, SEQ ID NO: 299, SEQ ID NO: 301, SEQ ID NO: 303, SEQ ID NO: 305, SEQ ID NO: 307, SEQ ID NO: 309, SEQ ID NO: 311, SEQ ID NO: 313, SEQ ID NO: 315, SEQ ID NO: 317, SEQ ID NO: 326, SEQ ID NO: 330, SEQ ID NO: 334, SEQ ID NO: 338, SEQ ID NO: 342, SEQ ID NO: 346, SEQ ID NO: 350, SEQ ID NO: 354, SEQ ID NO: 358, SEQ ID NO: 362, SEQ ID NO: 366, SEQ ID NO: 370, SEQ ID NO: 374, SEQ ID NO: 378, SEQ ID NO: 382, SEQ ID NO: 386, SEQ ID NO: 439, SEQ ID NO: 493, SEQ ID NO: 585, SEQ ID NO: 591, SEQ ID NO: 605, SEQ ID NO: 610 or SEQ ID NO: 747. In some aspects, the light chain CDR3 comprises the amino acid sequence of SEQ ID NO: 237, SEQ ID NO: 244, SEQ ID NO: 251, SEQ ID NO: 254, SEQ ID NO: 256, SEQ ID NO: 257, SEQ ID NO: 258, SEQ ID NO: 268, SEQ ID NO: 269, SEQ ID NO: 270, SEQ ID NO: 273, SEQ ID NO: 275, SEQ ID NO: 321, SEQ ID NO: 324, SEQ ID NO: 328, SEQ ID NO: 332, SEQ ID NO: 336, SEQ ID NO: 340, SEQ ID NO: 344, SEQ ID NO: 348, SEQ ID NO: 352, SEQ ID NO: 356, SEQ ID NO: 360, SEQ ID NO: 364, SEQ ID NO: 368, SEQ ID NO: 372, SEQ ID NO: 376, SEQ ID NO: 380, SEQ ID NO: 384, SEQ ID NO: 388, SEQ ID NO: 441, SEQ ID NO: 495, SEQ ID NO: 587, SEQ ID NO: 594, SEQ ID NO: 595, SEQ ID NO: 596, SEQ ID NO: 597, SEQ ID NO: 598, SEQ ID NO: 599, SEQ ID NO: 600, SEQ ID NO: 601, SEQ ID NO: 602, SEQ ID NO: 603, SEQ ID NO: 604, SEQ ID NO: 606 or SEQ ID NO: 612, and in some aspects, the light chain CDR3 comprises an amino acid sequence having at least about 85%, at least about 90%, at least about 92%, at least about 93%, at least about 94%, at least about 95%, at least about 96%, at least about 97%, at least about 98%, or at least about 99% sequence identity with the amino acid sequence of SEQ ID NO: 237, SEQ ID NO: 244, SEQ ID NO: 251, SEQ ID NO: 254, SEQ ID NO: 256, SEQ ID NO: 257, SEQ ID NO: 258, SEQ ID NO: 268, SEQ ID NO: 269, SEQ ID NO: 270, SEQ ID NO: 273, SEQ ID NO: 275, SEQ ID NO: 321, SEQ ID NO: 324, SEQ ID NO: 328, SEQ ID NO: 332, SEQ ID NO: 336, SEQ ID NO: 340, SEQ ID NO: 344, SEQ ID NO: 348, SEQ ID NO: 352, SEQ ID NO: 356, SEQ ID NO: 360, SEQ ID NO: 364, SEQ ID NO: 368, SEQ ID NO: 372, SEQ ID NO: 376, SEQ ID NO: 380, SEQ ID NO: 384, SEQ ID NO: 388, SEQ ID NO: 441, SEQ ID NO: 495, SEQ ID NO: 587, SEQ ID NO: 594, SEQ ID NO: 595, SEQ ID NO: 596, SEQ ID NO: 597, SEQ ID NO: 598, SEQ ID NO: 599, SEQ ID NO: 600, SEQ ID NO: 601, SEQ ID NO: 602, SEQ ID NO: 603, SEQ ID NO: 604, SEQ ID NO: 606 or SEQ ID NO: 612. It will be understood that antibodies comprising amino acid changes in the light chain complementarity determining region(s) (CDR1, CDR2, and/or CDR3) retain the capability to specifically bind to CD38. The retained CD38 specific binding activity (including affinity) is preferably about the same as the binding activity (including affinity) of an antibody without any amino acid changes in any light chain complementarity determining region(s), although the binding activity (including affinity) may be lesser or greater than an antibody without any amino acid changes in any light chain complementarity determining region(s).

In some aspects, the antibody comprises particular heavy and light chain pairs. The heavy chains having the amino acid sequences of SEQ ID NO: 659 may be paired with any light chains having the amino acid sequences of SEQ ID NO: 664, or the heavy chains having the amino acid sequences of SEQ ID NO: 665 may be paired with any light chains having the amino acid sequences of SEQ ID NO: 666, or the heavy chain having the amino acid sequences of SEQ ID NO: 736 may be paired with any light chains having the amino acid sequences of SEQ ID NO: 664.

Variable heavy and variable light chain pairs may comprise pairs from the following table:

| Antibody Name | Variable Heavy SEQ ID NO: (amino acid) | Variable Light SEQ ID NO: (amino acid) |
|---|---|---|
| A02.10 | 19 | 14 |
| A02.11 | 20 | 14 |
| A02.112 | 34 | 65 |
| A02.12 | 34 | 65 |
| A02.13 | 35 | 65 |
| A02.16 | 34 | 92 |
| A02.17 | 34 | 93 |
| A02.18 | 34 | 73 |
| A02.19 | 34 | 74 |
| A02.2 | 13 | 65 |
| A02.20 | 34 | 75 |
| A02.21 | 34 | 76 |
| A02.22 | 34 | 77 |
| A02.23 | 34 | 78 |
| A02.24 | 34 | 79 |
| A02.25 | 34 | 80 |
| A02.26 | 34 | 81 |
| A02.27 | 34 | 82 |
| A02.28 | 34 | 83 |
| A02.29 | 34 | 84 |
| A02.3 | 17 | 65 |
| A02.30 | 34 | 85 |
| A02.31 | 34 | 86 |
| A02.32 | 34 | 87 |
| A02.33 | 34 | 88 |
| A02.34 | 34 | 89 |
| A02.35 | 34 | 90 |
| A02.36 | 34 | 91 |
| A02.37 | 34 | 66 |
| A02.38 | 34 | 113 |
| A02.39 | 34 | 112 |
| A02.4 | 18 | 65 |
| A02.40 | 111 | 65 |
| A02.41 | 110 | 65 |
| A02.43 | 110 | 113 |
| A02.44 | 111 | 112 |
| A02.46 | 34 | 67 |
| A02.47 | 34 | 68 |
| A02.48 | 34 | 69 |
| A02.49 | 34 | 70 |
| A02.5 | 19 | 65 |
| A02.50 | 34 | 71 |
| A02.51 | 34 | 72 |
| A02.52 | 34 | 94 |
| A02.53 | 34 | 95 |
| A02.54 | 34 | 96 |
| A02.55 | 34 | 97 |
| A02.56 | 34 | 98 |
| A02.57 | 34 | 99 |
| A02.58 | 34 | 100 |
| A02.59 | 34 | 101 |
| A02.6 | 20 | 65 |
| A02.60 | 34 | 102 |
| A02.61 | 34 | 103 |
| A02.62 | 34 | 104 |
| A02.63 | 34 | 105 |
| A02.64 | 34 | 106 |
| A02.65 | 34 | 107 |
| A02.66 | 34 | 108 |
| A02.67 | 34 | 109 |
| A02.8 | 17 | 14 |
| A02.9 | 18 | 14 |
| A10.1 | 165 | 161 |
| A10.10 | 174 | 161 |
| A10.11 | 175 | 161 |
| A10.12 | 176 | 161 |
| A10.13 | 177 | 161 |
| A10.14 | 178 | 161 |
| A10.15 | 179 | 161 |
| A10.16 | 180 | 161 |
| A10.17 | 156 | 181 |
| A10.18 | 156 | 182 |
| A10.19 | 156 | 183 |

| Antibody Name | Variable Heavy SEQ ID NO: (amino acid) | Variable Light SEQ ID NO: (amino acid) |
| --- | --- | --- |
| A10.2 | 166 | 161 |
| A10.20 | 156 | 184 |
| A10.21 | 156 | 185 |
| A10.22 | 156 | 186 |
| A10.23 | 156 | 187 |
| A10.24 | 156 | 188 |
| A10.25 | 156 | 189 |
| A10.26 | 156 | 190 |
| A10.27 | 156 | 191 |
| A10.28 | 156 | 192 |
| A10.29 | 156 | 193 |
| A10.3 | 167 | 161 |
| A10.30 | 156 | 194 |
| A10.31 | 156 | 195 |
| A10.32 | 156 | 196 |
| A10.35 | 197 | 161 |
| A10.36 | 156 | 198 |
| A10.38 | 152 | 161 |
| A10.39 | 152 | 181 |
| A10.4 | 168 | 161 |
| A10.40 | 152 | 182 |
| A10.41 | 152 | 183 |
| A10.42 | 152 | 184 |
| A10.43 | 152 | 185 |
| A10.44 | 152 | 186 |
| A10.45 | 152 | 187 |
| A10.46 | 152 | 188 |
| A10.47 | 152 | 189 |
| A10.48 | 152 | 190 |
| A10.49 | 152 | 191 |
| A10.5 | 169 | 161 |
| A10.50 | 152 | 192 |
| A10.51 | 152 | 193 |
| A10.52 | 152 | 194 |
| A10.53 | 152 | 195 |
| A10.54 | 152 | 196 |
| A10.57 | 152 | 198 |
| A10.59 | 156 | 161 |
| A10.6 | 170 | 161 |
| A10.7 | 171 | 161 |
| A10.8 | 172 | 161 |
| A10.9 | 173 | 161 |
| A10A2.0 (chimeric) | 148 | 157 |
| A10A2.1 | 149 | 158 |
| A10A2.10 | 150 | 160 |
| A10A2.11 | 150 | 161 |
| A10A2.12 | 150 | 162 |
| A10A2.13 | 150 | 163 |
| A10A2.14 | 150 | 164 |
| A10A2.15 | 151 | 158 |
| A10A2.16 | 151 | 159 |
| A10A2.17 | 151 | 160 |
| A10A2.18 | 151 | 161 |
| A10A2.19 | 151 | 162 |
| A10A2.2 | 149 | 159 |
| A10A2.20 | 151 | 163 |
| A10A2.21 | 151 | 164 |
| A10A2.22 | 152 | 158 |
| A10A2.23 | 152 | 159 |
| A10A2.24 | 152 | 160 |
| A10A2.25 | 152 | 161 |
| A10A2.26 | 152 | 162 |
| A10A2.27 | 152 | 163 |
| A10A2.28 | 152 | 164 |
| A10A2.29 | 153 | 158 |
| A10A2.3 | 149 | 160 |
| A10A2.30 | 153 | 159 |
| A10A2.31 | 153 | 160 |
| A10A2.32 | 153 | 161 |
| A10A2.33 | 153 | 162 |
| A10A2.34 | 153 | 163 |
| A10A2.35 | 153 | 164 |
| A10A2.36 | 154 | 158 |
| A10A2.37 | 154 | 159 |
| A10A2.38 | 154 | 160 |
| A10A2.39 | 154 | 161 |
| A10A2.4 | 149 | 161 |
| A10A2.40 | 154 | 162 |
| A10A2.41 | 154 | 163 |
| A10A2.42 | 154 | 164 |
| A10A2.43 | 154 | 158 |
| A10A2.44 | 155 | 159 |
| A10A2.45 | 155 | 160 |
| A10A2.46 | 155 | 161 |
| A10A2.47 | 155 | 162 |
| A10A2.48 | 155 | 163 |
| A10A2.49 | 155 | 164 |
| A10A2.5 | 149 | 162 |
| A10A2.50 | 156 | 158 |
| A10A2.51 | 156 | 159 |
| A10A2.52 | 156 | 160 |
| A10A2.53 | 156 | 161 |
| A10A2.54 | 156 | 162 |
| A10A2.55 | 156 | 163 |
| A10A2.56 | 156 | 164 |
| A10A2.6 | 149 | 163 |
| A10A2.7 | 149 | 164 |
| A10A2.8 | 150 | 158 |
| A10A2.9 | 150 | 159 |
| A5D1.0 (chimeric) | 114 | 125 |
| A5D1.1 | 115 | 126 |
| A5D1.10 | 116 | 129 |
| A5D1.11 | 116 | 130 |
| A5D1.12 | 116 | 131 |
| A5D1.13 | 117 | 126 |
| A5D1.14 | 117 | 127 |
| A5D1.15 | 117 | 128 |
| A5D1.16 | 117 | 129 |
| A5D1.17 | 117 | 130 |
| A5D1.18 | 117 | 131 |
| A5D1.19 | 118 | 126 |
| A5D1.2 | 115 | 127 |
| A5D1.20 | 118 | 127 |
| A5D1.21 | 118 | 128 |
| A5D1.22 | 118 | 129 |
| A5D1.23 | 118 | 130 |
| A5D1.24 | 118 | 131 |
| A5D1.25 | 119 | 126 |
| A5D1.26 | 119 | 127 |
| A5D1.27 | 119 | 128 |
| A5D1.28 | 119 | 129 |
| A5D1.29 | 119 | 130 |
| A5D1.3 | 115 | 128 |
| A5D1.30 | 119 | 131 |
| A5D1.31 | 120 | 126 |
| A5D1.32 | 120 | 127 |
| A5D1.33 | 120 | 128 |
| A5D1.34 | 120 | 129 |
| A5D1.35 | 120 | 130 |
| A5D1.36 | 120 | 131 |
| A5D1.37 | 121 | 126 |
| A5D1.38 | 121 | 127 |
| A5D1.39 | 121 | 128 |
| A5D1.4 | 115 | 129 |
| A5D1.40 | 121 | 129 |
| A5D1.41 | 121 | 130 |
| A5D1.42 | 121 | 131 |
| A5D1.43 | 122 | 126 |
| A5D1.44 | 122 | 127 |
| A5D1.45 | 122 | 128 |
| A5D1.46 | 122 | 129 |
| A5D1.47 | 122 | 130 |
| A5D1.48 | 122 | 131 |
| A5D1.49 | 123 | 126 |
| A5D1.5 | 115 | 130 |
| A5D1.50 | 123 | 127 |
| A5D1.51 | 123 | 128 |
| A5D1.52 | 123 | 129 |
| A5D1.53 | 123 | 130 |
| A5D1.54 | 123 | 131 |

| Antibody Name | Variable Heavy SEQ ID NO: (amino acid) | Variable Light SEQ ID NO: (amino acid) |
|---|---|---|
| A5D1.55 | 124 | 126 |
| A5D1.56 | 124 | 127 |
| A5D1.57 | 124 | 128 |
| A5D1.58 | 124 | 129 |
| A5D1.59 | 124 | 130 |
| A5D1.6 | 115 | 131 |
| A5D1.60 | 124 | 131 |
| A5D1.7 | 116 | 126 |
| A5D1.8 | 116 | 127 |
| A5D1.9 | 116 | 128 |
| A5E8.0 (chimeric) | 132 | 143 |
| A5E8.1 | 133 | 144 |
| A5E8.10 | 135 | 145 |
| A5E8.11 | 135 | 146 |
| A5E8.12 | 135 | 147 |
| A5E8.13 | 136 | 144 |
| A5E8.14 | 136 | 145 |
| A5E8.15 | 136 | 146 |
| A5E8.16 | 136 | 147 |
| A5E8.17 | 137 | 144 |
| A5E8.18 | 137 | 145 |
| A5E8.19 | 137 | 146 |
| A5E8.2 | 133 | 145 |
| A5E8.20 | 137 | 147 |
| A5E8.21 | 138 | 144 |
| A5E8.22 | 138 | 145 |
| A5E8.23 | 138 | 146 |
| A5E8.24 | 138 | 147 |
| A5E8.25 | 139 | 144 |
| A5E8.26 | 139 | 145 |
| A5E8.27 | 139 | 146 |
| A5E8.28 | 139 | 147 |
| A5E8.29 | 140 | 144 |
| A5E8.3 | 133 | 146 |
| A5E8.30 | 140 | 145 |
| A5E8.31 | 140 | 146 |
| A5E8.32 | 140 | 147 |
| A5E8.33 | 141 | 144 |
| A5E8.34 | 141 | 145 |
| A5E8.35 | 141 | 146 |
| A5E8.36 | 141 | 147 |
| A5E8.37 | 142 | 144 |
| A5E8.38 | 142 | 145 |
| A5E8.39 | 142 | 146 |
| A5E8.4 | 133 | 147 |
| A5E8.40 | 142 | 147 |
| A5E8.5 | 134 | 144 |
| A5E8.6 | 134 | 145 |
| A5E8.7 | 134 | 146 |
| A5E8.8 | 134 | 147 |
| A5E8.9 | 135 | 144 |
| X02.10 | 19 | 14 |
| X02.100 | 13 | 58 |
| X02.101 | 13 | 59 |
| X02.102 | 13 | 60 |
| X02.103 | 13 | 61 |
| X02.104 | 13 | 62 |
| X02.105 | 13 | 63 |
| X02.106 | 13 | 64 |
| X02.107 | 13 | 65 |
| X02.108 | 32 | 14 |
| X02.11 | 20 | 14 |
| X02.110 | 33 | 14 |
| X02.114 | 13 | 660 |
| X02.115 | 13 | 661 |
| X02.116 | 13 | 662 |
| X02.117 | 13 | 663 |
| X02.118 | 34 | 700 |
| X02.119 | 34 | 701 |
| X02.120 | 728 | 700 |
| X02.121 | 729 | 700 |
| X02.122 | 730 | 700 |
| X02.123 | 731 | 700 |
| X02.124 | 728 | 701 |
| X02.125 | 729 | 701 |
| X02.126 | 730 | 701 |
| X02.127 | 731 | 701 |
| X02.68 | 21 | 14 |
| X02.69 | 22 | 14 |
| X02.70 | 23 | 14 |
| X02.71 | 24 | 14 |
| X02.72 | 25 | 14 |
| X02.73 | 26 | 14 |
| X02.74 | 27 | 14 |
| X02.75 | 28 | 14 |
| X02.76 | 29 | 14 |
| X02.77 | 30 | 14 |
| X02.78 | 31 | 14 |
| X02.8 | 17 | 14 |
| X02.80 | 13 | 38 |
| X02.81 | 13 | 39 |
| X02.82 | 13 | 40 |
| X02.83 | 13 | 41 |
| X02.84 | 13 | 42 |
| X02.85 | 13 | 43 |
| X02.86 | 13 | 44 |
| X02.87 | 13 | 45 |
| X02.88 | 13 | 46 |
| X02.89 | 13 | 47 |
| X02.9 | 18 | 14 |
| X02.90 | 13 | 48 |
| X02.91 | 13 | 49 |
| X02.92 | 13 | 50 |
| X02.93 | 13 | 51 |
| X02.94 | 13 | 52 |
| X02.95 | 13 | 53 |
| X02.96 | 13 | 54 |
| X02.97 | 13 | 55 |
| X02.98 | 13 | 56 |
| X02.99 | 13 | 57 |
| X10.100 | 720 | 706 |
| X10.101 | 721 | 706 |
| X10.102 | 722 | 706 |
| X10.103 | 723 | 706 |
| X10.104 | 739 | 706 |
| X10.105 | 740 | 706 |
| X10.106 | 741 | 706 |
| X10.107 | 742 | 706 |
| X10.108 | 720 | 707 |
| X10.109 | 721 | 707 |
| X10.110 | 722 | 707 |
| X10.111 | 723 | 707 |
| X10.112 | 739 | 707 |
| X10.113 | 740 | 707 |
| X10.114 | 741 | 707 |
| X10.115 | 742 | 707 |
| X10.116 | 720 | 708 |
| X10.117 | 721 | 708 |
| X10.118 | 722 | 708 |
| X10.119 | 723 | 708 |
| X10.120 | 739 | 708 |
| X10.121 | 740 | 708 |
| X10.122 | 741 | 708 |
| X10.123 | 742 | 708 |
| X10.124 | 720 | 709 |
| X10.125 | 721 | 709 |
| X10.126 | 722 | 709 |
| X10.127 | 723 | 709 |
| X10.128 | 739 | 709 |
| X10.129 | 740 | 709 |
| X10.130 | 741 | 709 |
| X10.131 | 742 | 709 |
| X10.132 | 720 | 710 |
| X10.133 | 721 | 710 |
| X10.134 | 722 | 710 |
| X10.135 | 723 | 710 |
| X10.136 | 739 | 710 |
| X10.137 | 740 | 710 |
| X10.138 | 741 | 710 |
| X10.139 | 742 | 710 |

-continued

| Antibody Name | Variable Heavy SEQ ID NO: (amino acid) | Variable Light SEQ ID NO: (amino acid) |
|---|---|---|
| X10.140 | 720 | 711 |
| X10.141 | 721 | 711 |
| X10.142 | 722 | 711 |
| X10.143 | 723 | 711 |
| X10.144 | 739 | 711 |
| X10.145 | 740 | 711 |
| X10.146 | 741 | 711 |
| X10.147 | 742 | 711 |
| X10.60 | 156 | 704 |
| X10.61 | 156 | 705 |
| X10.62 | 156 | 706 |
| X10.63 | 156 | 707 |
| X10.64 | 156 | 708 |
| X10.65 | 156 | 709 |
| X10.66 | 156 | 710 |
| X10.67 | 156 | 711 |
| X10.68 | 720 | 161 |
| X10.69 | 721 | 161 |
| X10.70 | 722 | 161 |
| X10.71 | 723 | 161 |
| X10.72 | 739 | 161 |
| X10.73 | 740 | 161 |
| X10.74 | 741 | 161 |
| X10.75 | 742 | 161 |
| X10.76 | 152 | 704 |
| X10.77 | 152 | 705 |
| X10.78 | 152 | 706 |
| X10.79 | 152 | 707 |
| X10.80 | 152 | 708 |
| X10.81 | 152 | 709 |
| X10.82 | 152 | 710 |
| X10.83 | 152 | 711 |
| X10.84 | 720 | 704 |
| X10.85 | 721 | 704 |
| X10.86 | 722 | 704 |
| X10.87 | 723 | 704 |
| X10.88 | 739 | 704 |
| X10.89 | 740 | 704 |
| X10.90 | 741 | 704 |
| X10.91 | 742 | 704 |
| X10.92 | 720 | 705 |
| X10.93 | 721 | 705 |
| X10.94 | 722 | 705 |
| X10.95 | 723 | 705 |
| X10.96 | 739 | 705 |
| X10.97 | 740 | 705 |
| X10.98 | 741 | 705 |
| X10.99 | 742 | 705 |
| X910/12-HC-L0-IFN-alpha (A145D) IgG4 | 110 | 112 |
| X913/15-HC-L0-IFN-alpha (A145D) IgG4 | 111 | 113 |

The antibodies may be fused to attenuated ligands, for example, to form antibody-attenuated ligand constructs, which show an elevated antigen-specificity index with respect to activating signaling pathways due to the action of the attenuated ligand on a cell surface receptor. These constructs are based on the observation that, in the context of an antibody-ligand construct, the ligand portion can be mutated in such a way that the ligand activity on antigen-negative cells is dramatically attenuated, while the ligand activity on antigen-positive cells is only modestly, if at all, attenuated. Such constructs display one, two, three, four or five orders of magnitude greater potency on antigen-positive cells compared to antigen negative cells than does the free ligand. In some aspects, the antibody-attenuated ligand construct retains at least 1%, at least 10%, at least 20%, at least 30%, at least 40% or at least 50% of the potency on antigen-positive cells as the non-attenuated free (i.e., not attached to an antibody) ligand. In some aspects, the antibody-attenuated ligand construct retains at least 30%, at least 50%, at least 75% or at least 90% of the maximal activity of the non-attenuated free (i.e. not attached to an antibody) ligand. Maximal activity includes the amount of signaling activity (or downstream effect thereof) at the high, plateau portion of a dose-response curve, where further increases in the agent does not further increase the amount of response.

In some aspects, the antibody fusion to and inclusion of an attenuating mutation(s) in the interferon ligand increases the antigen-specificity index (ASI) by greater than 10-fold, preferably greater than 50-fold, preferably greater than 100-fold, preferably greater than 1000-fold, or preferably greater than 10,000 fold, relative to an antibody without a fusion. The ASI comprises the fold-increased potency in signaling activity of the antibody-IFN ligand construct relative to the free non-mutated polypeptide ligand on target antigen-positive cells, multiplied by the fold decreased potency in signaling activity relative to the free non-mutated polypeptide ligand on target antigen-negative cells. Potency may be quantitatively represented by the $EC_{50}$ value, which is the mathematical midpoint of a dose-response curve, in which the dose refers to the concentration of ligand or antibody-ligand construct in an assay, and response refers to the quantitative response of the cells to the signaling activity of the ligand at a particular dose. Thus, for example, when a first compound is shown to possess an $EC_{50}$ (expressed for example in Molar units) that is 10-fold lower than a second compound's $EC_{50}$ on the same cells, typically when measured by the same method, the first compound is said to have a 10-fold higher potency. Conversely, when a first compound is shown to possess an $EC_{50}$ that is 10-fold higher than a second compound's $EC_{50}$ on the same cells, typically when measured by the same method, the first compound is said to have a 10-fold lower potency.

The antibodies are preferably capable of binding to CD38-positive cells. The antibody may bind to a CD38-positive cell with an $EC_{50}$ value of less than about 100 nM. The antibody may bind to a CD38-positive cell with an $EC_{50}$ value of less than about 75 nM. The antibody may bind to a CD38-positive cell with an $EC_{50}$ value of less than about 50 nM. The antibody may bind to a CD38-positive cell with an $EC_{50}$ value of less than about 30 nM. The antibody may bind to a CD38-positive cell with an $EC_{50}$ value of less than about 25 nM. The antibody may bind to a CD38-positive cell with an $EC_{50}$ value of less than about 20 nM. The antibody may bind to a CD38-positive cell with an $EC_{50}$ value of less than about 18 nM. The antibody may bind to a CD38-positive cell with an $EC_{50}$ value of less than about 15 nM. The antibody may bind to a CD38-positive cell with an $EC_{50}$ value of less than about 13 nM. The antibody may bind to a CD38-positive cell with an $EC_{50}$ value of less than about 10 nM.

The interferon joined to the antibody preferably comprises alterations in its amino acid sequence, including point mutations and/or deletions that render the interferon less active in stimulating its respective receptors on cells that lack cell surface expression of the CD38 antigen to which the antibody binds. A highly preferred variant of interferon alpha comprises an amino acid change at position 168 of the interferon alpha 2b molecule of SEQ ID NO: 7. For example, the amino acid at position 168, which is an alanine in the parent IFN-alpha2b molecule, is preferably changed to a glycine (Gly/G) (SEQ ID NO: 650) or aspartic acid (Asp/D) (SEQ ID NO: 647). In some aspects, the IFN-alpha2b is truncated at its N-terminus when the IFN-alpha2b is fused to an IgG heavy chain constant domain such as the human IgG1 or human IgG4 heavy chain constant domain. The truncated IFN-alpha2b does not have the twenty three N-terminal amino acids of SEQ ID NO:7 (Met 1 through Gly 23 are deleted), and the truncated IFN-alpha2b comprises the amino acid sequence of SEQ ID NO: 648. The truncated IFN-alpha2b may also comprise the amino acid change at what was formerly position 168, but which becomes position 145 in the truncated protein (e.g., alanine 168 becomes alanine 145). In the truncated IFN-alpha2b, the alanine is preferably changed to a glycine (Gly/G) (SEQ ID NO: 651) or aspartic acid (Asp/D) (SEQ ID NO: 649). Interferon with A145D alteration (SEQ ID NO: 647 or SEQ ID NO: 649) is particularly preferred as the attenuated ligand fused to the antibodies of the disclosure. Any of these point-mutated, attenuated versions of IFN-alpha may be joined to any antibody described herein, for example, as an antibody-attenuated interferon construct.

The linkage between the antibody and the interferon preferably comprises a fusion, for example, a peptide bond between the N- or the C-terminus of the interferon and the N- or C-terminus of the heavy or the light chain of the antibody. In highly preferred aspects, no linker is present between the antibody and the interferon, and the antibody and interferon are thus directly fused. It is believed that direct fusion, without an intervening linker peptide, provides at least a measurable degree of attenuation of the interferon protein, and it is also believed that this attenuation is additive with the attenuation of the interferon protein that stems from the mutations introduced into the interferon protein, including those described or exemplified herein.

Polynucleotide sequences that encode antibodies and their subdomains (e.g., FWRs and CDRs) are featured in the disclosure. Polynucleotides include, but are not limited to, RNA, DNA, cDNA, hybrids of RNA and DNA, and single, double, or triple stranded strands of RNA, DNA, or hybrids thereof.

In some aspects, the polynucleotides encode the heavy chain of an antibody that specifically binds to an epitope on CD38. The polynucleotide may encode a heavy chain comprising the amino acid sequence of any of SEQ ID NO: 667, SEQ ID NO: 668, SEQ ID NO: 679, SEQ ID NO: 680, SEQ ID NO: 681, SEQ ID NO: 682, SEQ ID NO: 683, SEQ ID NO: 684, SEQ ID NO:, SEQ ID NO: 685, SEQ ID NO: 686, SEQ ID NO: 695, SEQ ID NO: 724, SEQ ID NO: 725, SEQ ID NO: 726, SEQ ID NO: 727, SEQ ID NO: 732, SEQ ID NO: 733, SEQ ID NO: 734, SEQ ID NO: 735, SEQ ID NO: 743, SEQ ID NO: 744, SEQ ID NO: 745 or SEQ ID NO: 746. The polynucleotide may encode a light chain comprising the amino acid sequence of any of SEQ ID NO: 669, SEQ ID NO: 670, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 688, SEQ ID NO: 689, SEQ ID NO: 690, SEQ ID NO: 691, SEQ ID NO: 692, SEQ ID NO: 693, SEQ ID NO: 702, SEQ ID NO: 703, SEQ ID NO: 712, SEQ ID NO: 713, SEQ ID NO: 714, SEQ ID NO: 715, SEQ ID NO: 716, SEQ ID NO: 717, SEQ ID NO: 718 or SEQ ID NO: 719. The polynucleotide may comprise the nucleic acid sequence of any of SEQ ID NO: 667, SEQ ID NO: 668, SEQ ID NO: 679, SEQ ID NO: 680, SEQ ID NO: 681, SEQ ID NO: 682, SEQ ID NO: 683, SEQ ID NO: 684, SEQ ID NO:, SEQ ID NO: 685, SEQ ID NO: 686, SEQ ID NO:695, SEQ ID NO: 724, SEQ ID NO: 725, SEQ ID NO: 726, SEQ ID NO: 727, SEQ ID NO: 732, SEQ ID NO: 733, SEQ ID NO: 734, SEQ ID NO: 735, SEQ ID NO: 743, SEQ ID NO: 744, SEQ ID NO: 745, SEQ ID NO: 746, SEQ ID NO: 669, SEQ ID NO: 670, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 688, SEQ ID NO: 689, SEQ ID NO: 690, SEQ ID NO: 691, SEQ ID NO: 692, SEQ ID NO: 693, SEQ ID NO: 702, SEQ ID NO: 703, SEQ ID NO: 712, SEQ ID NO: 713, SEQ ID NO: 714, SEQ ID NO: 715, SEQ ID NO: 716, SEQ ID NO: 717, SEQ ID NO: 718 or SEQ ID NO: 719. The polynucleotide may comprise a nucleic acid sequence having at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity with any of SEQ ID NO: 667, SEQ ID NO: 668, SEQ ID NO: 679, SEQ ID NO: 680, SEQ ID NO: 681, SEQ ID NO: 682, SEQ ID NO: 683, SEQ ID NO: 684, SEQ ID NO:, SEQ ID NO: 685, SEQ ID NO: 686, SEQ ID NO:695, SEQ ID NO: 724, SEQ ID NO: 725, SEQ ID NO: 726, SEQ ID NO: 727, SEQ ID NO: 732, SEQ ID NO: 733, SEQ ID NO: 734, SEQ ID NO: 735, SEQ ID NO: 743, SEQ ID NO: 744, SEQ ID NO: 745, SEQ ID NO: 746, SEQ ID NO: 669, SEQ ID NO: 670, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 688, SEQ ID NO: 689, SEQ ID NO: 690, SEQ ID NO: 691, SEQ ID NO: 692, SEQ ID NO: 693, SEQ ID NO: 702, SEQ ID NO: 703, SEQ ID NO: 712, SEQ ID NO: 713, SEQ ID NO: 714, SEQ ID NO: 715, SEQ ID NO: 716, SEQ ID NO: 717, SEQ ID NO: 718 or SEQ ID NO: 719, and in some aspects such variants preferably encode the same amino acids encoded by the polynucleotide sequence of SEQ ID NO: 667, SEQ ID NO: 668, SEQ ID NO: 679, SEQ ID NO: 680, SEQ ID NO: 681, SEQ ID NO: 682, SEQ ID NO: 683, SEQ ID NO: 684, SEQ ID NO:, SEQ ID NO: 685, SEQ ID NO: 686, SEQ ID NO:695, SEQ ID NO: 724, SEQ ID NO: 725, SEQ ID NO: 726, SEQ ID NO: 727, SEQ ID NO: 732, SEQ ID NO: 733, SEQ ID NO: 734, SEQ ID NO: 735, SEQ ID NO: 743, SEQ ID NO: 744, SEQ ID NO: 745, SEQ ID NO: 746, SEQ ID NO: 669, SEQ ID NO: 670, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 688, SEQ ID NO: 689, SEQ ID NO: 690, SEQ ID NO: 691, SEQ ID NO: 692, SEQ ID NO: 693, SEQ ID NO: 702, SEQ ID NO: 703, SEQ ID NO: 712, SEQ ID NO: 713, SEQ ID NO: 714, SEQ ID NO: 715, SEQ ID NO: 716, SEQ ID NO: 717, SEQ ID NO: 718 or SEQ ID NO: 719. Preferably, the antibodies encoded by the polynucleotide variants will specifically bind to CD38 with an affinity about equal to the affinity of the antibody encoded by the parent (non-variant) polynucleotide sequence. Affinity may be measured, for example, according to any technique described or exemplified herein, including techniques described in the Examples. Complements of the polynucleotide sequences and the variant polynucleotide sequences are also within the scope of the disclosure.

Also encompassed within the disclosure are vectors comprising the polynucleotides of the disclosure. The vectors may be expression vectors. Recombinant expression vectors containing a sequence encoding a polypeptide of interest are thus provided. The expression vector may contain one or more additional sequences, such as but not limited to regulatory sequences, a selection marker, a purification tag, or a polyadenylation signal. Such regulatory elements may include a transcriptional promoter, enhancers, mRNA ribosomal binding sites, or sequences that control the termination of transcription and translation.

Expression vectors, especially mammalian expression vectors, may include one or more nontranscribed elements, such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a specific host may also be incorporated.

The vectors may be used to transform any of a wide array of host cells well known to those of skill in the art, and preferably host cells capable of expressing antibodies. Vectors include without limitation, plasmids, phagemids, cosmids, baculoviruses, bacmids, bacterial artificial chromosomes (BACs), yeast artificial chromosomes (YACs), and baculovirus, as well as other bacterial, eukaryotic, yeast, and viral vectors. Suitable host cells include without limitation CHO cells, HEK293 cells, or any eukaryotic stable cell line known or produced, and also include bacteria, yeast, and insect cells.

The antibodies may also be produced by hybridoma cells; methods to produce hybridomas being well known and established in the art.

It has been observed in accordance with the disclosure that when interferon alpha ligand, having one or more mutations that substantially decrease the affinity of the ligand for an interferon receptor, is linked to an anti-CD38 antibody that targets the mutated interferon alpha ligand to target cells which display the antibody's corresponding antigen, the ligand's activity on target antigen-positive cells is maintained while the ligand's activity on non-target antigen-negative cells is substantially reduced. The net result is a ligand signaling molecule that has a much greater potency in activation of its receptors on antigen-positive target cells compared to antigen-negative non-target cells, which provides a means for reducing toxicity arising from off-target ligand activity.

In some aspects, a polypeptide construct comprises an IFN-alpha variant linked to an anti-CD38 antibody or antigen binding portion thereof. Such a polypeptide will be capable of exerting with high potency the IFN's antiproliferative activity on CD38-positive tumor cells while exerting a much lower potency on CD38-negative, non-tumor cells within the body.

The disclosure also provides compositions comprising the antibodies and antibody-attenuated interferon constructs of the disclosure. These compositions can further comprise at least one of any suitable auxiliary, such as, but not limited to one or more, diluents, binders, stabilizers, buffers, salts, lipophilic solvents, preservatives, adjuvants, or other suitable carrier and/or excipient. Pharmaceutically acceptable auxiliaries are preferred. The compositions may comprise any of the antibodies and antibody-attenuated interferon constructs described and/or exemplified herein and an acceptable carrier such as a pharmaceutically acceptable carrier. Suitable carriers include any media that does not interfere with the biological activity of the antibody and/or the interferon and preferably is not toxic to a host to which it is administered. The carrier may be an aqueous solution, such as water, saline, or alcohol, or a physiologically compatible buffer, such as Hanks's solution, Ringer's solution, or physiological saline buffer. The carrier may contain formulatory agents, such as suspending, stabilizing and/or dispersing agents Pharmaceutical excipients and additives useful in the composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and other known sugars; and polysaccharides or sugar polymers), which can be present singly or in combination, comprising alone or in combination any suitable weight or volume. Exemplary protein excipients include serum albumin, such as human serum albumin (HSA), recombinant human albumin (rHA), gelatin, casein, and other known proteins. Representative amino acids which can also function in a buffering capacity include alanine, glycine, arginine, betaine, histidine, glutamic acid, aspartic acid, cysteine, lysine, leucine, isoleucine, valine, methionine, phenylalanine, and aspartame. One preferred amino acid is histidine. A second preferred amino acid is arginine.

Carbohydrate excipients suitable for use in the composition include, for example, monosaccharides, such as fructose, maltose, galactose, glucose, D-mannose, and sorbose; disaccharides, such as lactose, sucrose, trehalose, and cellobiose; polysaccharides, such as raffinose, melezitose, maltodextrins, dextrans, and starches; and alditols, such as mannitol, xylitol, maltitol, lactitol, xylitol sorbitol (glucitol), and myoinositol. Preferred carbohydrate excipients for use in the disclosure are mannitol, trehalose, and raffinose.

Antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, the compositions of the disclosure can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, antimicrobial agents, antioxidants, antistatic agents, surfactants (e.g., polysorbates such as "TWEEN® 20" and "TWEEN® 80"), lipids (e.g., phospholipids, fatty acids), steroids (e.g., cholesterol), and chelating agents (e.g., EDTA).

The compositions may also be formulated in sustained release vehicles or depot preparations. For example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administrations. The compositions may be formulated in a suitable controlled-release vehicle, with an adjuvant, or as a depot formulation.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

An anti-CD38-attenuated interferon alpha-2b fusion construct may be used, for example, to inhibit, reduce, decrease, block, or prevent proliferation of a cell that expressed CD38 on its surface. In some aspects, methods for inhibiting or reducing proliferation of a cell that expresses CD38 on its surface generally comprise contacting a cell expressing CD38 with an anti-CD38-attenuated interferon alpha-2b fusion construct in an amount effective to inhibit or reduce proliferation of the cell. The antibody that specifically binds to CD38 may be any antibody described or exemplified herein. The attenuated interferon alpha 2b may comprise IFN-alpha2b A145D or IFN-alpha2b A145G. The cell may be a lymphocyte, an autoimmune lymphocyte, or a tumor cell such as a leukemia cell, a multiple myeloma cell, or a lymphoma cell. The anti-CD38-attenuated interferon alpha-2b fusion construct may be comprised in a composition, for example, with a pharmaceutically acceptable carrier and optionally one or more auxiliaries or excipients, including any such carrier, auxiliary, or excipient described or exemplified herein. The methods may be carried out in vitro, ex vivo, in vivo, or in situ.

An anti-CD38-attenuated interferon alpha-2b fusion construct may also be used, for example, to induce, facilitate, or enhance apoptosis of a cell that expressed CD38 on its surface. In some aspects, methods for inducing apoptosis in a cell that expresses CD38 on its surface generally comprise contacting a cell expressing CD38 with an anti-CD38-attenuated interferon alpha-2b fusion construct in an amount effective to induce apoptosis in the cell. The antibody that specifically binds to CD38 may be any antibody described or exemplified herein. The attenuated interferon alpha 2b may comprise IFN-alpha2b A145D or IFN-alpha2b A145G. The cell may be a lymphocyte, an autoimmune lymphocyte, or a tumor cell such as a leukemia cell, a multiple myeloma cell, or a lymphoma cell. The anti-CD38-attenuated interferon alpha-2b fusion construct may be comprised in a composition, for example, with a pharmaceutically acceptable carrier and optionally one or more auxiliaries or excipients, including any such carrier, auxiliary, or excipient described or exemplified herein. The methods may be carried out in vitro, ex vivo, in vivo, or in situ.

An anti-CD38-attenuated interferon alpha-2b fusion construct may also be used to treat a subject having a tumor that comprises and/or is mediated, at least in part, by cells that express CD38 on their surface. In some aspects, methods for treating a tumor comprising cells expressing CD38 on their surface generally comprise administering to a subject in need thereof an anti-CD38-attenuated interferon alpha-2b fusion construct in an amount effective to treat the tumor in the subject. Effective treatment may include, for example, inhibiting or reducing proliferation of CD38-positive cells in the tumor and/or inducing apoptosis of CD38-positive cells in the tumor. The antibody that specifically binds to CD38 may be any antibody described or exemplified herein. The attenuated interferon alpha 2b may comprise IFN-alpha2b A145D or IFN-alpha2b A145G. The anti-CD38-attenuated interferon alpha-2b fusion construct may be comprised in a composition, for example, with a pharmaceutically acceptable carrier and optionally one or more auxiliaries or excipients, including any such carrier, auxiliary, or excipient described or exemplified herein.

The anti-CD38-attenuated interferon alpha-2b fusion constructs or composition comprising such constructs may be administered to the tumor by administering the constructs of composition to the blood. The anti-CD38-attenuated interferon alpha-2b fusion constructs or composition comprising such constructs may be administered such that the construct diffuses via blood flow to and/or into the tumor cells. The construct may be internalized by a tumor cell.

Use of an anti-CD38 antibody or anti-CD38 antibody-attenuated interferon alpha-2b fusion construct in the treatment of tumors are provided. Methods for treating tumors with an anti-CD38 antibody or anti-CD38 antibody-attenuated interferon alpha-2b fusion construct are provided. Any anti-CD38 antibody or anti-CD38 antibody-attenuated interferon alpha-2b fusion construct described or exemplified herein may be used. Tumors that may be treated include, but are not limited to AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, hematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, multiple myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor. In an embodiment the tumor is selected from a group of multiple myeloma or non-hodgkin's lymphoma.

In preferred aspects, the methods are used for treatment of multiple myeloma, leukemia, or lymphoma in a subject in need thereof. Such methods may further comprise treating the subject with a retinoid, such as all-trans retinoic acid. In some preferred aspects in which the cell surface associated antigen is CD38, the tumor or cancer may be selected from multiple myeloma, non-Hodgkin's lymphoma, chronic myelogenous leukemia, chronic lymphocytic leukemia or acute myelogenous leukemia.

An anti-CD38-attenuated interferon alpha-2b fusion construct may be combined with other drugs and/or used in addition to other cancer treatment regimens or modalities such as radiation therapy or surgery. When anti-CD38-attenuated interferon alpha-2b fusion constructs are used in combination with known therapeutic agents the combination may be administered either in sequence (either continuously or broken up by periods of no treatment) or concurrently or as a mixture. In the case of cancer, there are numerous known anticancer agents that may be used in this context. Treatment in combination is also contemplated to encompass the treatment with either the anti-CD38-attenuated interferon alpha-2b fusion construct followed by a known treatment, or treatment with a known agent followed by treatment with the anti-CD38-attenuated interferon alpha-2b fusion construct, for example, as maintenance therapy. For example, in the treatment of cancer it is contemplated that the anti-CD38-attenuated interferon alpha-2b fusion construct may be administered in combination with an alkylating agent (such as mechlorethamine, cyclophosphamide, chlorambucil, ifosfamidecysplatin, or platinum-containing alkylating-like agents such as cisplatin, carboplatin and oxaliplatin), an antimetabolite (such as a purine or pyrimidine analogue or an antifolate agent, such as azathioprine and mercaptopurine), an anthracycline (such as Daunorubicin, Doxorubicin, Epirubicinldarubicin, Valrubicin, Mitoxantrone, or anthracycline analog), a plant alkaloid (such as a *vinca* alkaloid or a taxane, such as Vincristine, Vinblastine, Vinorelbine, Vindesine, paclitaxel or Dosetaxel), a topoisomerase inhibitor (such as a type I or type II topoisomerase inhibitor), a Podophyllotoxin (such as etoposide or teniposide), or a tyrosine kinase inhibitor (such as imatinibmesylate, Nilotinib, or Dasatinib).

In the case of the treatment of multiple myeloma, an anti-CD38-attenuated interferon alpha-2b fusion construct may be administered in combination with other suitable therapies, such as treatment of the subject with the administration of steroids such as dexamethasone, proteasome inhibitors (such as bortezomib or carfilzomib), immuno-modulatory drugs (such as thalidomide, lenalidomide or pomalidomide), or induction chemotherapy followed by autologous hematopoietic stem cell transplantation, with or without other chemotherapeutic agents such as Melphalan hydrochloride or the chemotherapeutic agents listed above.

In the case of the treatment of Hodgkin's lymphoma, an anti-CD38-attenuated interferon alpha-2b fusion construct may be administered in combination with current therapeutic approaches, such as ABVD (Adriamycin (doxorubicin), bleomycin, vinblastine, and dacarbazine), or Stanford V (doxorubicin, bleomycin, vinblastine, vincristine, mechlorethamine, etoposide, prednisone), or BEACOPP (doxorubicin, bleomycin, vincristine, cyclophosphamide, procarbazine, etoposide, prednisone).

In the case of non-Hodgkin's lymphoma or other lymphomas, an anti-CD38-attenuated interferon alpha-2b fusion construct may be administered in combination current therapeutic approaches. Examples of drugs approved for non-Hodgkin lymphoma include Abitrexate (Methotrexate), Adriamycin PFS (Doxorubicin Hydrochloride), Adriamycin RDF (Doxorubicin Hydrochloride), Ambochlorin (Chlorambucil), Amboclorin (Chlorambucil), Arranon (Nelarabine), Bendamustine Hydrochloride, Bexxar (Tositumomab and Iodine I 131 Tositumomab), Blenoxane (Bleomycin), Bleomycin, Bortezomib, Chlorambucil, Clafen (Cyclophosphamide), Cyclophosphamide, Cytoxan (Cyclophosphamide), DenileukinDiftitox, DepoCyt (Liposomal Cytarabine), Doxorubicin Hydrochloride, DTIC-Dome (Dacarbazine), Folex (Methotrexate), Folex PFS (Methotrexate), Folotyn (Pralatrexate), IbritumomabTiuxetan, Istodax (Romidepsin), Leukeran (Chlorambucil), Linfolizin (Chlorambucil), Liposomal Cytarabine, Matulane (Procarbazine Hydrochloride), Methotrexate, Methotrexate LPF (Methotrexate), Mexate (Methotrexate), Mexate-AQ (Methotrexate), Mozobil (Plerixafor), Nelarabine, Neosar (Cyclophosphamide), Ontak (DenileukinDiftitox), Plerixafor, Pralatrexate, Rituxan (Rituximab), Rituximab, Romidepsin, Tositumomab and Iodine I 131 Tositumomab, Treanda (Bendamustine Hydrochloride), Velban (Vinblastine Sulfate), Velcade (Bortezomib), and Velsar (Vinblastine Sulfate), Vinblastine Sulfate, Vincasar PFS (Vincristine Sulfate), Vincristine Sulfate, Vorinostat, Zevalin (IbritumomabTiuxetan), Zolinza (Vorinostat). Examples of drug combinations used in treating non-Hodgkin lymphoma include CHOP (C=Cyclophosphamide, H=Doxorubicin Hydrochloride (Hydroxydaunomycin), O=Vincristine Sulfate (Oncovin), P=Prednisone); COPP (C=Cyclophosphamide, O=Vincristine Sulfate (Oncovin), P=Procarbazine Hydrochloride, P=Prednisone); CVP (C=Cyclophosphamide, V=Vincristine Sulfate, P=Prednisone); EPOCH (E=Etoposide, P=Prednisone, O=Vincristine Sulfate (Oncovin), C=Cyclophosphamide, H=Doxorubicin Hydrochloride (Hydroxydaunomycin)); ICE (I=Ifosfamide, C=Carboplatin, E=Etoposide) and R-CHOP (R=Rituximab, C=Cyclophosphamide, H=Doxorubicin Hydrochloride (Hydroxydaunomycin), O=Vincristine Sulfate (Oncovin), P=Prednisone.

An anti-CD38 antibody, or an anti-CD38-attenuated interferon alpha-2b fusion construct may be used to detect CD38-positive cells, including CD38-positive tumor cells. In some aspects, they may be used in methods for detecting a CD38-positive tumor cell in a tissue sample isolated from a subject, which methods may generally comprise contacting an anti-CD38 antibody, or an anti-CD38-attenuated interferon alpha-2b fusion construct, with a tissue sample isolated from a subject and detecting a complex of the antibody or construct and a CD38-positive cell in the tissue sample. The tissue sample preferably is blood. The cell may be a CD38-positive B-cell lymphoma cell, multiple myeloma cell, non-Hodgkin's lymphoma cell, chronic myelogenous leukemia cell, chronic lymphocytic leukemia cell, or acute myelogenous leukemia cell. The method may further comprise isolating the tissue sample from the subject.

The disclosure also features kits comprising any of the antibodies and anti-CD38-attenuated interferon alpha-2b fusion constructs described and exemplified herein. The kits may be used to supply antibodies and other agents for use in diagnostic, basic research, or therapeutic methods, among others.

In some aspects, a kit comprises an anti-CD38-attenuated interferon alpha-2b fusion construct, the construct optionally comprised in a composition comprising a pharmaceutically acceptable carrier, and instructions for using the kit in one or more of a method for inhibiting or reducing proliferation of a tumor cell expressing CD38 on its surface, a method for inducing apoptosis in a tumor cell expressing CD38 on its surface, and/or a method for treating a tumor that comprises and/or is mediated by cells expressing CD38 on their surface. Such methods may be any method described or exemplified herein. The kits may comprise a pharmaceutically acceptable carrier. The kits may comprise one or more pharmaceutically acceptable auxiliaries and/or one or more pharmaceutically acceptable excipients. In the kits, the anti-CD38 antibody may be any antibody described or exemplified herein, and the attenuated interferon alpha-2b may comprise any attenuated interferon alpha-2b described or exemplified herein. The constructs may be comprised in sterile solutions ready for injection or intravenous administration, or may comprise a sterile, lyophilized form ready to be combined with a carrier just prior to use.

In some aspects, a kit comprises an anti-CD38 antibody and instructions for using the kit in a method for detecting CD38-positive cells in a sample, including a tissue sample isolated from a subject. The anti-CD38 antibody may be any antibody described or exemplified herein. The antibody may optionally be fused to an attenuated interferon alpha-2b protein.

The following examples are provided to describe the disclosure in greater detail. They are intended to illustrate, not to limit, the disclosure.

Example 1

Optimization of X355/02-HC-L0-IFN-alpha (A145D) IgG4

Other anti-CD38-attenuated IFN fusion proteins are described in PCT Application No. PCT/AU2012/001323. These include the antibody construct designated in the PCT application as X355/02-HC-L0-IFN-alpha (A145D) IgG4. In this specification, X355/02-HC-L0-IFN-alpha (A145D) IgG4 has been renamed as A02.1. The heavy chain sequence of the antibody comprises the amino acid sequence of SEQ ID NO: 11, and the light chain sequence comprises the amino acid sequence of SEQ ID NO: 12. The variable light chain of A02.1 (SEQ ID NO: 14) was co-expressed with its variable heavy chain A02.1 (SEQ ID NO: 13) formatted on a human IgG4 constant region containing the substitution S228P (EU Numbering) (SEQ ID NO: 3). This antibody is referred to herein as X02.1. A02.1 includes a fusion to IFN-alpha2b whilst X02.1 does not, despite both antibodies sharing identical heavy chain and light chains sequences.

A BLAST search (Altschul S F (1997) Nucleic Acids Res. 25:3389-3402) against a database of human germline immunoglobulin genes was performed using the amino acid sequence of the variable heavy chain of X02.1. The closest human germline variable heavy chain gene was IGHV4-61*01 (SEQ ID NO: 16). An alignment of the X02.1 VH and IGHV4-61*01 is shown in FIG. 2. The X02.1 variable heavy region differs by eight amino acids from its closest germline amino acid sequence. In order to reduce the immunogenicity of the X02.1 heavy chain variable region, germline amino acid residue substitutions could be produced at residues where it differs from the germline sequence and the resulting antibody variants tested for anti-CD38 binding activity.

Several heavy chain variants of the X02.1 parental sequence are detailed in FIG. 2. These heavy chain variable regions were formatted onto the IgG4 S228P constant region, and co-expressed with the A02.1 light chain. Tables 1a and 1b detail the sequences of the variants tested along with their ability to bind human CD38 as assessed using flow cytometry and surface plasmon resonance (SPR). Briefly, antibody chains were transiently co-expressed in CHO cells and purified via Protein A chromatography as described in the Example 5. Flow binding assays as described in Example 5 were used to assess the variants. The $EC_{50}$ of the dose response curve obtained for each antibody is also given in Tables 1a and 1b.

TABLE 1a

| Antibody Designation | Variable Heavy Chain Amino Acid Substitution (Relative to X02.1) | Variable Heavy SEQ ID NO: | Variable Light SEQ ID NO: | CD38 binding by SPR | ARP-1 flow binding assay ($EC_{50}$ in µg/mL) |
|---|---|---|---|---|---|
| X02.8 | L74S | 17 | 14 | $2.30 \times 10^{-8}$ | 18.3 |
| X02.9 | H40P | 18 | 14 | $2.63 \times 10^{-8}$ | N/T |
| X02.10 | T(82A)S | 19 | 14 | $2.07 \times 10^{-8}$ | N/T |
| X02.11 | L74S, I78F R81K, T(82A)S | 20 | 14 | $2.39 \times 10^{-8}$ | 18.1 |
| X02.108 | I78F | 32 | 14 | $2.63 \times 10^{-8}$ | N/T |
| X02.110 | R81K | 33 | 14 | $2.07 \times 10^{-8}$ | N/T |

N/T—Protein was not able to be purified and was not tested.

TABLE 1b

| Antibody Designation | Variable Heavy Chain Amino Acid Substitution (Relative to X02.1) | Variable Heavy SEQ ID NO: | Variable Light SEQ ID NO: | CD38 binding by SPR | ARP-1 flow binding assay ($EC_{50}$ in µg/mL) |
|---|---|---|---|---|---|
| X02.69 | Q2V | 22 | 14 | $3.68 \times 10^{-11}$ | 16.8 |
| X02.71 | I29V | 24 | 14 | $1.29 \times 10^{-10}$ | 3.5 |
| X02.78 | S32G | 31 | 14 | $2.04 \times 10^{-11}$ | N/T |

N/T—Protein not purified or tested.

SPR binding of the variants detailed in Table 1a was evaluated separately to those of Table 1b. The $K_D$ (M) of the parental antibody X02.1 ranged from $2.7 \times 10^{-8}$ to $3.78 \times 10^{-10}$ in the SPR binding experiments. Flow cytometry binding experiments showed antibodies X02.8, X02.11, X02.69 and X02.71 bound strongly to the CD38 positive cell line ARP-1.

Antibodies with the above amino acid substitutions were subsequently explored in the context of a fusion protein through conjugation to attenuated IFN-alpha2b (termed A02 when linked to IFN, with the number following the decimal representing the same variant having the X02 designation). These heavy chain variable regions were formatted onto an IgG4 constant region comprising the substitution S228P fused to A145D attenuated IFN-alpha2b and co-expressed in CHO or HEK cells with the A02.1 light chain as described in the Example 5. Proteins that were successfully purified from cell supernatant were then tested in a flow binding assay to the cell line ARP-1. The $EC_{50}$ value of the dose response curve for each antibody is given in Table 2. All antibody-attenuated IFN fusion constructs tested bound to the CD38 positive cell line ARP-1. It was observed that heavy chain variant X02.9 (not fused to IFN) could not easily be purified whereas an identical variant fused to IFN (A02.9) was purified. In some cases, attenuated IFN fusion proteins could be expressed and purified, when the equivalent monoclonal antibody appeared more difficult to be expressed and/or purify.

TABLE 2

| Anti-CD38-attenuated IFN fusion protein | Variable Heavy Chain Amino Acid Substitution (Relative to A02.1) | Variable Heavy SEQ ID NO: | Variable Light SEQ ID NO: | Protein Acapture by SPR (RU)* | CD38 binding by SPR (RU) at 350 sec* | ARP-1 flow binding assay ($EC_{50}$ in μg/mL) |
|---|---|---|---|---|---|---|
| A02.8 | L74S | 17 | 14 | 4697 | 833 | 1.9 |
| A02.9 | H40P | 18 | 14 | 4718 | 841 | 1.0 |
| A02.10 | T(82A)S | 19 | 14 | 4647 | 804 | 1.5 |
| A02.11 | L74S, I78F, R81K, T(82A)S | 20 | 14 | 4483 | 827 | 3.5 |

*Note:
The amount of Anti-CD38 attenuated IFN fusion protein in the cell culture supernatant is indicated by the Protein A capture by SPR. The CD38 binding by SPR refers to the amount of CD38 that remains bound to the surface after 350 seconds of the dissociation phase.

BLAST searches using the amino acid sequence of the A02.1 variable light chain were performed against the database of human germline immunoglobulin genes. The closest human germline variable light chain gene was IGLV5-37*01. An amino acid sequence alignment of A02.1VL and IGLV5-37*01 is given in FIG. 3. This alignment illustrates a 12 amino acid difference between these sequences.

Several amino acid substitutions were made in the X02.1 variable light chain. These substitutions are shown in FIG. 3. Co-expression of these light chain variable regions with the X02.1 variable heavy chain formatted onto an IgG4 constant region containing the substitution S228P was performed in CHO cells as described in Example 5.

Antibodies purified from CHO cell supernatants were subsequently tested in flow cytometry-based binding assays to the CD38 positive cell line ARP-1. Table 3 details $EC_{50}$ values of the dose response curve obtained for each antibody.

TABLE 3

| Antibody Designation | Variable Light Chain Amino Acid Substitution (Relative to A02.1) | Variable Heavy SEQ ID NO: | Variable Light SEQ ID NO: | CD38 binding by SPR (KD) | ARP-1 flow binding assay ($EC_{50}$ in μg/mL) | Protein A HPLC mg/L |
|---|---|---|---|---|---|---|
| X02.95 | A2P | 13 | 53 | $4.40 \times 10^{-12}$ | N/T | 11.1 |
| X02.96 | A8P | 13 | 54 | $2.50 \times 10^{-10}$ | 30.0 | 19.9 |
| X02.97 | L11S | 13 | 55 | $7.51 \times 10^{-12}$ | Low Binding | 15.0 |
| X02.98 | R29S | 13 | 56 | $5.84 \times 10^{-12}$ | N/T | 8.7 |
| X02.99 | Y30S | 13 | 57 | $3.21 \times 10^{-12}$ | 4.4 | 11.5 |
| X02.100 | H(54A)D | 13 | 58 | $1.60 \times 10^{-7}$ | Low Binding | 18.9 |
| X02.101 | V(66B)A | 13 | 59 | $2.89 \times 10^{-11}$ | 13.7 | 21.0 |
| X02.102 | T68A | 13 | 60 | $1.20 \times 10^{-10}$ | 20.4 | 18.0 |
| X02.103 | S70T | 13 | 61 | $1.28 \times 10^{-9}$ | 9.4 | 27.9 |
| X02.104 | T90I | 13 | 62 | $1.0 \times 10^{-8}$ | 9.7 | 23.1 |
| X02.105 | S92P | 13 | 63 | $3.31 \times 10^{-8}$ | 12.7* | 19.3 |
| X02.106 | G95A | 13 | 64 | $4.47 \times 10^{-8}$ | N/T | 11.6 |

N/T - Protein not purified or not tested.

Low Binding - Minimal binding observed, not sufficient for an $EC_{50}$ value.

*Antibody was tested in a flow binding assay against H929 cell line. Reported value is the $EC_{50}$ in μg/mL.

Antibodies X02.96, X02.99, X02.101, X02.102, X02.103 and X02.104 bound strongly to the CD38 positive ARP-1 cell line. X02.105 was able to bind strongly to the CD38 positive, H929 cell line.

Amino acid sequence analysis of the variable heavy chain sequence of X02.1 and A02.1 identified amino acids that could potentially undergo oxidation or isomerization. These include a potential isomerization site at D101 and a potential oxidation site at M(100C). To remove the potential isomerization and oxidation sites, amino acid substitutions were made as follows: D(101)E (SEQ ID NO: 30), M(100C)L (SEQ ID NO: 29) and the combination of both D(101)E and M(100C)L (SEQ ID NO: 27) (FIG. 2). Antibodies were made with combinations of these amino acid substitutions in the variable heavy chain as shown in Table 4. Antibody heavy chain variable regions were formatted with an IgG4 constant region containing the substitution S228P and co-expressed with the A02.1 light chain in CHO cells. Antibodies were then purified by Protein A chromatography and screened for binding to ARP-1 cells by flow cytometry. The binding data obtained is shown in Table 4.

X02.94 bound the CD38 positive cell line ARP-1 indicating that the substitution M89L had little impact on CD38

TABLE 4

| Antibody Designation | Variable Heavy Chain Amino Acid Substitution (Relative to X02.1) | Variable Heavy SEQ ID NO: | Variable Light SEQ ID NO: | CD38 binding by SPR (KD) | ARP-1 flow binding assay (EC$_{50}$ in µg/mL) | Protein A HPLC mg/L |
|---|---|---|---|---|---|---|
| X02.76 | M(100C)L | 29 | 14 | $1.58 \times 10^{-13}$ | 4.1 | 24.8 |
| X02.77 | D101E | 30 | 14 | $9.11 \times 10^{-12}$ | 3.7 | 15.6 |
| X02.74 | M(100C)L, D101E | 27 | 14 | $6.85 \times 10^{-11}$ | N/T | 21.8 |

N/T - Protein was not purified or not tested.

Antibodies X02.76 and X02.77 maintained their strong binding to the ARP-1 cell line indicating that the amino acids substitutions to remove the potential oxidation and isomerization sites in the X02.1 and A02.1 heavy chain had little impact on their CD38 binding activity. Combining these substitutions to form antibody X02.74 resulted in an antibody that did not purify using the protocol in Example 5.

Amino acid analysis of the variable light chain sequence of X02.1 and A02.1 identified amino acids that could potentially undergo oxidation or deamidation. These included a potential deamidation site at N69 and potential oxidation site at M89. Additionally a putative N-linked glycosylation site was predicted to exist within CDR3 of the light chain at position N94. The presence of N-linked glycans can cause heterogeneity in therapeutic proteins, complicating development. To remove these potential issues the following point variants were synthesized: N69A (SEQ ID NO: 39), M89L (SEQ ID NO: 52) and M89I (SEQ ID NO: 51), N94T (SEQ ID NO: 48), N94Q (SEQ ID NO: 38), G95P (SEQ ID NO: 50) and S96A (SEQ ID NO: 45) (see FIG. 3). Antibodies were generated by co-expression of the heavy- and light chains in CHO cells as detailed in Table 5. Antibodies were purified by Protein A chromatography and screened for binding to ARP-1 cells by flow cytometry. The binding data obtained is presented in Table 5.

binding activity. The substitution N94Q in antibody X02.80 removed the potential N-linked glycosylation motif with minimal impact on CD38 binding activity as measure by flow cytometry (Table 5). Other substitutions that remove this glycosylation motif either resulted in antibodies that could not easily be purified or antibodies that exhibited attenuated binding to the CD38 positive cell line ARP-1. The potential deamidation site at position 69 was removed through substitution to alanine, though this antibody (X02.81) was not easily purified.

Other antibodies tested that comprised X02.1 variable heavy chain variants are listed in Table 6. These heavy chain variable regions were formatted on an IgG4 constant region containing an S228P substitution. These heavy chains were co-expressed with the A02.1 light chain in CHO cells. The antibodies were expressed and the resulting antibodies tested in flow cytometry-based assays for binding to the CD38-positive cell ARP-1. All variable heavy chain substitutions with the exception of T23K (SEQ ID NO:21; X02.68) had minimal impact on binding to the CD38 positive cell line ARP-1 in flow cytometry-based assays.

TABLE 5

| Antibody Designation | Variable Light Chain Amino Acid Substitution (Relative to A02.1) | Variable Heavy SEQ ID NO: | Variable Light SEQ ID NO: | CD38 binding by SPR | ARP-1 flow binding assay (EC$_{50}$ in µg/mL) | Protein A HPLC mg/L |
|---|---|---|---|---|---|---|
| X02.81 | N69A | 13 | 39 | $2.67 \times 10^{-10}$ | N/T | 12.6 |
| X02.93 | M89I | 13 | 51 | $2.56 \times 10^{-11}$ | 18.7 | 20.0 |
| X02.94 | M89L | 13 | 52 | $3.48 \times 10^{-12}$ | 8.7 | 18.9 |
| X02.90 | N94T | 13 | 48 | $5.52 \times 10^{-10}$ | 26.2 | 23.0 |
| X02.80 | N94Q | 13 | 38 | $1.44 \times 10^{-9}$ | 13.2 | 30.3 |
| X02.92 | G95P | 13 | 50 | Low Binding | Low Binding | 18.1 |
| X02.87 | S96A | 13 | 45 | $1.99 \times 10^{-9}$ | 37.5 | 18.9 |

N/T - Protein was not purified or tested

Low Binding - Minimal binding observed, not sufficient for an EC$_{50}$ or KD value.

TABLE 6

| Antibody Designation | Variable Heavy Chain Amino Acid Substitution (Relative to X02.1) | Variable Heavy SEQ ID NO: | Variable Light SEQ ID NO: | CD38 binding by SPR | ARP-1 flow binding assay ($EC_{50}$ in μg/mL) | Protein A HPLC mg/L |
|---|---|---|---|---|---|---|
| X02.73 | S19K | 26 | 14 | $3.85 \times 10^{-10}$ | 4.3 | 20.6 |
| X02.68 | T23K | 21 | 14 | $1.06 \times 10^{-11}$ | N/T | 17.0 |
| X02.70 | V71R | 23 | 14 | $3.54 \times 10^{-9}$ | 7.2 | 32.8 |
| X02.75 | T73K | 28 | 14 | $6.38 \times 10^{-10}$ | 4.9 | 17.8 |
| X02.72 | T83R | 25 | 14 | $1.63 \times 10^{-9}$ | 3.6 | 30.6 |

N/T - Protein not purified or tested.

Antibodies comprising other light chain variable region substitutions in the X02.1 sequence were also produced. These variant light chains were combined with the X02.1 heavy chain formatted onto an IgG4 constant region containing the substitution S228P and expressed in CHO cells as described in Example 5. A summary of the heavy- and light chains used to produce these antibody variants is given in Table 7. Antibodies X02.83, X02.85, X02.91, X02.82 bound strongly to the CD38 positive cell line ARP-1.

TABLE 7

| Antibody Designation | Variable Light Chain Amino Acid Substitution (Relative to A02.1) | Variable Heavy SEQ ID NO: | Variable Light SEQ ID NO: | CD38 binding via SPR | ARP-1 flow binding assay ($EC_{50}$ in μg/mL) | Protein A HPLC mg/L |
|---|---|---|---|---|---|---|
| X02.83 | E17A | 13 | 41 | $2.69 \times 10^{-9}$ | 8.2 | 32.8 |
| X02.86 | D(27A)G | 13 | 44 | $4.28 \times 10^{-9}$ | 120.4 | 30.0 |
| X02.85 | ΔD(L66A)*** ΔV(L66B)*** | 13 | 43 | $2.70 \times 10^{-10}$ | 6.3 | 17.6 |
| X02.107 | E83I, D85T | 13 | 65 | $2.47 \times 10^{-8}$## | N/T | 10.0* |
| X02.91 | P26R | 13 | 49 | $7.07 \times 10^{-10}$ | 17.6 | 21.1 |
| X02.88 | N32R | 13 | 46 | Low binding | Low Binding | 33.5 |
| X02.82 | Y49R | 13 | 40 | N/T | 3.8 | 27.9 |
| X02.89 | Y51R | 13 | 47 | Low binding | No Binding | 25.7 |
| X02.84 | Y49R, Y51R | 13 | 42 | Low binding | No Binding | 35.0 |

N/T - Protein was not purified or tested.
Low Binding - Minimal binding observed, not sufficient for an EC50 value
***Δ indicates that this amino acid present in A02.1 light chain was removed from this sequence
*estimated protein value based on protein A capture level by SPR
The SPR binding for X02.107 was evaluated in a separate experiment in which the KD of the parental antibody X02.1 was $2.7 \times 10^{-8}$. The KD of the parental antibody X02.1 is $3.78 \times 10^{-10}$ in the SPR binding experiment for all other antibodies tested.

Figure 4D:
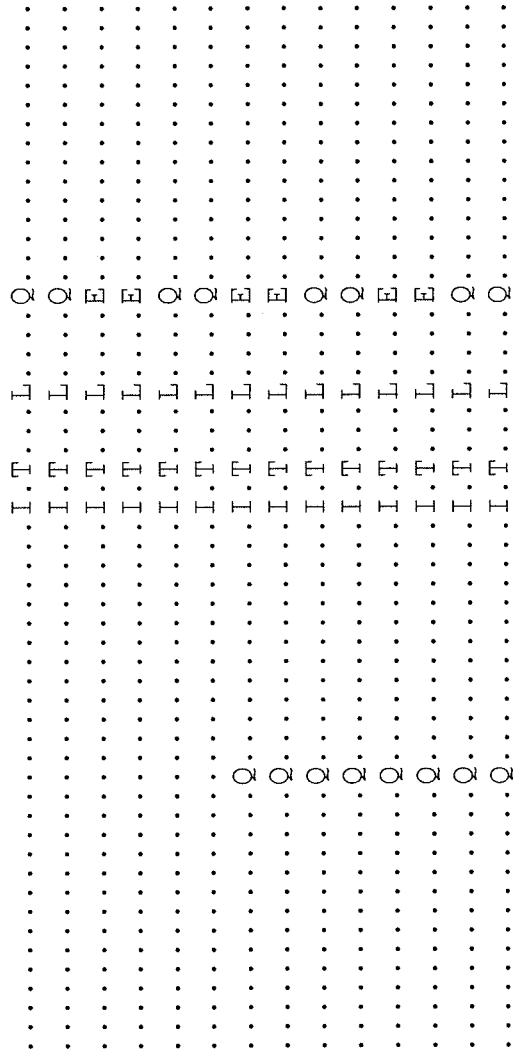
Figure 13:
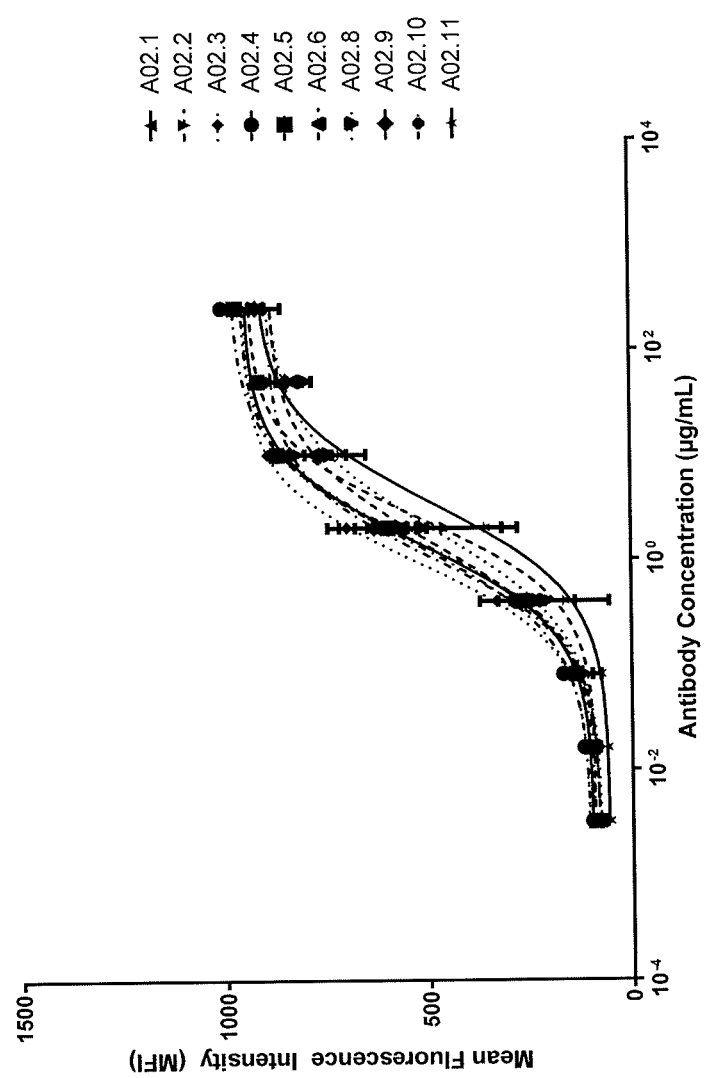
FIG. 13 shows the binding activity of A02.1 variants to the CD38-expressing multiple myeloma cell line ARP-1 as measured by flow cytometry. The assay details are described in the Examples of this specification.
Figure 14:
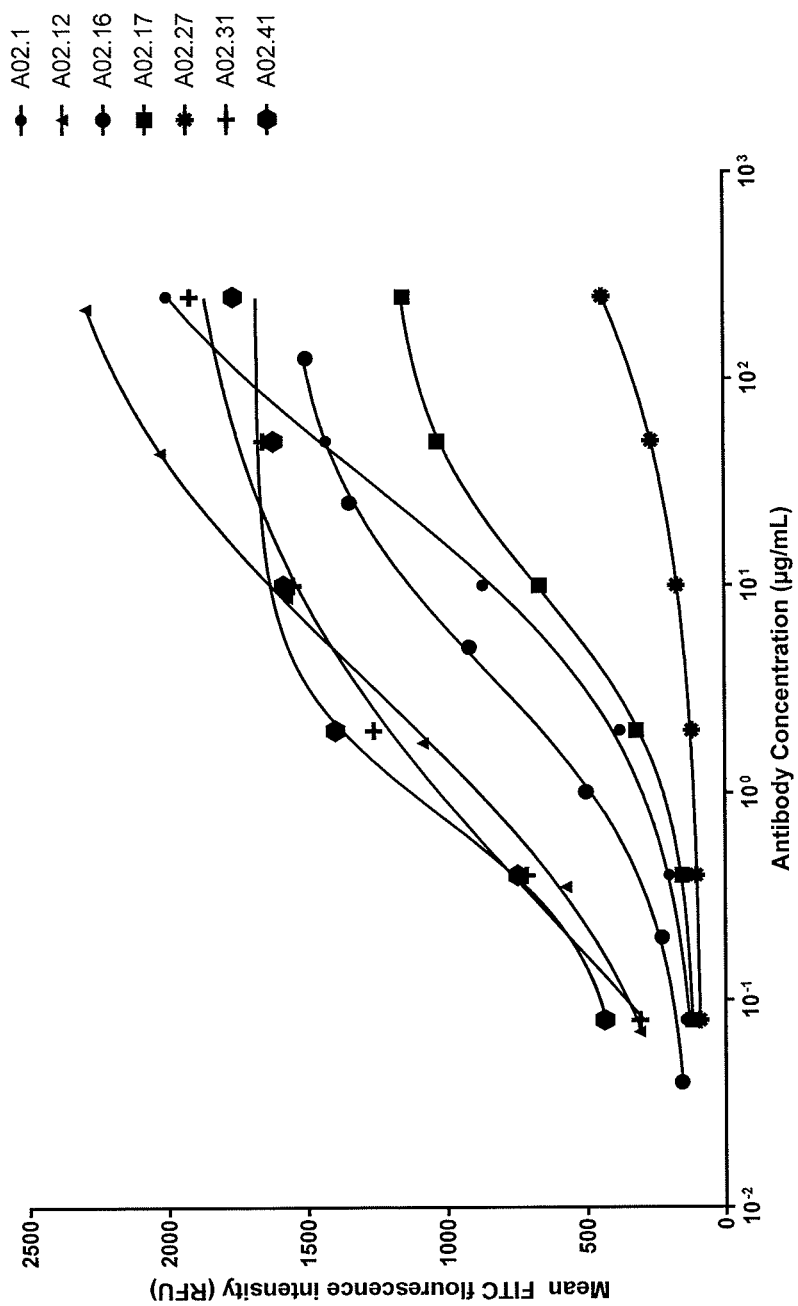
FIG. 14 shows the binding activity of A02.1 variants to the CD38-expressing multiple myeloma cell line NCI-H929 as measured by flow cytometry. The assay details are described in the Examples of this specification.
Figure 15:
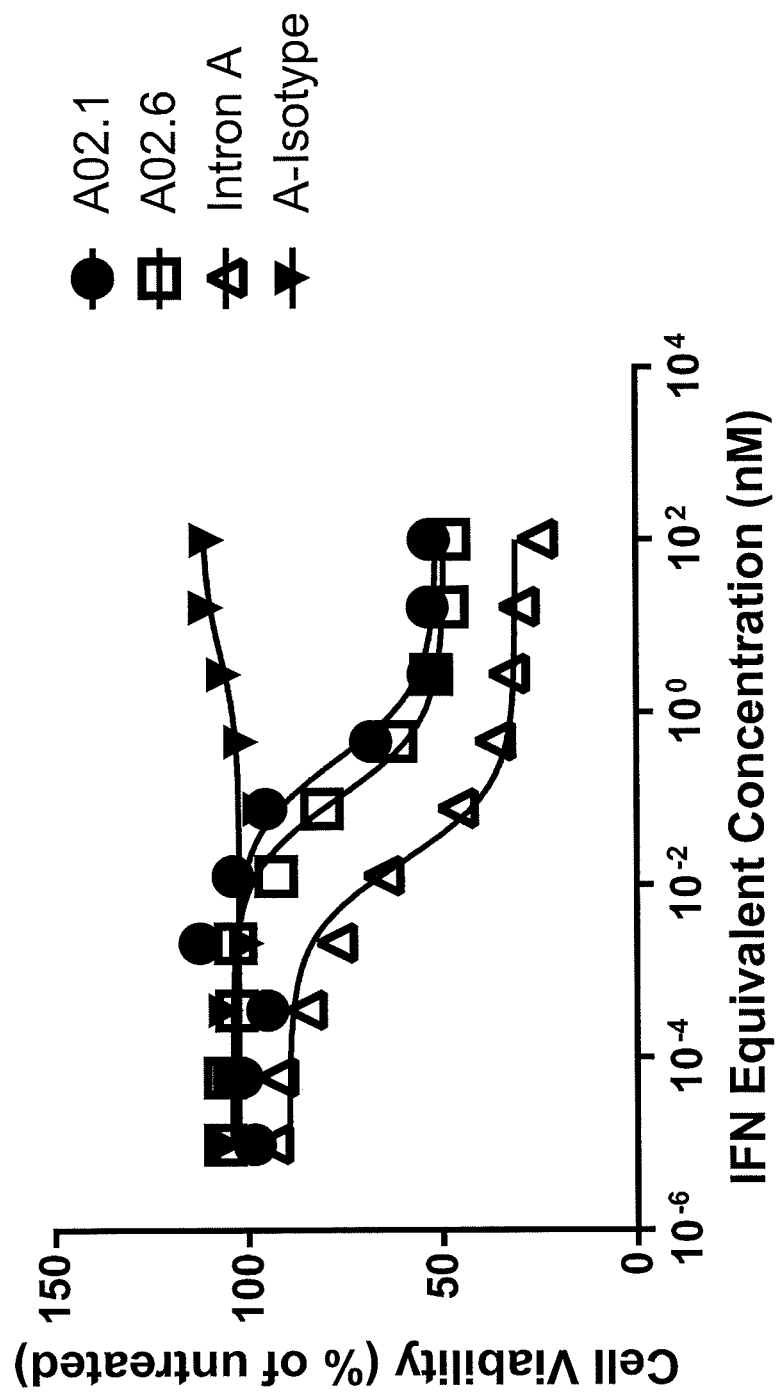
FIGS. 15 and 16 show the anti-proliferative activity of A02.1 variants on the multiple myeloma cell line ARP-1. A-isotype is an irrelevant specificity antibody fused with the attenuated interferon as a control. The assay details are described in the Examples (Cell proliferation assay).
Figure 16:
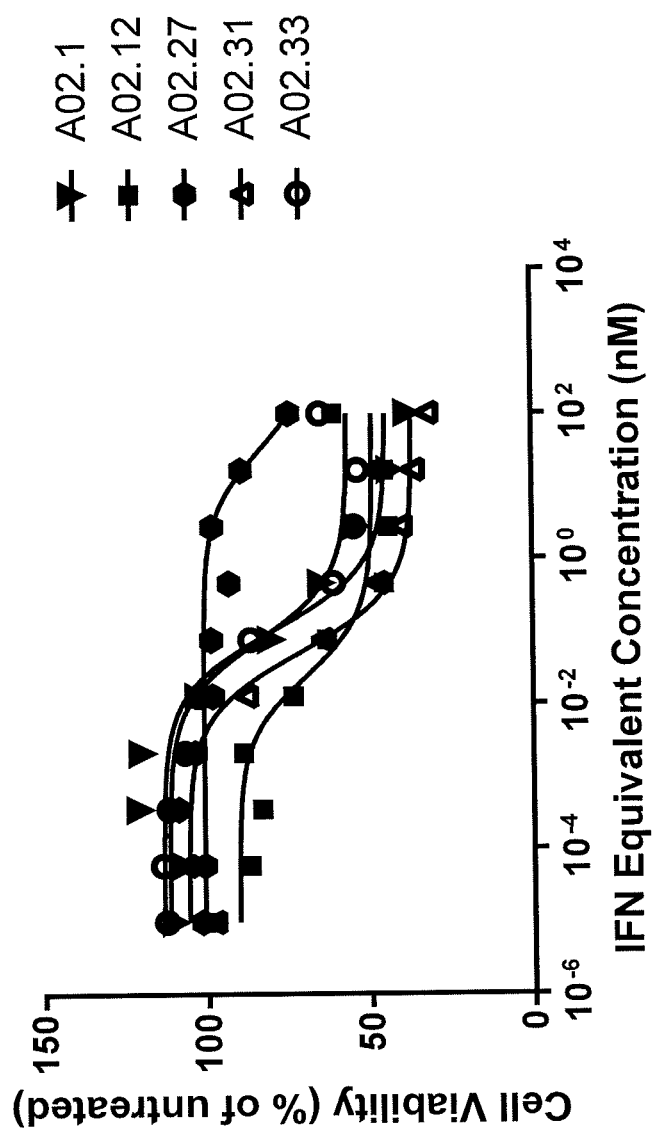
Figure 17:
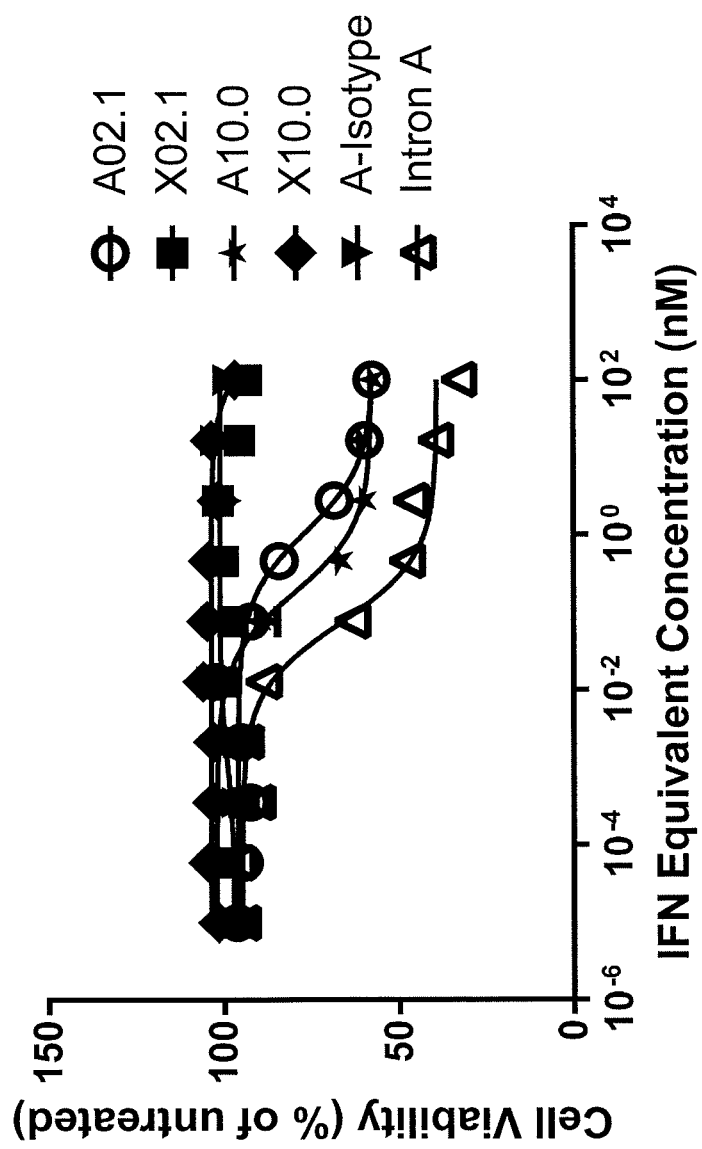
FIG. 17 shows the anti-proliferative activity of IFN-alpha2b (Intron A) compared with A02.1 and A10.0 and their corresponding unfused antibodies X02.1 and X10.0 on the multiple myeloma cell line ARP-1. A-isotype is an irrelevant specificity antibody fused with the attenuated interferon as a control. The assay details are described in the Examples (Cell proliferation assay).

Substitutions causing little impact on CD38 binding activity and the purification of X02 variant antibodies were subsequently produced as armed antibodies through fusion to A145D attenuated IFN-alpha2b. X02.1 light chain substitutions were combined and the resulting variants co-expressed with point- and combinatorial variants of the X02.1 heavy chain in HEK293E cells, as listed in Table 8. These antibodies were primarily focused on removing the potential X02.1 light chain deamidation site, an oxidation site from CDR3 of the X02.1 heavy chain and a putative strong MHC Class II binding peptide from framework region 3 of the X02.1 heavy chain predicted via in silico analyses (Epibase, Lonza, UK), FIG. 4.

TABLE 8

| Anti-CD38-attenuated IFN fusion protein | Variable Heavy Chain Amino Acid Substitution (Relative to A02.1) | Variable Heavy SEQ ID NO: | Variable Light Chain Amino Acid Substitution (Relative to A02.1) | Variable Light SEQ ID NO: |
|---|---|---|---|---|
| A02.2 | None | 13 | E83I, D85T | 65 |
| A02.3 | L74S | 17 | E83I, D85T | 65 |
| A02.4 | H40P | 18 | E83I, D85T | 65 |
| A02.5 | T(82A)S | 19 | E83I, D85T | 65 |
| A02.6 | L74S, I78F, R81K, T(82A)S | 20 | E83I, D85T | 65 |

TABLE 8-continued

| Anti-CD38-attenuated IFN fusion protein | Variable Heavy Chain Amino Acid Substitution (Relative to A02.1) | Variable Heavy SEQ ID NO: | Variable Light Chain Amino Acid Substitution (Relative to A02.1) | Variable Light SEQ ID NO: |
|---|---|---|---|---|
| A02.12 | L74S, I78F, R81K, T(82A)S, M(100C)L | 34 | E83I, D85T | 65 |
| A02.13 | H40P, L74S, I78F, R81K, T(82A)S | 35 | E83I, D85T | 65 |
| A02.37 | L74S, I78F, R81K, T(82A)S, M(100C)L | 34 | E83I, D85T, M89L | 66 |
| A02.46 | L74S, I78F, R81K, T(82A)S, M(100C)L | 34 | E83I, D85T, N69Q | 67 |
| A02.47 | L74S, I78F, R81K, T(82A)S, M(100C)L | 34 | E83I, D85T, N69T | 68 |
| A02.48 | L74S, I78F, R81K, T(82A)S, M(100C)L | 34 | E83I, D85T, N69G | 69 |
| A02.49 | L74S, I78F, R81K, T(82A)S, M(100C)L | 34 | E83I, D85T, N69H | 70 |
| A02.50 | L74S, I78F, R81K, T(82A)S, M(100C)L | 34 | E83I, D85T, N69K | 71 |
| A02.51 | L74S, I78F, R81K, T(82A)S, M(100C)L | 34 | E83I, D85T, N69P | 72 |

The antibodies listed in Table 8 were analyzed for protein expression and binding to CD38 via surface plasmon resonance (SPR). Potency assays were also performed using cell culture supernatant taken from transfected cells to assess the relative activity of each of these anti-CD38-attenuated IFN fusion proteins as outlined in Example 5. The data obtained is given in Table 9.

TABLE 9

| Anti-CD38-attenuated IFN fusion protein | Protein A HPLC (mg/L) | CD38 binding by SPR (RU) at 350 sec* | Annexin V Assay (Fold change relative to untreated cells) | Caspase Assay (Fold change relative to untreated cells) | Cell Proliferation Assay IC$_{50}$ (μM) |
|---|---|---|---|---|---|
| A02.2 | 30.2 | 756 | N/T | N/T | N/T |
| A02.3 | 21.6 | 835 | N/T | N/T | N/T |
| A02.4 | 27.3 | 809 | N/T | N/T | N/T |
| A02.5 | 22.0 | 788 | N/T | N/T | N/T |
| A02.6 | 33.7 | 895 | N/T | N/T | N/T |
| A02.12 | 25.3 | N/A | 2.7 | 7.0 | 236 |
| A02.46 | 3.1 | 914 | 2.2 | 5.8 | 1190 |
| A02.47 | 26.5 | 1455 | 3.10 | 4.44 | N/T |
| A02.48 | 3.4 | 921 | 2.0 | 5.6 | 562 |
| A02.49 | 3.0 | 946 | 2.1 | 5.5 | 875 |
| A02.50 | 3.1 | 809 | 1.9 | 6.1 | 1681 |
| A02.51 | 1.8 | 368 | 2.0 | 5.8 | 3741 |

Note:
The CD38 binding by SPR refers to the amount of CD38 that remains bound to the surface after 350 seconds of the dissociation phase. Annexin V Assay refers to cells positively stained by Annexin V-FITC after 24 h treatment with antibody constructs at 20 nM. Caspase Assay refers to caspase activation of cells after 24 h treatment with antibody constructs at 20 nM.
N/A—Not Available;
N/T—Not Tested Of the proteins tested A02.12 expressed well and demonstrated potency in the Annexin V, Caspase and cell proliferation assays. Substitution of N69T in antibody A02.47 did not affect expression levels or potency in Annexin V or Caspase Assays suggesting that removal of this deamidation site is possible. Substitution N69T could be incorporated into other constructs herein to remove this putative deamidation site with minimal losses in the functional activity of the resulting antibody.

Example 2

In Silico Immunogenicity Analysis of the A02.1 Light Chain Amino Acid Sequence Putative immunogenic epitopes were identified in the light chain variable region amino acid sequence of A02.1 using the Epibase analysis software (Lonza, UK). To remove putative immunogenic epitopes, substitutions were introduced into the A02.1 variable light chain (FIG. 4). Light chains with lower predicted immunogenicity were co-expressed in HEK293E cells with the A02.12 heavy chain variable region (SEQ ID NO: 34) formatted onto an IgG4 constant region containing the substitution S228P fused to A145D-attenuated IFN. The antibody variants produced are detailed in Table 10.

TABLE 10

| Anti-CD38-attenuated IFN fusion protein | Variable Heavy Chain Amino Acid Substitution (Relative to A02.1) | Variable Heavy SEQ ID NO: | Variable Light Chain Amino Acid Substitution (Relative to A02.1) | Variable Light SEQ ID NO: |
|---|---|---|---|---|
| A02.18 | L74S, I78F, R81K, T(82A)S, M(100C)L | 34 | E83I, D85T, L47E | 73 |
| A02.19 | L74S, I78F, R81K, T(82A)S, M(100C)L | 34 | E83I, D85T, L47G | 74 |
| A02.20 | L74S, I78F, R81K, T(82A)S, M(100C)L | 34 | E83I, D85T, L47N | 75 |
| A02.21 | L74S, I78F, R81K, T(82A)S, M(100C)L | 34 | E83I, D85T, L47P | 76 |
| A02.22 | L74S, I78F, R81K, T(82A)S, M(100C)L | 34 | E83I, D85T, L47S | 77 |
| A02.23 | L74S, I78F, R81K, T(82A)S, M(100C)L | 34 | E83I, D85T, L48E | 78 |
| A02.24 | L74S, I78F, R81K, T(82A)S, M(100C)L | 34 | E83I, D85T, L48P | 79 |
| A02.25 | L74S, I78F, R81K, T(82A)S, M(100C)L | 34 | E83I, D85T, Y49E | 80 |
| A02.26 | L74S, I78F, R81K, T(82A)S, M(100C)L | 34 | E83I, D85T, Y49Q | 81 |
| A02.27 | L74S, I78F, R81K, T(82A)S, M(100C)L | 34 | E83I, D85T, Y50P | 82 |
| A02.28 | L74S, I78F, R81K, T(82A)S, M(100C)L | 34 | E83I, D85T, Y50N | 83 |
| A02.29 | L74S, I78F, R81K, T(82A)S, M(100C)L | 34 | E83I, D85T, Y50T | 84 |
| A02.30 | L74S, I78F, R81K, T(82A)S, M(100C)L | 34 | E83I, D85T, Y51D | 85 |
| A02.31 | L74S, I78F, R81K, T(82A)S, M(100C)L | 34 | E83I, D85T, S52E | 86 |

TABLE 10-continued

| Anti-CD38-attenuated IFN fusion protein | Variable Heavy Chain Amino Acid Substitution (Relative to A02.1) | Variable Heavy SEQ ID NO: | Variable Light Chain Amino Acid Substitution (Relative to A02.1) | Variable Light SEQ ID NO: |
|---|---|---|---|---|
| A02.32 | L74S, I78F, R81K, T(82A)S, M(100C)L | 34 | E83I, D85T, S52H | 87 |
| A02.33 | L74S, I78F, R81K, T(82A)S, M(100C)L | 34 | E83I, D85T, S52Q | 88 |
| A02.34 | L74S, I78F, R81K, T(82A)S, M(100C)L | 34 | E83I, D85T, H(54A)N | 89 |
| A02.35 | L74S, I78F, R81K, T(82A)S, M(100C)L | 34 | E83I, D85T, H(54A)P | 90 |
| A02.36 | L74S, I78F, R81K, T(82A)S, M(100C)L | 34 | E83I, D85T, K(54B)D | 91 |

The above antibodies were analyzed for protein expression, binding to CD38 via SPR, and potency using the cell culture supernatant screen as described in Example 5. The results of these assays are detailed in Table 11. These data indicate that substitution of some residues to lower the predicted immunogenicity of the antibody results in Anti-CD38-attenuated IFN fusion proteins that express and have functional potency in the Annexin V, Caspase and Cell Proliferation Assays.

TABLE 11

| Anti-CD38-attenuated IFN fusion protein | Protein A HPLC (mg/L) | CD38 binding by SPR (RU) at 350 sec* | Annexin V Assay (Fold change relative to untreated cells) | Caspase Assay (Fold change relative to untreated cells) | Cell Proliferation Assay IC$_{50}$ (pm) |
|---|---|---|---|---|---|
| A02.18 | 9.3 | 745 | N/T | N/T | N/T |
| A02.19 | 8.0 | 741 | N/T | N/T | N/T |
| A02.20 | 9.1 | N/T | 2.2 | 5.6 | 37 |
| A02.21 | 3.3 | DNB | N/T | N/T | N/T |
| A02.22 | 10.4 | 738 | N/T | N/T | N/T |
| A02.23 | 15.9 | 192 | 2.7 | 6.9 | N/T |
| A02.24 | 23.5 | 87 | 1.4 | 2.3 | N/T |
| A02.25 | 25.7 | 80 | 3.0 | 4.3 | 2477 |
| A02.26 | 35.0 | 383 | 3.2 | 6.0 | 66 |
| A02.27 | 12.3 | DNB | 1.3 | 2.5 | 29910 |
| A02.28 | 16.1 | 422 | 2.7 | 6.3 | N/T |
| A02.29 | 19.7 | 150 | 2.7 | 5.8 | 133 |
| A02.30 | 25.2 | 122 | 1.9 | 2.5 | N/T |
| A02.31 | 28.4 | 359 | 3.0 | 7.1 | 514 |
| A02.32 | 13.5 | 663 | 2.7 | 7.7 | 60 |
| A02.33 | 11.2 | 107 | N/T | N/T | N/T |
| A02.34 | 16.6 | 407 | 4.8 | 5.1 | 503 |
| A02.35 | 11.2 | 738 | 2.4 | 4.8 | 3050 |
| A02.36 | 16.7 | 192 | 2.8 | 8.0 | N/T |

Note:
The CD38 binding by SPR refers to the amount of CD38 that remains bound to the surface after 350 seconds of the dissociation phase. Annexin V Assay refers to cells positively stained by Annexin V-FITC after 24 h treatment with antibody constructs at 20 nM. Caspase Assay refers to caspase activation of cells after 24 h treatment with antibody constructs at 20 nM.
DNB—Did not bind;
N/T—Not Tested Example 3

Multiple Amino Acid Substitutions Yield Optimized A02.1 Variants

By combining substitutions that improve the immunogenicity, manufacturability or potency of the anti-CD38 antibodies described above into a single gene construct, highly optimized anti-CD38 antibodies and anti-CD38-attenuated IFN fusion proteins were obtained. Table 12 summarizes such combinatorial substitutions and details heavy- and light chain combinations co-expressed in HEK293E cells and subsequently tested.

TABLE 12

| Anti-CD38-attenuated IFN fusion protein | Variable Heavy Chain Amino Acid Substitution (Relative to A02.1) | Variable Heavy SEQ ID NO: | Variable Light Chain Amino Acid Substitution (Relative to A02.1) | Variable Light SEQ ID NO: |
|---|---|---|---|---|
| A02.16 | L74S, I78F, R81K, T(82A)S, M(100C)L | 34 | R29G, Y30S, E83I, D85T, M89L, N94Q | 92 |
| A02.17 | L74S, I78F, R81K, T(82A)S, M(100C)L | 34 | R29G, Y30S, E83I, D85T, M89L, N94E | 93 |
| A02.52 | L74S, I78F, R81K, T(82A)S, M(100C)L | 34 | R29G, Y30S, S52Q, E83I, D85T, M89L, N94E | 94 |
| A02.53 | L74S, I78F, R81K, T(82A)S, M(100C)L | 34 | Y30S, S52Q, E83I, D85T, M89L, N94E | 95 |
| A02.54 | L74S, I78F, R81K, T(82A)S, M(100C)L | 34 | R29G, Y30S, S52Q, E83I, D85T, M89L, N94Q | 96 |
| A02.55 | L74S, I78F, R81K, T(82A)S, M(100C)L | 34 | Y30S, S52Q, E83I, D85T, M89L, N94Q | 97 |
| A02.56 | L74S, I78F, R81K, T(82A)S, M(100C)L | 34 | R29G, Y30S, S52E, M89L, E83I, D85T, N94E | 98 |
| A02.57 | L74S, I78F, R81K, T(82A)S, M(100C)L | 34 | Y30S, S52E, E83I, D85T, M89L, N94E | 99 |
| A02.58 | L74S, I78F, R81K, T(82A)S, M(100C)L | 34 | R29G, Y30S, S52E, E83I, D85T, M89L, N94Q | 100 |
| A02.59 | L74S, I78F, R81K, T(82A)S, M(100C)L | 34 | Y30S, S52E, E83I, D85T, M89L, N94Q | 101 |
| A02.60 | L74S, I78F, R81K, T(82A)S, M(100C)L | 34 | R29G, Y30S, S52Q, N69Q, E83I, D85T, M89L, N94E | 102 |
| A02.61 | L74S, I78F, R81K, T(82A)S, M(100C)L | 34 | Y30S, S52Q, N69Q, E83I, D85T, M89L, N94E | 103 |
| A02.62 | L74S, I78F, R81K, T(82A)S, M(100C)L | 34 | R29G, Y30S, S52Q, N69Q, E83I, D85T, M89L, N94Q | 104 |
| A02.63 | L74S, I78F, R81K, T(82A)S, M(100C)L | 34 | Y30S, S52Q, N69Q, E83I, D85T, M89L, N94Q | 105 |
| A02.64 | L74S, I78F, R81K, T(82A)S, M(100C)L | 34 | R29G, Y30S, S52E, N69Q, E83I, D85T, M89L, N94E | 106 |

TABLE 12-continued

| Anti-CD38-attenuated IFN fusion protein | Variable Heavy Chain Amino Acid Substitution (Relative to A02.1) | Variable Heavy SEQ ID NO: | Variable Light Chain Amino Acid Substitution (Relative to A02.1) | Variable Light SEQ ID NO: |
|---|---|---|---|---|
| A02.65 | L74S, I78F, R81K, T(82A)S, M(100C)L | 34 | Y30S, S52E, N69Q, E83I, D85T, M89L, N94E | 107 |
| A02.66 | L74S, I78F, R81K, T(82A)S, M(100C)L | 34 | R29G, Y30S, S52E, N69Q, E83I, D85T, M89L, N94Q | 108 |
| A02.67 | L74S, I78F, R81K, T(82A)S, M(100C)L | 34 | Y30S, S52E, N69Q, E83I, D85T, M89L, N94Q | 109 |

Each antibody described in Table 12 was analyzed for protein expression, binding to CD38 via SPR, and potency using cell culture supernatant. The resulting data is given in Table 13. These results demonstrate that combining substitutions predicted to be beneficial in silico gave rise to some Anti-CD38-attenuated IFN fusion proteins that expressed and had functional potency in the Annexin V, Caspase and Cell Proliferation Assays.

TABLE 13

| Anti-CD38-attenuated IFN fusion protein | Protein A HPLC (mg/L) | CD38 binding by SPR (RU) at 350 sec* | Annexin V Assay (Fold change relative to untreated cells) | Caspase Assay (Fold change relative to untreated cells) | Cell Proliferation Assay $IC_{50}$ (pm) |
|---|---|---|---|---|---|
| A02.14 | 8.1 | 1247 | 2.18 | 5.47 | 398 |
| A02.15 | 29.6 | 1409 | 3.92 | 5.62 | 491 |
| A02.16 | 5.7 | 1050 | 2.4 | 7.9 | 636 |
| A02.17 | 10.0 | 1103 | 3.7 | 5.7 | 467 |
| A02.52 | 2.8 | 416 | 2.0 | 5.4 | 2665 |
| A02.53 | 3.0 | 545 | 2.2 | 4.7 | 6338 |
| A02.54 | 1.8 | 250 | 1.9 | 5.9 | 15350 |
| A02.55 | 2.1 | 436 | 2.2 | 4.5 | 12740 |
| A02.56 | 2.0 | 178 | 1.7 | 4.3 | 13860 |
| A02.57 | 2.7 | 345 | 2.5 | 6.6 | 6363 |
| A02.58 | 2.3 | 273 | 1.9 | 4.9 | 9142 |
| A02.59 | 1.2 | 388 | 2.0 | 4.7 | 6176 |
| A02.60 | 1.3 | DNB | 1.5 | 3.3 | 185600 |
| A02.61 | 1.2 | DNB | 1.7 | 4.1 | 65160 |
| A02.62 | 1.3 | DNB | 1.8 | 5.0 | 55590 |
| A02.63 | 1.2 | DNB | 1.7 | 3.4 | 152100 |
| A02.64 | 1.1 | DNB | 1.8 | 3.2 | 89120 |
| A02.65 | 1.4 | DNB | 1.6 | 4.1 | 37240 |
| A02.66 | 1.3 | DNB | 1.6 | 4.0 | 57540 |
| A02.67 | 1.6 | DNB | 2.3 | 3.9 | 82760 |

Note:
The CD38 binding by SPR refers to the amount of CD38 that remains bound to the surface after 350 seconds of the dissociation phase. Annexin V Assay refer to cells positively stained by Annexin V-FITC after 24 h treatment with antibody constructs at 20 nM. Caspase Assay refers to caspase activation of cells after 24 h treatment with antibody constructs at 20 nM
DNB—Did not bind;
N/T—Not Tested

Example 4

Pairing of Different Heavy and Light Chain Anti-CD38 Antibodies

In order to determine if functional anti-CD38-attenuated IFN fusion proteins could be obtained, the heavy (SEQ ID NO: 110) and light (SEQ ID NO: 112) chains from the antibody X910/12-HC-L0-IFN-alpha (A145D) IgG4 described in PCT/AU2012/001323, and the heavy (SEQ ID NO: 111) and light (SEQ ID NO: 113) chains from the antibody X913/15-HC-L0-IFN-alpha (A145D) IgG4 described in PCT/AU12/001323, were paired with each other in various combinations and with heavy and lights chains described in the foregoing examples. A summary of the heavy and light chain pairings is provided listed in Table 14.

TABLE 14

| Anti-CD38-attenuated IFN fusion protein | Variable Heavy SEQ ID NO: | Variable Light SEQ ID NO: |
|---|---|---|
| A02.38 | 34 | 113 |
| A02.39 | 34 | 112 |
| A02.40 | 111 | 65 |
| A02.41 | 110 | 65 |
| X913/15-HC-L0-IFN-alpha (A145D) IgG4 | 111 | 113 |
| A02.43 | 110 | 113 |
| A02.44 | 111 | 112 |
| X910/12-HC-L0-IFN-alpha (A145D) IgG4 | 110 | 112 |

Each antibody produced was analyzed for protein expression, binding to CD38 via SPR, and potency using the cell culture supernatant potency assays. The results of these assays are presented in Table 15a. These data show that pairing different heavy and light chains from distinct antibodies gave rise to some Anti-CD38-attenuated IFN fusion proteins that expressed and had functional potency in the Annexin V, Caspase and Cell Proliferation Assays.

TABLE 15a

| Anti-CD38-attenuated IFN fusion protein | Protein A HPLC (mg/L) | CD38 binding by SPR (RU) at 350 sec* | Annexin V Assay (Fold change relative to untreated cells) | Caspase Assay (Fold change relative to untreated cells) |
|---|---|---|---|---|
| A02.38 | 2.9 | DNB | 0.9 | 4.3 |
| A02.39 | 21.3 | 66 | 2.5 | 6.6 |
| A02.40 | 2.1 | DNB | 1.0 | 4.4 |
| A02.41 | 50.0 | 165 | 2.6 | 6.7 |
| X913/15-HC-L0-IFN-alpha (A145D) IgG4 | 8.2 | 96 | 2.2 | 5.4 |
| A02.43 | 2.5 | DNB | 0.9 | 4.1 |
| A02.44 | 2.2 | DNB | 1.0 | 4.5 |
| X910/12-HC-L0-IFN-alpha (A145D) IgG4 | 27.1 | 125 | 2.6 | 5.9 |

Note:
The CD38 binding by SPR refers to the amount of CD38 that remains bound to the surface after 350 seconds of the dissociation phase. Annexin V Assay refer to cells positively stained by Annexin V-FITC after 24 h treatment with antibody constructs at 20 nM. Caspase Assay refers to caspase activation of cells after 24 h treatment with antibody constructs at 20 nM.
DNB—Did not bind.

A selection of the above Anti-CD38-attenuated IFN fusion proteins were purified and analyzed for binding to CD38 positive cells in cell based assays. In addition potency assays were repeated to give a more accurate determination of the relative activity of each Anti-CD38-attenuated IFN fusion protein. The results of these assays are given in Table 15b.

TABLE 15b

| Anti-CD38-attenuated IFN fusion protein | ARP-1 Flow binding ($EC_{50}$, in µg/mL) | Annexin V Assay (Fold change relative to untreated cells) | Caspase Assay (Fold change relative to untreated cells) | Cell Proliferation Assay IC50 (pM) | Figures |
|---|---|---|---|---|---|
| A02.1 | 1.45 | 1.86 | 4.2 | 278.2 | 13, 14, 15, 16, 17, 18, 19 |
| A02.2 | 2.46 | 1.94 | 4.4 | 175.7 | 13, 19 |
| A02.3 | 0.96 | 1.86 | 3.5 | 254.9 | 13, 19 |
| A02.4 | 1.50 | 1.88 | 3.8 | 198.3 | 13, 19 |
| A02.5 | 1.45 | 1.88 | 4.3 | 146.3 | 13, 19 |
| A02.6 | 1.42 | 2.03 | 3.5 | 102.3 | 13, 15, 19, 20 |
| A02.8 | 1.93 | 1.91 | 3.8 | 125.5 | 13, 19 |
| A02.9 | 1.03 | 1.96 | 3.6 | 107.1 | 13, 19 |
| A02.10 | 1.48 | 1.95 | 3.8 | 125.6 | 13, 19 |
| A02.11 | 3.48 | 1.98 | 3.9 | 374 | 13, 19 |
| A02.12 | 3.40* | 1.40 | 3.4 | 23.66 | 14, 16, 19, 21 |
| A02.14 | 10.01* | 1.82 | 2.5 | 398.20 | 19 |
| A02.15 | 1.97* | 3.09 | 6.8 | 491.70 | 19 |
| A02.16 | 3.89* | 2.66 | 5.2 | 636.80 | 14, 19 |
| A02.17 | 9.32* | 2.23 | 3.2 | 467.1 | 14, 19 |
| A02.18 | 1.64 | 1.55 | 3.7 | 78.72 | 19 |
| A02.19 | 1.07 | 1.63 | 3.5 | 230.3 | 19 |
| A02.20 | 15.92* | 1.61 | 2.9 | 36 | 19 |
| A02.22 | 1.58 | 1.91 | 3.8 | 207 | 19 |
| A02.25 | 0.37* | 1.42 | 2.4 | 2477 | 19 |
| A02.26 | 37.99* | 1.56 | 2.0 | 66 | 19 |
| A02.27 | LB* | 1.06 | 1.0 | 29910 | 14, 16, 19 |
| A02.29 | 0.48* | 1.55 | 3.0 | 133 | 19 |
| A02.31 | 0.26* | 1.78 | 2.1 | 514 | 14, 16, 19 |
| A02.32 | LB* | 1.83 | 3.3 | 605 | 19 |
| A02.33 | 1.54 | 1.96 | 3.7 | 741 | 16, 19 |
| A02.34 | 0.89* | 3.06 | 4.7 | 503 | 19 |
| A02.35 | 3.44* | 1.71 | 1.5 | 3050 | 19 |
| A02.37 | LB* | 2.05 | 4.3 | 128 | 19 |
| A02.39 | LB* | 1.92 | 4.3 | 3714 | 19 |
| A02.41 | 0.78* | 2.01 | 3.4 | 554 | 14, 19 |
| A02.42 | LB* | 1.52 | 3.3 | 310 | 19 |
| A02.45 | 0.71* | 1.66 | 1.6 | 1697 | 19 |
| A02.47 | 16.35* | 1.53 | 4.69 | 144.3 | 19 |

The flow binding refers to the concentration of antibody required to achieve 50% of maximal mean fluorescence intensity. Annexin V Assay refer to cells positively stained by Annexin V-FITC after 24 h treatment with antibody constructs at 20 nM. Caspase Assay refers to caspase activation of cells after 24 h treatment with antibody constructs at 20 nM. LB—low binding, not sufficient for an $EC_{50}$ value.
*Antibody was tested in a flow binding assay against H929 cell line. Reported value is the $EC_{50}$ in µg/mL.

FIG. 5 lists the consensus variable heavy chain and FIG. 6 lists the consensus variable light chain of A02.1 related constructs with functional activity. It could be further envisioned that combinations of substitutions could be made such as those described for Anti-CD38 antibodies X02.114, X02.115, X02.116, X02.117, X02.118, X02.119 (FIG. 6), X02.120, X02.121, X02.122, X02.123, X02.124, X02.125, X02.126 or X02.127 (FIG. 30). Further the above Anti-CD38 antibodies could also be constructed as Anti-CD38-attenuated IFN fusion proteins and tested for functional activity as described herein.

H929 Multiple Myeloma Xenograft Model

The in vivo potency of A02.1 has been tested previously in the NCI-H929 s.c. multiple myeloma model as described in Example 5. A02.1 was shown to have potent anti-tumor activity. The data is presented in PCT/AU2012/001323.

The H929 multiple myeloma xenograft model could be used to test the anti-tumor activity of any of the Anti-CD38-attenuated IFN fusion proteins described above.

Figure 18:
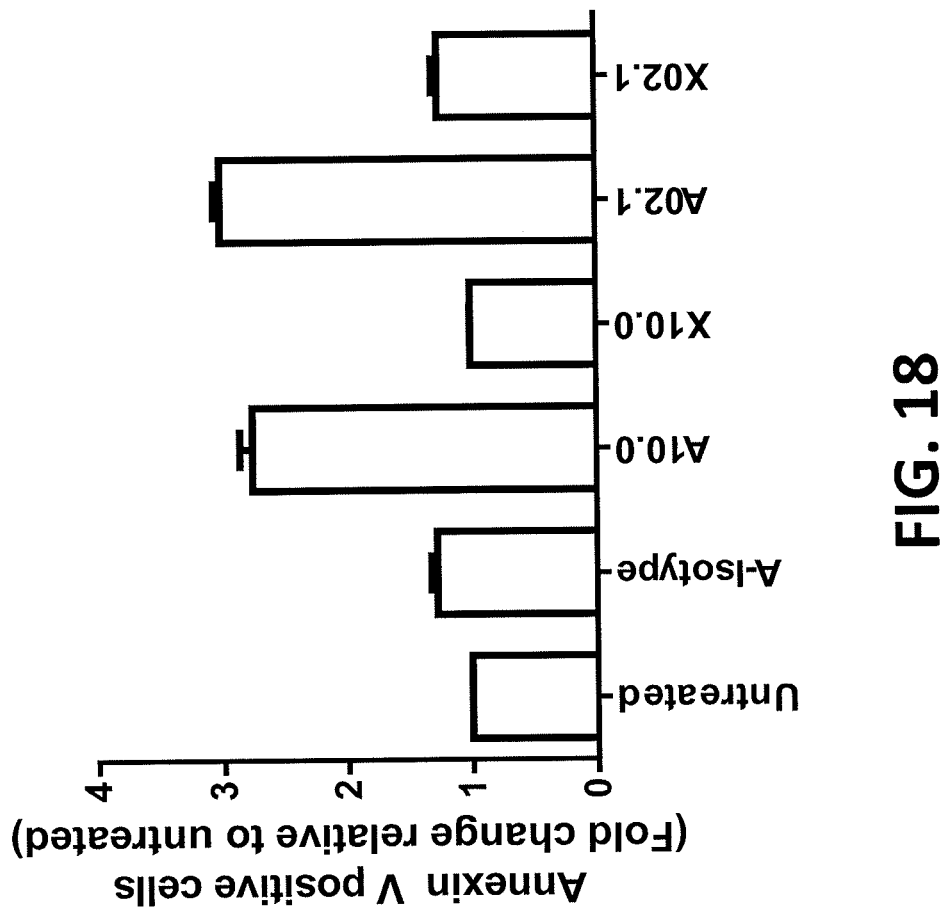
FIG. 18 shows the relative fold change of Annexin V production in the CD38-expressing multiple myeloma cell line NCI-H929 when treated with A02.1 and A10.0 and their corresponding unfused antibodies X02.1 and X10.0 for 24 hours compared to an untreated control. A-isotype is an irrelevant specificity antibody fused with the attenuated interferon as a control. The assay details are described in the Examples (Annexin V assay).
Figure 19:
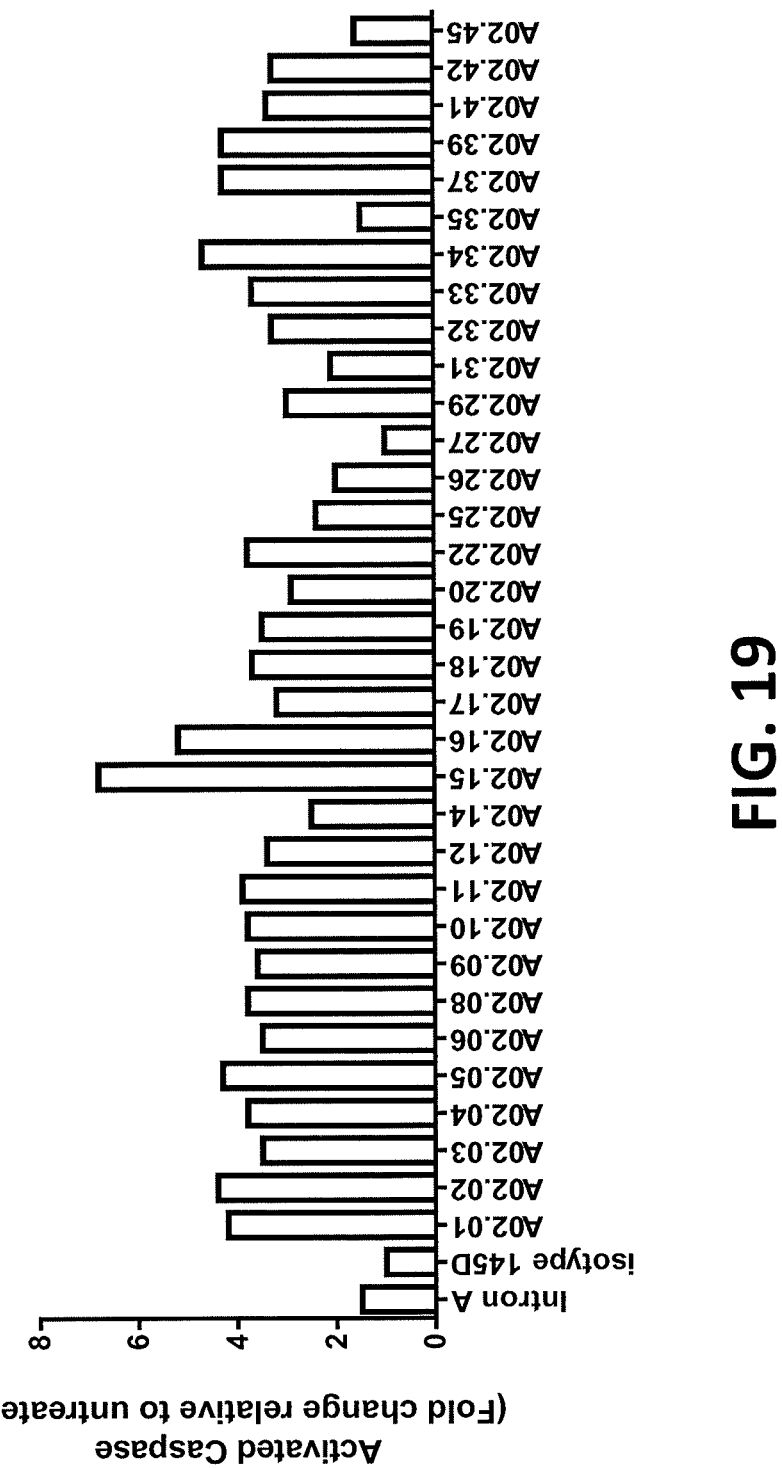
FIG. 19 shows the relative fold change of caspase activation in the CD38-expressing multiple myeloma cell line H929 of IFN-alpha2b (Intron A) vs. A02.1 and related constructs in comparison to untreated cells. Isotype 145D is an irrelevant specificity antibody fused with the attenuated interferon as a control. The assay details are described in the Examples (Caspase assay).
Figure 20:
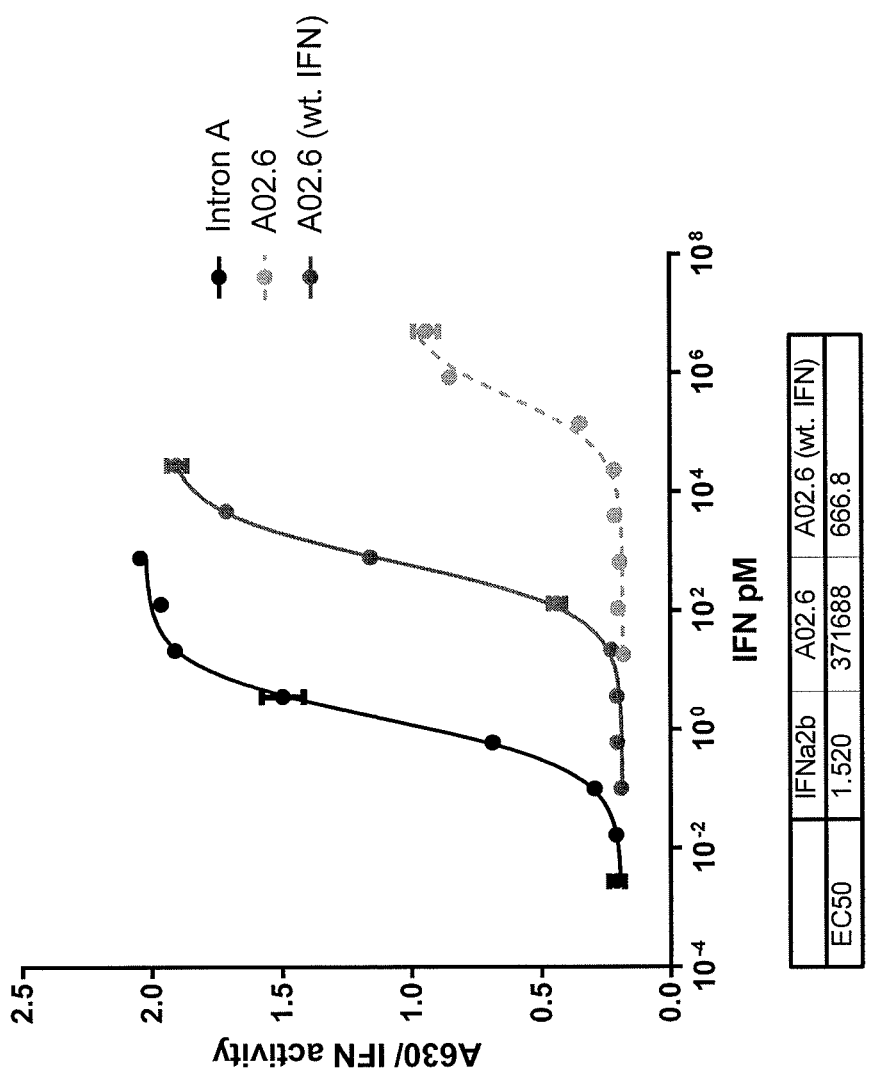
FIG. 20 shows the off target activity of IFN-alpha2b (Intron A) versus A02.6 and A02.6 fused to wild-type IFN-alpha2b (A02.6 (wt. IFN)) on the CD38-negative cells. The assay details are described in the Examples (HEK-BLUE™).

Attenuated IFN is Required for Potent Apoptotic and Caspase Activation in Tumor Cell Lines Using the Annexin V assay and the Caspase Assay it was demonstrated that the potent apoptotic activity and caspase activation is dependent on the Anti-CD38-attenuated IFN fusion proteins containing an attenuated IFN (Table 16a, FIG. 18). In the Annexin V Assay the attenuated IFN containing proteins (A02.1 and A02.6) had 2-fold greater activity than the proteins not containing attenuated IFN (X02.1 and X02.6).

TABLE 16a

| Anti-CD38-attenuated IFN fusion protein | Annexin V Assay (Fold change relative to untreated cells) | Caspase Assay (Fold change relative to untreated cells) |
|---|---|---|
| A02.1 | 3.57 | 5.60 |
| X02.1 | 1.50 | 2.34 |
| A02.6 | 2.03 | 3.5 |
| X02.6 | 1.04 | 0.40 |

Annexin V Assay refer to cells positively stained by Annexin V-FITC after 24 h treatment with antibody constructs at 20 nM. Caspase Assay refers to caspase activation of cells after 24 h treatment with antibody constructs at 20 nM.

Example 5

General Methods

Production of antibodies and antibody-fusion constructs in HEK-293E cells. DNA plasmids encoding protein constructs (antibodies and antibody-IFN-alpha2b related constructs) were prepared using HiSpeed Plasmid Maxi Kit (Qiagen, Valencia, Calif.) and then transfected into HEK293E cells (CNRC, Montreal, Canada), grown in F17 synthetic medium supplemented with 0.45% (w/v) D-(+)-Glucose (Sigma, Castle Hill, NSW), 25 µg/mL Geneticin (Invitrogen, Carlsbad, Calif.), and 1×GlutaMAX (Invitrogen, Carlsbad, Calif.) using a commercially available transfection reagent and OptiMEM medium (Invitrogen, Carlsbad, Calif.). After allowing for expression for 6 days in an incubator supplied with 5% $CO_2$ and 120 rpm shaking, the culture media was isolated and subjected to affinity purification using Protein A Mab Select SuRe™ agarose beads (GE Healthcare, Piscataway, N.J.). Purified protein constructs were buffer-exchanged into 0.2M arginine HCl, 25 mM citric acid, 71.5 mM sodium hydroxide at pH 6.0 using a PD Midi-Trap G-25 column (GE Healthcare, Piscataway, N.J.) or a HiPrep 26/10 Desalting column (HiTrap Desalting HiPrep 26/10 Desalting). Purified protein constructs were then concentrated using 50 kDaAmicon Ultra centrifugal filter devices (Millipore, Billerica, Mass.), followed by protein concentration determination by reading absorbance at 280 nm.

Production of Antibodies and Antibody-Fusion Constructs in CHO Cells.

DNA plasmids encoding protein constructs (antibodies and antibody-IFN-alpha2b related constructs) were prepared using HiSpeed Plasmid Maxi Kit (Qiagen, Valencia, Calif.) and then transfected into CHO cells (Lonza) grown in Freestyle™ CHO Expression Medium (Invitrogen, Carlsbad, Calif.) using a commercially available transfection reagent and OptiPro SFM™ medium (Invitrogen, Carlsbad, Calif.). After allowing for expression for 6 days in an incubator supplied with 10% $CO_2$ and 120 rpm shaking, the culture media was isolated and subjected to affinity purification using Protein A Mab Select SuReagarose beads (GE Healthcare, Piscataway, N.J.). Purified protein constructs were buffer-exchanged into 0.2M arginine.HCl, 25 mM citric acid, 71.5 mM sodium hydroxide at pH 6.0 using a PD Midi-Trap G-25 column (GE Healthcare, Piscataway, N.J.) or a HiPrep 26/10 Desalting column (HiTrap Desalting HiPrep 26/10 Desalting). Purified protein constructs were then concentrated using 50 kDaAmicon Ultra centrifugal filter devices (Millipore, Billerica, Mass.), followed by protein concentration determination by reading absorbance at 280 nm.

Anti-CD38-attenuated IFN fusion proteins binding to CD38 as measured by Surface Plasmon Resonance (SPR). The capacity of anti-CD38 antibodies and anti-CD38-attenuated IFN fusion proteins to bind to human CD38 were measured using unpurified transfected cell supernatant prepared 7:1 with Non Specific Binding Reducer (GE Healthcare, Piscataway, N.J.). Briefly, using a Biacore™ 3000 or a T200, Protein A was immobilized onto Flow Cell (FC) 1 (FC1) and FC2 (or alternatively FC3 and FC4) of a CM5 research grade sensor chip using amine coupling, giving approximately 1500 RU. FC2 (or FC4) was used as a reference throughout the experiments. The experiments were run at 37° C. in HBS-P+ buffer (0.01 M HEPES, 0.15 M NaCl, 0.005% v/v Surfactant P20, pH 7.4). At a flow rate of 20 µl/min, both flow cells were regenerated with 10 µL 50 mM sodium hydroxide before 40 µL supernatant containing the protein was passed over FC1 (or FC3) only. 30 µL of CD38 (10 g/mL in running buffer) or 30 µL running buffer was injected over FC1 and FC2 with a 5 minute dissociation time. Both surfaces were regenerated twice with sodium hydroxide. Results were generated using the BIAevaluation software provided with the machine. Microsoft Excel was used for calculations. BIAevaluation software automatically subtracted the reference sensorgram giving a trace of FC2-1 (or FC4-3) for each sample. A double reference was performed for each antibody tested by subtracting the sensorgram with a CD38 injection from the sensorgram with a blank running buffer injection. The Protein A capture refers to the response units measured from a sensorgram at a fixed timepoint of 412.5 s and this corresponds to the level of protein captured on the Protein A surface. CD38 binding is the response units measured at 507.5 s and is an indication of the level of bound CD38 to the protein captured sensor. CD38 dissociation is the response units measured at 865.5 s and is an indication of the level of CD38 bound to the protein captured surface after approximately 300 s of dissociation phase. BIAevalution was used to fit the sensorgram using a Langmuir 1:1 equation in order to generate an equilibrium association constant (KD)
Protein A HPLC.

Supernatants were analyzed by Protein A HPLC using a POROS A/20 2.1×30 mm Id column (Applied Biosystems) connected to an Agilent 1100 chromatography system. The column was equilibrated with PBS pH7.4, and protein was eluted with PBS adjusted to pH 2.2. A standard curve was generated using known amounts of a monoclonal antibody in PBS. The chromatograms, at the wavelengths of 215 nm or 280 nm, were integrated using the manufacturer's software and the area under the curve (AUC) reported and interpolated against the generated standard curve to estimate concentration.
Flow Cytometry Binding of Antibodies and Anti-CD38-Attenuated IFN Fusion Proteins to a Human CD38 Positive Cell Line, ARP-1 and H929.

The multiple myeloma cell line ARP-1 was a gift from Bart Barlogie MD, PhD, Director of the Myeloma Institute at the University of Arkansas Medical Center (Little Rock, Ak.). It is described in Hardin J. et al. (1994) Blood. 84:3063-70). The multiple myeloma cell line NCI-H929 (H929) was purchased from ATCC (CRL-9068, Gazdar, Blood 67: 1542-1549, 1986).

The ability of the antibodies or antibody-interferon constructs to bind the human CD38-positive myeloma cell lines ARP-1 or H929 in flow cytometry-based assays was tested. ARP-1 cells or H929 cells ($5×10^5$, as judged by trypan blue exclusion) were incubated with each protein or with a human IgG4 monoclonal antibody with irrelevant specificity protein construct at various concentrations in 50 µL of FACS buffer (PBS plus 1% fetal calf serum, FCS, 0.2M HEPES, 0.5M EDTA) in 96 well plates for 60 minutes on ice in the dark. Cells were washed three times with FACS buffer before incubation for 30 minutes in 50 µL of FACS buffer containing goat anti-human IgG (Fc-specific, conjugated to fluorescein isothiocyanate, FITC; Sigma-Aldrich, St. Louis, Mo.). After washing three times with FACS buffer, cells were fixed with 50 µL of PBS containing 4% formaldehyde v/v and incubated at 4° C. in the dark for 16 hours. Incubated cells in suspension were diluted with an additional 150 µL of FACS buffer and analyzed for binding by flow cytometry on a FACS Canto II (BD Biosciences, San Diego, Calif.) using forward scatter, side scatter and fluorescence intensity in the FITC channel. The value reported is the mean fluorescence intensity (MFI).

Target Assays

Daudi cell proliferation assay: This assay was used to quantify the anti-proliferative activity of IFNs and antibody-IFN fusion protein constructs on cells that display CD38. Daudi cells express CD38 as a cell surface associated antigen. The viability of cells was measured using the reagent CellTiter-Glo®, Cat #G7570, from Promega (Madison, Wis.). This is a luminescence-based assay that determines the viability of cells in culture based on quantitation of ATP. The signal strength is proportional to the number of viable cells in a microtiter plate well. The details of the assay are as follows: Daudi cells (obtained from ATCC, Manassas, Va.) were cultured in a T75 flask (TPP, Trasadingen, Switzerland, cat #90076) to a preferred density of between $0.5×10^5$ and $0.8×10^5$ viable cells/mL in RPMI 1640 (Mediatech, Inc., Manassas, Va., cat #10-040-CV) with 10% Fetal Bovine Serum (FBS; Hyclone, Logan, Utah cat #SH30070.03). Cells were harvested by centrifuging at 400×g for five minutes, decanting the supernatant, and resuspending the cell pellet in RPMI 1640+10% FBS. Cells were then counted and the density was adjusted to $3.0×10^5$ cells/mL in RPMI 1640+10% FBS. Then, 50 µL of cell suspension was aliquoted into each well of a 96 well round bottom tissue culture plate (hereafter, "experimental plate") (TPP, cat #92067). On a separate, sterile 96 well plate (hereafter, "dilution plate"; Costar, Corning, N.Y. cat #3879), test articles were serially diluted in duplicate in RPMI 1640+10% FBS. Then, 50 µL/well was transferred from the dilution plate to the experimental plate. The experimental plate was then incubated for four days at 37° C. with 5% $CO_2$. A mixture of the manufacturer-supplied assay buffer and assay substrate (hereafter, "CellTiter-Glo® reagent", mixed according to the manufacturer's instructions) was added to the experimental plate at 100 µL/well. The plate was shaken for two minutes.

Then, 100 µL/well was transferred from the experimental plate to a 96 well flat bottom white opaque plate (hereafter, "assay plate"; BD Biosciences, Franklin 5 Lakes, N.J. cat #35 3296). The content of the assay plate was then allowed to stabilize in the dark for 15 minutes at room temperature.

The plate was read on a Victor 3V Multilabel Counter (Perkin Elmer, Waltham, Mass., model #1420-041) on the luminometry channel and the luminescence was measured. Results are presented as "relative luminescence units" (RLU). Data was analyzed using Prism 5 (Graphpad, San Diego, Calif.) using non-linear regression and three parameter curve fit to determine the midpoint of the curve (EC50).

ARP-1 Cell proliferation assay. This assay was used to quantify the anti-proliferative activity of IFNs and antibody-IFN fusion protein constructs against CD38 antigen positive cells. ARP1 cells express CD38 as cell surface associated antigens. The viability of cells was measured using the reagent CellTiter-Glo®, Cat #G7570, from Promega (Madison, Wis.). This is a luminescence-based assay that determines the viability of cells in culture by quantitation of ATP. The signal strength is proportional to the number of viable cells in a microtiter plate well.

The details of the assay are as follows: ARP-1 cells were cultured in a T175 flask (Costar, Corning, N.Y. Lakes, N.J., cat #CLS431080) to a preferred density of between $2.0 \times 10^5$ and $2.0 \times 10^6$ viable cells/mL in RPMI 1640 (Life Technologies, Mulgrave, VIC, cat #11875-093) with 10% Fetal Bovine Serum (FBS; AusGeneX, Molendinar, QLD, Australia cat #FBS500S). Cells were harvested by centrifuging at 400×g for five minutes, decanting the supernatant, and resuspending the cell pellet in RPMI 1640+10% FBS. Cells were then counted and the density was adjusted to $2.0 \times 10^5$ cells/mL in RPMI 1640+10% FBS. Then, 50 μL of the cell suspension was aliquoted into each well of a 96-well flat bottom white opaque plate (hereafter, "experimental plate"; Costar, Corning, N.Y. Lakes, N.J., cat #CLS3917). On a separate, sterile 96-well plate (hereafter, "dilution plate"; Costar, Corning, N.Y. cat #3799), test articles were serially diluted in duplicate in RPMI 1640+10% FBS. Subsequently, 50 μL/well was transferred from the dilution plate to the experimental plate. The experimental plate was then incubated for four days at 37° C. with 5% $CO_2$. Each experimental plate included the parental antibody IFN construct as the relative control.

A mixture of the manufacturer-supplied assay buffer and assay substrate (CellTiter-Glo® reagent, mixed according to the manufacturer's instructions) was added to the experimental plate at 100 μL/well. The plate was shaken for two minutes. The content of the assay plate was then allowed to stabilize in the dark for 15 minutes at room temperature. The plate was read on a FLUOstar Galaxy plate reader (BMG Labtech, Durham, N.C.) on the luminometry channel and the luminescence was measured. Data was analyzed using Prism 5 (Graphpad, San Diego, Calif.) using non-linear regression and three parameter curve fit to determine the midpoint of the curve ($EC_{50}$).

Annexin V assay. H929 cells were harvested by centrifuging at 400×g for five minutes, decanting the supernatant, and resuspending the cell pellet in RPMI 1640+10% FBS. Cells were then counted and the density was adjusted to $1.0 \times 10^6$ cells/mL in RPMI 1640+10% FBS. Then, 50 μL of the cell suspension was aliquoted into each well of 96-well round bottom clear plates (hereafter, "experimental plate;" Costar, Corning, N.Y. cat #CL3799). On a separate, sterile 96-well plate (hereafter, "dilution plate"; Costar, Corning, N.Y. cat #CL3799), test articles were diluted to 40 nM in quaduplicate in RPMI 1640+10% FBS. Subsequently, 50 μL/well was transferred from the dilution plate to the experimental plate. The experimental plate was then incubated for 24 hours at 37° C. with 5% $CO_2$. The cells were then centrifuged at 400×g for 5 min, supernatant decanted and resuspended in 100 μL of HEPES buffer containing Annexin V-FITC (1/200) and 7-AAD (1/50). The cells were then incubated for 15 min at room temperature and subsequently analyzed for Annexin V and 7-AAD staining by flow cytometry on a FACS Canto II (BD Biosciences, San Diego, Calif.) using forward scatter, side scatter, FITC and PerCP-Cy5.5 channels. Annexin V positive cells refer to cells positively stained by Annexin V-FITC after 24 h treatment with antibody constructs at 20 nM and is expressed as fold change relative to untreated cells.

Caspase assay. Activated caspases 2, 3, 6, 7, 8, 9, 10 were measured with the reagent Homogeneous Caspases Assay, fluorimetric Cat #12236869001, from Roche (West Sussex, UK) after treatment with test antibodies. The details of the assay follow.

ARP-1 cells, which express high levels of CD38, were cultured in a T175 flask (Costar, Corning, N.Y., cat #CLS431080) to a preferred density of between $2.0 \times 10^5$ and $2.0 \times 10^6$ viable cells/mL in RPMI 1640 (Life Technologies, Mulgrave, VIC, cat #11875-093) with 10% FBS (AusGeneX, Molendinar, QLD, Australia cat #FBS500S). Cells were harvested by centrifuging at 400×g for five minutes, decanting the supernatant, and resuspending the cell pellet in RPMI 1640 Phenol red-free (Life Technologies, Mulgrave, VIC, cat #11835-030) +10% FBS. Cells were then counted and the density was adjusted to $2.0 \times 10^5$ cells/mL in RPMI 1640 Phenol red free+10% FBS. Then, 50 μL of the cell suspension was aliquoted into each well of a 96-well flat bottom black-walled clear bottom plate (hereafter, "experimental plate"; Costar, Corning, N.Y. cat #CLS3603). On a separate, sterile 96-well plate (hereafter, "dilution plate"; Costar, Corning, N.Y. cat #3799), test articles were diluted to 40 nM in quadruplicate in RPMI 1640 Phenol red free+10% FBS. Subsequently, 50 μL/well was transferred from the dilution plate to the experimental plate. The experimental plate was then incubated for 24 hours at 37° C. with 5% $CO_2$. The manufacturer-supplied assay buffer was added to the manufacturer-supplied substrate and mixed according to the manufacturer's instructions to create the "substrate solution." Then, 100 μL of the substrate solution was added to each well of the assay plate. The plate was shaken for 2 minutes. The plate was then incubated at room temperature for 15 minutes in the dark and finally read on FluoStar Galaxy plate reader (BMG Labtech, Durham, N.C.) with an excitation filter 470-500 nm and emission filter 500-560 nm and the fluorescence measured and presented as fold change relative to untreated cells. Caspase Assay refers to caspase activation of cells after 24 h treatment with antibody constructs at 20 nM.

Off-Target Assays iLite gene reporter assay. The "off-target" iLite assay (PBL Interferon Source, Piscataway, N.J., Cat #51100) was performed largely as described by the manufacturer, with the addition of a human IgG blocking step. The iLite cell line is described by the manufacturer as "a stable transfected cell line derived from a commercially available pro-monocytic human cell line characterized by the expression of MHC Class II antigens, in particular the human lymphocyte antigen (HLADR), on the cell surface." The cell line contains a stably transfected luciferase gene, the expression of which is driven by an interferon-response element (IRE), which allows for interferon activity to be quantified based on luminescence output. The manufacturer supplied iLite plate (hereafter, assay plate) and diluent were removed from the −80° C. freezer and allowed to equilibrate to room temperature. Then, 50 μL of the diluent was added per well to the assay plate. The vial of manufacturer-supplied reporter cells was removed from the −80° C. freezer and thawed in a 37° C. water bath. Then, 25 μL aliquots of cells were dispensed into each well of the assay plate. Next, 12.5 μL of 8 mg/mL human IgG that was diluted into RPMI 1640+10% FBS (Sigma Chemicals, St. Louis, Mo.; cat #14506) was added per well. The contents were mixed and incubated at 37° C. for 15 minutes. On a separate "dilution plate," test articles were serially diluted in duplicate in RPMI 1640+10% FBS. Then, 12.5 μL of the test articles were transferred from the dilution plate to the assay plate. The assay plate was then incubated at 37° C. with 5% $CO_2$ for 17 hours. The manufacturer-supplied assay buffer and substrate were removed from the −80° C. freezer and allowed to equilibrate to room temperature for two hours. The manufacturer-supplied assay buffer was added to the manufacturer-supplied substrate vial and mixed well according to the manufacturer's instructions to create the "luminescence solution." Then, 100 μL of the luminescence solution was added to each well of the assay plate. The plate was shaken for 2 minutes. The plate was then incubated at room temperature for 5 minutes in the dark and finally read on a Victor 3V Multilabel Counter on a luminometry channel and the luminescence measured and presented as RLU. The data was analyzed with Graphpad Prism 5 as described for the "on-target (Daudi) assay." To test anti-CD38 antibody-IFN fusion protein constructs in the iLite assay, manufacturer-supplied diluent was supplemented with 0.25 mg/mL anti-CD38 antibody (same antibody clone being tested as an antibody-IFN fusion protein construct, to block any binding of the anti-CD38 antibody-IFN fusion protein constructs to the CD38 expressed on the iLite cells).

HEK-Blue Off-target assay. The assay was used to quantify the ability of antibody-IFN fusion constructs to bind interferon-alpha/β receptor (IFNAR) using the HEK-Blue™ IFN-alpha/β cell line (InvivoGen, San Diego, Calif.). The "off-target (HB-IFN) assay" was performed largely as described by the manufacturer of the HEK-Blue IFN-alpha/β cell line. HEK-Blue™ IFN-alpha/β Cells are specifically designed to monitor the activation of the JAK-STAT pathway, which is induced by type I IFNs. The cells were generated by introducing the human STAT2 and IRF9 genes into HEK293 cells to obtain a fully active type I IFN signalling pathway. The HEK-Blue™ IFN-alpha/β Cells stably express a reporter gene, secreted embryonic alkaline phosphatase (SEAP), under the control of the ISG54 promoter. ISG54 is a well-known ISG activated through an ISRE-dependent mechanism by type I IFNs. Upon IFN-alpha or IFNβ stimulation, HEK-Blue™ IFN-alpha/3 cells activate the JAK-STAT pathway and then the expression of the SEAP reporter gene. SEAP is secreted into the media and can be quantitated using the colorimetric reagent QUANTI-Blue™. Briefly, HEK-Blue IFN-alpha/β cells (Invivogen, San Diego Calif. cat #hkb-ifnab) were thawed and cultured in DMEM media (Mediatech, Manassas Va., cat #10-013-CV)+10% FBS (Hyclone, Logan Utah, cat #SH30070.03) that had been heat inactivated (HI FBS). When the cells reached 60-80% confluence, they were lifted with Cell Stripper (Mediatech, cat #25-056-CI). Cells were washed twice in DMEM+HI FBS and counted. Cells were adjusted to $3.3 \times 10^5$ viable cells/mL in DMEM+HI FBS and 150 μL was aliquoted per well into a flat bottom 96 well tissue culture plate (hereafter, the "experimental plate"). Then, 50 μL of IFN-alpha2b or fusion protein construct, diluted in DMEM+HI FBS, was added per well. The plate was incubated at 37° C. 5% $CO_2$ for 16-24 hours. QUANTI-Blue (Invivogen, cat #rep-qb1) was prepared according to the manufacturer's directions. QUANTI-Blue (150 μL) was aliquoted into each well of a flat bottom plate (hereafter, the "assay plate"). Then, 50 μL supernatant per well from the experimental plate was transferred to assay plate. Assay plate was then incubated at 37° C. for 1-3 hours. Assay plate absorbance at 630 nm was read on a model 1420-41 Victor 3V Multilabel Counter from Perkin-Elmer. Data was analyzed using Graph Pad Prism.

H929 Xenograft Model

The effect of different doses of the A10.38 and A10.0 anti-CD38-attenuated IFN-alpha fusion protein constructs, were compared to the non-CD38-targeted fusion protein construct, on myeloma tumor growth. For these comparisons, the NCI-H929 s.c. multiple myeloma model was used.

The multiple myeloma cell line, NCI-H929 (ATCC CRL-9068, Gazdar, Blood 67: 1542-1549, 1986) is grown subcutaneously in immunocompromised (SCID) mice.

Eight to twelve week old CB.17 SCID mice were injected subcutaneously in the flank with $1 \times 10^7$ NCI-H929 tumor cells in 50% Matrigel. When average tumor size reached 170-350 mm³, mice were grouped into 4 cohorts of 7 mice each and treatment began at time zero (TO). All treatments were given by intraperitoneal injection, (i.p.) twice weekly for 3 weeks (indicated by bar under graph). All compounds were dosed at 100 μg/dose (approximately 4.5 mg/kg) except vehicle group. Tumor volume was measured twice weekly by caliper measurement. Endpoint was tumor volume of 2,000 mm³.

The effect of different doses of the A02. 6, A10.0 and A10.38 anti-CD38-attenuated IFN-alpha fusion protein constructs, were compared to vehicle, on myeloma tumor growth. For these comparisons, the NCI-H929 s.c. multiple myeloma model was used.

The multiple myeloma cell line, NCI-H929 (ATCC CRL-9068, Gazdar, Blood 67: 1542-1549, 1986) is grown subcutaneously in immunocompromised (SCID) mice.

Eight to twelve week old CB.17 SCID mice were injected subcutaneously in the flank with $1 \times 10^7$ NCI-H929 tumor cells in 50% Matrigel. When average tumor size reaches 90 mm³, mice will be grouped into 4 cohorts of 5 mice each and treatment begin at time zero (TO). All treatments will be given by intraperitoneal injection, (i.p.) twice weekly for 3 weeks (indicated by bar under graph). All compounds will be dosed at 100 μg/dose (approximately 4.5 mg/kg) except vehicle group. Tumor volume will be measured twice weekly by caliper measurement.

Example 6

Anti-CD38-Attenuated IFN Fusion Protein with Alternative Constant Region

A02.12 comprises an anti-CD38-attenuated IFN fusion protein in which the constant region of the protein is HC-L0-IFN-alpha (A145D) IgG4 (SEQ ID NO: 9). The heavy chain variable region of this antibody was reformatted onto an IgG1 constant region fused to A145D attenuated IFN-alpha2b (SEQ ID NO: 10). Co-expression of this heavy chain with the light chain of X02.107 (SEQ ID NO: 65) in HEK293E cells yielded antibody A02.112. Comparison of antibodies A02.12 and A02.112 using flow cytometry-based CD38-binding assays and potency assays demonstrates that other antibody constant regions, such as human IgG1, may also be used resulting in antibody-attenuated IFN fusion proteins with potent biologic activity equivalent to those generated using a human IgG4 constant region (Table 16b).

TABLE 16b

Figure 21:
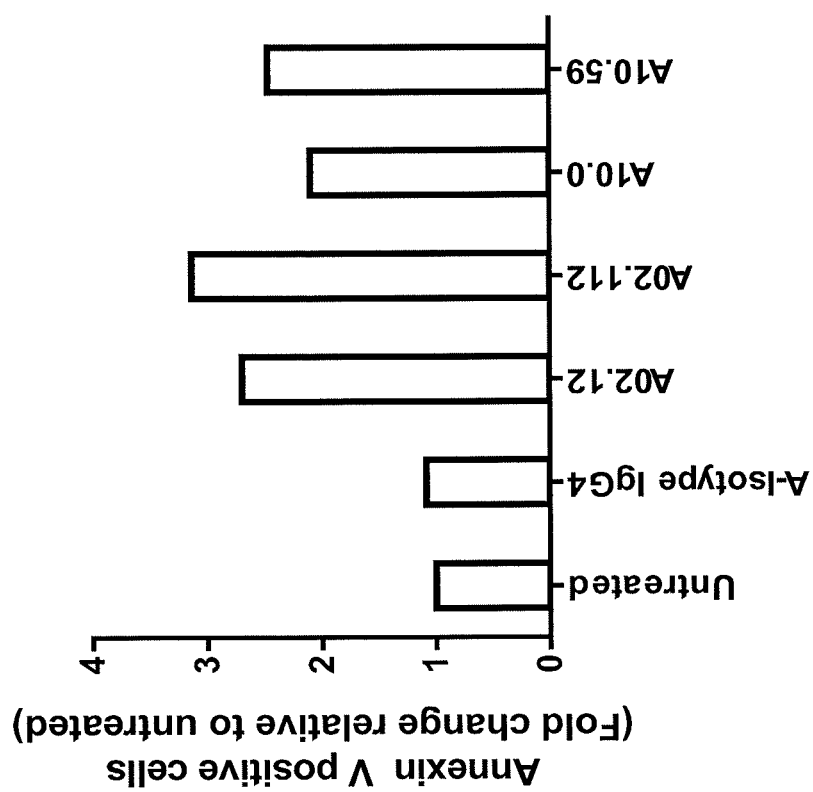
FIG. 21 shows the relative fold change of Annexin V production in the CD38-expressing multiple myeloma cell line H929 between IgG1 and IgG4 subtypes of anti-CD38-attenuated IFN-alpha fusion protein constructs. A-isotype is a non-specific IgG4 antibody fused with the attenuated interferon as a control. The antibodies, A02.12 and A10.0 contain IgG4 constant regions fused to attenuated IFN-alpha while A02.112 and A10.59 contain IgG1 constant regions fused to attenuated IFN-alpha. The assay details are described in the Examples (Annexin V/7AAD assay).
Figure 22:
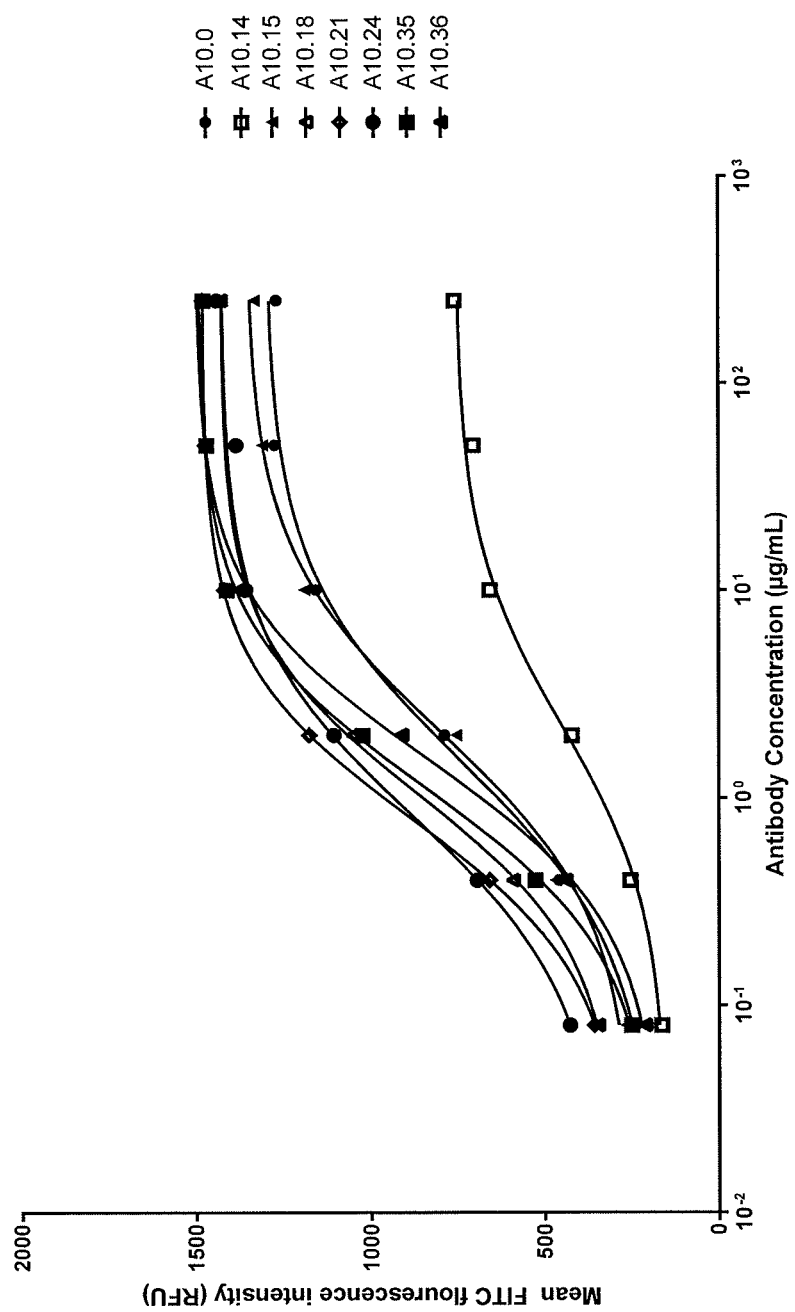
FIG. 22 shows the binding activity of A10.0 variants to the CD38-expressing multiple myeloma cell line NCI-H929 as measured by flow cytometry. The assay details are described in the Examples of this specification.
Figure 23:
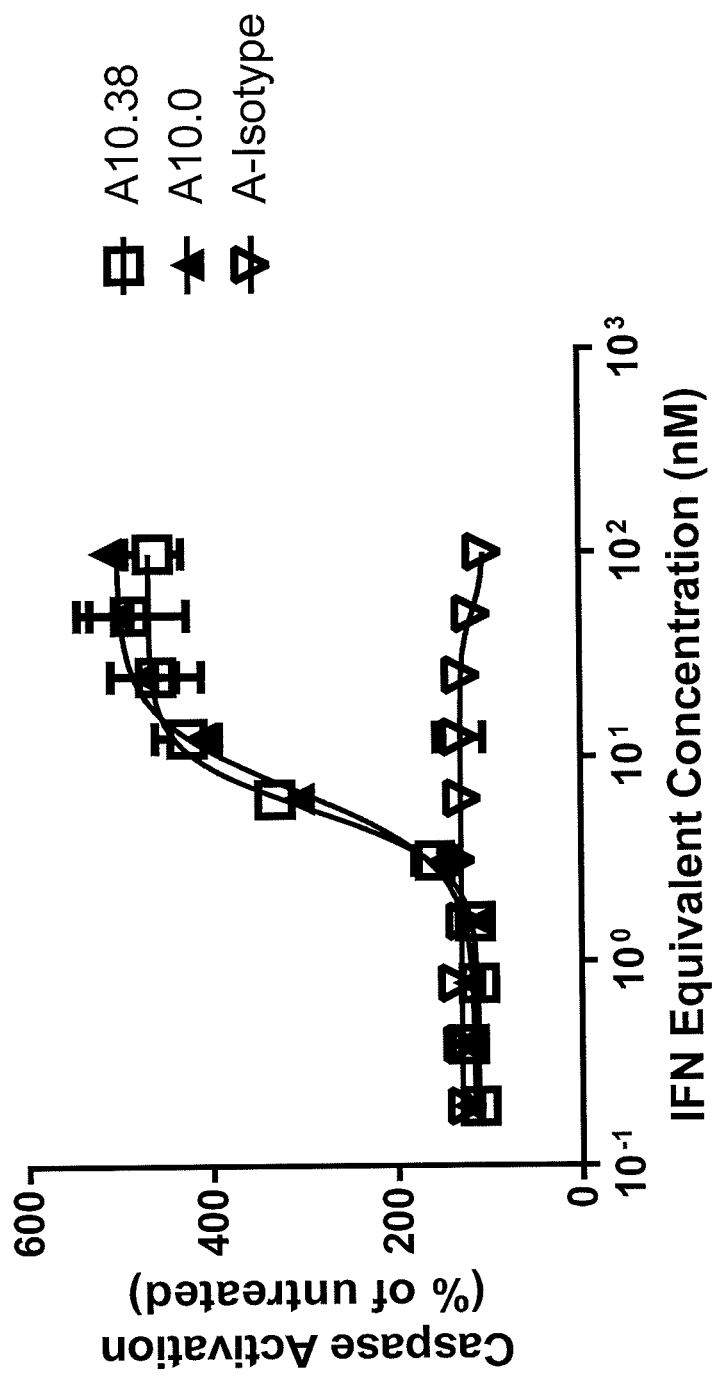
FIG. 23 shows caspase activation in the CD38-expressing multiple myeloma cell line H929 of A10.0 and A10.38 compared to untreated cells. A-isotype is an irrelevant specificity antibody fused to the attenuated IFN as a control. The assay details are described in the Examples (Caspase assay).
Figure 24:
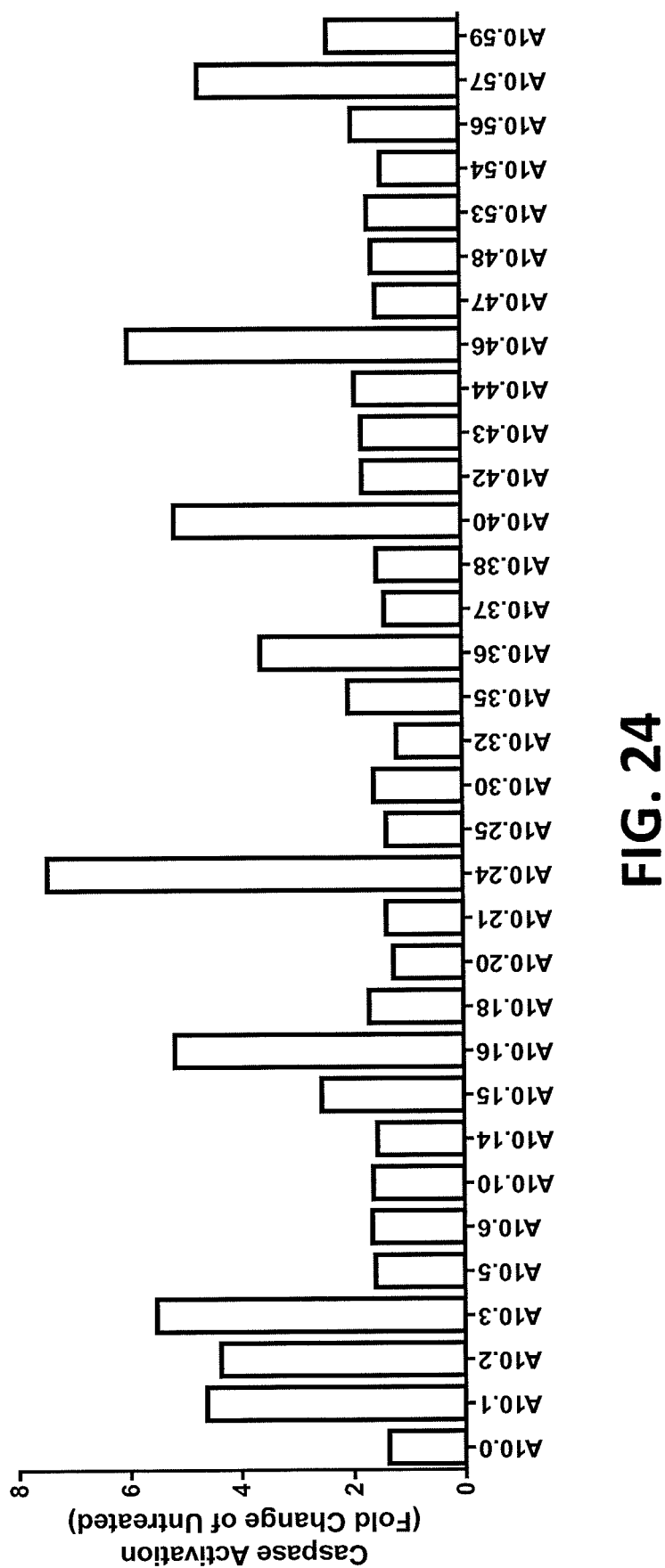
FIG. 24 shows the relative fold change of caspase activation in the CD38 expressing multiple myeloma cell line H929 by A10.0 variants compared to untreated cells. The assay details are described in the Examples (Caspase assay).

| Anti-CD38-attenuated IFN fusion protein | Flow binding (EC$_{50}$ in μg/mL) | Annexin V Assay (Fold change relative to untreated cells) | Caspase Assay (Fold change relative to untreated cells) | Cell Proliferation Assay IC$_{50}$ (pm) | Figures |
|---|---|---|---|---|---|
| A02.12 | 3.40* | 1.40 | 2.70 | 23.66 | FIG. 21 |
| A02.112 | <0.3* | 3.14 | 3.74 | N/T | FIG. 21 |

Note:
*Antibody was tested in a flow binding assay against H929 cell line. Reported value is the EC$_{50}$ in μg/mL. Annexin V Assay refer to cells positively stained by Annexin V-FITC after 24 h treatment with antibody constructs at 20 nM. Caspase Assay refers to caspase activation of cells after 24 h treatment with antibody constructs at 20 nM.
N/T—Not Tested

Example 7

Humanization of R5D1, R5E8 and R10A2 Variable Regions

Rat-derived anti-CD38 antibodies R5D1, R5E8 and R10A2 are described in PCT/AU12/001323 and were selected for humanization. The variable regions of these antibodies were superhumanized as described in U.S. Publ. No. 2003/0039649. Briefly, canonical structures were assigned to each rodent heavy and light chain through inspection of their respective amino acid sequences. R10A2 was assigned the canonical structure 2-1-1/1-2 ($V_L/V_H$), R5E8 was assigned the canonical structure 4-1-1/1-2, and R5D1 was assigned the canonical structure 2-1-1/1-2. Human germline sequences of the same canonical structure were used as acceptor frameworks for the grafting of donor CDRs. Variants of the resulting superhumanized antibody genes containing amino acid substitutions at positions within their sequences deemed likely to be important for maintenance of their binding activity were also designed. The different heavy chain superhumanized variable regions are shown in FIG. 7. The different light chain superhumanized variable regions are shown in FIG. 8.

Heavy chain variable region sequences were subcloned into vector pEE6.4 containing a human IgG4 constant region possessing the substitution S228P fused to A145D attenuated IFN-alpha2b (SEQ ID NO: 9). Light chain variable regions were subcloned into vector pEE12.4 containing a human kappa constant region (SEQ ID NO: 5). Antibodies were produced through co-expression of heavy chains in pEE6.4 and light chains in pEE12.4 in CHO cells as described previously. Table 17 summarises the heavy- and light chain pairings used to produce each superhumanized 5D1-based protein. Table 18 details the heavy- and light chain pairings for the superhumanized 5E8-based protein generated, whilst the heavy- and light chain pairings used to generate superhumanized 10A2-based proteins are given in Table 19. One-shot equilibrium dissociation constant (K$_D$) ranking of the superhumanized antibodies was performed by BIAcore™ analysis of the resulting CHO transfection supernatants. The method was used to determine if the antibodies expressed (Protein A capture) and had a level of binding activity to human CD38.

TABLE 17

| Anti-CD38-attenuated IFN fusion protein | Variable Heavy SEQ ID NO: | Variable Light SEQ ID NO: | K$_D$ (M) | Protein A capture (RU) |
|---|---|---|---|---|
| A5D1.0 (chimeric) | 114 | 125 | 2.28 × 10$^{-9}$ | N/A |
| A5D1.1 | 115 | 126 | 2.95 × 10$^{-8}$ | 175 |
| A5D1.2 | 115 | 127 | 2.95 × 10$^{-8}$ | 289 |
| A5D1.3 | 115 | 128 | 2.35 × 10$^{-8}$ | 248 |
| A5D1.4 | 115 | 129 | 2.85 × 10$^{-8}$ | 427 |
| A5D1.5 | 115 | 130 | 1.84 × 10$^{-7}$ | 269 |
| A5D1.6 | 115 | 131 | 2.32 × 10$^{-8}$ | 338 |
| A5D1.7 | 116 | 126 | 1.05 × 10$^{-8}$ | 132 |
| A5D1.8 | 116 | 127 | 6.80 × 10$^{-9}$ | 263 |
| A5D1.9 | 116 | 128 | 9.93 × 10$^{-8}$ | 128 |
| A5D1.10 | 116 | 129 | 5.69 × 10$^{-9}$ | 358 |
| A5D1.11 | 116 | 130 | 1.64 × 10$^{-8}$ | 250 |
| A5D1.12 | 116 | 131 | 5.61 × 10$^{-9}$ | 345 |
| A5D1.13 | 117 | 126 | 1.44 × 10$^{-8}$ | 213 |
| A5D1.14 | 117 | 127 | 1.52 × 10$^{-8}$ | 344 |
| A5D1.15 | 117 | 128 | 1.46 × 10$^{-8}$ | 167 |
| A5D1.16 | 117 | 129 | 1.37 × 10$^{-8}$ | 524 |
| A5D1.17 | 117 | 130 | 3.28 × 10$^{-8}$ | 410 |
| A5D1.18 | 117 | 131 | 1.01 × 10$^{-8}$ | 396 |
| A5D1.19 | 118 | 126 | 1.01 × 10$^{-8}$ | 245 |
| A5D1.20 | 118 | 127 | 1.07 × 10$^{-8}$ | 282 |
| A5D1.21 | 118 | 128 | 7.94 × 10$^{-9}$ | 351 |
| A5D1.22 | 118 | 129 | 8.97 × 10$^{-9}$ | 566 |
| A5D1.23 | 118 | 130 | 2.14 × 10$^{-8}$ | 336 |
| A5D1.24 | 118 | 131 | 8.01 × 10$^{-9}$ | 319 |
| A5D1.25 | 119 | 126 | DNB | 165 |
| A5D1.26 | 119 | 127 | DNB | 286 |
| A5D1.27 | 119 | 128 | DNB | 265 |
| A5D1.28 | 119 | 129 | DNB | 493 |
| A5D1.29 | 119 | 130 | DNB | 275 |
| A5D1.30 | 119 | 131 | DNB | 263 |
| A5D1.31 | 120 | 126 | 1.05 × 10$^{-7}$ | 206 |
| A5D1.32 | 120 | 127 | 1.20 × 10$^{-7}$ | 318 |
| A5D1.33 | 120 | 128 | 9.83 × 10$^{-8}$ | 176 |
| A5D1.34 | 120 | 129 | 1.06 × 10$^{-7}$ | 497 |
| A5D1.35 | 120 | 130 | 6.07 × 10$^{-7}$ | 211 |
| A5D1.36 | 120 | 131 | 8.58 × 10$^{-8}$ | 331 |
| A5D1.37 | 121 | 126 | 1.01 × 10$^{-7}$ | 184 |
| A5D1.38 | 121 | 127 | 1.21 × 10$^{-7}$ | 315 |
| A5D1.39 | 121 | 128 | 9.55 × 10$^{-8}$ | 191 |
| A5D1.40 | 121 | 129 | 1.22 × 10$^{-7}$ | 460 |
| A5D1.41 | 121 | 130 | 5.60 × 10$^{-7}$ | 409 |
| A5D1.42 | 121 | 131 | 8.54 × 10$^{-8}$ | 301 |
| A5D1.43 | 122 | 126 | 1.78 × 10$^{-8}$ | 150 |
| A5D1.44 | 122 | 127 | 1.76 × 10$^{-8}$ | 226 |
| A5D1.45 | 122 | 128 | 1.42 × 10$^{-8}$ | 177 |
| A5D1.46 | 122 | 129 | 1.51 × 10$^{-8}$ | 401 |
| A5D1.47 | 122 | 130 | 1.89 × 10$^{-8}$ | 364 |
| A5D1.48 | 122 | 131 | 1.20 × 10$^{-8}$ | 273 |
| A5D1.49 | 123 | 126 | 6.32 × 10$^{-9}$ | 141 |
| A5D1.50 | 123 | 127 | 5.64 × 10$^{-9}$ | 212 |
| A5D1.51 | 123 | 128 | 4.97 × 10$^{-9}$ | 188 |
| A5D1.52 | 123 | 129 | 4.07 × 10$^{-9}$ | 493 |
| A5D1.53 | 123 | 130 | 6.98 × 10$^{-9}$ | 561 |
| A5D1.54 | 123 | 131 | 4.49 × 10$^{-9}$ | 253 |
| A5D1.55 | 124 | 126 | 6.48 × 10$^{-9}$ | 203 |
| A5D1.56 | 124 | 127 | 8.44 × 10$^{-9}$ | 144 |
| A5D1.57 | 124 | 128 | 5.59 × 10$^{-9}$ | 233 |
| A5D1.58 | 124 | 129 | 5.37 × 10$^{-9}$ | 376 |
| A5D1.59 | 124 | 130 | 1.05 × 10$^{-8}$ | 313 |
| A5D1.60 | 124 | 131 | 4.57 × 10$^{-9}$ | 429 |

DNB—did not bind.
N/A—Not available

TABLE 18

| Anti-CD38-attenuated IFN fusion protein | Variable Heavy SEQ ID NO: | Variable Light SEQ ID NO: | K$_D$ (M) | Protein A capture (RU) |
|---|---|---|---|---|
| A5E8.0 (chimeric) | 132 | 143 | 5.50 × 10$^{-9}$ | N/A |
| A5E8.1 | 133 | 144 | 2.31 × 10$^{-7}$ | 267 |

TABLE 18-continued

| Anti-CD38-attenuated IFN fusion protein | Variable Heavy SEQ ID NO: | Variable Light SEQ ID NO: | $K_D$ (M) | Protein A capture (RU) |
|---|---|---|---|---|
| A5E8.2 | 133 | 145 | $2.37 \times 10^{-7}$ | 459 |
| A5E8.3 | 133 | 146 | $3.59 \times 10^{-7}$ | 281 |
| A5E8.4 | 133 | 147 | DNB | 420 |
| A5E8.5 | 134 | 144 | $1.75 \times 10^{-7}$ | 172 |
| A5E8.6 | 134 | 145 | $1.57 \times 10^{-7}$ | 611 |
| A5E8.7 | 134 | 146 | $2.58 \times 10^{-7}$ | 201 |
| A5E8.8 | 134 | 147 | $8.09 \times 10^{-7}$ | 308 |
| A5E8.9 | 135 | 144 | $1.05 \times 10^{-8}$ | 153 |
| A5E8.10 | 135 | 145 | $2.13 \times 10^{-8}$ | 503 |
| A5E8.11 | 135 | 146 | $2.69 \times 10^{-8}$ | 372 |
| A5E8.12 | 135 | 147 | DNB | 212 |
| A5E8.13 | 136 | 144 | $3.98 \times 10^{-8}$ | 301 |
| A5E8.14 | 136 | 145 | $1.26 \times 10^{-7}$ | 543 |
| A5E8.15 | 136 | 146 | $1.39 \times 10^{-7}$ | 504 |
| A5E8.16 | 136 | 147 | DNB | 284 |
| A5E8.17 | 137 | 144 | $2.76 \times 10^{-8}$ | 397 |
| A5E8.18 | 137 | 145 | $8.81 \times 10^{-8}$ | 430 |
| A5E8.19 | 137 | 146 | $1.09 \times 10^{-7}$ | 220 |
| A5E8.20 | 137 | 147 | DNB | 397 |
| A5E8.21 | 138 | 144 | DNB | 277 |
| A5E8.22 | 138 | 145 | DNB | 409 |
| A5E8.23 | 138 | 146 | DNB | 339 |
| A5E8.24 | 138 | 147 | DNB | 266 |
| A5E8.25 | 139 | 144 | DNB | 283 |
| A5E8.26 | 139 | 145 | DNB | 395 |
| A5E8.27 | 139 | 146 | DNB | 277 |
| A5E8.28 | 139 | 147 | DNB | 290 |
| A5E8.29 | 140 | 144 | $3.91 \times 10^{-8}$ | 207 |
| A5E8.30 | 140 | 145 | $5.00 \times 10^{-8}$ | 255 |
| A5E8.31 | 140 | 146 | $6.61 \times 10^{-8}$ | 267 |
| A5E8.32 | 140 | 147 | DNB | 42 |
| A5E8.33 | 141 | 144 | $1.12 \times 10^{-8}$ | 134 |
| A5E8.34 | 141 | 145 | $1.63 \times 10^{-8}$ | 301 |
| A5E8.35 | 141 | 146 | $1.85 \times 10^{-8}$ | 177 |
| A5E8.36 | 141 | 147 | DNB | 10 |
| A5E8.37 | 142 | 144 | $8.19 \times 10^{-8}$ | 200 |
| A5E8.38 | 142 | 145 | $1.55 \times 10^{-8}$ | 328 |
| A5E8.39 | 142 | 146 | $1.74 \times 10^{-8}$ | 232 |
| A5E8.40 | 142 | 147 | DNB | 126 |

DNB—did not bind.
N/A—not available

TABLE 19

| Anti-CD38-attenuated IFN fusion protein | SEQ ID: Variable Heavy | SEQ ID: Variable Light | $K_D$ (M) | Protein A capture (RU) |
|---|---|---|---|---|
| A10A2.0 (chimeric) | 148 | 157 | $5.98 \times 10^{-10}$ | N/A |
| A10A2.1 | 149 | 158 | DNB | 728 |
| A10A2.2 | 149 | 159 | DNB | 689 |
| A10A2.3 | 149 | 160 | DNB | 850 |
| A10A2.4 | 149 | 161 | DNB | 996 |
| A10A2.5 | 149 | 162 | DNB | 761 |
| A10A2.6 | 149 | 163 | DNB | 890 |
| A10A2.7 | 149 | 164 | DNB | 725 |
| A10A2.8 | 150 | 158 | $7.18 \times 10^{-7}$ | 718 |
| A10A2.9 | 150 | 159 | $6.62 \times 10^{-7}$ | 627 |
| A10A2.10 | 150 | 160 | $9.13 \times 10^{-7}$ | 850 |
| A10A2.11 | 150 | 161 | $2.37 \times 10^{-7}$ | 956 |
| A10A2.12 | 150 | 162 | $1.18 \times 10^{-6}$ | 864 |
| A10A2.13 | 150 | 163 | $6.80 \times 10^{-7}$ | 765 |
| A10A2.14 | 150 | 164 | DNB | 645 |
| A10A2.15 | 151 | 158 | $1.15 \times 10^{-7}$ | 488 |
| A10A2.16 | 151 | 159 | $8.11 \times 10^{-8}$ | 759 |
| A10A2.17 | 151 | 160 | $1.84 \times 10^{-7}$ | 684 |
| A10A2.18 | 151 | 161 | $3.39 \times 10^{-8/}$ | 907 |
| A10A2.19 | 151 | 162 | $1.84 \times 10^{-9}$ | 831 |
| A10A2.20 | 151 | 163 | $1.23 \times 10^{-7}$ | 560 |
| A10A2.21 | 151 | 164 | DNB | 337 |
| A10A2.22 | 152 | 158 | $2.70 \times 10^{-9}$ | 890 |
| A10A2.23 | 152 | 159 | $2.17 \times 10^{-9}$ | 828 |

TABLE 19-continued

| Anti-CD38-attenuated IFN fusion protein | SEQ ID: Variable Heavy | SEQ ID: Variable Light | $K_D$ (M) | Protein A capture (RU) |
|---|---|---|---|---|
| A10A2.24 | 152 | 160 | $3.04 \times 10^{-9}$ | 803 |
| A10A2.25 | 152 | 161 | $1.51 \times 10^{-9}$ | 1054 |
| A10A2.26 | 152 | 162 | $3.51 \times 10^{-9}$ | 741 |
| A10A2.27 | 152 | 163 | $2.42 \times 10^{-9}$ | 603 |
| A10A2.28 | 152 | 164 | $3.69 \times 10^{-8}$ | 384 |
| A10A2.29 | 153 | 158 | $2.77 \times 10^{-8}$ | 93 |
| A10A2.30 | 153 | 159 | $2.15 \times 10^{-8}$ | 86 |
| A10A2.31 | 153 | 160 | $5.82 \times 10^{-8}$ | 33 |
| A10A2.32 | 153 | 161 | $8.49 \times 10^{-9}$ | 169 |
| A10A2.33 | 153 | 162 | $5.66 \times 10^{-8}$ | 62 |
| A10A2.34 | 153 | 163 | $3.88 \times 10^{-8}$ | 56 |
| A10A2.35 | 153 | 164 | DNB | DNE |
| A10A2.36 | 154 | 158 | $8.38 \times 10^{-9}$ | 221 |
| A10A2.37 | 154 | 159 | $1.39 \times 10^{-9}$ | 858 |
| A10A2.38 | 154 | 160 | $1.08 \times 10^{-8}$ | 178 |
| A10A2.39 | 154 | 161 | $3.80 \times 10^{-9}$ | 357 |
| A10A2.40 | 154 | 162 | $1.34 \times 10^{-8}$ | 217 |
| A10A2.41 | 154 | 163 | $8.73 \times 10^{-9}$ | 202 |
| A10A2.42 | 154 | 164 | $2.09 \times 10^{-7}$ | 175 |
| A10A2.43 | 154 | 158 | $2.45 \times 10^{-7}$ | 621 |
| A10A2.44 | 155 | 159 | $6.23 \times 10^{-9}$ | 220 |
| A10A2.45 | 155 | 160 | $2.84 \times 10^{-7}$ | 881 |
| A10A2.46 | 155 | 161 | $1.39 \times 10^{-7}$ | 1000 |
| A10A2.47 | 155 | 162 | $3.28 \times 10^{-7}$ | 9 |
| A10A2.48 | 155 | 163 | $2.52 \times 10^{-7}$ | 565 |
| A10A2.49 | 155 | 164 | DNB | 499 |
| A10A2.50 | 156 | 158 | $1.61 \times 10^{-9}$ | 567 |
| A10A2.51 | 156 | 159 | $2.00 \times 10^{-7}$ | 603 |
| A10A2.52 | 156 | 160 | $1.69 \times 10^{-9}$ | 723 |
| A10A2.53 | 156 | 161 | $1.20 \times 10^{-9}$ | 729 |
| A10A2.54 | 156 | 162 | $1.92 \times 10^{-9}$ | 639 |
| A10A2.55 | 156 | 163 | $1.47 \times 10^{-9}$ | 692 |
| A10A2.56 | 156 | 164 | $1.97 \times 10^{-7}$ | 383 |

DNB—did not bind.

DNE—did not express.

For each family of humanized antibodies—5D1, 5E8 and 10A2—several humanized heavy and light chain combinations failed to either express protein, or to bind to human CD38. A considerable number of antibodies across all 3 families of humanized antibodies expressed and bound to human CD38 with equilibrium dissociation constants in the nanomolar (nM) range. A10A2.53 and A10A2.25, which share a common light chain were chosen for further optimization. A10A2.53 was renamed A10.0 and A10A2.25 was renamed A10.38.

Example 8

Improved Variants of A10.0

The A10.0 antibody was optimized through alterations to the variable heavy and/or light chain sequences with the aim of yielding a positive effect on the biophysical and in silico immunogenicity of the antibody whilst causing minimal impact on the functional activity of the antibody.

In-Silico Immunogenicity Analysis of A10.0 Heavy- and Light Chains

In silico immunogenicity analyses of the A10.0 heavy- and light chain variable regions were made using the Epibase software package. Several amino acid substitutions were introduced into the heavy- and light chain variable regions of A10.0 to remove potential immunogenic epitopes. An amino acid sequence alignment of the heavy chain variable region variants produced aligned with the humanised heavy chain (SEQ ID NO: 156) is shown in FIG. 9. An amino acid sequence alignment of the light chain variable region variants aligned with the humanised light chain (SEQ ID NO: 161) is shown in FIG. 10. Details of the heavy- and light chains variants co-expressed in HEK293E cells to produce proteins are summarised in Table 20.

TABLE 20

| Anti-CD38-attenuated IFN fusion protein | VH Amino Acid Substitution (Relative to A10.0) | Variable Heavy SEQ ID NO: | VK Amino Acid Substitution (Relative to A10.0) | Variable Light SEQ ID NO: |
|---|---|---|---|---|
| A10.1 | A40E | 165 | N/A | 161 |
| A10.2 | A40G | 166 | N/A | 161 |
| A10.3 | A40H | 167 | N/A | 161 |
| A10.4 | A40Q | 168 | N/A | 161 |
| A10.5 | A40S | 169 | N/A | 161 |
| A10.6 | A40V | 170 | N/A | 161 |
| A10.7 | N35E | 171 | N/A | 161 |
| A10.8 | N35P | 172 | N/A | 161 |
| A10.9 | N35Q | 173 | N/A | 161 |
| A10.10 | N35S | 174 | N/A | 161 |
| A10.11 | R94E | 175 | N/A | 161 |
| A10.12 | R94G | 176 | N/A | 161 |
| A10.13 | R94P | 177 | N/A | 161 |
| A10.14 | R94T | 178 | N/A | 161 |
| A10.15 | K96G | 179 | N/A | 161 |
| A10.16 | K96T | 180 | N/A | 161 |
| A10.17 | N/A | 156 | K24E | 181 |
| A10.18 | N/A | 156 | K24G | 182 |
| A10.19 | N/A | 156 | K24P | 183 |
| A10.20 | N/A | 156 | K24Q | 184 |
| A10.21 | N/A | 156 | R54D | 185 |
| A10.22 | N/A | 156 | I48D | 186 |
| A10.23 | N/A | 156 | Y49E | 187 |
| A10.24 | N/A | 156 | M89A | 188 |
| A10.25 | N/A | 156 | M89E | 189 |
| A10.26 | N/A | 156 | M89H | 190 |
| A10.27 | N/A | 156 | M89K | 191 |
| A10.28 | N/A | 156 | M89P | 192 |
| A10.29 | N/A | 156 | M89Q | 193 |
| A10.30 | N/A | 156 | M89S | 194 |
| A10.31 | N/A | 156 | M89V | 195 |
| A10.32 | N/A | 156 | Q90D | 196 |

Each antibody generated using the heavy- and light chain pairings outlined in Table 20 was assessed for protein expression level and binding to CD38 via SPR. Furthermore, potency assays were performed using cell culture supernatants to assess the relative functional activity of each of these anti-CD38 antibody-attenuated IFN fusion proteins, Table 21.

TABLE 21

| Anti-CD38-attenuated IFN fusion protein | Protein A HPLC (mg/L) | CD38 binding by SPR (RU) at 350 sec* | Annexin V (Fold change relative to untreated cells) Assay | Caspase Assay (Fold change relative to untreated cells) | Cell Proliferation Assay (IC$_{50}$ pM) |
|---|---|---|---|---|---|
| A10.1 | 16.9 | 1824 | 1.66 | 3.41 | 4078 |
| A10.2 | 16.7 | 1821 | 1.66 | 5.19 | 7622 |
| A10.3 | 25.0 | 2166 | 1.63 | 5.46 | 2148 |
| A10.4 | 23.7 | 2169 | 1.63 | 5.78 | 4108 |
| A10.5 | 28.0 | 2240 | 1.64 | 5.80 | 3046 |
| A10.6 | 31.0 | 2097 | 1.57 | 5.76 | 2283 |
| A10.7 | 26.5 | DNB | 1.18 | 1.09 | No IC$_{50}$ |
| A10.8 | 2.4 | DNB | N/T | N/T | N/T |
| A10.9 | 18.3 | 176 | 1.48 | 2.07 | No IC$_{50}$ |
| A10.10 | 32.2 | 1072 | 1.57 | 4.97 | 18870 |
| A10.11 | 28.3 | 98 | 1.57 | 3.64 | No IC$_{50}$ |
| A10.12 | 30.7 | DNB | 1.22 | 1.99 | No IC$_{50}$ |
| A10.13 | 30.6 | 123 | 1.31 | 2.67 | No IC$_{50}$ |
| A10.14 | 30.5 | 247 | 1.19 | 5.11 | 68270 |
| A10.15 | 41.8 | 1254 | 1.52 | 5.44 | 5169 |
| A10.16 | 24.2 | 1210 | 1.70 | 4.57 | 5224 |
| A10.17 | 18.2 | 1686 | 1.79 | 6.11 | 3054 |
| A10.18 | 32.5 | 2457 | 1.89 | 6.16 | 2178 |
| A10.19 | 1.6 | DNB | 1.73 | 2.39 | No IC$_{50}$ |
| A10.20 | 12.2 | 1355 | 4.65 | 7.72 | 564 |
| A10.21 | 19.9 | 1837 | 1.84 | 5.56 | 5330 |
| A10.22 | 5.5 | 480 | N/T | N/T | N/T |
| A10.23 | 20.6 | 255 | 1.71 | 3.85 | 59720 |
| A10.24 | 34.6 | 1943 | 4.14 | 6.75 | 399 |
| A10.25 | 28.3 | 1778 | 1.87 | 6.09 | 4910 |
| A10.26 | 5.7 | 706 | N/T | N/T | N/T |
| A10.27 | 7.4 | 136 | N/T | N/T | N/T |
| A10.28 | 2.2 | 48 | N/T | N/T | N/T |
| A10.29 | 10.9 | 1443 | N/T | N/T | No IC$_{50}$ |
| A10.30 | 25.4 | 1865 | 1.98 | 6.21 | 1438 |
| A10.31 | 5.8 | 469 | N/T | N/T | N/T |
| A10.32 | 34.5 | 615 | 3.80 | 6.97 | 3628 |

The CD38 binding by SPR refers to the amount of CD38 that remains bound to the surface after 350 seconds of the dissociation phase. Annexin V Assay refer to cells positively stained by Annexin V-FITC after 24 h treatment with antibody constructs at 20 nM. Caspase Assay refers to caspase activation of cells after 24 h treatment with antibody constructs at 20 nM.
DNB—Did not bind;
N/T—not tested;
No IC$_{50}$-potency not sufficient for an IC$_{50}$ value.

Analyses of the amino acid sequences of the variable heavy- and light chain sequences of A10.0 identified several potential deamidation sites and one potential oxidation site. Variable heavy chain substitution N98Q was prepared to remove a deamidation site from CDR3 of the heavy chain, SEQ ID NO: 197. A further variant of the A10.0 variable light chain containing the CDR2 substitution N53Q (SEQ ID NO: 198) was generated to remove this putative deamidation site. M89 within CDR3 of the light chain was also altered through amino acid substitutions at this position with the combined aims of removing this potential oxidation site and reducing the predicted immunogenicity of this region of the light chain. These substitutions are outlined in Table 22, along with the heavy and light chain pairings co-expressed to produce each anti-CD38-attenuated IFN fusion protein.

TABLE 22

| Anti-CD38-attenuated IFN fusion protein | Amino Acid Substitution (Relative to A10.0) | Variable Heavy SEQ ID NO: | Variable Light SEQ ID NO: |
|---|---|---|---|
| A10.35 | Heavy Chain N(98)Q | 197 | 161 |
| A10.36 | Light Chain N(53)Q | 156 | 198 |

Each antibody generated using the heavy- and light chain pairings outlined in Table 22 was assessed for protein expression level and binding to CD38 via SPR. Furthermore, potency assays were performed using cell culture supernatants to assess the relative functional activity of each of these anti-CD38-attenuated IFN fusion proteins, Table 23

TABLE 23

| Anti-CD38-attenuated IFN fusion protein | Protein A HPLC (mg/L) | CD38 binding by SPR (RU) at 350 sec* | Annexin V assay (Fold change relative to untreated cells)Assay | Caspase Assay (Fold change relative to untreated cells) | Cell Proliferation Assay IC$_{50}$ (pM) |
|---|---|---|---|---|---|
| A10.35 | 34.5 | 1889 | 1.83 | 6.16 | 6241 |
| A10.36 | 52.4 | 1895 | 3.95 | 5.90 | 534.9 |

The CD38 binding by SPR refers to the amount of CD38 that remains bound to the surface after 350 seconds of the dissociation phase. Annexin V Assay refer to cells positively stained by Annexin V-FITC after 24 h treatment with antibody constructs at 20 nM. Caspase Assay refers to caspase activation of cells after 24 h treatment with antibody constructs at 20 nM.

Example 9

Generating Improved Variants of A10.38

A10.0 and A10.38 share a common light chain. The optimized light chain sequences of A10.0 were paired with the heavy chain of the A10.38 antibody with the aim of yielding a positive effect on the antibody's biophysical and in silico immunogenicity properties whilst having a minimal impact on functional activity. A summary of the changes and the pairings of heavy and light chains are described in Table 24.

TABLE 24

| Anti-CD38-attenuated IFN fusion protein | SEQ ID: Variable Heavy | VK Amino Acid Substitution (Relative to A10.38) | SEQ ID: Variable Light |
|---|---|---|---|
| A10.38 | 152 | N/A | 161 |
| A10.39 | 152 | K24E | 181 |
| A10.40 | 152 | K24G | 182 |
| A10.41 | 152 | K24P | 183 |
| A10.42 | 152 | K24Q | 184 |
| A10.43 | 152 | R54D | 185 |
| A10.44 | 152 | I48D | 186 |
| A10.45 | 152 | Y49E | 187 |
| A10.46 | 152 | M89A | 188 |
| A10.47 | 152 | M89E | 189 |
| A10.48 | 152 | M89H | 190 |
| A10.49 | 152 | M89K | 191 |
| A10.50 | 152 | M89P | 192 |
| A10.51 | 152 | M89Q | 193 |
| A10.52 | 152 | M89S | 194 |
| A10.53 | 152 | M89V | 195 |
| A10.54 | 152 | Q90D | 196 |
| A10.57 | 152 | N53Q | 198 |

Each of the above antibodies was assessed for protein expression level and binding to CD38 via SPR. Potency assays were performed using cell culture supernatants to assess the relative functional activity of each of these anti-CD38 antibody-attenuated IFN fusion proteins, Table 25.

TABLE 25

| Anti-CD38-attenuated IFN fusion protein | Protein A HPLC (mg/L) | CD38 binding by SPR (RU) at 350 sec* | Annexin V Assay (Fold change relative to untreated cells) | Caspase Assay (Fold change relative to untreated cells) |
|---|---|---|---|---|
| A10.38 | 119.7 | 1540 | 3.22 | 5.17 |
| A10.39 | 113.4 | 1444 | 3.39 | 4.79 |
| A10.40 | 117.8 | 1562 | 3.28 | 5.12 |
| A10.41 | 89.7 | 1459 | 3.27 | 5.12 |
| A10.42 | 111.7 | 1443 | 3.32 | 5.60 |
| A10.43 | 94.1 | 1426 | 3.21 | 6.15 |
| A10.44 | 51.9 | 969 | 3.08 | 5.66 |
| A10.45 | 111.7 | 333 | 2.76 | 5.01 |
| A10.46 | 120.0 | 1547 | 3.24 | 4.80 |
| A10.47 | 107.3 | 1337 | 3.45 | 4.25 |
| A10.48 | 45.5 | 865 | 3.06 | 5.48 |
| A10.49 | 55.8 | 213 | 3.46 | 7.63 |
| A10.50 | 11.3 | 172 | 2.96 | 5.61 |
| A10.51 | 51.6 | 1320 | 2.34 | 6.16 |
| A10.52 | 70.0 | 1512 | 3.21 | 5.62 |
| A10.53 | 40.0 | 536 | 3.46 | 4.68 |
| A10.54 | 61.3 | 583 | 3.10 | 6.20 |
| A10.57 | 67.1 | 1431 | 3.06 | 6.04 |

The CD38 binding by SPR refers to the amount of CD38 that remains bound to the surface after 350 seconds of the dissociation phase. Annexin V Assay refer to cells positively stained by Annexin V-FITC after 24 h treatment with antibody constructs at 20 nM. Caspase Assay refers to caspase activation of cells after 24 h treatment with antibody constructs at 20 nM.
N/T—Not Tested Attenuated IFN is Required for Potent Apoptotic and Caspase Activation in Tumor Cell Lines The relative potency of anti-CD38 antibodies A10.0 (attenuated IFN fusion) and X10.0 (no fusion) were compared using the Annexin V, Caspase and the Cell Proliferation Assays outlined in Example 5. The relative potency of A10.38 and X10.38 was also compared, Table 26.

TABLE 26

Figure 25:
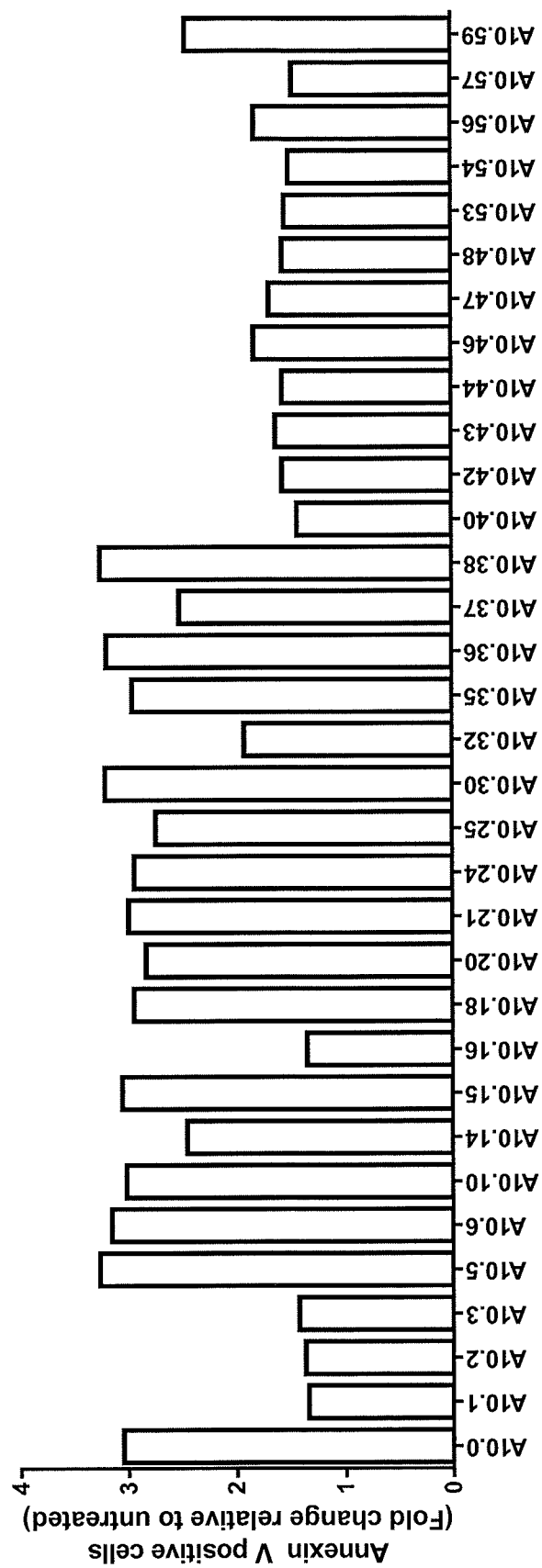
FIG. 25 shows the relative fold change of production of Annexin V in the CD38-expressing multiple myeloma cell line H929 by A10.0 variants. The assay details are described in the Examples (Annexin V/7AAD assay).
Figure 26:
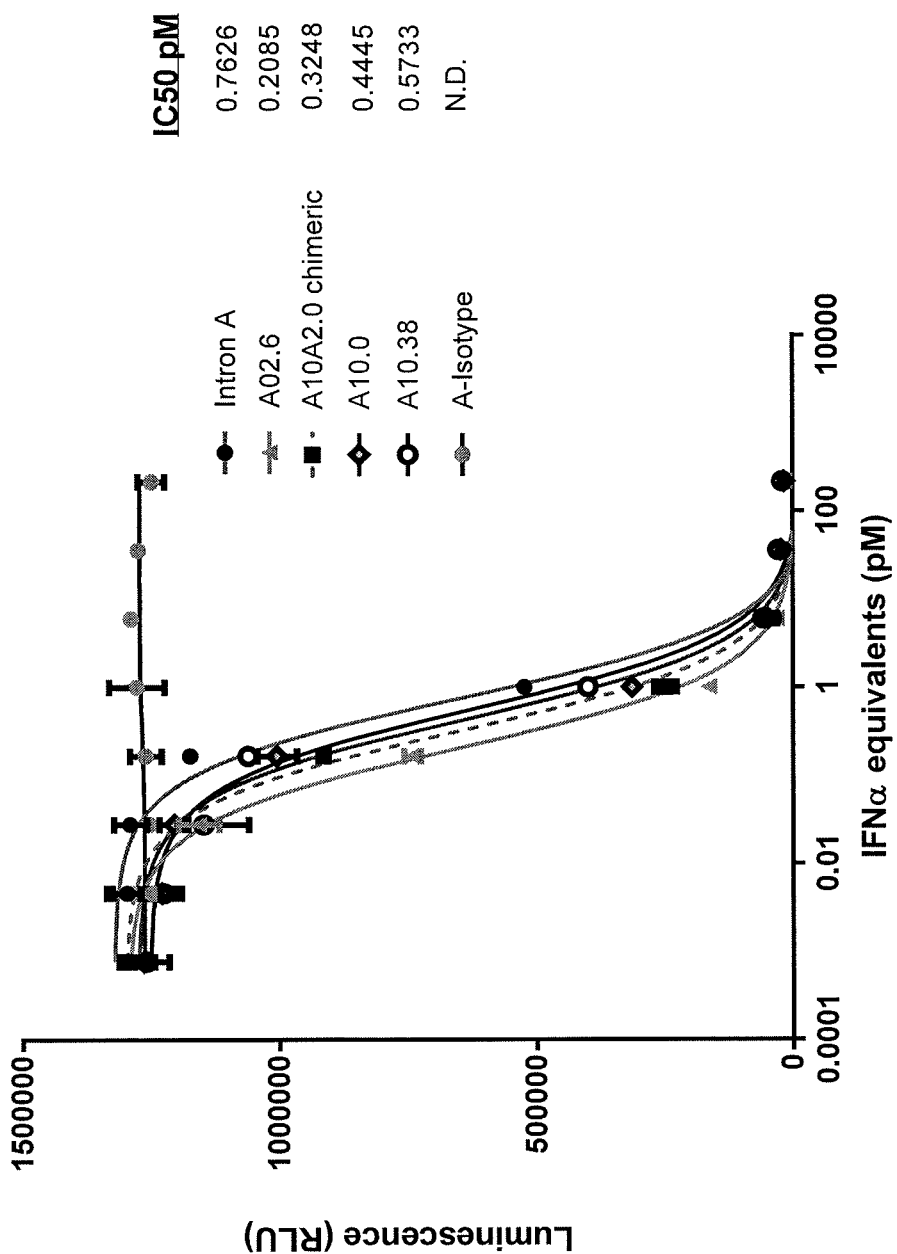
FIG. 26 shows the anti-proliferative activity of IFN-alpha2b (Intron A) compared with A02.6, A10.0, A10.38 and parental A10A2.0 chimeric antibody constructs on the Burkitt's lymphoma cell line Daudi. A-isotype is an irrelevant specificity antibody fused to the attenuated IFN as a control. The assay details are described in the Examples (Cell proliferation assay).

| Anti-CD38-attenuated IFN fusion protein | Annexin V Assay (Fold change relative to untreated cells) | Caspase Assay (Fold change relative to untreated cells) | Cell Proliferation Assay IC$_{50}$ (pM) | Figures |
|---|---|---|---|---|
| A10.0 | 2.10 | 4.23 | 2081 | FIG. 18 |
| X10.0 | 1.27 | 1.70 | No IC50 | FIG. 18 |
| A10.38 | 3.22 | 5.17 | 1118 | FIG. 25 |
| X10.38 | 1.46 | 2.09 | No IC50 | FIG. 25 |

Annexin V Assay refer to cells positively stained by Annexin V-FITC after 24 h treatment with antibody constructs at 20 nM. Caspase Assay refers to caspase activation of cells after 24 h treatment with antibody constructs at 20 nM.

These data demonstrate the potent apoptotic activity exhibited by antibodies A10.0 and A10.38 relative to X10.0 and X10.38 respectively necessitates the presence of the attenuated IFN fusion. No anti-proliferative activity was observed with antibodies without an attenuated IFN.

A consensus sequence alignment of heavy chain variable regions from proteins with functional activity is shown in FIG. 11. A consensus sequence alignment of light chain variable regions from proteins with functional activity is shown in FIG. 12. It could be further envisioned that combinations of substitutions could be made such as those described for Anti-CD38 antibodies X10.60, X10.61, X10.62, X10.63, X10.64, X10.65, X10.66, X10.67, X10.68, X10.69, X10.70, X10.71, X10.72, X10.73, X10.74, X10.75, X10.76, X10.77, X10.78, X10.79, X10.80, X10.81, X10.82, X10.83, X10.84, X10.85, X10.86, X10.87, X10.88, X10.89, X10.90, X10.91, X10.92, X10.93, X10.94, X10.95, X10.96, X10.97, X10.98, X10.99, X10.100, X10.101, X10.102, X10.103, X10.104, X10.105, X10.106, X10.107, X10.108, X10.109, X10.110, X10.111, X10.112, X10.113, X10.114, X10.115, X10.116, X10.117, X10.118, X10.119, X10.120, X10.121, X10.122, X10.123, X10.124, X10.125, X10.126, X10.127, X10.128, X10.129, X10.130, X10.131, X10.132, X10.133, X10.134, X10.135, X10.136, X10.137, X10.138, X10.139, X10.140, X10.141, X10.142, X10.143, X10.144, X10.145, X10.146, X10.147 (FIG. 11, FIG. 12). Further the above Anti-CD38 antibodies could also be constructed as Anti-CD38-attenuated IFN fusion proteins and tested for functional activity as described herein.

Further In-Vitro Potency Data for A10.0 and Related Constructs

A selection of the above Anti-CD38-attenuated IFN fusion proteins were purified and analysed for binding to CD38 positive cells in cell based assays. In addition potency assays were repeated to more accurately determine the relative activity of each of these Anti-CD38-attenuated IFN fusion proteins. The methods for these various assays are described in Example 5. The results of each of these assays are given in Table 27.

TABLE 27

| Anti-CD38-attenuated IFN fusion protein | H929 Flow binding ($EC_{50}$ in μg/mL) | Annexin V Assay (Fold change relative to untreated cells) | Caspase Assay (Fold change relative to untreated cells) | Cell Proliferation Assay $IC_{50}$ (pM) | Figures |
|---|---|---|---|---|---|
| A10.0 | 1.49 | 3.05 | 1.38 | 120.8 | 17, 18, 21, 22, 23, 24, 25, 26, 27 28, 29 |
| A10.1 | 1.03 | 1.34 | 4.63 | 63.6 | 24, 25 |
| A10.2 | 0.57 | 1.37 | 4.37 | 45.6 | 24, 25 |
| A10.3 | 0.55 | 1.43 | 5.52 | 65.8 | 24, 25 |
| A10.5 | 0.48 | 3.27 | 1.61 | 53.79 | 24, 25 |
| A10.6 | 0.35 | 3.16 | 1.66 | 98.85 | 24, 25 |
| A10.10 | 6.84 | 3.02 | 1.64 | 1967.00 | 24, 25 |
| A10.14 | 2.26 | 2.46 | 1.56 | 2207 | 22, 24, 25 |
| A10.15 | 2.06 | 3.06 | 2.55 | 174.4 | 22, 24, 25 |
| A10.16 | 1.17 | 1.35 | 5.18 | 49.5 | 24, 25 |
| A10.18 | 1.03 | 2.95 | 1.70 | 124.2 | 22, 24, 25 |
| A10.20 | 2.11 | 2.84 | 1.26 | 656 | 24, 25 |
| A10.21 | 0.78 | 3.0 | 1.39 | 147.3 | 22, 24, 25 |
| A10.24 | 0.81 | 2.95 | 7.47 | 87.99 | 22, 24, 25 |
| A10.25 | 1.37 | 2.75 | 1.38 | 27.69 | 24, 25 |
| A10.30 | 0.88 | 3.22 | 1.60 | 18.73 | 24, 25 |
| A10.32 | 51.69 | 1.93 | 1.19 | 381.4 | 24, 25 |
| A10.35 | 1.10 | 2.97 | 2.05 | 93.96 | 22, 24, 25 |
| A10.36 | 1.53 | 3.21 | 3.61 | 57.83 | 22, 24, 25 |
| A10.37 | 18.57 | 2.53 | 1.40 | 163.5 | 24, 25 |
| A10.38 | 1.13 | 3.27 | 1.53 | 36.79 | 23, 24, 25, 26, 29 |
| A10.40 | 0.99 | 1.44 | 5.16 | 3.02 | 24, 25 |
| A10.42 | 1.61 | 1.58 | 1.78 | 155.3 | 24, 25 |
| A10.43 | 1.20 | 1.64 | 1.79 | 120.9 | 24, 25 |
| A10.44 | 1.65 | 1.58 | 1.91 | 308.6 | 24, 25 |
| A10.46 | 0.73 | 1.84 | 5.99 | 2.63 | 24, 25 |
| A10.47 | 0.79 | 1.70 | 1.53 | 5.707 | 24, 25 |
| A10.48 | 1.72 | 1.58 | 1.60 | 22.33 | 24, 25 |
| A10.53 | 1.32 | 1.56 | 1.67 | 56.01 | 24, 25 |
| A10.54 | 5.90 | 1.52 | 1.43 | 2008 | 24, 25 |
| A10.56 | 2.43 | 1.84 | 1.95 | 141.7 | 24, 25 |
| A10.57 | 1.54 | 1.49 | 4.71 | 126.1 | 24, 25 |
| A10.59 | 0.89 | 2.48 | 2.38 | 45.75 | 21, 24, 25 |

The flow binding was determined in H929 cell line. Annexin V Assay refer to cells positively stained by Annexin V-FITC after 24 h treatment with antibody constructs at 20 nM. Caspase Assay refers to caspase activation of cells after 24 h treatment with antibody constructs at 20 nM.

H929 Multiple Myeloma Xenograft Model

Figure 27:
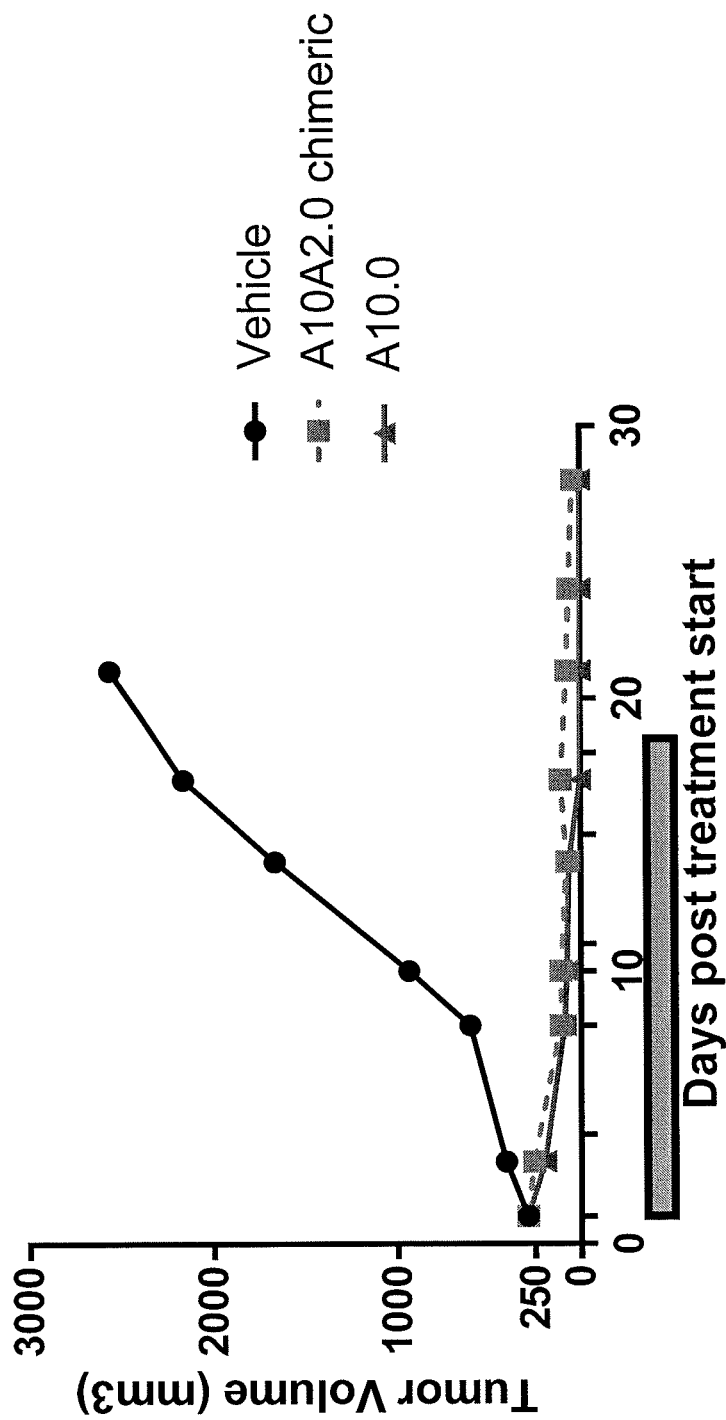
FIG. 27 shows the effects of humanized A10.0 versus the parental A10A2.0 chimeric antibody attenuated interferon construct on the growth of subcutaneous H929 myeloma tumors in SCID mice. The bar labeled "treatment phase" shows the duration of treatment with the compounds.

The in vivo potency of 10A2 variants A10.0 and A10A2.0 were evaluated in an NCI-H929 s.c. mouse multiple myeloma model, FIG. 27. Both were shown to have potent anti-tumour activity in this model. Such a model could be used to test for anti-tumor activity of other protein constructs described within.

Off-Target Activity for the 10A2 Variants

Figure 28:
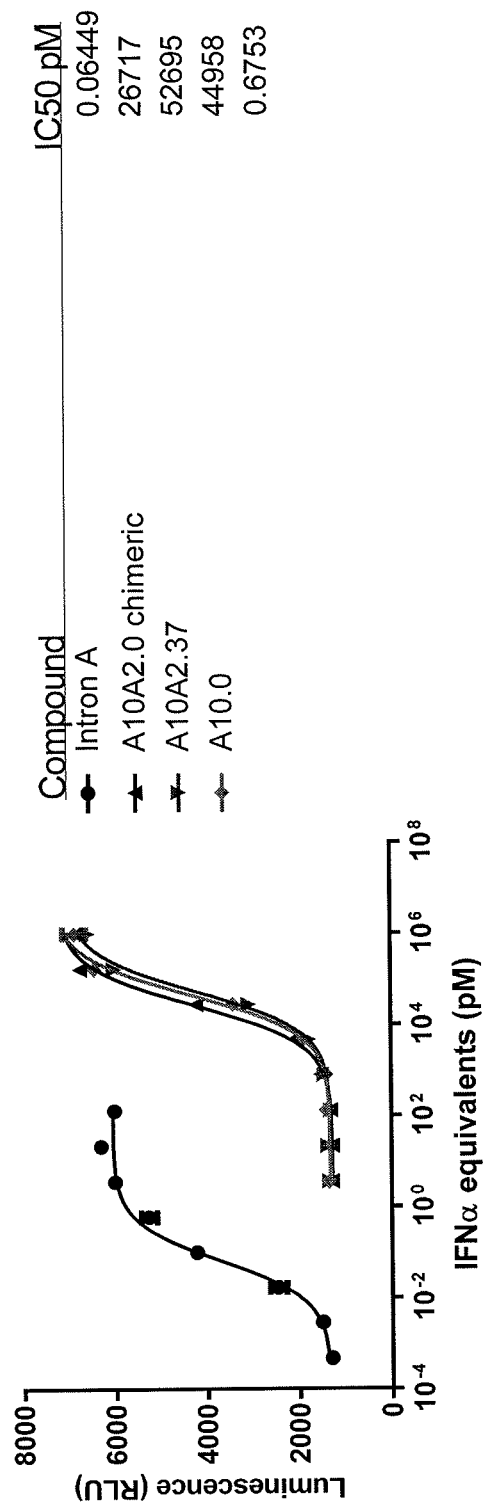
FIG. 28 shows the non-antibody antigen targeted IFN activity of A10.0 variants fused to the same attenuated IFN-alpha2b protein. The assay details are described in the Examples ("Off-target assays"—iLite gene reporter assay).
Figure 29:
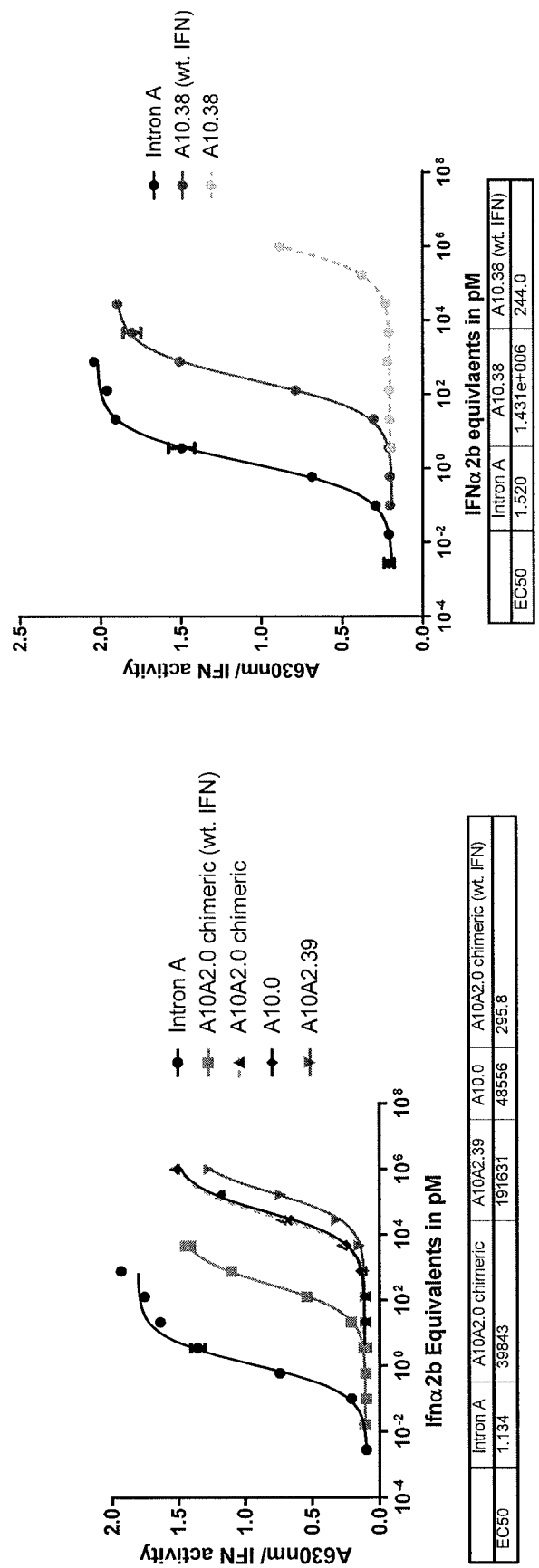
FIG. 29 shows the "Off-target" activity of IFN-alpha2b (Intron A) compared with A10.0 variants and the parental A10A2.0 chimeric antibody fused to wild-type IFN-alpha2b (A10A2.0 chimeric (wt.IFN)). The assay details are described in the Examples ("Off-target assays"—HEK-BLUE™).

The off-target activity of the 10A2 variants A10.0, A10.38, A10A2.37 and A10A2.39 in comparison with the parental A10A2.0 chimeric antibody fused to wildtype and attenuated interferon 145D was assessed in either the iLite reporter gene assay and/or the HEK Blue assay and is shown in FIG. 28 and FIG. 29. The $EC_{50}$ values are provided in FIG. 28 and FIG. 29. The off-target activity confirms the attenuation of the interferon and the need for the antibody to be targeted to CD38 to restore function.

Anti-CD38-Attenuated IFN Fusion Protein with Alternative Constant Region

A10.0 comprises an anti-CD38-attenuated IFN fusion protein in which the constant region of the protein is HC-L0-IFN-alpha (A145D) IgG4 (SEQ ID NO: 9). Using gene synthesis, the constant region of this protein was replaced with HC-L0-IFN-alpha (A145D) IgG1 (SEQ ID NO: 10), paired with A10.0 light chain (SEQ ID NO: 161) and given the designation A10.59. The protein was expressed and was found to be potent in functional assays (Table 28). While the majority of the proteins tested in the foregoing examples were constructed on the human IgG4 constant region, these data demonstrate that other antibody constant regions, such as human IgG1, may also be used, with the resultant antibody-attenuated IFN fusion construct having potent biologic activity equivalent to constructs that utilize a human IgG4 constant region.

TABLE 28

| Anti-CD38-attenuated IFN fusion protein | H929 Flow binding (EC$_{50}$ in μg/mL) | Annexin V Assay (Fold change relative to untreated cells) | Caspase Assay (Fold change relative to untreated cells) | Cell Proliferation Assay IC$_{50}$ (pM)* | Figures |
|---|---|---|---|---|---|
| A10.0 | 1.50 | 3.05 | 1.89 | 2081 | 21, 24, 25 |
| A10.59 | 0.89 | 2.48 | 2.38 | 328.6 | 21, 24, 25 |

Annexin V Assay refer to cells positively stained by Annexin V-FITC after 24 h treatment with antibody constructs at 20 nM. Caspase Assay refers to caspase activation of cells after 24 h treatment with antibody constructs at 20 nM.
N/T is Not Tested,
*Data obtained from Cell Proliferation Assay assessed with cell culture supernatant.

Table 29 lists the pairing of variable heavy chain, variable light chain and constant region for each antibody described herein.

TABLE 29

| Antibody Name | Variable Heavy SEQ ID NO: (amino acid) | Variable Light SEQ ID NO: (amino acid) | Heavy Chain Constant Region SEQ ID NO: (amino acid) |
|---|---|---|---|
| A02.10 | 19 | 14 | 9 |
| A02.11 | 20 | 14 | 9 |
| A02.112 | 34 | 65 | 10 |
| A02.12 | 34 | 65 | 9 |
| A02.13 | 35 | 65 | 9 |
| A02.16 | 34 | 92 | 9 |
| A02.17 | 34 | 93 | 9 |
| A02.18 | 34 | 73 | 9 |
| A02.19 | 34 | 74 | 9 |
| A02.2 | 13 | 65 | 9 |
| A02.20 | 34 | 75 | 9 |
| A02.21 | 34 | 76 | 9 |
| A02.22 | 34 | 77 | 9 |
| A02.23 | 34 | 78 | 9 |
| A02.24 | 34 | 79 | 9 |
| A02.25 | 34 | 80 | 9 |
| A02.26 | 34 | 81 | 9 |
| A02.27 | 34 | 82 | 9 |
| A02.28 | 34 | 83 | 9 |
| A02.29 | 34 | 84 | 9 |
| A02.3 | 17 | 65 | 9 |
| A02.30 | 34 | 85 | 9 |
| A02.31 | 34 | 86 | 9 |
| A02.32 | 34 | 87 | 9 |
| A02.33 | 34 | 88 | 9 |
| A02.34 | 34 | 89 | 9 |
| A02.35 | 34 | 90 | 9 |
| A02.36 | 34 | 91 | 9 |
| A02.37 | 34 | 66 | 9 |
| A02.38 | 34 | 113 | 9 |
| A02.39 | 34 | 112 | 9 |
| A02.4 | 18 | 65 | 9 |
| A02.40 | 111 | 65 | 9 |
| A02.41 | 110 | 65 | 9 |
| A02.43 | 110 | 113 | 9 |
| A02.44 | 111 | 112 | 9 |
| A02.46 | 34 | 67 | 9 |
| A02.47 | 34 | 68 | 9 |
| A02.48 | 34 | 69 | 9 |
| A02.49 | 34 | 70 | 9 |
| A02.5 | 19 | 65 | 9 |
| A02.50 | 34 | 71 | 9 |
| A02.51 | 34 | 72 | 9 |
| A02.52 | 34 | 94 | 9 |
| A02.53 | 34 | 95 | 9 |
| A02.54 | 34 | 96 | 9 |
| A02.55 | 34 | 97 | 9 |
| A02.56 | 34 | 98 | 9 |
| A02.57 | 34 | 99 | 9 |
| A02.58 | 34 | 100 | 9 |
| A02.59 | 34 | 101 | 9 |
| A02.6 | 20 | 65 | 9 |
| A02.60 | 34 | 102 | 9 |
| A02.61 | 34 | 103 | 9 |
| A02.62 | 34 | 104 | 9 |
| A02.63 | 34 | 105 | 9 |
| A02.64 | 34 | 106 | 9 |
| A02.65 | 34 | 107 | 9 |
| A02.66 | 34 | 108 | 9 |
| A02.67 | 34 | 109 | 9 |
| A02.8 | 17 | 14 | 9 |
| A02.9 | 18 | 14 | 9 |
| A10.1 | 165 | 161 | 9 |
| A10.10 | 174 | 161 | 9 |
| A10.11 | 175 | 161 | 9 |
| A10.12 | 176 | 161 | 9 |
| A10.13 | 177 | 161 | 9 |
| A10.14 | 178 | 161 | 9 |
| A10.15 | 179 | 161 | 9 |
| A10.16 | 180 | 161 | 9 |
| A10.17 | 156 | 181 | 9 |
| A10.18 | 156 | 182 | 9 |
| A10.19 | 156 | 183 | 9 |
| A10.2 | 166 | 161 | 9 |
| A10.20 | 156 | 184 | 9 |
| A10.21 | 156 | 185 | 9 |
| A10.22 | 156 | 186 | 9 |
| A10.23 | 156 | 187 | 9 |
| A10.24 | 156 | 188 | 9 |
| A10.25 | 156 | 189 | 9 |
| A10.26 | 156 | 190 | 9 |
| A10.27 | 156 | 191 | 9 |
| A10.28 | 156 | 192 | 9 |
| A10.29 | 156 | 193 | 9 |
| A10.3 | 167 | 161 | 9 |
| A10.30 | 156 | 194 | 9 |
| A10.31 | 156 | 195 | 9 |
| A10.32 | 156 | 196 | 9 |
| A10.35 | 197 | 161 | 9 |
| A10.36 | 156 | 198 | 9 |
| A10.38 | 152 | 161 | 9 |
| A10.39 | 152 | 181 | 9 |
| A10.4 | 168 | 161 | 9 |
| A10.40 | 152 | 182 | 9 |
| A10.41 | 152 | 183 | 9 |
| A10.42 | 152 | 184 | 9 |
| A10.43 | 152 | 185 | 9 |
| A10.44 | 152 | 186 | 9 |
| A10.45 | 152 | 187 | 9 |
| A10.46 | 152 | 188 | 9 |
| A10.47 | 152 | 189 | 9 |
| A10.48 | 152 | 190 | 9 |
| A10.49 | 152 | 191 | 9 |
| A10.5 | 169 | 161 | 9 |
| A10.50 | 152 | 192 | 9 |
| A10.51 | 152 | 193 | 9 |
| A10.52 | 152 | 194 | 9 |
| A10.53 | 152 | 195 | 9 |
| A10.54 | 152 | 196 | 9 |
| A10.57 | 152 | 198 | 9 |
| A10.59 | 156 | 161 | 10 |
| A10.6 | 170 | 161 | 9 |
| A10.7 | 171 | 161 | 9 |
| A10.8 | 172 | 161 | 9 |
| A10.9 | 173 | 161 | 9 |
| A10A2.0 (chimeric) | 148 | 157 | 9 |
| A10A2.1 | 149 | 158 | 9 |
| A10A2.10 | 150 | 160 | 9 |
| A10A2.11 | 150 | 161 | 9 |
| A10A2.12 | 150 | 162 | 9 |
| A10A2.13 | 150 | 163 | 9 |
| A10A2.14 | 150 | 164 | 9 |
| A10A2.15 | 151 | 158 | 9 |
| A10A2.16 | 151 | 159 | 9 |
| A10A2.17 | 151 | 160 | 9 |
| A10A2.18 | 151 | 161 | 9 |

TABLE 29-continued

| Antibody Name | Variable Heavy SEQ ID NO: (amino acid) | Variable Light SEQ ID NO: (amino acid) | Heavy Chain Constant Region SEQ ID NO: (amino acid) |
|---|---|---|---|
| A10A2.19 | 151 | 162 | 9 |
| A10A2.2 | 149 | 159 | 9 |
| A10A2.20 | 151 | 163 | 9 |
| A10A2.21 | 151 | 164 | 9 |
| A10A2.22 | 152 | 158 | 9 |
| A10A2.23 | 152 | 159 | 9 |
| A10A2.24 | 152 | 160 | 9 |
| A10A2.25 | 152 | 161 | 9 |
| A10A2.26 | 152 | 162 | 9 |
| A10A2.27 | 152 | 163 | 9 |
| A10A2.28 | 152 | 164 | 9 |
| A10A2.29 | 153 | 158 | 9 |
| A10A2.3 | 149 | 160 | 9 |
| A10A2.30 | 153 | 159 | 9 |
| A10A2.31 | 153 | 160 | 9 |
| A10A2.32 | 153 | 161 | 9 |
| A10A2.33 | 153 | 162 | 9 |
| A10A2.34 | 153 | 163 | 9 |
| A10A2.35 | 153 | 164 | 9 |
| A10A2.36 | 154 | 158 | 9 |
| A10A2.37 | 154 | 159 | 9 |
| A10A2.38 | 154 | 160 | 9 |
| A10A2.39 | 154 | 161 | 9 |
| A10A2.4 | 149 | 161 | 9 |
| A10A2.40 | 154 | 162 | 9 |
| A10A2.41 | 154 | 163 | 9 |
| A10A2.42 | 154 | 164 | 9 |
| A10A2.43 | 154 | 158 | 9 |
| A10A2.44 | 155 | 159 | 9 |
| A10A2.45 | 155 | 160 | 9 |
| A10A2.46 | 155 | 161 | 9 |
| A10A2.47 | 155 | 162 | 9 |
| A10A2.48 | 155 | 163 | 9 |
| A10A2.49 | 155 | 164 | 9 |
| A10A2.5 | 149 | 162 | 9 |
| A10A2.50 | 156 | 158 | 9 |
| A10A2.51 | 156 | 159 | 9 |
| A10A2.52 | 156 | 160 | 9 |
| A10A2.53 | 156 | 161 | 9 |
| A10A2.54 | 156 | 162 | 9 |
| A10A2.55 | 156 | 163 | 9 |
| A10A2.56 | 156 | 164 | 9 |
| A10A2.6 | 149 | 163 | 9 |
| A10A2.7 | 149 | 164 | 9 |
| A10A2.8 | 150 | 158 | 9 |
| A10A2.9 | 150 | 159 | 9 |
| A5D1.0 (chimeric) | 114 | 125 | 9 |
| A5D1.1 | 115 | 126 | 9 |
| A5D1.10 | 116 | 129 | 9 |
| A5D1.11 | 116 | 130 | 9 |
| A5D1.12 | 116 | 131 | 9 |
| A5D1.13 | 117 | 126 | 9 |
| A5D1.14 | 117 | 127 | 9 |
| A5D1.15 | 117 | 128 | 9 |
| A5D1.16 | 117 | 129 | 9 |
| A5D1.17 | 117 | 130 | 9 |
| A5D1.18 | 117 | 131 | 9 |
| A5D1.19 | 118 | 126 | 9 |
| A5D1.2 | 115 | 127 | 9 |
| A5D1.20 | 118 | 127 | 9 |
| A5D1.21 | 118 | 128 | 9 |
| A5D1.22 | 118 | 129 | 9 |
| A5D1.23 | 118 | 130 | 9 |
| A5D1.24 | 118 | 131 | 9 |
| A5D1.25 | 119 | 126 | 9 |
| A5D1.26 | 119 | 127 | 9 |
| A5D1.27 | 119 | 128 | 9 |
| A5D1.28 | 119 | 129 | 9 |
| A5D1.29 | 119 | 130 | 9 |
| A5D1.3 | 115 | 128 | 9 |
| A5D1.30 | 119 | 131 | 9 |
| A5D1.31 | 120 | 126 | 9 |
| A5D1.32 | 120 | 127 | 9 |
| A5D1.33 | 120 | 128 | 9 |
| A5D1.34 | 120 | 129 | 9 |
| A5D1.35 | 120 | 130 | 9 |
| A5D1.36 | 120 | 131 | 9 |
| A5D1.37 | 121 | 126 | 9 |
| A5D1.38 | 121 | 127 | 9 |
| A5D1.39 | 121 | 128 | 9 |
| A5D1.4 | 115 | 129 | 9 |
| A5D1.40 | 121 | 129 | 9 |
| A5D1.41 | 121 | 130 | 9 |
| A5D1.42 | 121 | 131 | 9 |
| A5D1.43 | 122 | 126 | 9 |
| A5D1.44 | 122 | 127 | 9 |
| A5D1.45 | 122 | 128 | 9 |
| A5D1.46 | 122 | 129 | 9 |
| A5D1.47 | 122 | 130 | 9 |
| A5D1.48 | 122 | 131 | 9 |
| A5D1.49 | 123 | 126 | 9 |
| A5D1.5 | 115 | 130 | 9 |
| A5D1.50 | 123 | 127 | 9 |
| A5D1.51 | 123 | 128 | 9 |
| A5D1.52 | 123 | 129 | 9 |
| A5D1.53 | 123 | 130 | 9 |
| A5D1.54 | 123 | 131 | 9 |
| A5D1.55 | 124 | 126 | 9 |
| A5D1.56 | 124 | 127 | 9 |
| A5D1.57 | 124 | 128 | 9 |
| A5D1.58 | 124 | 129 | 9 |
| A5D1.59 | 124 | 130 | 9 |
| A5D1.6 | 115 | 131 | 9 |
| A5D1.60 | 124 | 131 | 9 |
| A5D1.7 | 116 | 126 | 9 |
| A5D1.8 | 116 | 127 | 9 |
| A5D1.9 | 116 | 128 | 9 |
| A5E8.0 (chimeric) | 132 | 143 | 9 |
| A5E8.1 | 133 | 144 | 9 |
| A5E8.10 | 135 | 145 | 9 |
| A5E8.11 | 135 | 146 | 9 |
| A5E8.12 | 135 | 147 | 9 |
| A5E8.13 | 136 | 144 | 9 |
| A5E8.14 | 136 | 145 | 9 |
| A5E8.15 | 136 | 146 | 9 |
| A5E8.16 | 136 | 147 | 9 |
| A5E8.17 | 137 | 144 | 9 |
| A5E8.18 | 137 | 145 | 9 |
| A5E8.19 | 137 | 146 | 9 |
| A5E8.2 | 133 | 145 | 9 |
| A5E8.20 | 137 | 147 | 9 |
| A5E8.21 | 138 | 144 | 9 |
| A5E8.22 | 138 | 145 | 9 |
| A5E8.23 | 138 | 146 | 9 |
| A5E8.24 | 138 | 147 | 9 |
| A5E8.25 | 139 | 144 | 9 |
| A5E8.26 | 139 | 145 | 9 |
| A5E8.27 | 139 | 146 | 9 |
| A5E8.28 | 139 | 147 | 9 |
| A5E8.29 | 140 | 144 | 9 |
| A5E8.3 | 133 | 146 | 9 |
| A5E8.30 | 140 | 145 | 9 |
| A5E8.31 | 140 | 146 | 9 |
| A5E8.32 | 140 | 147 | 9 |
| A5E8.33 | 141 | 144 | 9 |
| A5E8.34 | 141 | 145 | 9 |
| A5E8.35 | 141 | 146 | 9 |
| A5E8.36 | 141 | 147 | 9 |
| A5E8.37 | 142 | 144 | 9 |
| A5E8.38 | 142 | 145 | 9 |
| A5E8.39 | 142 | 146 | 9 |
| A5E8.4 | 133 | 147 | 9 |
| A5E8.40 | 142 | 147 | 9 |
| A5E8.5 | 134 | 144 | 9 |
| A5E8.6 | 134 | 145 | 9 |
| A5E8.7 | 134 | 146 | 9 |
| A5E8.8 | 134 | 147 | 9 |
| A5E8.9 | 135 | 144 | 9 |

TABLE 29-continued

| Antibody Name | Variable Heavy SEQ ID NO: (amino acid) | Variable Light SEQ ID NO: (amino acid) | Heavy Chain Constant Region SEQ ID NO: (amino acid) |
|---|---|---|---|
| X02.10 | 19 | 14 | 3 |
| X02.100 | 13 | 58 | 3 |
| X02.101 | 13 | 59 | 3 |
| X02.102 | 13 | 60 | 3 |
| X02.103 | 13 | 61 | 3 |
| X02.104 | 13 | 62 | 3 |
| X02.105 | 13 | 63 | 3 |
| X02.106 | 13 | 64 | 3 |
| X02.107 | 13 | 65 | 3 |
| X02.108 | 32 | 14 | 3 |
| X02.11 | 20 | 14 | 3 |
| X02.110 | 33 | 14 | 3 |
| X02.114 | 13 | 660 | 3 |
| X02.115 | 13 | 661 | 3 |
| X02.116 | 13 | 662 | 3 |
| X02.117 | 13 | 663 | 3 |
| X02.118 | 34 | 700 | 3 |
| X02.119 | 34 | 701 | 3 |
| X02.120 | 728 | 700 | 3 |
| X02.121 | 729 | 700 | 3 |
| X02.122 | 730 | 700 | 3 |
| X02.123 | 731 | 700 | 3 |
| X02.124 | 728 | 701 | 3 |
| X02.125 | 729 | 701 | 3 |
| X02.126 | 730 | 701 | 3 |
| X02.127 | 731 | 701 | 3 |
| X02.68 | 21 | 14 | 3 |
| X02.69 | 22 | 14 | 3 |
| X02.70 | 23 | 14 | 3 |
| X02.71 | 24 | 14 | 3 |
| X02.72 | 25 | 14 | 3 |
| X02.73 | 26 | 14 | 3 |
| X02.74 | 27 | 14 | 3 |
| X02.75 | 28 | 14 | 3 |
| X02.76 | 29 | 14 | 3 |
| X02.77 | 30 | 14 | 3 |
| X02.78 | 31 | 14 | 3 |
| X02.8 | 17 | 14 | 3 |
| X02.80 | 13 | 38 | 3 |
| X02.81 | 13 | 39 | 3 |
| X02.82 | 13 | 40 | 3 |
| X02.83 | 13 | 41 | 3 |
| X02.84 | 13 | 42 | 3 |
| X02.85 | 13 | 43 | 3 |
| X02.86 | 13 | 44 | 3 |
| X02.87 | 13 | 45 | 3 |
| X02.88 | 13 | 46 | 3 |
| X02.89 | 13 | 47 | 3 |
| X02.9 | 18 | 14 | 3 |
| X02.90 | 13 | 48 | 3 |
| X02.91 | 13 | 49 | 3 |
| X02.92 | 13 | 50 | 3 |
| X02.93 | 13 | 51 | 3 |
| X02.94 | 13 | 52 | 3 |
| X02.95 | 13 | 53 | 3 |
| X02.96 | 13 | 54 | 3 |
| X02.97 | 13 | 55 | 3 |
| X02.98 | 13 | 56 | 3 |
| X02.99 | 13 | 57 | 3 |
| X10.100 | 720 | 706 | 3 |
| X10.101 | 721 | 706 | 3 |
| X10.102 | 722 | 706 | 3 |
| X10.103 | 723 | 706 | 3 |
| X10.104 | 739 | 706 | 3 |
| X10.105 | 740 | 706 | 3 |
| X10.106 | 741 | 706 | 3 |
| X10.107 | 742 | 706 | 3 |
| X10.108 | 720 | 707 | 3 |
| X10.109 | 721 | 707 | 3 |
| X10.110 | 722 | 707 | 3 |
| X10.111 | 723 | 707 | 3 |
| X10.112 | 739 | 707 | 3 |
| X10.113 | 740 | 707 | 3 |
| X10.114 | 741 | 707 | 3 |
| X10.115 | 742 | 707 | 3 |
| X10.116 | 720 | 708 | 3 |
| X10.117 | 721 | 708 | 3 |
| X10.118 | 722 | 708 | 3 |
| X10.119 | 723 | 708 | 3 |
| X10.120 | 739 | 708 | 3 |
| X10.121 | 740 | 708 | 3 |
| X10.122 | 741 | 708 | 3 |
| X10.123 | 742 | 708 | 3 |
| X10.124 | 720 | 709 | 3 |
| X10.125 | 721 | 709 | 3 |
| X10.126 | 722 | 709 | 3 |
| X10.127 | 723 | 709 | 3 |
| X10.128 | 739 | 709 | 3 |
| X10.129 | 740 | 709 | 3 |
| X10.130 | 741 | 709 | 3 |
| X10.131 | 742 | 709 | 3 |
| X10.132 | 720 | 710 | 3 |
| X10.133 | 721 | 710 | 3 |
| X10.134 | 722 | 710 | 3 |
| X10.135 | 723 | 710 | 3 |
| X10.136 | 739 | 710 | 3 |
| X10.137 | 740 | 710 | 3 |
| X10.138 | 741 | 710 | 3 |
| X10.139 | 742 | 710 | 3 |
| X10.140 | 720 | 711 | 3 |
| X10.141 | 721 | 711 | 3 |
| X10.142 | 722 | 711 | 3 |
| X10.143 | 723 | 711 | 3 |
| X10.144 | 739 | 711 | 3 |
| X10.145 | 740 | 711 | 3 |
| X10.146 | 741 | 711 | 3 |
| X10.147 | 742 | 711 | 3 |
| X10.60 | 156 | 704 | 3 |
| X10.61 | 156 | 705 | 3 |
| X10.62 | 156 | 706 | 3 |
| X10.63 | 156 | 707 | 3 |
| X10.64 | 156 | 708 | 3 |
| X10.65 | 156 | 709 | 3 |
| X10.66 | 156 | 710 | 3 |
| X10.67 | 156 | 711 | 3 |
| X10.68 | 720 | 161 | 3 |
| X10.69 | 721 | 161 | 3 |
| X10.70 | 722 | 161 | 3 |
| X10.71 | 723 | 161 | 3 |
| X10.72 | 739 | 161 | 3 |
| X10.73 | 740 | 161 | 3 |
| X10.74 | 741 | 161 | 3 |
| X10.75 | 742 | 161 | 3 |
| X10.76 | 152 | 704 | 3 |
| X10.77 | 152 | 705 | 3 |
| X10.78 | 152 | 706 | 3 |
| X10.79 | 152 | 707 | 3 |
| X10.80 | 152 | 708 | 3 |
| X10.81 | 152 | 709 | 3 |
| X10.82 | 152 | 710 | 3 |
| X10.83 | 152 | 711 | 3 |
| X10.84 | 720 | 704 | 3 |
| X10.85 | 721 | 704 | 3 |
| X10.86 | 722 | 704 | 3 |
| X10.87 | 723 | 704 | 3 |
| X10.88 | 739 | 704 | 3 |
| X10.89 | 740 | 704 | 3 |
| X10.90 | 741 | 704 | 3 |
| X10.91 | 742 | 704 | 3 |
| X10.92 | 720 | 705 | 3 |
| X10.93 | 721 | 705 | 3 |
| X10.94 | 722 | 705 | 3 |
| X10.95 | 723 | 705 | 3 |
| X10.96 | 739 | 705 | 3 |
| X10.97 | 740 | 705 | 3 |
| X10.98 | 741 | 705 | 3 |

TABLE 29-continued

| Antibody Name | Variable Heavy SEQ ID NO: (amino acid) | Variable Light SEQ ID NO: (amino acid) | Heavy Chain Constant Region SEQ ID NO: (amino acid) |
|---|---|---|---|
| X10.99 | 742 | 705 | 3 |
| X910/12-HC-L0-IFN-alpha (A145D) IgG4 | 110 | 112 | 9 |
| X913/15-HC-L0-IFN-alpha (A145D) IgG4 | 111 | 113 | 9 |

TABLE 30

| SEQ ID NO: | Type | Description |
|---|---|---|
| 1 | AA | Human CD38 |
| 2 | AA | Cynomolgus CD38 |
| 3 | AA | Human IgG4 constant heavy chain |
| 4 | AA | Human IgG1 constant heavy chain |
| 5 | AA | Human kappa constant region |
| 6 | AA | Human lambda constant region |
| 7 | AA | IFN-alpha2b |
| 8 | AA | Intron A |
| 9 | AA | HC-L0-IFN-alpha (A145D) IgG4 |
| 10 | AA | HC-L0-IFN-alpha (A145D) IgG1 |
| 11 | AA | A02.1 heavy chain |
| 12 | AA | A02.1 light chain |
| 13 | AA | A02.1 variable heavy chain |
| 14 | AA | A02.1 variable light chain |
| 15 | AA | X02.1VH variable heavy chain |
| 16 | AA | IGHV4-61*01 germline sequence |
| 17 | AA | X02.8VH variable heavy chain |
| 18 | AA | X02.9VH variable heavy chain |
| 19 | AA | X02.10VH variable heavy chain |
| 20 | AA | X02.11VH variable heavy chain |
| 21 | AA | X02.68VH variable heavy chain |
| 22 | AA | X02.69VH variable heavy chain |
| 23 | AA | X02.70VH variable heavy chain |
| 24 | AA | X02.71VH variable heavy chain |
| 25 | AA | X02.72VH variable heavy chain |
| 26 | AA | X02.73VH variable heavy chain |
| 27 | AA | X02.74VH variable heavy chain |
| 28 | AA | X02.75VH variable heavy chain |
| 29 | AA | X02.76VH variable heavy chain |
| 30 | AA | X02.77VH variable heavy chain |
| 31 | AA | X02.78VH variable heavy chain |
| 32 | AA | X02.108VH variable heavy chain |
| 33 | AA | X02.110VH variable heavy chain |
| 34 | AA | A02.12VH variable heavy chain |
| 35 | AA | A02.13VH variable heavy chain |
| 36 | AA | A02.1VL variable light chain |
| 37 | AA | IGLV5-37*01 germline sequence |
| 38 | AA | X02.80VL variable light chain |
| 39 | AA | X02.81VL variable light chain |
| 40 | AA | X02.82VL variable light chain |
| 41 | AA | X02.83VL variable light chain |
| 42 | AA | X02.84VL variable light chain |
| 43 | AA | X02.85VL variable light chain |
| 44 | AA | X02.86VL variable light chain |
| 45 | AA | X02.87VL variable light chain |
| 46 | AA | X02.88VL variable light chain |
| 47 | AA | X02.89VL variable light chain |
| 48 | AA | X02.90VL variable light chain |
| 49 | AA | X02.91VL variable light chain |
| 50 | AA | X02.92VL variable light chain |
| 51 | AA | X02.93VL variable light chain |
| 52 | AA | X02.94VL variable light chain |
| 53 | AA | X02.95VL variable light chain |
| 54 | AA | X02.96VL variable light chain |
| 55 | AA | X02.97VL variable light chain |
| 56 | AA | X02.98VL variable light chain |
| 57 | AA | X02.99VL variable light chain |
| 58 | AA | X02.100VL variable light chain |
| 59 | AA | X02.101VL variable light chain |
| 60 | AA | X02.102VL variable light chain |
| 61 | AA | X02.103VL variable light chain |
| 62 | AA | X02.104VL variable light chain |
| 63 | AA | X02.105VL variable light chain |
| 64 | AA | X02.106VL variable light chain |
| 65 | AA | X02.107VL variable light chain |
| 66 | AA | A02.37VL variable light chain |
| 67 | AA | A02.46VL variable light chain |
| 68 | AA | A02.47VL variable light chain |
| 69 | AA | A02.48VL variable light chain |
| 70 | AA | A02.49VL variable light chain |
| 71 | AA | A02.50VL variable light chain |
| 72 | AA | A02.51VL variable light chain |
| 73 | AA | A02.18VL variable light chain |
| 74 | AA | A02.19VL variable light chain |
| 75 | AA | A02.20VL variable light chain |
| 76 | AA | A02.21VL variable light chain |
| 77 | AA | A02.22VL variable light chain |
| 78 | AA | A02.23VL variable light chain |
| 79 | AA | A02.24VL variable light chain |
| 80 | AA | A02.25VL variable light chain |
| 81 | AA | A02.26VL variable light chain |
| 82 | AA | A02.27VL variable light chain |
| 83 | AA | A02.28VL variable light chain |
| 84 | AA | A02.29VL variable light chain |
| 85 | AA | A02.30VL variable light chain |
| 86 | AA | A02.31VL variable light chain |
| 87 | AA | A02.32VL variable light chain |
| 88 | AA | A02.33VL variable light chain |
| 89 | AA | A02.34VL variable light chain |
| 90 | AA | A02.35VL variable light chain |
| 91 | AA | A02.36VL variable light chain |
| 92 | AA | X02.16VL variable light chain |
| 93 | AA | A02.17VL variable light chain |
| 94 | AA | A02.52VL variable light chain |
| 95 | AA | A02.53VL variable light chain |
| 96 | AA | A02.54VL variable light chain |
| 97 | AA | A02.55VL variable light chain |
| 98 | AA | A02.56VL variable light chain |
| 99 | AA | A02.57VL variable light chain |
| 100 | AA | A02.58VL variable light chain |
| 101 | AA | A02.59VL variable light chain |
| 102 | AA | A02.60VL variable light chain |
| 103 | AA | A02.61VL variable light chain |
| 104 | AA | A02.62VL variable light chain |
| 105 | AA | A02.63VL variable light chain |
| 106 | AA | A02.64VL variable light chain |
| 107 | AA | A02.65VL variable light chain |
| 108 | AA | A02.66VL variable light chain |
| 109 | AA | A02.67VL variable light chain |
| 110 | AA | 910VH variable heavy chain |
| 111 | AA | 915 VH variable heavy chain |
| 112 | AA | 912VL variable light chain |
| 113 | AA | 913VL variable light chain |
| 114 | AA | Chimeric 5D1-E2-VH |
| 115 | AA | 5d1_1-f*01VH |
| 116 | AA | 5d1_1-f*01VH94R |
| 117 | AA | 5d1_1-18*01VH |
| 118 | AA | 5d1_1-18*01VH71A |
| 119 | AA | 5d1_1-24*01VH |
| 120 | AA | 5d1_1-24*01VH71A |
| 121 | AA | 5d1_1-24*01VH29F |
| 122 | AA | 5d1_1-24*01VH94R |
| 123 | AA | 5d1_1-45*01VH |
| 124 | AA | 5d1_1-45*01VH71A |
| 125 | AA | Chimeric 5D1VK |
| 126 | AA | 5d1_1-5*01VK |
| 127 | AA | 5d1_1-9*01VK |
| 128 | AA | 5d1_1-12*01VK |
| 129 | AA | 5d1_1D-13*01VK |
| 130 | AA | 5d1_1D-16*01VK |
| 131 | AA | 5d1_3-15*01VK |
| 132 | AA | Chimeric 5E8 |
| 133 | AA | 5E8-1-f*01VH |
| 134 | AA | 5E8-1-f*01VH30I |
| 135 | AA | 5E8-1-f*01VH94R |
| 136 | AA | 5E8-1-18*01VH |
| 137 | AA | 5E8-1-18*01VH71A |
| 138 | AA | 5E8-1-24*01VH |
| 139 | AA | 5E8-1-24*01VH71A |

TABLE 30-continued

| SEQ ID NO: | Type | Description |
|---|---|---|
| 140 | AA | 5E8-1-24*01VH94R |
| 141 | AA | 5E8-1-45*01VH |
| 142 | AA | 5E8-1-45*01VH71A |
| 143 | AA | chimeric 5E8VK |
| 144 | AA | 5E8-2-24*01VK |
| 145 | AA | 5E8-2D-28*01VK |
| 146 | AA | 5E8-2D-29*01VK |
| 147 | AA | 5E8-2-30*01VK |
| 148 | AA | 10A2 chimeric VH |
| 149 | AA | 10A2_1-24*01VH |
| 150 | AA | 10A2_1-24*01VH71A |
| 151 | AA | 10A2_1-24*01VH94R |
| 152 | AA | 10A2_1-24*0171A94R |
| 153 | AA | 10A2_1-45*01VH |
| 154 | AA | 10A2_1-45*01VH71A |
| 155 | AA | 10A2_1-f*01VH |
| 156 | AA | 10A2_1-f*01VH94R |
| 157 | AA | 10A2 chimeric VK |
| 158 | AA | 10A2_1-9*01Vk |
| 159 | AA | 10A2_1-12*01Vk |
| 160 | AA | 10A2_1D-13*01Vk |
| 161 | AA | 10A2_1-33*01Vk |
| 162 | AA | 10A2_3-11*02Vk |
| 163 | AA | 10A2_3-15*01Vk |
| 164 | AA | 10A2_6-21*01Vk |
| 165 | AA | 10A2VH + A40E |
| 166 | AA | 10A2VH + A40G |
| 167 | AA | 10A2VH + A40H |
| 168 | AA | 10A2VH + A40Q |
| 169 | AA | 10A2VH + A40S |
| 170 | AA | 10A2VH + A40V |
| 171 | AA | 10A2VH + N35E |
| 172 | AA | 10A2VH + N35P |
| 173 | AA | 10A2VH + N35Q |
| 174 | AA | 10A2VH + N35S |
| 175 | AA | 10A2VH + R94E |
| 176 | AA | 10A2VH + R94G |
| 177 | AA | 10A2VH + R94P |
| 178 | AA | 10A2VH + R94T |
| 179 | AA | 10A2VH + K96G |
| 180 | AA | 10A2VH + K96T |
| 181 | AA | 10A2VK + K24E |
| 182 | AA | 10A2VK + K24G |
| 183 | AA | 10A2VK + K24P |
| 184 | AA | 10A2VK + K24Q |
| 185 | AA | 10A2VK + R54D |
| 186 | AA | 10A2VK + I48D |
| 187 | AA | 10A2VK + Y49E |
| 188 | AA | 10A2VK + M89A |
| 189 | AA | 10A2VK + M89E |
| 190 | AA | 10A2VK + M89H |
| 191 | AA | 10A2VK + M89K |
| 192 | AA | 10A2VK + M89P |
| 193 | AA | 10A2VK + M89Q |
| 194 | AA | 10A2VK + M89S |
| 195 | AA | 10A2VK + M89V |
| 196 | AA | 10A2VK + Q90D |
| 197 | AA | 10A2VH (AQ) + N98Q |
| 198 | AA | 10A2VK (AV) + N53Q |
| 199 | AA | X02.1VH FWR1 |
| 200 | AA | X02.1VH CDR1 |
| 201 | AA | X02.1VH FWR2 |
| 202 | AA | X02.1VH CDR2 |
| 203 | AA | X02.1VH FWR3 |
| 204 | AA | X02.1VH CDR3 |
| 205 | AA | X02.1VH FWR4 |
| 206 | AA | IGHV4-61*01 FWR1 |
| 207 | AA | IGHV4-61*01 CDR1 |
| 208 | AA | IGHV4-61*01 FWR2 |
| 209 | AA | IGHV4-61*01 FWR3 |
| 210 | AA | X02.8VH FWR3 |
| 211 | AA | X02.9VH FWR2 |
| 212 | AA | X02.10VH FWR3 |
| 213 | AA | X02.11VH FWR3 |
| 214 | AA | X02.68VH FWR1 |
| 215 | AA | X02.69VH FWR1 |
| 216 | AA | X02.70VH FWR3 |
| 217 | AA | X02.71VH FWR1 |
| 218 | AA | X02.72VH FWR3 |
| 219 | AA | X02.73VH FWR1 |
| 220 | AA | X02.74VH CDR3 |
| 221 | AA | X02.75VH FWR3 |
| 222 | AA | X02.76VH CDR3 |
| 223 | AA | X02.77VH CDR3 |
| 224 | AA | X02.78VH CDR1 |
| 225 | AA | X02.108 FWR3 |
| 226 | AA | X02.110VH FWR3 |
| 227 | AA | A02.12VH FWR3 |
| 228 | AA | A02.12VH CDR3 |
| 229 | AA | A02.13VH FWR2 |
| 230 | AA | A02.13VH FWR3 |
| 231 | AA | A02.13VH CDR3 |
| 232 | AA | A02.1VL FWR1 |
| 233 | AA | A02.1VL CDR1 |
| 234 | AA | A02.1VL FWR2 |
| 235 | AA | A02.1VL CDR2 |
| 236 | AA | A02.1VL FWR3 |
| 237 | AA | A02.1VL CDR3 |
| 238 | AA | A02.1VL FWR4 |
| 239 | AA | IGLV5-37*01 FWR1 |
| 240 | AA | IGLV5-37*01 CDR1 |
| 241 | AA | IGLV5-37*01 CDR2 |
| 242 | AA | IGLV5-37*01 FWR3 |
| 243 | AA | IGLV5-37*01 CDR3 |
| 244 | AA | X02.80VL CDR3 |
| 245 | AA | X02.81VL FWR3 |
| 246 | AA | X02.82VL FWR2 |
| 247 | AA | X02.83VL FWR1 |
| 248 | AA | X02.84VL FWR2 |
| 249 | AA | X02.84VL CDR2 |
| 250 | AA | X02.86VL CDR1 |
| 251 | AA | X02.87VL CDR3 |
| 252 | AA | X02.88VL CDR1 |
| 253 | AA | X02.89VL CDR2 |
| 254 | AA | X02.90VL CDR3 |
| 255 | AA | X02.91VL CDR1 |
| 256 | AA | X02.92VL CDR3 |
| 257 | AA | X02.93VL CDR3 |
| 258 | AA | X02.94VL CDR3 |
| 259 | AA | X02.95VL FWR1 |
| 260 | AA | X02.96VL FWR1 |
| 261 | AA | X02.97VL FWR1 |
| 262 | AA | X02.98VL CDR1 |
| 263 | AA | X02.99VL CDR1 |
| 264 | AA | X02.100VL CDR2 |
| 265 | AA | X02.101VL FWR3 |
| 266 | AA | X02.102VL FWR3 |
| 267 | AA | X02.103VL FWR3 |
| 268 | AA | X02.104VL CDR3 |
| 269 | AA | X02.105VL CDR3 |
| 270 | AA | X02.106VL CDR3 |
| 271 | AA | X02.107VL FWR3 |
| 272 | AA | A02.37VL FWR3 |
| 273 | AA | A02.37VL CDR3 |
| 274 | AA | A02.46VL FWR3 |
| 275 | AA | A02.46VL CDR3 |
| 276 | AA | A02.47VL FWR3 |
| 277 | AA | A02.48VL FWR3 |
| 278 | AA | A02.49VL FWR3 |
| 279 | AA | A02.50VL FWR3 |
| 280 | AA | A02.51VL FWR3 |
| 281 | AA | A02.18VL FWR2 |
| 282 | AA | A02.18VL FWR3 |
| 283 | AA | A02.19VL FWR2 |
| 284 | AA | A02.19VL FWR3 |
| 285 | AA | A02.20VL FWR2 |
| 286 | AA | A02.20VL FWR3 |
| 287 | AA | A02.21VL FWR2 |
| 288 | AA | A02.21VL FWR3 |
| 289 | AA | A02.22VL FWR2 |
| 290 | AA | A02.22VL FWR3 |
| 291 | AA | A02.23VL FWR2 |
| 292 | AA | A02.23VL FWR3 |
| 293 | AA | A02.24VL FWR2 |
| 294 | AA | A02.24VL FWR3 |
| 295 | AA | A02.25VL FWR2 |

TABLE 30-continued

| SEQ ID NO: | Type | Description |
|---|---|---|
| 296 | AA | A02.25VL FWR3 |
| 297 | AA | A02.26VL FWR2 |
| 298 | AA | A02.26VL FWR3 |
| 299 | AA | A02.27VL CDR2 |
| 300 | AA | A02.27VL FWR3 |
| 301 | AA | A02.28VL CDR2 |
| 302 | AA | A02.28VL FWR3 |
| 303 | AA | A02.29VL CDR2 |
| 304 | AA | A02.29VL FWR3 |
| 305 | AA | A02.30VL CDR2 |
| 306 | AA | A02.30VL FWR3 |
| 307 | AA | A02.31VL CDR2 |
| 308 | AA | A02.31VL FWR3 |
| 309 | AA | A02.32VL CDR2 |
| 310 | AA | A02.32VL FWR3 |
| 311 | AA | A02.33VL CDR2 |
| 312 | AA | A02.33VL FWR3 |
| 313 | AA | A02.34VL CDR2 |
| 314 | AA | A02.34VL FWR3 |
| 315 | AA | A02.35VL CDR2 |
| 316 | AA | A02.35VL FWR3 |
| 317 | AA | A02.36VL CDR2 |
| 318 | AA | A02.36VL FWR3 |
| 319 | AA | X02.16VL CDR1 |
| 320 | AA | X02.16VL FWR3 |
| 321 | AA | X02.16VL CDR3 |
| 322 | AA | X02.17VL CDR1 |
| 323 | AA | X02.17VL FWR3 |
| 324 | AA | X02.17VL CDR3 |
| 325 | AA | A02.52VL CDR1 |
| 326 | AA | A02.52VL CDR2 |
| 327 | AA | A02.52VL FWR3 |
| 328 | AA | A02.52VL CDR3 |
| 329 | AA | A02.53VL CDR1 |
| 330 | AA | A02.53VL CDR2 |
| 331 | AA | A02.53VL FWR3 |
| 332 | AA | A02.53VL CDR3 |
| 333 | AA | A02.54VL CDR1 |
| 334 | AA | A02.54VL CDR2 |
| 335 | AA | A02.54VL FWR3 |
| 336 | AA | A02.54VL CDR3 |
| 337 | AA | A02.55VL CDR1 |
| 338 | AA | A02.55VL CDR2 |
| 339 | AA | A02.55VL FWR3 |
| 340 | AA | A02.55VL CDR3 |
| 341 | AA | A02.56VL CDR1 |
| 342 | AA | A02.56VL CDR2 |
| 343 | AA | A02.56VL FWR3 |
| 344 | AA | A02.56VL CDR3 |
| 345 | AA | A02.57VL CDR1 |
| 346 | AA | A02.57VL CDR2 |
| 347 | AA | A02.57VL FWR3 |
| 348 | AA | A02.57VL CDR3 |
| 349 | AA | A02.58VL CDR1 |
| 350 | AA | A02.58VL CDR2 |
| 351 | AA | A02.58VL FWR3 |
| 352 | AA | A02.58VL CDR3 |
| 353 | AA | A02.59VL CDR1 |
| 354 | AA | A02.59VL CDR2 |
| 355 | AA | A02.59VL FWR3 |
| 356 | AA | A02.59VL CDR3 |
| 357 | AA | A02.60VL CDR1 |
| 358 | AA | A02.60VL CDR2 |
| 359 | AA | A02.60VL FWR3 |
| 360 | AA | A02.60VL CDR3 |
| 361 | AA | A02.61VL CDR1 |
| 362 | AA | A02.61VL CDR2 |
| 363 | AA | A02.61VL FWR3 |
| 364 | AA | A02.61VL CDR3 |
| 365 | AA | A02.62VL CDR1 |
| 366 | AA | A02.62VL CDR2 |
| 367 | AA | A02.62VL FWR3 |
| 368 | AA | A02.62VL CDR3 |
| 369 | AA | A02.63VL CDR1 |
| 370 | AA | A02.63VL CDR2 |
| 371 | AA | A02.63VL FWR3 |
| 372 | AA | A02.63VL CDR3 |
| 373 | AA | A02.64VL CDR1 |
| 374 | AA | A02.64VL CDR2 |
| 375 | AA | A02.64VL FWR3 |
| 376 | AA | A02.64VL CDR3 |
| 377 | AA | A02.65VL CDR1 |
| 378 | AA | A02.65VL CDR2 |
| 379 | AA | A02.65VL FWR3 |
| 380 | AA | A02.65VL CDR3 |
| 381 | AA | A02.66VL CDR1 |
| 382 | AA | A02.66VL CDR2 |
| 383 | AA | A02.66VL FWR3 |
| 384 | AA | A02.66VL CDR3 |
| 385 | AA | A02.67VL CDR1 |
| 386 | AA | A02.67VL CDR2 |
| 387 | AA | A02.67VL FWR3 |
| 388 | AA | A02.67VL CDR3 |
| 389 | AA | 5D1.1VH FWR1 |
| 390 | AA | 5D1.1VH CDR1 |
| 391 | AA | 5D1.1VH FWR2 |
| 392 | AA | 5D1.1VH CDR2 |
| 393 | AA | 5D1.1VH FWR3 |
| 394 | AA | 5D1.1VH CDR3 |
| 395 | AA | 5D1.1VH FWR4 |
| 396 | AA | 5D1.2VH FWR1 |
| 397 | AA | 5D1.2VH FWR2 |
| 398 | AA | 5D1.2VH CDR2 |
| 399 | AA | 5D1.2VH FWR3 |
| 400 | AA | 5D1.3VH FWR1 |
| 401 | AA | 5D1.3VH FWR2 |
| 402 | AA | 5D1.3VH CDR2 |
| 403 | AA | 5D1.3VH FWR3 |
| 404 | AA | 5D1.4VH FWR1 |
| 405 | AA | 5D1.4VH FWR2 |
| 406 | AA | 5D1.4VH CDR2 |
| 407 | AA | 5D1.4VH FWR3 |
| 408 | AA | 5D1.5VH FWR1 |
| 409 | AA | 5D1.5VH FWR2 |
| 410 | AA | 5D1.5VH CDR2 |
| 411 | AA | 5D1.5VH FWR3 |
| 412 | AA | 5D1.6VH FWR1 |
| 413 | AA | 5D1.6VH FWR2 |
| 414 | AA | 5D1.6VH CDR2 |
| 415 | AA | 5D1.6VH FWR3 |
| 416 | AA | 5D1.7VH FWR1 |
| 417 | AA | 5D1.7VH FWR2 |
| 418 | AA | 5D1.7VH CDR2 |
| 419 | AA | 5D1.7VH FWR3 |
| 420 | AA | 5D1.8VH FWR1 |
| 421 | AA | 5D1.8VH FWR2 |
| 422 | AA | 5D1.8VH CDR2 |
| 423 | AA | 5D1.8VH FWR3 |
| 424 | AA | 5D1.9VH FWR1 |
| 425 | AA | 5D1.9VH FWR2 |
| 426 | AA | 5D1.9VH CDR2 |
| 427 | AA | 5D1.9VH FWR3 |
| 428 | AA | 5D1.10VH FWR1 |
| 429 | AA | 5D1.10VH FWR2 |
| 430 | AA | 5D1.10VH CDR2 |
| 431 | AA | 5D1.10VH FWR3 |
| 432 | AA | 5D1.11VH FWR1 |
| 433 | AA | 5D1.11VH FWR2 |
| 434 | AA | 5D1.11VH CDR2 |
| 435 | AA | 5D1.11VH FWR3 |
| 436 | AA | 5D1.1VL FWR1 |
| 437 | AA | 5D1.1VL CDR1 |
| 438 | AA | 5D1.1VL FWR2 |
| 439 | AA | 5D1.1VL CDR2 |
| 440 | AA | 5D1.1VL FWR3 |
| 441 | AA | 5D1.1VL CDR3 |
| 442 | AA | 5D1.1VL FWR4 |
| 443 | AA | 5D1.2VL FWR1 |
| 444 | AA | 5D1.2VL FWR2 |
| 445 | AA | 5D1.2VL FWR3 |
| 446 | AA | 5D1.2VL FWR4 |
| 447 | AA | 5D1.3VL FWR1 |
| 448 | AA | 5D1.3VL FWR2 |
| 449 | AA | 5D1.3VL FWR3 |
| 450 | AA | 5D1.3VL FWR4 |
| 451 | AA | 5D1.4VL FWR1 |

TABLE 30-continued

| SEQ ID NO: | Type | Description |
|---|---|---|
| 452 | AA | 5D1.4VL FWR2 |
| 453 | AA | 5D1.4VL FWR3 |
| 454 | AA | 5D1.4VL FWR4 |
| 455 | AA | 5D1.5VL FWR1 |
| 456 | AA | 5D1.5VL FWR2 |
| 457 | AA | 5D1.5VL FWR3 |
| 458 | AA | 5D1.5VL FWR4 |
| 459 | AA | 5D1.6VL FWR1 |
| 460 | AA | 5D1.6VL FWR2 |
| 461 | AA | 5D1.6VL FWR3 |
| 462 | AA | 5D1.6VL FWR4 |
| 463 | AA | 5D1.7VL FWR1 |
| 464 | AA | 5D1.7VL FWR2 |
| 465 | AA | 5D1.7VL FWR3 |
| 466 | AA | 5E8.1VH FWR1 |
| 467 | AA | 5E8.1VH CDR2 |
| 468 | AA | 5E8.1VH FWR3 |
| 469 | AA | 5E8.1VH CDR3 |
| 470 | AA | 5E8.2VH FWR1 |
| 471 | AA | 5E8.2VH CDR2 |
| 472 | AA | 5E8.3VH FWR1 |
| 473 | AA | 5E8.3VH CDR2 |
| 474 | AA | 5E8.4VH FWR1 |
| 475 | AA | 5E8.4VH CDR2 |
| 476 | AA | 5E8.5VH FWR1 |
| 477 | AA | 5E8.5VH CDR2 |
| 478 | AA | 5E8.6VH FWR1 |
| 479 | AA | 5E8.6VH CDR2 |
| 480 | AA | 5E8.7VH FWR1 |
| 481 | AA | 5E8.7VH CDR2 |
| 482 | AA | 5E8.8VH FWR1 |
| 483 | AA | 5E8.8VH CDR2 |
| 484 | AA | 5E8.9VH FWR1 |
| 485 | AA | 5E8.9VH CDR2 |
| 486 | AA | 5E8.10VH FWR1 |
| 487 | AA | 58E.10VH CDR2 |
| 488 | AA | 5E8.11VH FWR1 |
| 489 | AA | 58E.11VH CDR2 |
| 490 | AA | 5E8.1VL FWR1 |
| 491 | AA | 5E8.1VL CDR1 |
| 492 | AA | 5E8.1VL FWR2 |
| 493 | AA | 5E8.1VL CDR2 |
| 494 | AA | 5E8.1VL FWR3 |
| 495 | AA | 5E8.1VL CDR3 |
| 496 | AA | 5E8.1VL FWR4 |
| 497 | AA | 5E8.2VL FWR1 |
| 498 | AA | 5E8.2VL FWR2 |
| 499 | AA | 5E8.2VL FWR3 |
| 500 | AA | 5E8.2VL FWR4 |
| 501 | AA | 5E8.3VL FWR1 |
| 502 | AA | 5E8.3VL FWR2 |
| 503 | AA | 5E8.3VL FWR3 |
| 504 | AA | 5E8.3VL FWR4 |
| 505 | AA | 5E8.4VL FWR1 |
| 506 | AA | 5E8.4VL FWR2 |
| 507 | AA | 5E8.4VL FWR3 |
| 508 | AA | 5E8.4VL FWR4 |
| 509 | AA | 5E8.5VL FWR1 |
| 510 | AA | 5E8.5VL FWR2 |
| 511 | AA | 5E8.5VL FWR3 |
| 512 | AA | 5E8.5VL FWR4 |
| 513 | AA | 10A2.1VH FWR1 |
| 514 | AA | 10A2.1VH CDR1 |
| 515 | AA | 10A2.1VH FWR2 |
| 516 | AA | 10A2.1VH CDR2 |
| 517 | AA | 10A2.1VH FWR3 |
| 518 | AA | 10A2.1VH CDR3 |
| 519 | AA | 10A2.1VH FWR4 |
| 520 | AA | 10A2.2VH FWR2 |
| 521 | AA | 10A2.3VH FWR2 |
| 522 | AA | 10A2.4VH FWR2 |
| 523 | AA | 10A2.5VH FWR2 |
| 524 | AA | 10A2.6VH FWR2 |
| 525 | AA | 10A2.7VH FWR2 |
| 526 | AA | 10A2.8VH CDR1 |
| 527 | AA | 10A2.9VH CDR1 |
| 528 | AA | 10A2.10VH CDR1 |
| 529 | AA | 10A2.11VH CDR1 |
| 530 | AA | 10A2.12VH FWR3 |
| 531 | AA | 10A2.13VH FWR3 |
| 532 | AA | 10A2.14VH FWR3 |
| 533 | AA | 10A2.15VH FWR3 |
| 534 | AA | 10A2.16VH CDR3 |
| 535 | AA | 10A2.17VH CDR3 |
| 536 | AA | 10A2.18VH CDR3 |
| 537 | AA | 10A2.19VH FWR1 |
| 538 | AA | 10A2.19VH FWR2 |
| 539 | AA | 10A2.19VH CDR2 |
| 540 | AA | 10A2.19VH FWR3 |
| 541 | AA | 10A2.19VH FWR4 |
| 542 | AA | 10A2.20VH FWR1 |
| 543 | AA | 10A2.20VH FWR2 |
| 544 | AA | 10A2.20VH CDR2 |
| 545 | AA | 10A2.20VH FWR3 |
| 546 | AA | 10A2.20VH FWR4 |
| 547 | AA | 10A2.21VH FWR1 |
| 548 | AA | 10A2.21VH FWR2 |
| 549 | AA | 10A2.21VH CDR2 |
| 550 | AA | 10A2.21VH FWR3 |
| 551 | AA | 10A2.21VH FWR4 |
| 552 | AA | 10A2.22VH FWR1 |
| 553 | AA | 10A2.22VH FWR2 |
| 554 | AA | 10A2.22VH CDR2 |
| 555 | AA | 10A2.22VH FWR3 |
| 556 | AA | 10A2.22VH FWR4 |
| 557 | AA | 10A2.23VH FWR1 |
| 558 | AA | 10A2.23VH FWR2 |
| 559 | AA | 10A2.23VH CDR2 |
| 560 | AA | 10A2.23VH FWR3 |
| 561 | AA | 10A2.23VH FWR4 |
| 562 | AA | 10A2.24VH FWR1 |
| 563 | AA | 10A2.24VH FWR2 |
| 564 | AA | 10A2.24VH CDR2 |
| 565 | AA | 10A2.24VH FWR3 |
| 566 | AA | 10A2.24VH FWR4 |
| 567 | AA | 10A2.25VH FWR1 |
| 568 | AA | 10A2.25VH FWR2 |
| 569 | AA | 10A2.25VH CDR2 |
| 570 | AA | 10A2.25VH FWR3 |
| 571 | AA | 10A2.25VH FWR4 |
| 572 | AA | 10A2.26VH FWR1 |
| 573 | AA | 10A2.26VH FWR2 |
| 574 | AA | 10A2.26VH CDR2 |
| 575 | AA | 10A2.26VH FWR3 |
| 576 | AA | 10A2.26VH FWR4 |
| 577 | AA | 10A2.27VH FWR1 |
| 578 | AA | 10A2.27VH FWR2 |
| 579 | AA | 10A2.27VH CDR2 |
| 580 | AA | 10A2.27VH FWR3 |
| 581 | AA | 10A2.27VH FWR4 |
| 582 | AA | 10A2.1VL FWR1 |
| 583 | AA | 10A2.1VL CDR1 |
| 584 | AA | 10A2.1VL FWR2 |
| 585 | AA | 10A2.1VL CDR2 |
| 586 | AA | 10A2.1VL FWR3 |
| 587 | AA | 10A2.1VL CDR3 |
| 588 | AA | 10A2.1VL FWR4 |
| 589 | AA | 10A2.2VL CDR1 |
| 590 | AA | 10A2.3VL CDR1 |
| 591 | AA | 10A2.4VL CDR2 |
| 592 | AA | 10A2.5VL FWR2 |
| 593 | AA | 10A2.6VL FWR2 |
| 594 | AA | 10A2.7VL CDR3 |
| 595 | AA | 10A2.8VL CDR3 |
| 596 | AA | 10A2.9VL CDR3 |
| 597 | AA | 10A2.10VL CDR3 |
| 598 | AA | 10A2.11VL CDR3 |
| 599 | AA | 10A2.12VL CDR3 |
| 600 | AA | 10A2.13VL CDR3 |
| 601 | AA | 10A2.14VL CDR3 |
| 602 | AA | 10A2.15VL CDR3 |
| 603 | AA | 10A2 16VL CDR3 |
| 604 | AA | 10A2.17VL CDR3 |
| 605 | AA | 10A2.18VL CDR2 |
| 606 | AA | 10A2.19VL CDR3 |
| 607 | AA | 10A2.20VL FWR1 |

TABLE 30-continued

| SEQ ID NO: | Type | Description |
|---|---|---|
| 608 | AA | 10A2.20VL CDR1 |
| 609 | AA | 10A2,20VL FWR2 |
| 610 | AA | 10A2.20VL CDR2 |
| 611 | AA | 10A2.20VL FWR3 |
| 612 | AA | 10A2.20VL CDR3 |
| 613 | AA | 10A2.20VL FWR4 |
| 614 | AA | 10A2.21VL FWR1 |
| 615 | AA | 10A2.21VL FWR2 |
| 616 | AA | 10A2.21VL FWR3 |
| 617 | AA | 10A2.21VL FWR4 |
| 618 | AA | 10A2.22VL FWR1 |
| 619 | AA | 10A2.22VL FWR2 |
| 620 | AA | 10A2.22VL FWR3 |
| 621 | AA | 10A2.22VL FWR4 |
| 622 | AA | 10A2.23VL FWR1 |
| 623 | AA | 10A2.23VL FWR2 |
| 624 | AA | 10A2.23VL FWR3 |
| 625 | AA | 10A2.23VL FWR4 |
| 626 | AA | 10A2.24VL FWR1 |
| 627 | AA | 10A2.24VL FWR2 |
| 628 | AA | 10A2.24VL FWR3 |
| 629 | AA | 10A2.24VL FWR4 |
| 630 | AA | 10A2.25VL FWR1 |
| 631 | AA | 10A2.25VL FWR2 |
| 632 | AA | 10A2.25VL FWR3 |
| 633 | AA | 10A2.25VL FWR4 |
| 634 | AA | 10A2.26VL FWR1 |
| 635 | AA | 10A2.26VL FWR2 |
| 636 | AA | 10A2.26VL FWR3 |
| 637 | AA | 10A2.26VL FWR4 |
| 638 | AA | 10A2.27VL FWR1 |
| 639 | AA | 10A2.27 VL FWR2 |
| 640 | AA | 10A2.27VL FWR3 |
| 641 | AA | 10A2.27VL FWR4 |
| 642 | AA | Gly4Ser1 |
| 643 | AA | Gly4Ser1 x 2 |
| 644 | AA | Gly4Ser1 x 3 |
| 645 | AA | Gly4Ser1 x 4 |
| 646 | AA | Gly4Ser1 x 5 |
| 647 | AA | IFN-alpha2b A145D |
| 648 | AA | Trunc IFN-alpha2b |
| 649 | AA | Trunc IFN-alpha2b A145D |
| 650 | AA | IFN-alpha2b A145G |
| 651 | AA | Trunc IFN-alpha2b A145G |
| 652 | AA | IgG4 IFN-alpha2b A145D |
| 653 | AA | IgG4 IFN-alpha2b A145G |
| 654 | AA | IgG4 S228P IFN-alpha2b A145G |
| 655 | AA | IgG1 IFN-alpha2b A145G |
| 656 | AA | IgG1 YTE IFN-alpha2b A145D |
| 657 | AA | IgG1 YTE IFN-alpha2b A145G |
| 658 | AA | IgG4 YTE IFN-alpha2b A145D |
| 659 | AA | A02 consensus variable heavy |
| 660 | AA | X02.114VL |
| 661 | AA | X02.115VL |
| 662 | AA | X02.116VL |
| 663 | AA | X02.117VL |
| 664 | AA | A02 consensus variable light |
| 665 | AA | A10 consensus variable heavy |
| 666 | AA | A10 consensus variable light |
| 667 | DNA | A02.12VH |
| 668 | DNA | X02.9VH |
| 669 | DNA | X02.107VL |
| 670 | DNA | A02.47VL |
| 671 | DNA | A02.31VL |
| 672 | DNA | A02.33VL |
| 673 | DNA | X02.16VL |
| 674 | DNA | X02.17VL |
| 675 | DNA | X02.114VL |
| 676 | DNA | X02.115VL |
| 677 | DNA | X02.116VL |
| 678 | DNA | X02.117VL |
| 679 | DNA | 10A2VH + A40E |
| 680 | DNA | 10A2VH + A40G |
| 681 | DNA | 10A2VH + A40H |
| 682 | DNA | 10A2VH + A40Q |
| 683 | DNA | 10A2VH + K96G |
| 684 | DNA | 10A2VH + K96T |
| 685 | DNA | 10A2_1-f*01VH94R |
| 686 | DNA | 10A2VH (AQ) + N98Q |
| 687 | DNA | 10A2-1-24*0171A94R |
| 688 | DNA | 10A2_1-33*01Vk |
| 689 | DNA | 10A2VK + K24G |
| 690 | DNA | 10A2VK + K24Q |
| 691 | DNA | 10A2VK + R54D |
| 692 | DNA | 10A2VK + M89A |
| 693 | DNA | 10A2VK (AV) + N53Q |
| 694 | AA | IgG4 YTE IFN-alpha2b A145G |
| 695 | DNA | 910VH variable heavy chain |
| 696 | AA | 10A2VK + K24G CDR1 |
| 697 | AA | 910VH CDR1 |
| 698 | AA | 910VH CDR2 |
| 699 | AA | 910VH CDR3 |
| 700 | AA | X02.118 variable light chain |
| 701 | AA | X02.119 variable light chain |
| 702 | DNA | X02.118 variable light chain |
| 703 | DNA | X02.119 variable light chain |
| 704 | AA | X10.60 variable light chain |
| 705 | AA | X10.61 variable light chain |
| 706 | AA | X10.62 variable light chain |
| 707 | AA | X10.63 variable light chain |
| 708 | AA | X10.64 variable light chain |
| 709 | AA | X10.65 variable light chain |
| 710 | AA | X10.66 variable light chain |
| 711 | AA | X10.67 variable light chain |
| 712 | DNA | X10.60 variable light chain |
| 713 | DNA | X10.61 variable light chain |
| 714 | DNA | X10.62 variable light chain |
| 715 | DNA | X10.63 variable light chain |
| 716 | DNA | X10.64 variable light chain |
| 717 | DNA | X10.65 variable light chain |
| 718 | DNA | X10.66 variable light chain |
| 719 | DNA | X10.67 variable light chain |
| 720 | AA | X10.68 variable heavy chain |
| 721 | AA | X10.69 variable heavy chain |
| 722 | AA | X10.70 variable heavy chain |
| 723 | AA | X10.71 variable heavy chain |
| 724 | DNA | X10.68 variable heavy chain |
| 725 | DNA | X10.69 variable heavy chain |
| 726 | DNA | X10.70 variable heavy chain |
| 727 | DNA | X10.71 variable heavy chain |
| 728 | AA | X02.120 variable heavy chain |
| 729 | AA | X02.121 variable heavy chain |
| 730 | AA | X02.122 variable heavy chain |
| 731 | AA | X02.123 variabel heavy chain |
| 732 | DNA | X02.120 variable heavy chain |
| 733 | DNA | X02.121 variable heavy chain |
| 734 | DNA | X02.122 variable heavy chain |
| 735 | DNA | X02.123 variable heavy chain |
| 736 | AA | 910 variable heavy consensus |
| 737 | AA | X02.122VH CDR2 |
| 738 | AA | X02.123VH CDR2 |
| 739 | AA | X10.72 variable heavy chain |
| 740 | AA | X10.73 variable heavy chain |
| 741 | AA | X10.74 variable heavy chain |
| 742 | AA | X10.75 variable heavy chain |
| 743 | DNA | X10.72 variable heavy chain |
| 744 | DNA | X10.73 variable heavy chain |
| 745 | DNA | X10.74 variable heavy chain |
| 746 | DNA | X10.75 variable heavy chain |
| 747 | AA | X10.64VL CDR2 |
| 748 | AA | 910 VH FRW1 |
| 749 | AA | 910 VH FRW2 |
| 750 | AA | X10.120VH FRW2 |
| 751 | AA | 910 VH FRW3 |
| 752 | AA | X10.121VH FRW3 |
| 753 | AA | 910VH FRW4 |

The disclosure is not limited to the embodiments described and exemplified above, but is capable of variation and modification within the scope of the appended claims.

We claim:

1. A method for treating B-cell lymphoma, multiple myeloma, non-Hodgkin's lymphoma, chronic myelogenous leukemia, chronic lymphocytic leukemia, or acute myelogenous leukemia in a subject, the method comprising:
administering to the subject a recombinant antibody that specifically binds to CD38, the recombinant antibody comprising the heavy chain complementarity determining region 1 (CDR1), CDR2, and CDR3 of SEQ ID NO: 665 and the light chain CDR1, CDR2, and CDR3 of SEQ ID NO: 666 in an amount effective to thereby treat the B-cell lymphoma, multiple myeloma, non-Hodgkin's lymphoma, chronic myelogenous leukemia, chronic lymphocytic leukemia, or acute myelogenous leukemia.

2. The method of claim 1, wherein the recombinant antibody is a humanized antibody.

3. The method of claim 1, wherein the antibody is fused to an attenuated human interferon alpha-2b.

4. The method of claim 3, wherein the attenuated human interferon alpha-2b comprises an alanine to aspartic acid substitution at position 145 relative to the amino acid sequence of SEQ ID NO: 648.

5. The method of claim 3, wherein the attenuated human interferon alpha 2b comprises the amino acid sequence of SEQ ID NO: 647, SEQ ID NO: 649, SEQ ID NO: 650, or SEQ ID NO: 651.

6. The method of claim 5, wherein the attenuated human interferon alpha 2b comprises the amino acid sequence of SEQ ID NO: 649.

7. The method of claim 1, wherein the recombinant antibody comprises a human IgG1 heavy chain constant region.

8. The method of claim 1, wherein the recombinant antibody comprises a human IgG4 heavy chain constant region.

9. The method of claim 8, wherein the human IgG4 heavy chain constant region comprises a proline at position 228 according to the EU numbering system.

10. The method of claim 1, wherein the heavy chain CDR1 comprises the amino acid sequence of SEQ ID NO: 514, the heavy chain CDR2 comprises the amino acid sequence of SEQ ID NO: 516, the heavy chain CDR3 comprises the amino acid sequence of SEQ ID NO: 518, the light chain CDR1 comprises the amino acid sequence of SEQ ID NO: 608, the light chain CDR2 comprises the amino acid sequence of SEQ ID NO: 591, and the light chain CDR3 comprises the amino acid sequence of SEQ ID NO: 612.

11. The method of claim 10, wherein the recombinant antibody is fused to an attenuated human interferon alpha-2b comprising the amino acid sequence of SEQ ID NO: 649.

12. The method of claim 1, wherein the recombinant antibody comprises a heavy chain variable region comprising the amino acid sequence of SEQ ID NO: 156 and a light chain variable region comprising the amino acid sequence of SEQ ID NO: 185.

13. The method of claim 12, wherein the recombinant antibody is fused to an attenuated human interferon alpha-2b comprising the amino acid sequence of SEQ ID NO: 649.

* * * * *